(12) United States Patent
Ishihara et al.

(10) Patent No.: US 7,229,986 B2
(45) Date of Patent: Jun. 12, 2007

(54) MELANIN-CONCENTRATING HORMONE ANTAGONIST

(75) Inventors: Yuji Ishihara, Itami (JP); Jun Terauchi, Ikeda (JP); Nobuhiro Suzuki, Minoo (JP); Shiro Takekawa, Nishinomiya (JP); Kazuyoshi Aso, Takatsuki (JP)

(73) Assignee: Takeda Pharmaceutical Company Ltd., Osaka (JP)

( * ) Notice: Subject to any disclaimer, the term of this patent is extended or adjusted under 35 U.S.C. 154(b) by 0 days.

(21) Appl. No.: 10/276,288

(22) PCT Filed: May 15, 2001

(86) PCT No.: PCT/JP01/04015

§ 371 (c)(1),
(2), (4) Date: Nov. 12, 2002

(87) PCT Pub. No.: WO01/87834

PCT Pub. Date: Nov. 22, 2001

(65) Prior Publication Data

US 2003/0158177 A1    Aug. 21, 2003

(30) Foreign Application Priority Data

May 16, 2000  (JP) .............................. 2000-148647
Apr. 13, 2001  (JP) .............................. 2001-116219

(51) Int. Cl.
*C07D 209/08*  (2006.01)
*C07D 209/14*  (2006.01)
*C07D 401/12*  (2006.01)
*A61K 31/404*  (2006.01)
*A61P 3/04*  (2006.01)

(52) U.S. Cl. ................................. 514/217.01; 540/594
(58) Field of Classification Search ................ 540/594; 514/217.01
See application file for complete search history.

(56) References Cited

U.S. PATENT DOCUMENTS

| 3,752,818 A | 8/1973 | Plumpe .................... 260/287 R |
| 4,024,128 A | 5/1977 | Koch .......................... 260/239 |
| 4,156,734 A | 5/1979 | Stone ...................... 424/273 R |
| 4,160,835 A | 7/1979 | Stone .......................... 424/263 |
| 4,170,654 A | 10/1979 | Stone .......................... 424/283 |
| 4,245,123 A | 12/1980 | DeMarinis .................. 424/246 |
| 4,315,935 A | 2/1982 | Ali ................................ 424/258 |
| 4,335,123 A | 6/1982 | Grawinger .................. 424/246 |
| 4,482,560 A | 11/1984 | Banno ........................ 424/258 |
| 4,699,907 A | 10/1987 | Gasc .......................... 514/232 |
| 4,736,042 A | 4/1988 | Gasc .......................... 548/491 |
| 4,845,099 A | 7/1989 | Ruger ........................ 514/253 |
| 4,866,076 A | 9/1989 | Gribble ...................... 514/307 |
| 4,918,073 A | 4/1990 | Ruger ........................ 514/255 |
| 4,963,563 A | 10/1990 | DeBernardis .............. 514/307 |
| 5,026,856 A | 6/1991 | Yatsunami .................. 546/156 |
| 5,151,435 A | 9/1992 | Bagley ........................ 514/303 |
| 5,170,654 A | 12/1992 | Anagnostopoulos ......... 72/299 |
| 5,173,497 A | 12/1992 | Flanagan .................... 514/411 |
| 5,175,164 A | 12/1992 | Bagley ........................ 514/259 |
| 5,185,361 A | 2/1993 | Gilmore ...................... 514/415 |
| 5,256,789 A | 10/1993 | Stevens ...................... 514/311 |
| 5,264,587 A | 11/1993 | Flanagan .................... 548/429 |
| 5,280,032 A | 1/1994 | Ono ............................ 514/336 |
| 5,288,749 A | 2/1994 | Meyer ........................ 514/414 |

(Continued)

FOREIGN PATENT DOCUMENTS

| DE | 2060720 | 6/1972 |
| EP | 002792 | 7/1979 |
| EP | 025864 | 4/1981 |
| EP | 38177 | 10/1981 |

(Continued)

OTHER PUBLICATIONS

Dhanoa, et al. "Nonpeptide Angiotensin II (AII) Receptor Antagonists: N-substituted Indole, Dihydroindole, Phenylaminophenylacetic acid and Acylsulfonamide-Based AII Receptor Antagonists" PEPT.: Chem., Struct. Biol., Proc. Am Pept. Symp. 13th (1994) Meeting Date 1993,. 296-298. Abstract (Caplus File Search Results Attached).

Dhanoa, et al. "Nonpeptide angiotensin II receptor antagonists. 1. Design, synthesis, and biological activity of N- substituted indoles and dihydroindoles" Journal of Medicinal Chemistry 36(26): 4230-4238 (1993) (Caplus File Search Results Attached).

(Continued)

*Primary Examiner*—Bruck Kifle

(57) ABSTRACT

A melanin-concentrating hormone antagonist comprising a compound of the formula:

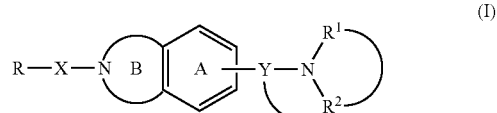

wherein R is hydrogen atom or a cyclic group which may be substituted; X is a bond or a spacer having a main chain of 1 to 10 atoms; Y is a spacer having a main chain of 1 to 6 atoms; ring A is benzene ring which may be further substituted; ring B is a 5- to 9-membered nitrogen-containing non-aromatic heterocyclic ring which may be further substituted; $R^1$ and $R^2$ are the same or different and are hydrogen atom, a hydrocarbon group which may be substituted or a heterocyclic group which may be substituted; or $R^1$ and $R^2$, together with the adjacent nitrogen atom, may form a nitrogen-containing heterocyclic ring which may be substituted; or $R^2$, together with the adjacent nitrogen atom and Y, may form a nitrogen-containing heterocyclic ring which may be substituted; or a salt thereof is useful as a preventive or therapeutic agent for obesity, etc.

15 Claims, No Drawings

U.S. PATENT DOCUMENTS

| | | | |
|---|---|---|---|
| 5,354,753 A | 10/1994 | Ohi | 514/258 |
| 5,374,643 A | 12/1994 | Atwal | 514/364 |
| 5,387,603 A | 2/1995 | Kitazawa | 514/415 |
| 5,387,685 A | 2/1995 | Powell | 546/143 |
| 5,391,556 A | 2/1995 | Heckel | 514/322 |
| 5,455,348 A | 10/1995 | Austel | 544/238 |
| 5,462,934 A | 10/1995 | Goto | 514/183 |
| 5,472,984 A | 12/1995 | Ono | 514/651 |
| 5,478,822 A | 12/1995 | Hoshino | 514/213 |
| 5,538,973 A | 7/1996 | Matsui | 514/253 |
| 5,541,218 A | 7/1996 | Ikeda | 514/419 |
| 5,547,966 A | 8/1996 | Atwal | 514/352 |
| 5,550,149 A | 8/1996 | Powell | 514/416 |
| 5,561,141 A | 10/1996 | Powell | 514/311 |
| 5,612,381 A | 3/1997 | Ono | 514/651 |
| 5,616,620 A | 4/1997 | Rudolf | 514/620 |
| 5,622,947 A | 4/1997 | Ogawa | 514/213 |
| 5,631,280 A | 5/1997 | Ciccarone et al. | 514/416 |
| 5,639,887 A | 6/1997 | Powell | 546/293 |
| 5,658,904 A | 8/1997 | Ono | 514/237.2 |
| 5,719,150 A | 2/1998 | Ono | 514/239.2 |
| 5,750,520 A | 5/1998 | Danilewicz | 514/212 |
| 5,753,644 A | 5/1998 | Ogawa | 514/213 |
| 5,767,129 A | 6/1998 | Yuen | 514/307 |
| 5,807,875 A | 9/1998 | Rudolf | 514/364 |
| 5,807,886 A | 9/1998 | MacDonald | 514/438 |
| 5,817,833 A | 10/1998 | Gaster | 548/484 |
| 5,856,530 A | 1/1999 | Webber | 549/478 |
| 5,861,393 A | 1/1999 | Danilewicz | 514/213 |
| 5,872,117 A | 2/1999 | Ono | 514/227.5 |
| 5,889,022 A | 3/1999 | Gaster | 514/314 |
| 5,929,103 A | 7/1999 | Yoon | 514/392 |
| 5,932,573 A | 8/1999 | Yuen | 514/229.8 |
| 5,932,742 A | 8/1999 | Yoon | 548/312.1 |
| 5,936,089 A | 8/1999 | Carpino | 546/143 |
| 6,004,977 A | 12/1999 | Kurys | 514/307 |
| 6,025,367 A | 2/2000 | Forbes | 514/307 |
| 6,100,284 A | 8/2000 | Oku | 514/394 |
| 6,117,898 A | 9/2000 | MacDonald | 514/438 |
| 6,143,762 A | 11/2000 | Nash | 514/307 |
| 6,143,791 A | 11/2000 | Goldin | 514/634 |
| 6,194,409 B1 | 2/2001 | vanBoeckel | 514/243 |
| 6,200,978 B1 | 3/2001 | Maw | 514/254.05 |
| 6,238,856 B1 | 5/2001 | Uchida et al. | 430/566 |

FOREIGN PATENT DOCUMENTS

| | | |
|---|---|---|
| EP | 229623 | 7/1987 |
| EP | 230179 | 7/1987 |
| EP | 263480 | 1/1988 |
| EP | 300725 | 1/1989 |
| EP | 343560 | 11/1989 |
| EP | 383281 | 8/1990 |
| EP | 422666 | 4/1991 |
| EP | 457318 | 11/1991 |
| EP | 47635 | 3/1992 |
| EP | 508723 | 10/1992 |
| EP | 517357 | 12/1992 |
| EP | 528369 | 2/1993 |
| EP | 555824 | 8/1993 |
| EP | 560235 | 9/1993 |
| EP | 587180 | 3/1994 |
| EP | 600675 | 6/1994 |
| EP | 634401 | 1/1995 |
| EP | 656350 | 6/1995 |
| EP | 801060 | 10/1997 |
| GB | 1244593 | 9/1971 |
| GB | 1313539 | 4/1973 |
| JP | 56-147768 | 11/1981 |
| JP | 63-290821 | 11/1988 |
| JP | 3-181478 | 8/1991 |
| JP | 4-095070 | 3/1992 |
| JP | 6 211800 | 8/1994 |
| JP | 6-239841 | 8/1994 |
| JP | 6-016558 | 1/1995 |
| JP | 7-330725 | 12/1995 |
| JP | 7-330726 | 12/1995 |
| JP | 2000-016984 | 1/2000 |
| JP | 2000-321732 | 11/2000 |
| JP | 2000-321736 | 11/2000 |
| WO | WO 91/01724 | 2/1991 |
| WO | WO 91/162298 | 10/1991 |
| WO | WO 92/03436 | 3/1992 |
| WO | WO 93/00335 | 1/1993 |
| WO | WO 93/12754 | 7/1993 |
| WO | WO 93/15077 | 8/1993 |
| WO | WO 93/20065 | 10/1993 |
| WO | WO 94/19340 | 1/1994 |
| WO | WO 94/02459 | 2/1994 |
| WO | WO 94/08582 | 4/1994 |
| WO | WO 94/17035 | 8/1994 |
| WO | WO 95/13274 | 5/1995 |
| WO | WO 95/17398 | 6/1995 |
| WO | WO 95/20950 | 8/1995 |
| WO | WO 96/06079 | 3/1996 |
| WO | WO 96/08491 | 3/1996 |
| WO | WO 96/17606 | 6/1996 |
| WO | WO 96/30014 | 10/1996 |
| WO | WO 96/35713 | 11/1996 |
| WO | WO 96/34871 | 12/1996 |
| WO | WO 96/39382 | 12/1996 |
| WO | WO 96/01817 | 1/1997 |
| WO | WO 97/06158 | 2/1997 |
| WO | WO 97/11069 | 3/1997 |
| WO | WO 97/40051 | 10/1997 |
| WO | WO 97/43305 | 11/1997 |
| WO | WO 97/49695 | 12/1997 |
| WO | WO 98/06699 | 2/1998 |
| WO | WO 98/07719 | 2/1998 |
| WO | WO 98/25611 | 6/1998 |
| WO | WO 98/29407 | 7/1998 |
| WO | WO 98/46590 | 10/1998 |
| WO | WO 98/47876 | 10/1998 |
| WO | WO 98/50346 | 11/1998 |
| WO | WO 99/00371 | 1/1999 |
| WO | WO 99/33798 | 7/1999 |
| WO | WO 99/43652 | 9/1999 |
| WO | WO 99/50237 | 10/1999 |
| WO | WO 99/62904 | 12/1999 |
| WO | WO 00/12074 | 3/2000 |
| WO | WO 00/15612 | 3/2000 |
| WO | WO 00/17190 | 3/2000 |
| WO | WO 00/21951 | 4/2000 |
| WO | WO 00/23437 | 4/2000 |
| WO | WO 00/42036 | 7/2000 |
| WO | WO 00/64866 | 11/2000 |
| WO | WO 00/76966 | 12/2000 |
| WO | WO 00/76970 | 12/2000 |
| WO | WO 00/77027 | 12/2000 |
| WO | WO 01/05784 | 1/2001 |
| WO | WO 01/07412 | 2/2001 |
| WO | WO 01/12600 | 2/2001 |
| WO | WO 01/21169 | 3/2001 |
| WO | WO 01/21577 | 3/2001 |
| WO | WO 01/21598 | 3/2001 |
| WO | WO 01/32626 | 5/2001 |
| WO | WO 01/44226 | 6/2001 |

OTHER PUBLICATIONS

Cannon, et al. "Derivatives of 4-(2-N,N-di-n-propylaminoethyl)-5-hydroxyindole: synthesis and pharmacological effects" Pharmaceutical Research 9(6):735-738 (1992) (Caplus File Search Results Attached).

MELANIN-CONCENTRATING HORMONE ANTAGONIST

This application is the National Phase filing of International Patent Application No. PCT/JP01/04015, filed 15 May 2001.

TECHNICAL FIELD

The present invention relates to a melanin-concentrating hormone antagonist which is useful as an agent for preventing or treating obesity, etc.

BACKGROUND ART

Feeding behavior is an essential action for many living beings including humans. Therefore, if irregularities in feeding behavior occur, disorders, often connected to diseases, will occur in normal life-maintaining activities. Accompanying recent changes of our dietary environment, obesity is now becoming a social problem. In addition, not only is obesity a serious risk factor for life-style diseases such as diabetes, hypertension, and arteriosclerosis; it is also widely known that increased body weight places excessive burdens on joints such as knee joints, causing arthritis and pain. The "diet boom," etc. show that there is a potentially great percentage of the population hoping to reduce body weight; on the other hand, many cases of feeding problems such as overeating, occurring due to causes such as hereditary neurosis or neurosis due to stress, have been reported.

Therefore, research on and development of agents for preventing or treating obesity, or agents for inhibiting eating, have been vigorously done for a long time. The centrally acting anorectic drug, Mazindol, is now being marketed.

Many appetite control factors such as leptin, have recently been discovered, and the development of anti-obesity agents or anorectic agents which will regulate the functions of these appetite control factors is progressing. In particular, it is known that melanin-concentrating hormone (hereinafter also abbreviated as "MCH") originates in the hypothalamus and has orexigenic action. In addition, it has been reported that even though the daily behavior of MCH knock-out mice was normal, the amount of feeding by MCH knock-out mice was significantly reduced and their body weights were lighter than those of normal mice [Nature, Vol. 396, p. 670, 1998]. This indicates that, if a MCH antagonist was produced, it can be expected to be an excellent anorectic agent or anti-obesity agent; but at present there are no known compound, especially non-peptide type compounds, which possess MCH antagonistic actions.

On the other hand, the following compounds are known as amine derivatives.

1) JP 10-504315 A describes a compound represented by the formula:

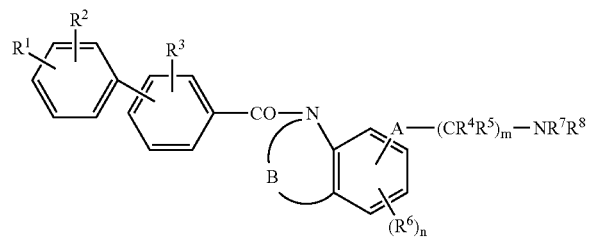

wherein $R^1$ is hydrogen, halogen, $C_{1-6}$ alkyl, $C_{3-6}$ cycloalky, $COC_{1-6}$ alkyl, $C_{1-6}$ alkoxy, hydroxy, hydroxy-$C_{1-6}$ alkyl, hydroxy-$C_{1-6}$ alkoxy, acyl, nitro, trifluoromethyl, cyano, CHO, $SR^9$, $SOR^9$, $SO_2R^9$, $SO_2NR^{10}R^{11}$, $CO_2R^{10}$, $NR^{10}SO_2R^{11}$, $CONR^{10}R^{11}$, $CO_2NR^{10}R^{11}$, $CONR^{10}(CH_2)_pCO_2R^{11}$, $(CH_2)_pNR^{10}$, $R^{11}$, $(CH_2)_pCONR^{10}R^{11}$, $(CH_2)_pNR^{10}COR^{11}$, $(CH_2)_pCO_2-C_{1-6}$ alkyl, $CO_2(CH_2)_pOR^{10}$, $CONHNR^{10}R^{11}$, $NR^{10}R^{11}$, $NR^{10}CO_2R^{11}$, $NR^{10}CONR^{10}R^{11}$, $CR^{10}=NOR^{11}$, $CNR^{10}=NOR^{11}$ (wherein $R^{10}$ and $R^{11}$ are independently hydrogen, or $C_{1-6}$ alkyl and p is 1 to 4);

$R^2$ and $R^3$ are independently hydrogen, halogen, $C_{1-6}$ alkyl, $C_{3-6}$ cycloalkyl, $C_{3-6}$ cycloalkenyl, $C_{1-6}$ alkoxy, acyl, aryl, acyloxy, hydroxy, nitro, trifluoromethyl, cyano, hydroxy-$C_{1-6}$ alkyl, $C_{1-6}$ alkyl-O—$C_{1-6}$ alkyl, $CO_2R^{10}$, $CONR^{10}R^{11}$, $NR^{10}R^{11}$ (wherein $R^{10}$ and $R^{11}$ are independently hydrogen, or $C_{1-6}$ alkyl);

$R^4$ and $R^5$ are independently hydrogen or $C_{1-6}$ alkyl;

$R^6$ is hydrogen, halogen, hydroxy, $C_{1-6}$ alkyl or $C_{1-6}$ alkoxy;

$R^7$ and $R^8$ are independently hydrogen, $C_{1-6}$ alkyl, aralkyl or they, together with the nitrogen to which they are attached, may form a 5- to 7-heterocyclic ring containing one or two heteroatoms selected from oxygen, nitrogen and sulfur which may be substituted;

A is oxygen, $S(O)_q$ (wherein q is 0, 1 or 2), $CR^4=CR^5$ or $CR^4R^5$ (wherein $R^4$ and $R^5$ are independently hydrogen or $C_{1-6}$ alkyl), or A is $NR^{12}$ (wherein $R^{12}$ is hydrogen or $C_{1-6}$ alkyl);

B is $(CR^{13}R^{14})_q$ (wherein q is 2, 3 or 4, $R^{13}$ and $R^{14}$ are independently hydrogen or $C_{1-6}$ alkyl), or B is $(CR^{13}R^{14})_r$-D (wherein r is 0, 1 or 2, D is oxygen, sulfur or $CR^{13}=CR^{14}$); m is 1 to 4; and n is 1 or 2; or a salt thereof, which has 5-HT$_{1D}$ antagonistic activity.

As specific examples thereof, there are described 1-(4'-acetamidomethyl-2'-methylbiphenyl-4-carbonyl)-5-chloro-2,3-dihydro-6-(2-dimethylaminoethoxy)-1H-indole, 1-(4'-acetamidomethyl-2'-methylbiphenyl-4-carbonyl)-2,3-dihydro-6-(3-dimethylaminopropyl)-5-ethoxy-1H-indole, etc.

2) JP 9-506885 A (WO95/17398) describes a compound represented by the formula:

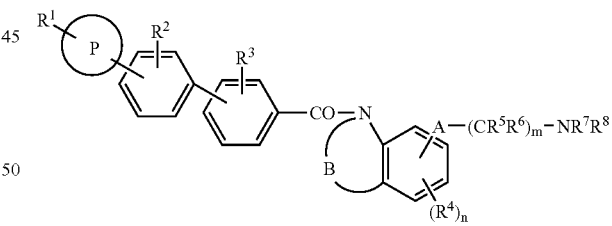

wherein P is a 5- to 7-membered heterocyclic ring containing one to three heteroatoms selected from oxygen, nitrogen and sulfur;

$R^1$, $R^2$ and $R^3$ are independently hydrogen, halogen, $C_{1-6}$ alkyl, $C_{3-6}$ cycloalky, $C_{3-6}$ cylcoalkenyl, $C_{1-6}$ alkoxy, acyl aryl, acyloxy, hydroxy, nitro, trifluoromethyl, cyano, $CO_2R^9$, $CONR^{10}R^{11}$, $NR^{10}R^{11}$ (wherein $R^9$, $R^{10}$ and $R^{11}$ are independently hydrogen, or $C_{1-6}$ alkyl);

$R^4$ is hydrogen, halogen, hydroxy, $C_{1-6}$ alkyl or $C_{1-6}$ alkoxy;

$R^5$ and $R^6$ are independently hydrogen or $C_{1-6}$ alkyl;

$R^7$ and $R^8$ are independently hydrogen, $C_{1-6}$ alkyl, aralkyl or they, together with the nitrogen to which they are attached, may form a 5- to 7-heterocyclic ring containing one or two heteroatoms selected from oxygen, nitrogen and sulfur which may be substituted;

A is oxygen, $S(O)_n$ (wherein n is 0, 1 or 2), or A is $NR^{12}$ (wherein $R^{12}$ is hydrogen or $C_{1-6}$ alkyl), or A is $CR^5=CR^6$ or $CR^5R^6$ (wherein $R^5$ and $R^6$ are independently hydrogen or $C_{1-6}$ alkyl);

m is 1 to 4;

n is 1 or 2;

B is $(CR^{13}R^{14})_q$ (wherein q is 2, 3 or 4, $R^{13}$ and $R^{14}$ are independently hydrogen or $C_{1-6}$ alkyl), or B is $(CR^{13}R^{14})_r$-D (wherein r is 0, 1 or 2, D is oxygen, sulfur or $CR^{13}=CR^{14}$); or a salt thereof, which has 5-$HT_{1D}$ antagonistic activity.

As specific examples thereof, there are described [7-(2-dimethylaminoethoxy)-6-methoxy-3,4-dihydro-2H-quinolin-1-yl]-[2'-methyl-4'-(5-methyl-1,2,4-oxadiazol-3-yl)biphenyl-4-yl]methanone, [7-(2-dimethylaminopropyl)-6-methoxy-3,4-dihydro-2H-quinolin-1-yl]-[2'-methyl-4'-(5-methyl-1,2,4-oxadiazol-3-yl)biphenyl-4-yl]methanone, etc.

3) JP 6-211800 A describes a compound represented by the formula:

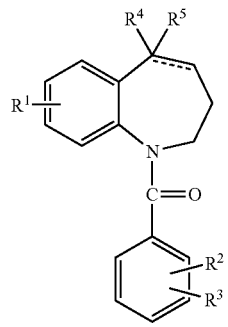

wherein $R^1$ is hydrogen atom, a halogen atom, hydroxy group, a lower alkanoyloxy group, amino-lower alkoxy group which may have a group selected from a lower alkyl group and a lower alkanoyl group as a substituent, a carboxy-substituted lower alkoxy group, a lower alkoxycarbonyl-substituted lower alkoxy group, or an aminocarbonyl lower alkoxy group which may have a lower alkyl group as a substituent; $R^4$ is hydrogen atom, a group of —$NR^6R^7$ (wherein $R^6$ and $R^7$ are the same or different and are hydrogen atom, a lower alkyl group, a lower alkenyl group or benzoyl group having a halogen atom on the phenyl ring), a lower alkenyloxy group, a hydroxy-substituted lower alkyl group, a group of —O—CO-$ANR^8R^9$ (wherein A is a lower alkylene group, $R^8$ and $R^9$ are the same or different and are hydrogen atom or a lower alkylene group, or $R^8$ and $R^9$, together with the nitrogen atom to which they are attached, may form a 5- to 6-membered saturated or unsaturated heterocyclic ring through or without through oxygen or nitrogen atom, said heterocyclic ring may have a lower alkyl group on the heterocyclic ring as a substituent), a group of —O—$R^{10}$ ($R^{10}$ is an amino acid residue), a lower alkoxycarbonyl-substituted lower alkylidene group, a lower alkoxycarbonyl-substituted lower alkyl group, a carboxy-substituted lower alkyl group, a group of -$ACONR^{11}R^{12}$ (A is as defined above, $R^{11}$ and $R^{12}$ are the same or different and are hydrogen atom, a lower alkyl group which may have hydroxy group, piperidinyl group which may have a phenyl-lower alkyl group on the piperidine ring, a carbamoyl-substituted lower alkyl group, a pyridyl-substituted lower alkyl group, pyridyl group, a group of -$ANR^{39}R^{40}$ (A is as defined above, $R^{39}$ and $R^{40}$ are the same or different and are hydrogen atom or a lower alkyl group which may have hydroxy group, or $R^{39}$ and $R^{40}$, together with the nitrogen atom to which they are attached, may form a 5- to 6-membered saturated heterocyclic ring thorough or without thorough nitrogen or oxygen atom, said heterocyclic ring may have a lower alkyl on the heterocyclic ring as a substituent), a pyrazinyl-substituted lower alkyl group which may have a lower alkyl group on the pyrazine ring as a substituent, a pyrrolyl-substituted lower alkyl group which may have a lower alkyl group on the pyrrole ring, a pyrrolidinyl-substituted lower alkyl group which may have a lower alkyl group on the pyrrolidine ring, or phenyl group which may have a halogen atom on the phenyl ring, or $R^{11}$ and $R^{12}$, together with the nitrogen atom to which they are attached, may form a 5- to 7-membered heterocyclic ring through or without thorough nitrogen or oxygen atom, said heterocyclic ring may be substituted with a lower alkyl group or a pyrrolidinylcarbonyl-lower alkyl group, each of which may have one to two groups selected from the group consisting of a lower alkyl group, a lower alkoxycarbonyl group, amino group which may have a group selected from the group consisting of a lower alkyl group or a lower alkanoyl group as a substituent), a lower alkoxycarbonyl-substituted lower alkyl group, phenyl group which may have a halogen atom on the phenyl ring, a cyano-substituted lower alkyl group, a lower alkenyl group, an oxiranyl-substituted lower alkyl group, a carbamoyl-substituted lower alkyl group and amino group which may have hydroxy group and a lower alkyl group as a substituent), a group —$OACONR^{23}R^{24}$ (A is as defined above, $R^{23}$ and $R^{24}$ are the same or different and are hydrogen atom, a lower alkyl group, a lower alkoxycarbonyl-substituted lower alkyl group, a carboxy-substituted lower alkyl group, piperidinyl group which may have a lower alkyl group on the piperidine ring, or a group of —B—$NR^{23A}R^{24A}$ (wherein B is a lower alkylene group, $R^{23A}$ and $R^{24A}$ are the same or different and are hydrogen atom or a lower alkyl group, or $R^{23A}$ and $R^{24A}$, together with the nitrogen atom to which they are attached, may form a 5- to 6-membered saturated heterocyclic ring through or without through nitrogen atom or oxygen atom), or $R^{23}$ and $R^{24}$, together with the nitrogen atom to which they are attached, may form a 5- to 7-membered saturated heterocyclic ring through or without through nitrogen atom or oxygen atom, said heterocyclic ring may have a lower alkyl group on the heterocyclic ring as a substituent), a pyrrolidinylcarbonyl-lower alkoxy group having a lower alkoxycarbonyl group on the pyrrolidine ring, a lower alkoxy-substituted lower alkanoyloxy group, a group of —$BOCOANR^{25}R^{26}$ (A is as defined above, B is lower alkylene group, $R^{25}$ and $R^{26}$ are the same or different and are hydrogen atom or a lower alkyl group), amino-substituted lower alkylidene group which may have a lower alkyl group as a substituent, a group of —$OANR^{27}R^{28}$ (A is as defined above, $R^{27}$ and $R^{28}$ are the same or different and are hydrogen atom, a lower alkyl group, a lower alkenyl group, a lower alkynyl group, a lower alkylsulfonyl group, an aminothiocarbonyl group which may have a lower alkyl group as a substituent, a group of

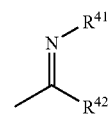

wherein $R^{41}$ is hydrogen atom or cyano group, $R^{42}$ is a lower alkyl group or amino group which may have a lower alkyl group as a substituent), carbamoyl group, a lower alkoxycarbonyl group, cycloalkyl group, a phenyl-lower alkyl group which may have a halogen atom as a substituent on the phenyl group, a cyano-substituted lower alkyl group, a halogen atom-substituted lower alkylsulfonyl group or an amino-substituted lower alkyl group which may have a lower alkyl group, or $R^{27}$ and $R^{28}$, together with the nitrogen atom to which they are attached, may form a 5- to 10-membered monocyclic or bicyclic, and saturated or unsaturated heterocyclic ring, said heterocyclic ring may have oxo group, a lower alkyl group, a lower alkoxycarbonyl group, a lower alkanoyl group or a lower alkanoylamino group on the heterocyclic ring as a substituent), cyano group, a cyano-substituted lower alkyl group, a lower alkoxy group having phenylsulfonyloxy group whose phenyl ring may have a lower alkyl group as a substituent or hydroxy group, a group -$ANR^{29}R^{30}$ (A is as defined above, $R^{29}$ is hydrogen atom or a lower alkyl group, $R^{30}$ is a lower alkenyl group, cycloalkyl group or a lower alkynyl group, or $R^{29}$ and $R^{30}$, together the nitrogen atom to which they are attached, may form a 5- or 6-membered saturated heterocyclic ring through or without through nitrogen atom or oxygen atom, said heterocyclic ring may have a lower alkyl group, a lower alkanoyl group, amino group which may have a group selected from the group consisting of a lower alkyl group and a lower alkanoyl group, a lower alkylsulfonyl group, a lower alkoxycarbonyl group, or aminocarbonyl group which may be substituted with a lower alkyl group on the heterocyclic ring as a substituent), a phenylsulfonyloxy-substituted lower alkyl group which may have an lower alkyl group on the phenyl ring, a phthalimide-substituted lower alkyl group, a cyano-substituted lower alkylidene group, a halogen atom-substituted alkyl group, an imidazolyl-substituted lower alkyl group, 1, 2, 4-triazolyl-substituted lower alkoxy group, 1, 2, 3, 4-tetrazolyl-substitued lower alkoxy group, 1, 2, 3, 5-tetrazolyl-substitued lower alkoxy group, 1, 2, 3, 4-tetrazolyl-substituted lower alkyl group, 1, 2, 3, 5-tetrzolyl-substituted lower alkyl group, 1, 2, 4-triazolyl-substituted lower alkyl group, a carboxy-substituted lower alkoxy group, a lower alkoxycarbonyl-substituted lower alkoxy group, a pyridylthio-substituted lower alkoxy group, a pyrimidinylthio-substituted lower alkoxy group which may have a lower alkyl group on the pyrimidine ring, an imidazolylthio-substituted lower alkoxy group, a pyridylsulfinyl-substituted lower alkoxy group, a pyridylsulfonyl-substituted lower alkoxy group, an imidazolylsulfinyl-substituted lower alkoxy group or an imidazolylsulfonyl-substituted lower alkoxy group; $R^5$ is hydrogen atom or hydroxy group, or $R^4$ and $R^5$ together form oxo group; $R^2$ is hydrogen atom, a lower alkyl group, hydroxy group, a halogen atom or a lower alkoxy group; $R^3$ is a group of

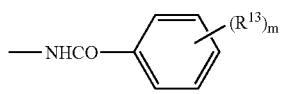

(wherein $R^{13}$ is a halogen atom, hydroxy group, carbamoyl group, a lower alkyl group, a piperazinyl-lower alkoxy group having a lower alkanoyl group at 4-position of the piperazine ring, an imidazolyl-substituted lower alkoxy group, piperidinyl-lower alkoxy group having a lower alkanoylamino group on the piperidine ring, a 1, 2, 4-triazolyl-substituted lower alkoxy group, a ureido-substituted lower alkoxy group which may have a lower alkyl group or an amino-substituted lower alkoxy group which may have a lower alkyl group as a substituent; m is 0 or an integer of 1 to 3, a phenyl-lower alkanoylamino group which have one to three groups selected from the group consisting of a halogen atom, a lower alkoxy group, a lower alkyl group and nitro group on the phenyl ring as a substituent, a group of

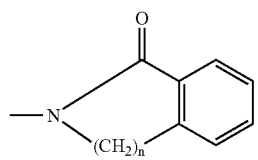

(n is 1 or 2) or a group of

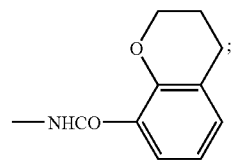

the bond between 4 and 5 positions of the benzazepine ring represent a single bond or a double bond; provided that, when $R^1$ is hydrogen atom or a halogen atom, and $R^4$ is hydrogen atom, a group of —$NR^6R^7$ ($R^6$ and $R^7$ are the above $R^6$ and $R^7$ other than benzoyl group having a halogen atom on the phenyl ring as a substituent), a group of —O—CO$ANR^8R^9$ (A is as defined above, $R^8$ and $R^9$ are the same or different and are hydrogen atom or a lower alkyl), a hydroxy group-substituted lower alkyl group, a carboxy-substituted lower alkoxy group, a lower alkoxycarbonyl-substituted lower alkoxy group or a group —O-A-$NR^{27}R^{28}$ (A is as defined above, $R^{27}$ and $R^{28}$ are the same or different and are hydrogen atom or a lower alkyl group), $R^5$ is hydrogen atom or hydroxy group or $R^4$ and $R^5$ together form oxo group, and further $R^3$ is a group of

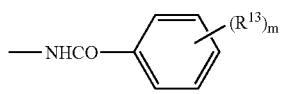

$R^{13}$ must be carbamoyl group, a piperazinyl-lower alkoxy group having a lower alkanoyl group at 4-position of the piperazine ring, a piperidinyl-lower alkoxy group having a lower alkanoylamino group on the piperidine ring, 1, 2, 4-triazolyl-substituted lower alkoxy group or a ureido-substituted lower alkoxy group which may have a lower alkyl group; or a salt thereof, which has vasopressin antagonistic activity or oxytocin antagonistic activity.

As specific examples, there are described N-[4-[[7-[3-(dimethylamino)propoxy]-2,3,4,5-tetrahydro-1H-1-benzazepin-1-yl]carbonyl]phenyl]-2-methylbenzamide, etc.

There has been great desire for the development of a melanin-concentrating hormone antagonist which is useful as an agent for preventing or treating obesity, excellent in oral absorbency, and safe.

DISCLOSURE OF INVENTION

As a result of intensive studies of compounds with a MCH antagonistic action, the present inventors found that a derivative which is obtained by introducing a group of the formula: R—X— where each symbol is as defined hereafter, into a compound of the formula:

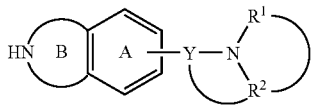

wherein each symbol is as defined hereinafter, had an excellent MCH antagonistic actions, to complete the present invention.

Namely, the present invention relates to:

1) A melanin-concentrating hormone antagonist which comprises a compound represented by the formula:

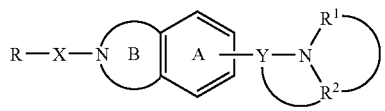

(I)

wherein R is hydrogen atom, a halogen atom or a cyclic group which may be substituted;
X is a bond or a spacer having a main chain of 1 to 10 atoms;
Y is a spacer having a main chain of 1 to 6 atoms;
ring A is benzene ring which may be further substituted;
ring B is a 5- to 9-membered nitrogen-containing non-aromatic heterocyclic ring which may be further substituted; and
$R^1$ and $R^2$ are the same or different and are hydrogen atom, a hydrocarbon group which may be substituted or a heterocyclic group which may be substituted; or $R^1$ and $R^2$, together with the adjacent nitrogen atom, may form a nitrogen-containing heterocyclic ring which may be substituted; or $R^2$, together with the adjacent nitrogen atom and Y, may form a nitrogen-containing heterocyclic ring which may be substituted;
or a salt thereof;

2) The antagonist according to the above 1), wherein R is a cyclic group which may be substituted; X is a spacer having a main chain of 1 to 6 atoms; and $R^1$ and $R^2$ are the same or different and are hydrogen atom or a hydrocarbon group which may be substituted; or $R^1$ and $R^2$, together with the adjacent nitrogen atom, form a nitrogen-containing heterocyclic ring which may be substituted; or $R^2$, together with the adjacent nitrogen atom and Y, form a nitrogen-containing heterocyclic ring which may be substituted;

3) The antagonist according to the above 1) which is an agent for preventing or treating diseases caused by melanin-concentrating hormone;

4) The antagonist according to the above 1) which is an agent for preventing or treating obesity;

5) A compound represented by the formula:

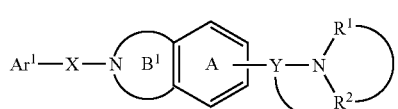

(I')

wherein $Ar^1$ is a cyclic group which may be substituted;
X is a bond or a spacer having a main chain of 1 to 10 atoms;
Y is a spacer having a main chain of 1 to 6 atoms;
ring A is benzene ring which may be further substituted;
ring $B^1$ is a 5- to 9-membered nitrogen-containing non-aromatic heterocyclic ring which may be further substituted; and
$R^1$ and $R^2$ are the same or different and are hydrogen atom, a hydrocarbon group which may be substituted or a heterocyclic group which may be substituted; or $R^1$ and $R^2$, together with the adjacent nitrogen atom, may form a nitrogen-containing heterocyclic ring which may be substituted; or $R^2$, together with the adjacent nitrogen atom and Y, may form a nitrogen-containing heterocyclic ring (except piperidine) which may be substituted;
provided that, when X is CO, ring $B^1$ is not azepane or 4,5-dihydroazepine each of which may be further substituted, or $Ar^1$ is not biphenylyl which may be substituted, and that Y is not —CO—(C(Ra)H)$_{na}$— (Ra is hydrogen atom or a hydrocarbon group which may be substituted, na is an integer of 1 to 10) and does not have a bicyclic nitrogen-containing heterocyclic ring substituted with amino group; or a salt thereof;

6) The compound according to the above 5), wherein X is a spacer having a main chain of 1 to 10 atoms; and $R^1$ and $R^2$ are the same or different and are hydrogen atom or a hydrocarbon group which may be substituted; or $R^1$ and $R^2$, together with the adjacent nitrogen atom, form a nitrogen-containing heterocyclic ring which may be substituted; or $R^2$, together with the adjacent nitrogen atom and Y, form a nitrogen-containing heterocyclic ring (except piperidine) which may be substituted;

7) The compound according to the above 5), wherein the cyclic group represented by $Ar^1$ is an aromatic group;

8) The compound according to the above 7), wherein the aromatic group is a group formed by removing an optional one hydrogen atom from an aromatic ring assembly formed by 2 or 3 members selected from $C_{6-14}$ monocyclic or condensed polycyclic aromatic hydrocarbon and 5- to 10-membered aromatic heterocyclic ring;

9) The compound according to the above 5), wherein the spacer represented by X and Y is a bivalent group consisting of 1 to 3 members selected from —O—, —S—, —CO—, —SO—, —SO$_2$—, —NR$^8$— ($R^8$ is hydrogen atom, optionally halogenated $C_{1-6}$ alkyl, optionally halogenated $C_{1-6}$ alkyl-carbonyl or optionally halogenated $C_{1-6}$ alkylsulfonyl), and a divalent $C_{1-6}$ non-cyclic hydrocarbon group which may be substituted;

10) The compound according to the above 5), wherein X is CO;

11) The compound according to the above 5), wherein Y is $C_{2-6}$ alkenylene which may be substituted;

12) The compound according to the above 5), wherein the group represented by the formula:

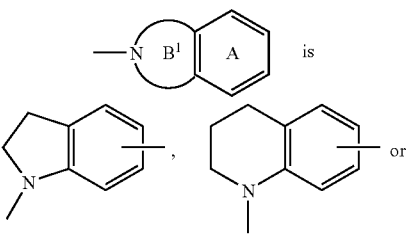

-continued

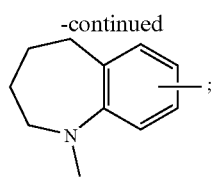

13) The compound according to the above 5), wherein $R^1$ and $R^2$, together with the adjacent nitrogen atom, form a nitrogen-containing heterocyclic ring which may be substituted;

14) The compound according to the above 5), wherein $R^1$ and $R^5$ are $C_{1-6}$ alkyl;

15) A pharmaceutical composition comprising the compound according to the above 5), or a salt thereof;

16) A prodrug of the compound according to the above 5);

17) A process for producing a compound represented by the formula:

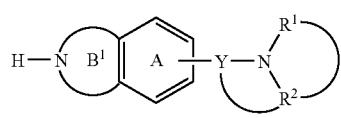
(I′)

wherein each symbol is as defined in the above 5), or a salt thereof, which comprises reacting a compound represented by the formula:

$Ar^1$—X-L     (IIb)

wherein L is a leaving group and the other symbols are as defined above, or a salt thereof with a compound represented by the formula:

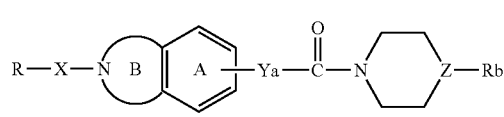
(IIIb)

wherein each symbol is as defined above, or a salt thereof;

18) A compound represented by the formula:

(I″)

wherein R is hydrogen atom, a halogen atom or a cyclic group which may be substituted;
X is a bond or a spacer having a main chain of 1 to 10 atoms;
Ya is a spacer having a main chain of 1 to 5 atoms;
ring A is benzene ring which may be further substituted; ring B is a 5- to 9-membered nitrogen-containing non-aromatic heterocyclic ring which may be further substituted;
Z is CH or N; and
Rb is hydrogen atom or a hydrocarbon group which may be substituted;
provided that Ya does not have a bicyclic nitrogen-containing heterocyclic ring substituted with amino group;
or a salt thereof;

19) The compound according to the above 18), wherein R is hydrogen atom;

20) The compound according to the above 18), wherein Ya is —$(CH_2)_{w1}CO(CH_2)_{w2}$— (w1 and w2 are an integer of 0 to 5 and w1+w2 is 0 to 5);

21) The compound according to the above 18), wherein Z is CH;

22) The compound according to the above 18), wherein Rb is $C_{6-14}$, aryl which may be substituted;

23) The compound according to the above 18), wherein the group represented by the formula:

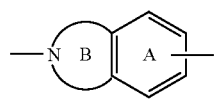

is

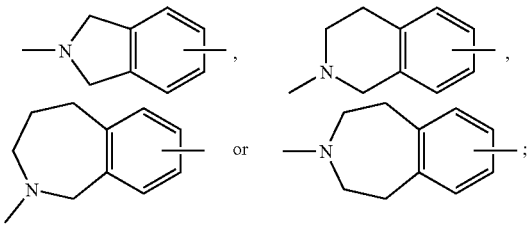

24) A pharmaceutical composition comprising the compound according to the above 18), or a salt thereof;

25) A prodrug of the compound according to the above 18);

26) A process for producing a compound represented by the formula:

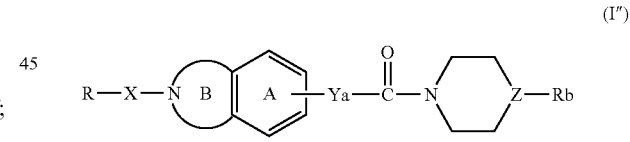
(I″)

wherein each symbol is as defined in the above 18), or a salt thereof, which comprises reacting a compound represented by the formula:

R—X-L     (IIa)

wherein L is a leaving group and the other symbols are as defined above, or a salt thereof, with a compound represented by the formula:

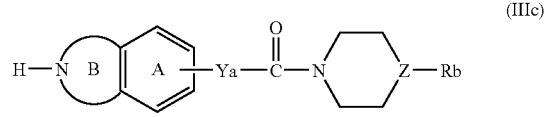
(IIIc)

wherein each symbol is as defined above, or a salt thereof;

27) A compound represented by the formula

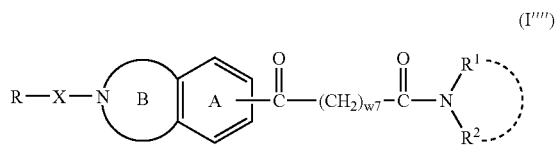

wherein R is hydrogen atom, a halogen atom or a cyclic group which may be substituted;
X is a bond or a spacer having a main chain of 1 to 10 atoms;
ring A is benzene ring which may be further substituted;
ring B is a 5- to 9-membered nitrogen-containing non-aromatic heterocyclic ring which may be further substituted;
w7 is an integer of 0 to 4; and
$R^1$ and $R^2$ are the same or different and are hydrogen atom, a hydrocarbon group which may be substituted or a heterocyclic group which may be substituted; or $R^1$ and $R^2$, together with the adjacent nitrogen atom, may form a nitrogen-containing heterocyclic ring which may be substituted; or a salt thereof;

28) A pharmaceutical composition comprising the compound according to the above 27) or a salt thereof;

29) A prodrug of the compound according to the above 27);

30) A compound represented by the formula:

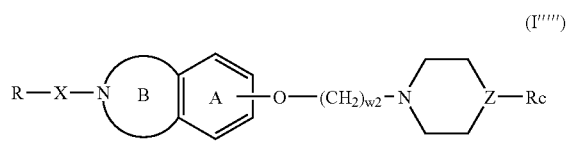

wherein R is hydrogen atom, a halogen atom or a cyclic group which may be substituted;
X is a bond or a spacer having a main chain of 1 to 10 atoms;
ring A is benzene ring which may be further substituted;
ring B is a 5- to 9-membered nitrogen-containing non-aromatic heterocyclic group which may be further substituted;
w2 is an integer of 0 to 5;
Z is CH or N;
Rc is a hydrocarbon group which may be substituted; or a salt thereof;

31) The compound according to the above 30), wherein Z is CH;

32) The compound according to the above 30), wherein Rc is $C_{6-14}$ aryl which may be substituted;

33) A pharmaceutical composition comprising the compound according to the above 30) or a salt thereof;

34) A prodrug of the compound according to the above 30);

35) The antagonist according to the above 1) which is an anorectic agent;

36) A pharmaceutical which comprises the melanin-concentrating hormone antagonist according to the above 1) in combination with at least one species selected from the group consisting of an agent for treating diabetes, an agent for treating hypertension and an agent for treating arteriosclerosis;

37) A method for preventing or treating diseases caused by a melanin-concentrating hormone in a mammal in need thereof, which comprises administering to said mammal an effective amount of a compound represented by the formula (I), or a salt thereof;

38) A method for preventing or treating obesity in a mammal in need thereof, which comprises administering to said mammal an effective amount of a compound represented by the formula:

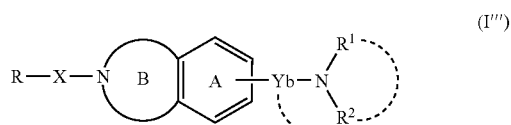

wherein R is hydrogen atom, a halogen atom or a cyclic group which may be substituted;
X is a bond or a spacer having a main chain of 1 to 10 atoms;
Yb is a spacer having a main chain of 1 to 6 atoms;
ring A is benzene ring which may be further substituted;
ring B is a 5- to 9-membered nitrogen-containing non-aromatic heterocyclic ring which may be further substituted; and
$R^1$ and $R^2$ are the same or different and are hydrogen atom, a hydrocarbon group which may be substituted or a heterocyclic group which may be substituted; or $R^1$ and $R^2$, together with the adjacent nitrogen atom, may form a nitrogen-containing heterocyclic ring (except piperidine) which may be substituted; or $R^2$, together with the adjacent nitrogen atom and Y, may form a nitrogen-containing heterocyclic ring which may be substituted;
provided that Yb is not —CO—(C(Ra)H)$_{na}$— (Ra is hydrogen atom or a hydrocarbon group which may be substituted, na is an integer of 1 to 10); or a salt thereof;

39) Use of a compound represented by the formula (I) or a salt thereof, for the manufacture of a pharmaceutical preparation for preventing or treating diseases caused by a melanin-concentrating hormone;

40) Use of a compound represented by the formula (I''') or a salt thereof, for the manufacture of a pharmaceutical preparation for preventing or treating obesity; and the like.

Examples of the "cyclic group" in the "cyclic group which may be substituted" represented by R and $Ar^1$ include aromatic groups, non-aromatic cyclic hydrocarbon groups, non-aromatic heterocyclic groups and the like.

Here, examples of the "aromatic groups" include monocyclic aromatic groups, condensed aromatic groups, ring assembly aromatic groups and the like.

Examples of the monocyclic aromatic groups include univalent groups which can be formed by removing an optional one hydrogen atom from a monocyclic aromatic ring. Example of the "monocyclic aromatic ring" include benzene ring and a 5- or 6-membered aromatic heterocyclic ring.

Examples of the "5- or 6-membered aromatic heterocyclic ring" include a 5- or 6-membered aromatic heterocyclic ring containing one or more (for example, 1 to 3) hetero atoms selected from nitrogen, sulfur and oxygen atoms in addition to carbon atoms, and the like. Specifically, thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, furazan, etc., can be mentioned.

Specific examples of the "monocyclic aromatic groups" include phenyl, 2- or 3-thienyl, 2-, 3-, or 4-pyridyl, 2- or 3-furyl, 2-, 4- or 5-thiazolyl, 2-, 4- or 5-oxazolyl, 1-, 3- or 4-pyrazolyl, 2-pyrazinyl, 2-, 4- or 5-pyrimidinyl, 1-, 2- or 3-pyrrolyl, 1-, 2- or 4-imidazolyl, 3- or 4-pyridazinyl, 3-isothiazolyl, 3-isoxazolyl, 1,2,4-oxadiazol-5-yl, 1,2,4-oxadiazol-3-yl, etc.

The "condensed aromatic groups" mean a univalent group that can be formed by removing an optional one hydrogen atom from condensed polycyclic (preferably bicyclic to tetracyclic, more preferably bicyclic or tricyclic) aromatic rings, etc. Examples of the "condensed aromatic groups" include condensed polycyclic aromatic hydrocarbons, condensed polycyclic aromatic heterocyclic rings, etc.

Examples of the "condensed polycyclic aromatic hydrocarbons" include $C_{9-14}$ condensed polycyclic (bicyclic or tricyclic) aromatic hydrocarbons (e.g. naphthalene, indene, fluorene, anthracene, etc.), etc.

Examples of the "condensed polycyclic aromatic heterocyclic rings" include 9- to 14-membered, preferably, 9- or 10-membered, condensed polycyclic aromatic heterocyclic rings containing one or more (for example, 1 to 4 atoms) hetero atoms selected from nitrogen, sulfur and oxygen atoms in addition to carbon atoms, and the like.

Specific examples of the "condensed polycyclic aromatic heterocyclic rings" include benzofuran, benzimidazole, benzoxazole, benzothiazole, benzisothiazole, naphtho[2,3-b]thiophene, isoquinoline, quinoline, indole, quinoxaline, phenanthridine, phenothiadine, phenoxazine, phthalazine, naphthyridine, quinazoline, cinnoline, carbazole, β-carboline, acridine, phenazine, phthalimide, thioxanthene, etc.

Specific examples of the "condensed aromatic groups" include 1-naphthyl; 2-naphthyl; 2-, 3-, 4-, 5- or 8-quinolyl; 1-, 3-, 4-, 5-, 6-, 7- or 8-isoquinolyl; 1-, 2-, 3-, 4-, 5-, 6- or 7-indolyl; 1-, 2-, 4- or 5-isoindolyl; 1-, 5- or 6-phthalazinyl; 2-, 3- or 5-quinoxalinyl; 2-, 3-, 4-, 5- or 6-benzofuranyl; 2-, 4-, 5- or 6-benzothiazolyl; 1-, 2-, 4-, 5- or 6-benzimidazolyl; etc.

The "ring assembly aromatic group" means a group formed by removing an optional one hydrogen atom from an aromatic ring assembly in which 2 or more (preferably 2 or 3) aromatic rings are directly bonded by single bonds, and in which the number of bonds which directly bond the rings, is less by one than the number of ring systems.

Examples of the aromatic ring assembly include an aromatic ring assemblies formed by 2 or 3 (preferably 2) species selected from $C_{6-14}$ monocyclic or condensed polycyclic aromatic hydrocarbons (e.g. benzene and naphthalene) and 5- to 10-membered (preferably 5 or 6 membered) aromatic heterocyclic rings, etc.

Preferred example of the aromatic ring assemblies include aromatic ring assembles comprising 2 or 3 aromatic rings selected from benzene, naphthalene, pyridine, pyrimidine, thiophene, furan, thiazole, isothiazole, oxazole, isoxazole, 1,2,4-oxadiazole, 1,3,4-oxadiazole, 1,2,4-thiadiazole, 1,3,4-thiadiazole, quinoline, isoquinoline, indole, benzothiophene, benzoxazole, benzothiazole and benzofuran.

Specific examples of the "ring assembly aromatic groups" include 2-, 3- or 4-biphenylyl; 3-(1-naphthyl)-1,2,4-oxadiazol-5-yl; 3-(2-naphthyl)-1, 2, 4-oxadiazol-5-yl; 3-(2-benzofuranyl)-1,2,4-oxadiazol-5-yl; 3-phenyl-1,2,4-oxadiazol-5-yl; 3-(2-benzoxazolyl)-1,2,4-oxadiazol-5-yl; 3-(3-indolyl)-1,2,4-oxadiazol-5-yl; 3-(2-indolyl)-1,2,4-oxadiazol-5-yl; 4-phenylthiazol-2-yl; 4-(2-benzofuranyl)thiazol-2-yl; 4-phenyl-1,3-oxazol-5-yl; 5-phenyl-isothiazol-4-yl; 5-phenyloxazol-2-yl; 4-(2-thienyl)phenyl; 4-(3-thienyl)phenyl; 3-(3-pyridyl)phenyl; 4-(3-pyridyl)phenyl; 6-phenyl-3-pyridyl; 5-phenyl-1,3,4-oxadiazol-2-yl; 4-(2-naphthyl)phenyl; 4-(2-benzofuranyl)phenyl; 4,4'-terphenyl; 5-phenyl-2-pyridyl; 2-phenyl-5-pyrimidinyl; 4-(4-pyridyl)phenyl; 2-phenyl-1,3-oxazol-5-yl; 2,4-diphenyl-1,3-oxazol-5-yl; 3-phenyl-isoxazol-5-yl; 5-phenyl-2-furyl; 4-(2-furyl)phenyl; etc.

Preferred groups among the above "aromatic groups" are "a group formed by removing an optional one hydrogen atom from an aromatic ring assembly formed by 2 or 3 members selected from a $C_{6-14}$ monocyclic or condensed polycyclic aromatic hydrocarbon and 5- to 10-membered aromatic heterocyclic ring (preferably, 2-, 3- or 4-biphenylyl; 6-phenyl-3-pyridyl, 5-phenyl-2-pyridyl, etc.)".

Examples of the "non-aromatic cyclic hydrocarbon groups" include $C_{3-8}$ cycloalkyl, $C_{3-8}$ cycloalkenyl, etc.

Here, specific examples of the $C_{3-8}$ cycloalkyl include cyclopropyl, cyclobutyl, cyclopentyl, cyclohexyl, cycloheptyl, cyclooctyl. etc.

Specific examples of the $C_{3-8}$ cycloalkenyl include cyclopropenyl, cyclobutenyl, cyclopentenyl, cyclohexenyl, cycloheptenyl, cyclooctenyl, etc.

Among the above "non-aromatic cyclic hydrocarbon groups", $C_{3-8}$ cycloalkyl is preferred, and cyclohexyl is particularly preferred.

Examples of "non-aromatic heterocyclic groups" include monocyclic non-aromatic heterocyclic groups, condensed polycyclic non-aromatic heterocyclic groups, and the like.

Examples of the "monocyclic non-aromatic heterocyclic groups" include univalent groups formed by removing an optional one hydrogen atom from monocyclic non-aromatic heterocyclic ring. Examples of the "monocyclic non-aromatic heterocyclic ring" include 5- to 8-membered monocyclic non-aromatic heterocyclic rings containing one or more (e.g. 1 to 3) hetero atoms selected from nitrogen, sulfur and oxygen atoms in addition to carbon atoms. Specifically, tetrahydrothiophene, tetrahydrofuran, pyrrolidine, imidazoline, imidazolidine, pyrazoline, pyrazolidine, tetrahydrothiazole, tetrahydroisothiazole, tetrahydrooxazole, tetrahydroisoxazole, piperidine, tetrahydropyridine, dihydropyridine, piperazine, morpholine, thiomorpholine, tetrahydropyrimidine, tetrahydropyridazine, hexamethyleneimine, etc. can be mentioned.

The "condensed polycyclic non-aromatic heterocyclic group" means a univalent group formed by removing an optional one hydrogen atom from a condensed polycyclic (preferably bicyclic to tetracyclic, more preferably bicyclic or tricyclic) non-aromatic heterocyclic ring. Examples of the "condensed polycyclic non-aromatic heterocyclic ring" include 9- to 14-membered, preferably 9- or 10-membered condensed polycyclic non-aromatic heterocyclic rings which contain one or more (e.g. 1 to 4) hetero atoms selected from nitrogen, sulfur and oxygen atoms in addition to carbon atoms. Specifically, dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, indoline, isoindoline, tetrahydroquinoxaline, tetrahydrophenanthridine, hexahydrophenothiadine, hexahydrophenoxazine, tetrahydrophthaladine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxantene, etc., can be mentioned.

Among the above "non-aromatic heterocyclic groups", "5- to 8-membered monocyclic non-aromatic heterocyclic groups (preferably piperidino; piperazinyl; pyrrolidinyl; etc.)" are preferred.

Examples of the "cyclic group" in the "cyclic group which may be substituted" represented by R and $Ar^1$ is preferably an aromatic group, more preferably a monocyclic aromatic group (preferably phenyl, pyrrolyl, etc.) or a ring assembly aromatic group (preferably biphenylyl, etc.).

Examples of the "substituent" in the "cyclic group which may be substituted" represented by R and $Ar^1$ include oxo, halogen atoms (e.g. fluorine, chlorine, bromine, iodine, etc.), $C_{1-3}$ alkylenedioxy (e.g. methylenedioxy, ethylenedioxy, etc.), nitro, cyano, optionally halogenated $C_{1-6}$ alkyl, hydroxy-$C_{1-6}$ alkyl, $C_{6-14}$ aryloxy-$C_{1-6}$ alkyl (e.g. phenoxymethyl, etc.), $C_{1-6}$ alkyl-$C_{6-14}$ aryl-$C_{2-6}$ alkenyl (e.g. methylphenylethenyl, etc.), optionally halogenated $C_{3-6}$ cycloalkyl, optionally halogenated $C_{1-6}$ alkoxy, optionally halogenated $C_{1-6}$ alkylthio, $C_{7-19}$ aralkyl which may be substituted, hydroxy, $C_{6-14}$ aryloxy which may be substituted, $C_{7-19}$ aralkyloxy which may be substituted, $C_{6-14}$ aryl-carbamoyl which may be substituted, amino, amino-$C_{1-6}$ alkyl (e.g. aminomethyl, aminoethyl, aminopropyl, aminobutyl, etc.), mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, dipropylamino, dibutylamino, ethylmethylamino, etc.), mono-$C_{1-6}$ alkylamino-$C_{1-6}$ alkyl (e.g. methylaminomethyl, ethylaminomethyl, propylaminomethyl, isopropylaminoethyl, butylaminoethyl, etc.), di-$C_{1-6}$ alkylamino-$C_{1-6}$ alkyl (e.g. dimethylaminomethyl, diethylaminomethyl, dipropylaminomethyl, diisopropylaminoethyl, dibutylaminoethyl, etc.), 5- to 7-membered saturated cyclic amino which may be substituted, 5- to 7-membered non-aromatic heterocyclic groups which may be substituted, acyl, acylamino, acyloxy, etc.

The "cyclic group" represented by R and $Ar^1$ may have 1 to 5, preferably 1 to 3, of the above-mentioned substituents at a substitutable position on the cyclic group. When the number of substituents is 2 or more, each substituents can be the same or different.

Also, when the "cyclic group" represented by R and $Ar^1$ is a non-aromatic cyclic hydrocarbon group or a non-aromatic heterocyclic group, the "cyclic group" may have as its substituent(s), $C_{6-14}$ aryl which may be substituted, 5- to 10-membered aromatic heterocyclic groups which may be substituted, etc.

Here, the groups exemplified as the "substituent" in the "5- to 7-membered saturated cyclic amino which may be substituted" mentioned hereinafter, can be mentioned as "$C_{6-14}$ aryl which may be substituted" and "5- to 10-membered aromatic heterocyclic groups which may be substituted". The number of substituents is, for example, 1 to 3. When the number of substituents is 2 or more, each substituents can be the same or different.

Specific examples of the above "optionally halogenated $C_{1-6}$ alkyl" include $C_{1-6}$ alkyl (e.g. methyl, ethyl, propyl, isopropyl, butyl, isobutyl, sec-butyl, tert-butyl, pentyl, hexyl, etc.) which may have 1 to 5, preferably 1 to 3, halogen atoms (e.g. fluorine, chlorine, bromine, iodine, etc.). Specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.

The $C_{1-6}$ alkyl in the above "optionally halogenated $C_{1-6}$ alkyl" can be mentioned as the $C_{1-6}$ alkyl in the above "hydroxy-$C_{1-6}$ alkyl".

Examples of the above "optionally halogenated $C_{3-6}$ cycloalkyl" include $C_{3-6}$ cycloalkyl (e.g. cyclopropyl, cyclobutyl, cyclopentyl, cyclohexyl, etc.) which may have 1 to 5, preferably 1 to 3, halogen atoms (e.g. fluorine, chlorine, bromine, iodine, etc.). Specific examples include cyclopropyl, cyclobutyl, cyclopentyl, cyclohexyl, 4,4-dichlorocyclohexyl, 2,2,3,3-tetrafluorocyclopentyl, 4-chlorocyclohexyl, etc.

Examples of the above "optionally halogenated $C_{1-6}$ alkoxy" include $C_{1-6}$ alkoxy (e.g. methoxy, ethoxy, propoxy, butoxy, pentyloxy, etc.) which may have 1 to 5, preferably 1 to 3, halogen atoms (e.g. fluorine, chlorine, bromine, iodine, etc.). Specific examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.

Examples of the above "optionally halogenated $C_{1-6}$ alkylthio" include $C_{1-6}$ alkylthio (e.g. methylthio, ethylthio, propylthio, isopropylthio, butylthio, sec-butylthio, tert-butylthio, etc.) which may have 1 to 5, preferably 1 to 3, halogen atoms (e.g. fluorine, chlorine, bromine, iodine, etc.). Specific examples include methylthio, difluoromethylthio, trifluoromethylthio, ethylthio, propylthio, isopropylthio, butylthio, 4,4,4-trifluorobutylthio, pentylthio, hexylthio, etc.

Examples of the "$C_{7-19}$ aralkyl" in the above "$C_{7-19}$ aralkyl which may be substituted" include benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, etc. Benzyl is particularly preferred.

Examples of the "substituent" in the above "$C_{7-19}$ aralkyl which may be substituted" include halogen atom (e.g. fluorine, chlorine, bromine, iodine, etc.), $C_{1-3}$ alkylenedioxy (e.g. methylenedioxy, ethylenedioxy, etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, dipropylamino, dibutylamino, ethylmethylamino, etc.), amino-$C_{1-6}$ alkyl (e.g. aminomethyl, aminoethyl, aminopropyl, aminobutyl, etc.), mono-$C_{1-6}$ alkylamino-$C_{1-6}$ alkyl (e.g. methylaminomethyl, ethylaminomethyl, propylaminomethyl, isopropylaminoethyl, butylaminoethyl, etc.), di-$C_{1-6}$ alkylamino-$C_{1-6}$ alkyl (e.g. dimethylaminomethyl, diethylaminomethyl, dipropylaminomethyl, diisopropylaminoethyl, dibutylaminoethyl, etc.), formyl, carboxy, carbamoyl, thiocarbamoyl, optionally halogenated $C_{1-6}$ alkyl-carbonyl, $C_{1-6}$ alkoxy-carbonyl (e.g., methoxycarbonyl, ethoxycarbonyl, propoxycarbonyl, tert-butoxycarbonyl, etc.), mono-$C_{1-6}$ alkyl-carbamoyl (e.g., methylcarbamoyl, ethylcarbamoyl, etc.), di-$C_{1-6}$ alkyl-carbamoyl (e.g. dimethylcarbamoyl, diethylcarbamoyl, ethylmethylcarbamoyl, etc.), optionally halogenated $C_{1-6}$ alkylsulfonyl, formylamino, optionally halogenated $C_{1-6}$ alkylcarboxamide, $C_{1-6}$ alkoxy-carboxamide (e.g. methoxycarboxamide, ethoxycarboxamide, prpoxycarboxamide, butoxycarboxamide, etc.), $C_{1-6}$ alkylsulfonylamino (e.g. methylsulfonylamino, ethylsulfonylamino, etc.), $C_{1-6}$ alkyl-carbonyloxy (e.g. acetoxy, propanoyloxy, etc.), $C_{1-6}$ alkoxy-carbonyloxy (e.g. methoxycarbonyloxy, ethoxycarbonyloxy, propoxycarbonyloxy, butoxycarbonyloxy, etc.), mono-$C_{1-6}$ alkyl-carbamoyloxy (e.g. methylcarbamoyloxy, ethylcarbamoyloxy, etc.), di-$C_{1-6}$ alkyl-carbamoyloxy (e.g. dimethylcarbamoyloxy, diethylcarbamoyloxy, etc.), hydroxy-$C_{1-6}$ alkyl (e.g., hydroxyethyl, etc.), etc. The number of substituents is, for example, 1 to 5, preferably 1 to 3. When the number of substituents is 2 or more, each substituents can be the same or different.

As the "optionally halogenated $C_{1-6}$ alkyl", "optionally halogenated $C_{3-6}$ cycloalkyl", "optionally halogenated $C_{1-6}$ alkoxy" and "optionally halogenated $C_{1-6}$ alkylthio", those exemplified as the "substituents" in the above "cyclic group which may be substituted" can be used, respectively.

Examples of the above "optionally halogenated $C_{1-6}$ alkylcarbonyl" include $C_{1-6}$ alkyl-carbonyl (e.g. acetyl, propanoyl, butanoyl, pentanoyl, hexanoyl, etc.) which may have 1 to 5, preferably 1 to 3, halogen atoms (e.g., fluorine, chlorine, bromine, iodine, etc.), etc. Specific examples include acetyl, monochloroacetyl, trifluoroacetyl, trichloroacetyl, propanoyl, butanoyl, pentanoyl, hexanoyl, etc.

Examples of the above "optionally halogenated $C_{1-6}$ alkylsulfonyl" include $C_{1-6}$ alkylsulfonyl (e.g. methylsulfonyl, ethylsulfonyl, propylsulfonyl, isopropylsulfonyl, butylsulfonyl, sec-butylsulfonyl, tert-butylsulfonyl, etc.) which may have 1 to 5, preferably 1 to 3, halogen atoms (e.g., fluorine, chlorine, bromine, iodine, etc.), etc. Specific examples include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl, hexylsulfonyl, etc.

Examples of the above "optionally halogenated $C_{1-6}$ alkyl-carboxamide" include $C_{1-6}$ alkyl-carboxamide (e.g. acetamide, propanamide, butanamide, etc.) which may have 1 to 5, preferably 1 to 3, halogen atoms (e.g. fluorine, chlorine, bromine, iodine, etc.), etc. Specific examples include acetamide, trifluoroacetamide, propanamide, butanamide, etc.

Examples of the "$C_{6-14}$ aryloxy" in the above "$C_{6-14}$ aryloxy which may be substituted" include phenyloxy, 1-naphthyloxy, 2-naphthyloxy, etc.

Examples of the "$C_{7-19}$ aralkyloxy" in the above "$C_{7-19}$ aralkyloxy which may be substituted" include benzyloxy, phenethyloxy, diphenylmethyloxy, triphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy, etc.

Examples of the "$C_{6-14}$ aryl-carbamoyl" in the above "$C_{6-14}$ aryl-carbamoyl which may be substituted" include phenylcarbamoyl, 1-naphthylcarbamoyl, 2-naphthylcarbamoyl, etc.

As the "substituents" in the "$C_{6-14}$ aryloxy which may be substituted", "$C_{7-19}$ aralkyloxy which may be substituted" and "$C_{6-14}$ aryl-carbamoyl which may be substituted", those exemplified for the "substituents" in the above "$C_{7-19}$ aralkyl which may be substituted" can be used. The number of substituents is, for example, 1 to 5, preferably 1 to 3. When the number of substituents is 2 or more, each substituents can be the same or different.

Examples of the "5- to 7-membered saturated cyclic amino" in the above "5 to 7 membered saturated cyclic amino which may be substituted" include morpholino, thiomorpholino, piperazin-1-yl, piperidino, pirrolidin-1-yl, etc. The "5- to 7-membered saturated cyclic amino" can be condensed with a benzene ring.

Examples of the "substituent" in the "5- to 7-membered saturated cyclic amino which may be substituted" include oxo, optionally halogenated $C_{1-6}$ alkyl, optionally halogenated $C_{1-6}$ alkyl-carbonyl, optionally halogenated $C_{1-6}$ alkylsulfonyl, $C_{6-14}$ aryl which may be substituted, $C_{7-19}$ aralkyl which may be substituted, $C_{6-14}$ aryl-carbonyl which may be substituted, 5- to 10-membered aromatic heterocyclic group which may be substituted, hydroxy, 5- to 8-membered monocyclic non-aromatic heterocyclic group (e.g., piperidinyl, piperazinyl, pyrrolidinyl, etc.), carbamoyl, hydroxy-$C_{1-6}$ alkyl, $C_{1-6}$ alkoxy-carbonyl-$C_{1-6}$ alkyl (e.g. ethoxycarbonylmethyl, etc.), $C_{8-19}$ arylalkenyl (e.g., styryl, 3-phenyl-2-prop-2-enyl, etc.), $C_{1-6}$ alkyl-carboxamide (e.g., methylcarboxamide, etc.), (N—$C_{1-6}$ alkyl)-$C_{1-6}$ alkyl-carboxamide (e.g., (N-ethyl)methylcarboxamide, etc.), amino, mono-$C_{1-6}$ alkylamino (e.g., methylamino, ethylamino, propylamino, isopropylamino, butylamino, etc.), di-$C_{1-6}$ alkylamino (e.g., dimethylamino, diethylamino, dipropylamino, dibutylamino, ethylmethylamino, etc.), 5- to 8-membered monocyclic non-aromatic heterocyclic group-$C_{1-6}$ alkyl (e.g., pyrrolidinylmethyl, etc.), $C_{6-14}$ aryl-amino-$C_{1-6}$ alkyl (e.g., 2,6-dimethylphenylaminomethyl, etc.) which may be substituted with one to three $C_{1-6}$ alkyl, etc. The number of substituents is, for example, 1 to 5, preferably 1 to 3. When the number of substituents is 2 or more, each substituents can be the same or different.

Here, as the "optionally halogenated $C_{1-6}$ alkyl" and "$C_{7-19}$ aralkyl which may be substituted", those exemplified as the "substituents" in the above "cyclic group which may be substituted" can be used, respectively.

Examples of the "optionally halogenated $C_{1-6}$ alkyl-carbonyl" and "optionally halogenated $C_{1-6}$ alkylsulfonyl" include those exemplified as the "substituents" in the above "$C_{7-19}$ aralkyl which may be substituted".

Examples of the "$C_{6-14}$ aryl" in the "$C_{6-14}$ aryl which may be substituted" include phenyl, 1-naphthyl, 2-naphthyl, 2-indenyl, 2-anthryl, etc. Phenyl is especially preferable.

As the "substituents" in the "$C_{6-14}$ aryl which may be substituted", those exemplified as the "substituents" in the above "$C_{7-19}$ aralkyl which may be substituted" can be used. The number of substituents is, for example, 1 to 5, preferably 1 to 3. When the number of substituents is 2 or more, each substituents can be the same or different.

Examples of the "$C_{6-14}$ aryl-carbonyl" in the "$C_{6-14}$ aryl-carbonyl which may be substituted" include benzoyl, 1-naphthoyl, 2-naphthoyl, etc.

As the "substituents" in the "$C_{6-14}$ aryl-carbonyl which may be substituted", those exemplified as "substituents" in the above "$C_{7-19}$ aralkyl which may be substituted" can be used. The number of substituents is, for example, 1 to 5, preferably 1 to 3. When the number of substituents is 2 or more, each substituents can be the same or different.

Examples of the "5- to 10-membered aromatic heterocyclic groups" in the "5- to 10-membered aromatic heterocyclic groups which may be substituted" include 5- to 10-membered (monocyclic or bicyclic) aromatic heterocyclic groups containing 1 or 2 kinds of, preferably 1 to 4 hetero atoms selected from nitrogen, sulfur and oxygen atom in addition to carbon atoms. Specific examples include 2- or 3-thienyl; 2-, 3- or 4-pyridyl; 2- or 3-furyl; 2-, 4- or 5-thiazolyl; 2-, 4- or 5-oxazolyl; 1-, 3- or 4-pyrazolyl; 2-pyrazinyl; 2-, 4- or 5-pyrimidinyl; 1-, 2- or 3-pyrrolyl; 1-, 2- or 4-imidazolyl; 3- or 4-pyridazinyl; 3-isothiazolyl; 3-isoxazolyl; 1,2,4-oxadiazol-5-yl; 1,2,4-oxadiazol-3-yl; 2-, 3-, 4-, 5- or 8-quinolyl; 1-, 3-, 4-, 5-, 6-, 7- or 8-isoquinolyl; 1-, 2-, 3-, 4-, 5-, 6- or 7-indolyl; 1-, 2-, 4- or 5-isoindolyl; 1-, 5- or 6-phthalazinyl; 2-, 3- or 5-quinoxalinyl; 2-, 3-, 4-, 5- or 6-benzofuranyl; 2-, 4-, 5- or 6-benzothiazolyl; 1-, 2-, 4-, 5- or 6-benzimidazolyl, etc.

Examples of the "substituents" in the "5- to 10-membered aromatic heterocyclic groups which may be substituted" include halogen atom (e.g. fluorine, chlorine, bromine and iodine, etc.), $C_{1-3}$ alkylenedioxy (e.g. methylenedioxy, ethylenedioxy, etc.), nitro, cyano, optionally halogenated $C_{1-6}$ alkyl, $C_{6-14}$ aryloxy-$C_{1-6}$ alkyl (e.g. phenoxymethyl, etc.), $C_{1-6}$ alkyl-$C_{6-14}$ aryl-$C_{2-6}$ alkenyl (e.g. methylphenylethenyl, etc.), optionally halogenated $C_{3-6}$ cycloalkyl, optionally halogenated $C_{1-6}$ alkoxy, optionally halogenated $C_{1-6}$ alkylthio, $C_{7-19}$ aralkyl which may be substituted, hydroxy, $C_{6-14}$ aryloxy which may be substituted, $C_{7-19}$ aralkyloxy which may be substituted, amino, amino-$C_{1-6}$ alkyl (e.g. aminomethyl, aminoethyl, aminopropyl, aminobutyl, etc.), mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, dipropylamino, dibutylamino, ethylmethylamino, etc.), mono-$C_{1-6}$ alkylamino-$C_{1-6}$ alkyl (e.g. methylaminomethyl, ethylaminomethyl, propylaminomethyl, isopropylaminoethyl, butylaminoethyl, etc.), di-$C_{1-6}$ alkylamino-$C_{1-6}$ alkyl (e.g. dimethylaminomethyl, diethylaminomethyl, dipropylaminomethyl, diisopropylaminoethyl, dibutylaminoethyl, etc.), 5- to 7-membered saturated cyclic amino, acyl, acylamino, acyloxy, etc. The number of substituents is, for example, 1 to 5, preferably 1 to 3. When the number of substituents is 2 or more, each substituents can be the same or different.

Here, as the "optionally halogenated $C_{1-6}$ alkyl", "optionally halogenated $C_{3-6}$ cycloalkyl", "optionally halogenated $C_{1-6}$ alkoxy", "optionally halogenated $C_{1-6}$ alkylthio", "$C_{7-19}$ aralkyl which may be substituted", "$C_{6-14}$ aryloxy which may be substituted", "$C_{7-19}$ aralkyloxy which may be substituted", those exemplified as the "substituents" in the above "cyclic group which may be substituted" can be used, respectively.

As the "5- to 7-membered saturated cyclic amino", those exemplified as "5-to 7-membered saturated cyclic amino" regarding "5- to 7-membered saturated cyclic amino which may be substituted" which is the "substituent" in the above "cyclic amino which may be substituted" can be used.

Examples of the above "acyl" include acyl of the formulas: —CO—$R^3$, —CO—$OR^3$, —CO—$NR^3R^4$, —CS—$NR^3R^4$, —$SO_2$—$R^{3a}$, —SO—$R^{3a}$, —PO(—$OR^3$)—$OR^4$ or —$PO_2$—$R^{3a}$ wherein $R^3$ is (i) hydrogen atom, (ii) a hydrocarbon group which may be substituted, or (iii) a heterocyclic group which may be substituted; $R^{3a}$ is (i) a hydrocarbon group which may be substituted, or (ii) a heterocyclic group which may be substituted; $R^4$ is hydrogen atom or $C_{1-6}$ alkyl; $R^3$ and $R^4$, together with the adjacent nitrogen atom, may form a nitrogen-containing heterocyclic ring which may be substituted, and the like.

Examples of the "hydrocarbon group" in "hydrocarbon group which may be substituted" represented by $R^3$ or $R^{3a}$ include straight-chain or cyclic hydrocarbon groups (e.g. alkyl, alkenyl, alkynyl, cycloalkyl, aryl, aralkyl, arylalkenyl, dihydroindene, etc.), etc. Among these, $C_{1-19}$ straight-chain or cyclic hydrocarbon groups as shown below are preferred.

a) $C_{1-6}$ alkyl (e.g. methyl, ethyl, propyl, isopropyl, butyl, isobutyl, sec-butyl, tert-butyl, pentyl, hexyl, etc.);
b) $C_{2-6}$ alkenyl (e.g., vinyl, allyl, isopropenyl, 2-butenyl, etc.);
c) $C_{2-6}$ alkynyl (e.g. ethynyl, propargyl, 2-butynyl, etc.);
d) $C_{3-6}$ cycloalkyl (e.g. cyclopropyl, cyclobutyl, cyclopentyl, cyclohexyl, etc.); the $C_{3-6}$ cycloalkyl may be condensed with one benzene ring;
e) $C_{6-14}$ aryl (e.g. phenyl, 1-naphthyl, 2-naphthyl, 2-indenyl, 2-anthryl, etc.), preferably phenyl;
f) $C_{7-19}$ aralkyl (e.g. benzyl, phenethyl, diphenylmethyl, triphenylmethyl, 1-methylmethyl, 2-naphthylmethyl, 2,2-diphenylethyl, 3-phenylpropyl, 4-phenylbutyl, 5-phenylpentyl, etc.), preferably benzyl, phenethyl, 3-phenylpropyl;
g) $C_{8-19}$ arylalkenyl (e.g., styryl, 3-phenyl-2-prop-2-enyl, etc.);
h) dihydroindene.

The "hydrocarbon groups" are preferably $C_{1-6}$ alkyl, $C_{6-14}$ aryl, $C_{7-19}$ aralkyl, etc.

Examples of the "substituent" in the "hydrocarbon groups which may be substituted" include halogen atom (e.g. fluorine, chlorine, bromine, iodine, etc.), $C_{1-3}$ alkylenedioxy (e.g. methylenedioxy, ethylenedioxy, etc.), nitro, cyano, optionally halogenated $C_{1-6}$ alkoxy, optionally halogenated $C_{1-6}$ alkylthio, hydroxy, amino, mono-$C_{1-6}$ alkylamino (e.g. methylamino, ethylamino, propylamino, isopropylamino, butylamino, etc.), di-($C_{1-6}$ alkyl optionally substituted with hydroxy)amino (e.g. dimethylamino, diethylamino, dipropylamino, diisopropylamino, dibutylamino, ethylmethylamino, di(hydroxyethyl)amino, etc.), $C_{6-14}$ aryl-amino which may be substituted with one to three $C_{1-6}$ alkyl (e.g., phenylamino, 2,6-dimethylphenylamino, etc.), N—$C_{1-6}$ alkyl-N—($C_{6-14}$ aryl optionally substituted with $C_{1-6}$ alkyl) amino (e.g., N-methyl-N-phenylamino, N-ethyl-N-(methylphenyl)amino, etc.), 5- or 6-membered monocyclic aromatic heterocyclic ring amino optionally substituted with nitro (e.g., nitropyridylamino, etc.), 5- to 8-membered monocyclic non-aromatic heterocyclic group optionally substituted with oxo or $C_{1-6}$ alkyl (e.g., tetrahydrofuryl, pyrrolidinyl, oxopyrrolidinyl, piperidinyl, methylpiperidinyl, morpholinyl, methylpiperazinyl, etc.), formyl, carboxy, carbamoyl, thiocarbamoyl, optionally halogenated $C_{1-6}$ alkylcarbonyl, $C_{1-6}$ alkoxy-carbonyl (e.g., methoxycarbonyl, ethoxycarbonyl, propoxycarbonyl, tert-butoxycarbonyl, etc.), 5- to 10-membered aromatic heterocyclic groups which may be substituted, $C_{6-14}$ aryl-carbonyl which may be substituted, $C_{6-14}$ aryloxy-carbonyl which may be substituted, $C_{7-19}$ aralkyloxy-carbonyl which may be substituted, 5- to 6-membered heterocyclic ring-carbonyl which may be substituted, mono-$C_{1-6}$ alkyl-carbamoyl (e.g. methylcarbamoyl, ethylcarbamoyl, etc.), di-$C_{1-6}$ alkyl-carbamoyl (e.g. dimethylcarbamoyl, diethylcarbamoyl, ethylmethylcarbamoyl, etc.), $C_{6-14}$ aryl-carbamoyl which may be substituted, 5- to 6-membered heterocyclic ring-carbamoyl which may be substituted, optionally halogenated $C_{1-6}$ alkylsulfonyl, $C_{6-14}$ arylsulfonyl which may be substituted, formylamino, optionally halogenated $C_{1-6}$ alkyl-carboxamide, $C_{1-6}$ alkoxy-carboxamide (e.g., methoxycarboxamide, ethoxycarboxamide, propoxycarboxamide, butoxycarboxamide, etc.), $C_{1-6}$ alkylsulfonylamino (e.g., methylsulfonylamino, ethylsulfonylamino, etc.), $C_{1-6}$ alkyl-carbonyloxy (e.g. acetoxy, propanoyloxy, etc.), $C_{6-14}$ aryl-carbonyloxy which may be substituted, $C_{1-6}$ alkoxy-carbonyloxy (e.g. methoxycarbonyloxy, ethoxycarbonyloxy, propoxycarbonyloxy, butoxycarbonyloxy, etc.), mono-$C_{1-6}$ alkyl-carbamoyloxy (e.g. methylcarbamoyloxy, ethylcarbamoyloxy, etc.), di-$C_{1-6}$ alkyl-carbamoyloxy (e.g. dimethylcarbamoyloxy, diethylcarbamoyloxy, etc.), $C_{6-14}$ aryl-carbamoyloxy which may be substituted, nicotinoyloxy, etc. The number of substituents is, for example, 1 to 5, preferably 1 to 3. When the number of substituents is 2 or more, each substituents can be the same or different.

Here, as the "optionally halogenated $C_{1-6}$ alkoxy", "optionally halogenated $C_{1-6}$ alkylthio" and "$C_{6-14}$ aryl-carbamoyl which may be substituted", those exemplified as the "substituent" in the above "cyclic group which may be substituted" can be used, respectively.

As the "optionally halogenated $C_{1-6}$ alkyl-carbonyl", "optionally halogenated $C_{1-6}$ alkylsulfonyl" and "optionally halogenated $C_{1-6}$ alkyl-carboxamide", those exemplified as the "substituent" in the above "$C_{7-19}$ aralkyl which may be substituted" can be used, respectively.

As the above "5- to 10-membered aromatic heterocyclic groups which may be substituted" and "$C_{6-14}$ aryl-carbonyl which may be substituted", those exemplified as the "substituent" in the above "5- to 7-membered saturated cyclic amino which may be substituted" can be used, respectively.

Examples of the "$C_{6-14}$ aryloxy-carbonyl" in the "$C_{6-14}$ aryloxy-carbonyl which may be substituted" include phenyloxycarbonyl, 1-naphthyloxycarbonyl, 2-naphthyloxycarbonyl, etc.

Examples of the "$C_{7-19}$ aralkyloxy-carbonyl" in "$C_{7-19}$ aralkyloxy-carbonyl which may be substituted" include benzyloxycarbonyl, phenethyloxycarbonyl, diphenylmethyloxycarbonyl, triphenylmethyloxycarbonyl, 1-naphthylmethyloxycarbonyl, 2-naphthylmethyloxycarbonyl, 2,2-diphenylethyloxycarbonyl, 3-phenylpropyloxycarbonyl, 4-phenylbutyloxycarbonyl, 5-phenylpentyloxycarbonyl, etc.

Examples of the "5- to 6-membered heterocyclic ring-carbonyl" in the above "5- to 6-membered heterocyclic ring-carbonyl which may be substituted" include nicotinoyl, isonicotinoyl, 2-thenoyl, 3-thenoyl, 2-furoyl, 3-furoyl, morpholinocarbonyl, pepiridinocarbonyl, pyrrolidin-1-ylcarbonyl, etc.

Examples of the "5- to 6-membered heterocyclic ring-carbamoyl" in the above "5- to 6-membered heterocyclic ring-carbamoyl which may be substituted" include morpholinocarbamoyl, pepiridinocarbamoyl, 2-pyridylcarbamoyl, 3-pyridylcarbamoyl, 4-pyridylcarbamoyl, 2-thienylcarbamoyl, 3-thienylcarbamoyl, etc.

Examples of the "$C_{6-14}$ arylsulfonyl" in the above "$C_{6-14}$ arylsulfonyl which may be substituted" include phenylsulfonyl, 1-naphthylsulfonyl, 2-naphthylsulfonyl, etc.

Examples of the "$C_{6-14}$ aryl-carbonyloxy" in the above "$C_{6-14}$ aryl-carbonyloxy which may be substituted" include benzoyloxy, 1-naphthoyloxy, 2-naphthoyloxy, etc.

Examples of the "$C_{6-14}$ aryl-carbamoyloxy" in the above "$C_{1-14}$ aryl-carbamoyloxy which may be substituted" include phenylcarbamoyloxy, naphthylcarbamoyloxy, etc.

As the "substituents" in the above "$C_{6-14}$ aryloxy-carbonyl which may be substituted", "$C_{7-19}$ aralkyloxy-carbonyl which may be substituted", "5- to 6-membered heterocyclic ring-carbonyl which may be substituted", "5- to 6-membered heterocyclic ring-carbamoyl which may be substituted", "$C_{6-14}$ arylsulfonyl which may be substituted", "$C_{6-14}$ aryl-carbonyloxy which may be substituted" and "$C_{6-14}$ aryl-carbamoyloxy which may be substituted", those exemplified as the "substituents" in the above "$C_{7-19}$ aralkyl which may be substituted" can be mentioned. The number of the substituents is, for example, 1 to 5, preferably 1 to 3. When the number of substituents is 2 or more, each substituents can be the same or different.

Examples of the "heterocyclic groups" in the "heterocyclic groups which may be substituted" represented by $R^3$ or $R^{3a}$ include a 5- to 14-membered (monocyclic, bicyclic or tricyclic) heterocyclic ring containing 1 or 2 kinds of, 1 to 4 hetero atoms selected from nitrogen, sulfur and oxygen atom in addition to carbon atoms. Preferably, univalent groups formed by removing an optional one hydrogen atom from (i) an aromatic heterocyclic ring, (ii) a 5- to 10-membered non-aromatic heterocyclic ring, or (iii) a 7- to 10-membered heterocyclic-bridge ring, etc., can be mentioned.

Here, examples of the "aromatic heterocyclic ring" include a 5- to 14-membered, preferably 5- to 10-membered, aromatic heterocyclic ring containing one or more hetero atoms (e.g. 1 to 4) selected from nitrogen, sulfur and oxygen atoms in addition to carbon atoms. Specific examples include aromatic heterocyclic rings such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, furazan, benzothiophene, benzofuran, benzimidazole, benzoxazole, benzothiazole, benzisothiazole, naphtho[2,3-b]thiophene, phenoxathiin, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazinephenothiadine, phenoxazine, phthalimide, etc.; or a ring formed by condensing these rings (preferably monocyclic rings) with one to multiple (preferably 1 or 2) aromatic rings (e.g. benzene ring, etc.), etc.

Examples of "5- to 10-membered non-aromatic heterocyclic rings" include 2- or 3-pyrroline, pyrrolidine, 2- or 3-imidazoline, 2-oxazoline, oxazolidine, 2- or 3-pyrazoline, pyrazolidine, 2-thiazoline, piperidine, piperazine, hexamethylenimine, morpholine, thiomorpholine, etc.

Examples of "7- to 10-membered heterocyclic-bridge rings" include quinuclidine, 7-azabicyclo[2.2.1]heptane, etc.

The "heterocyclic groups" are preferably 5- to 10-membered (monocyclic or bicyclic) heterocyclic groups containing 1 or 2 kinds of, preferably 1 to 4, hetero atoms selected from nitrogen, sulfur and oxygen atoms in addition to carbon atoms. Specific examples include aromatic heterocyclic groups such as 2- or 3-thienyl; 2-, 3- or 4-pyridyl; 2- or 3-furyl; 2-, 4- or 5-thiazolyl; 2-, 4- or 5-oxazolyl; 1-, 3- or 4-pyrazolyl; 2-pyrazinyl; 2-, 4- or 5-pyrimidinyl; 1-, 2- or 3-pyrrolyl; 1-, 2- or 4-imidazolyl; 3- or 4-pyridazinyl; 3-isothiazolyl; 3-isoxazolyl; 1,2,4-oxadiazol-5-yl; 1,2,4-oxadiazol-3-yl; 2-, 3-, 4-, 5- or 8-quinolyl; 1-, 3-, 4-, 5-, 6-, 7- or 8-isoquinolyl; 1-, 2-, 3-, 4-, 5-, 6- or 7-indolyl; 1-, 2-, 4- or 5-isoindolyl; 1-, 5- or 6-phthalazinyl; 2-, 3- or 5-quinoxalinyl; 2-, 3-, 4-, 5- or 6-benzofuranyl; 2-, 3-, 4-, 5- or 6-benzothienyl; 2-, 4-, 5- or 6-benzothiazolyl; 1-, 2-, 4-, 5- or 6-benzimidazolyl; etc.; and non-aromatic heterocyclic groups such as 1-, 2- or 3-pyrrolidinyl; 1-, 2-, 4- or 5-imidazolidinyl; 2- or 4-imidazolinyl; 2-, 3- or 4-pyrazolidinyl; piperidino; 2-, 3- or 4-piperidyl; 1- or 2-piperazinyl; morpholino; etc.

As the "substituents" in the "heterocyclic groups which may be substituted", those exemplified as the "substituents" in the above "5- to 10-membered aromatic heterocyclic groups which may be substituted" can be used. The number of substituents is, for example, 1 to 5, preferably 1 to 3. When the number of substituents is 2 or more, each substituents can be the same or different.

Examples of the "$C_{1-6}$ alkyl" represented by $R^4$ include methyl, ethyl, propyl, isopropyl, butyl, isobutyl, sec-butyl, tert-butyl, pentyl, hexyl, etc.

Examples of the "nitrogen-containing heterocyclic ring" in the "nitrogen-containing heterocyclic ring which may be substituted" formed by $R^3$ and $R^4$ together with the adjacent nitrogen atom include a 5- to 7-membered nitrogen-containing heterocyclic ring which contains at least one nitrogen atom in addition to carbon atoms and may contain 1 to 3 hetero atoms selected from nitrogen, sulfur and oxygen atoms. The "nitrogen-containing heterocyclic rings" are preferably piperidine, morpholine, thiomorpholine, piperazine, pyrrolidine, etc.

As the "substituents" in the "nitrogen-containing heterocyclic ring which may be substituted", those exemplified as the "substituents" in the above "5- to 10-membered aromatic heterocyclic groups which may be substituted" can be used. The number of substituents is, for example, 1 to 5, preferably 1 to 3. When the number of substituents is 2 or more, each substituents can be the same or different.

The "acyl" is preferably formyl, carboxy, carbamoyl, optionally halogenated $C_{1-6}$ alkyl-carbonyl (e.g. acetyl, etc.), $C_{1-6}$ alkoxy-carbonyl (e.g. methoxycarbonyl, ethoxycarbonyl, propoxycarbonyl, tert-butoxycarbonyl, etc.), $C_{6-14}$ arylcarbonyl which may be substituted (e.g. benzoyl, 1-naphthoyl, 2-naphthoyl, etc.), $C_{6-14}$ aryloxy-carbonyl which may be substituted (e.g. phenyloxycarbonyl, 1-naphthyloxycarbonyl, 2-naphthyloxycarbonyl, etc.), $C_{7-19}$ aralkyloxy-carbonyl which may be substituted (e.g. benzyloxycarbonyl, phenethyloxycarbonyl, etc.), a 5- to 6-membered heterocyclic ring-carbonyl which may be substituted (e.g. nicotinoyl, etc.), mono-$C_{1-6}$ alkyl-carbamoyl (e.g. methylcarbamoyl, ethylcarbamoyl, etc.), di-$C_{1-6}$ alkyl-carbamoyl (e.g. dimethylcarbamoyl, diethylcarbamoyl, ethylmethylcarbamoyl, etc.), $C_{6-14}$ aryl-carbamoyl which may be substituted (e.g. phenylcarbamoyl, 4-methoxyphenylcarbamoyl, 3,4-dimethoxyphenylcarbamoyl, etc.), aromatic heterocyclic ring-carbamoyl which may be substituted (e.g. 2-pyridinylcarbamoyl, 2-quinolinylcarbamoyl etc.), optionally halogenated $C_{1-6}$ alkylsulfonyl (e.g. methylsulfonyl, etc.), $C_{6-14}$ arylsulfonyl which may be substituted (e.g. phenylsulfonyl etc.), etc.

Here, as the "optionally halogenated $C_{1-6}$ alkyl-carbonyl" and "optionally halogenated $C_{1-6}$ alkylsulfonyl", those exemplified as the "substituents" in the above "$C_{7-19}$ aralkyl which may be substituted" can be used, respectively.

As the "$C_{6-14}$ aryl-carbonyl which may be substituted", those exemplified as the "substituents" in the above "5- to 7-membered saturated cyclic amino which may be substituted" can be used.

As the "$C_{6-14}$ aryloxy-carbonyl which may be substituted", "$C_{7-19}$ aralkyloxy-carbonyl which may be substituted", "5- to 6-membered heterocyclic ring-carbonyl which may be substituted", "aromatic heterocyclic ring-carbamoyl which may be substituted" and "$C_{6-14}$ arylsulfonyl which may be substituted", those exemplified as the "substituents" in the above "hydrocarbon groups which may be substituted" can be used, respectively.

As the "$C_{6-14}$ aryl-carbamoyl which may be substituted", those exemplified as the "substituents" in the above "cyclic group which may be substituted" can be used.

Examples of the above "acylamino" include amino which is substituted by 1 or 2 of the above "acyl". Preferably, acylamino of the formulas: —$NR^5$—$COR^6$—$NR^5$—$COOR^{6a}$, —$NR^5$—$SO_2R^{6a}$, —$NR^5$—$CONR^{6a}R^{6b}$, —$PO(—OR^5)$—$OR^6$, or —$PO_2$—$R^6$ wherein $R^5$ is hydrogen atom or $C_{1-6}$ alkyl; $R^6$ is as defined with respect to the above $R^3$; $R^{6a}$ is as defined with respect to the above $R^{3a}$; and $R^{6b}$ is as defined with respect to $R^4$], etc., can be mentioned.

As the "$C_{1-6}$ alkyl" represented by $R^5$, the same one as the "$C_{1-6}$ alkyl" for the above $R^4$ can be mentioned.

The "acylamino" is preferably formylamino, optionally halogenated $C_{1-6}$ alkyl-carboxamide (e.g. methylcarboxamide, trifluoromethylcarboxamide, etc.), $C_{6-14}$ aryl-carboxamide which may be substituted (e.g. phenylcarboxamide, 2-methoxyphenylcarboxamide, 4-methoxyphenylcarboxamide, etc.), N-($C_{6-14}$ aryl-carbonyl which may be substituted)-N—$C_{1-6}$ alkylamino (e.g. N-4-methoxybenzoyl-N-methylamino, etc.), $C_{7-19}$ aralkyl-carboxamide which may be substituted (e.g. benzylcarboxamide, etc.), aromatic heterocyclic ring-carboxamide which may be substituted (e.g. benzothiophen-2-ylcarboxamide, etc.), optionally halogenated $C_{1-6}$ alkoxy-carboxamide (e.g. methoxycarboxamide, ethoxycarboxamide, propoxycarboxamide, butoxycarboxamide, etc.), $C_{6-14}$ arylamino-carbonylamino which may be substituted (e.g. phenylaminocarbonylamino, etc.), optionally halogenated $C_{1-6}$ alkylsulfonylamino (e.g. methylsulfonylamino, trifluoromethylsulfonylamino, ethylsulfonylamino, etc.), $C_{6-14}$ arylsulfonylamino which may be substituted (e.g. 4-methoxyphenylsulfonylamino, etc.), etc.

Here, as the "substituents" in the "$C_{6-14}$ aryl-carboxamide which may be substituted", "N—($C_{6-14}$ aryl-carbonyl which may be substituted)-N—$C_{1-6}$ arylkylamino", "$C_{7-19}$ aralkyl-carboxamide which may be substituted", "aromatic heterocyclic ring-carboxamide which may be substituted", "$C_{6-14}$ arylamino-carbonylamino which may be substituted" and "$C_{6-14}$ arylsulfonylamino which may be substituted", those exemplified as the "substituents" in the above "$C_{7-19}$ aralkyl which may be subsituted" can be mentioned. The number of substituents is, for example, 1 to 5, preferably 1 to 3. When the number of substituents is 2 or more, each substituents can be the same or different.

Examples of the above "acyloxy" include oxy substituted by one of the above "acyl". Preferably, acyloxy of the formulas: —O—$COR^7$, —O—$COOR^7$, —O—$CONHR^7$, —PO(OH)—$OR^7$ or —$PO_2$—$R^7$ wherein $R^7$ is as defined with respect to the above $R^3$, etc., can be mentioned.

The "acyloxy" is preferably optionally halogenated $C_{1-6}$ alkyl-carbonyloxy (e.g. acetoxy, propanoyloxy, etc.), $C_{6-14}$ aryl-carbonyloxy which may be substituted (e.g. benzoyloxy, 4-methoxybenzoyloxy, etc.), optionally halogenated $C_{1-6}$ alkoxy-carbonyloxy (e.g. methoxycarbonyloxy, trifluoromethoxycarbonyloxy, ethoxycarbonyloxy, propoxycarbonyloxy, butoxycarbonyloxy, etc.), mono-$C_{1-6}$ alkyl-carbamoyloxy (e.g. methylcarbamoyloxy, ethylcarbamoyloxy, etc.), di-$C_{1-6}$ alkyl-carbamoyloxy (e.g. dimethylcarbamoyloxy, diethylcarbamoyloxy, etc.), $C_{6-14}$ aryl-carbamoyloxy which may be substituted (e.g. phenylcarbamoyloxy, naphthylcarbamoyloxy, etc.), nicotinoyloxy, etc.

As the "substituents" in "$C_{6-14}$ aryl-carbonyloxy which may be substituted" and "$C_{6-14}$ aryl-carbamoyloxy which may be substituted", those exemplified as the "substituents" in the above "$C_{7-19}$ aralkyl which may be substituted" can be mentioned. The number of substituents is, for example, 1 to 5, preferably 1 to 3. When the number of substituents is 2 or more, each substituents can be the same or different.

Examples of the "5- to 7-membered non-aromatic heterocyclic groups" in the "5- to 7-membered non-aromatic heterocyclic groups which may be substituted" which is the "substituents" in "cyclic group which may be substituted" represented by R and $Ar^1$, include 4,5-dihydro-1,3-oxazol-2-yl, 4,5-dihydro-1,3-thiazol-2-yl, 4,5-dihydro-1H-2-imidazolyl, etc. As the "substituents" in the "5- to 7-membered non-aromatic heterocyclic groups which may be substituted", those exemplified as the "substituents" in the above "5- to 7-membered saturated cyclic amino which may be substituted" can be used.

As the "acyl", "acyloxy" and "acylamino", which are the "substituents" in the "cyclic group which may be substituted" represented by R and $Ar^1$, those exemplified as the "substituents" in the above "5- to 10-membered aromatic heterocyclic groups which may be substituted" can be used.

The "substituents" in the "cyclic group which may be substituted" for R and $Ar^1$ are preferably a halogen atom (preferably fluorine, chlorine and bromine, etc.); nitro; $C_{1-3}$ alkylenedioxy (preferably methylenedioxy, etc.); optionally halogenated $C_{1-6}$ alkyl (preferably, methyl, ethyl, propyl, trifluoromethyl, tert-butyl, etc.); hydroxy-$C_{1-6}$ alkyl (preferably hydroxymethyl, etc.); optionally halogenated $C_{3-6}$ cycloalkyl (preferably cyclohexyl, etc.); optionally halogenated $C_{1-6}$ alkoxy (preferably methoxy, ethoxy, etc.); optionally halogenated $C_{1-6}$ alkylthio (preferably methylthio, etc.); hydroxy; $C_{7-19}$ aralkyloxy which may be substituted (preferably benzyloxy, 4-methoxybenzyloxy, 3-methoxybenzyloxy, 4-fluorobenzyloxy, 4-methylthiobenzyloxy, 4-ethylbenzyloxy, etc.); $C_{6-14}$ aryloxy which may be substituted (preferably phenyloxy, etc.); amino; mono-$C_{1-6}$ alkylamino (preferably methylamino, etc.); di-$C_{1-6}$ alkylamino (preferably dimethylamino, etc.); 5- to 7-membered saturated cyclic amino which may be substituted and may be condensed with a benzene ring (preferably 1,3-dioxo-1,3-dihydro-2H-isoindol-2-yl, etc.); 5- to 7-membered non-aromatic heterocyclic groups which may be substituted (preferably 4,5-dihydro-1,3-oxazol-2-yl, etc.); formyl; carboxy; $C_{6-14}$ aryl-carbonyl which may be substituted (preferably benzoyl, etc.); $C_{6-14}$ aryl-carbamoyl which may be substituted (preferably, phenylcarbamoyl, 4-methoxyphenylcarbamoyl, 3,4-dimethoxyphenylcarbamoyl, etc.); aromatic heterocyclic ring-carbamoyl which may be substituted (preferably 2-pyridinylcarbamoyl, 2-quinolinylcarbamoyl, etc.); $C_{1-6}$ alkoxy-carbonyl (preferably methoxycarbonyl, ethoxycarbonyl, etc.); optionally halogenated $C_{1-6}$ alkyl-carboxamide (preferably methylcarboxamide, trifluoromethylcarboxamide, etc.); $C_{6-14}$ aryl-carboxamide which may be substituted (preferably phenylcarboxamide, 2-methoxyphenylcarboxamide, 4-methoxyphenylcarboxamide, etc.); $C_{7-19}$ aralkyl-carboxamide which may be substituted (preferably benzylcarboxamide, etc.); aromatic heterocyclic ring-carboxamide which may be substituted (preferably benzothiophen-2-yl-carboxamide, etc.); N—($C_{6-14}$ aryl-carbonyl which may be substituted)-N—$C_{1-6}$ alkylamino (preferably N-4-methoxybenzoyl-N-methylamino, etc.); $C_{6-14}$ arylamino-carbonylamino which may be substituted (preferably phenylaminocarbonylamino, etc.); $C_{6-14}$ arylsulfonylamino which may be substituted (preferably 4-methoxyphenylsulfonylamino, etc.); $C_{6-14}$ aryl-carbonyloxy which may be substituted (preferably 4-methoxybenzoyloxy, etc.); oxo; etc.

When the "cyclic group" in the "cyclic group which may be substituted" represented by R and $Ar^1$ is a non-aromatic cyclic hydrocarbon group or a non-aromatic heterocyclic group, $C_{6-14}$ aryl which may be substituted (preferably phenyl), etc., can be used as a preferred substituent.

More preferably, the "substituent" of the "cyclic group which may be substituted" represented by R and $Ar^1$ is a halogen atom (preferably chlorine, etc.), $C_{1-6}$ alkyl (preferably methyl, etc.), $C_{7-19}$ aralkyloxy which may be substituted with $C_{1-6}$ alkoxy (preferably methoxybenzyloxy, etc.), etc.

R and $Ar^1$ are preferably phenyl, biphenylyl (preferably 4-biphenylyl), phenyl-pyridyl (preferably 6-phenyl-3-pyridyl, 5-phenyl-2-pyridyl), phenyl-furyl (preferably 5-phenyl-2-furyl), phenyl-isoxazole (preferably 3-phenyl-isoxazol-5-yl), diphenyl-oxazole (preferably 2,4-diphenyl-1,3-oxazol-5-yl), pyridyl-phenyl (preferably 4-(4-pyridyl)phenyl), phenyl-pyrimidinyl (preferably 2-phenyl-5-pyrimidinyl), benzofuranyl-phenyl (preferably 4-(2-benzofuranyl)phenyl), furyl-phenyl (preferably 4-(2-furyl)phenyl), pyrrolyl (preferably 1-pyrrolyl) or naphthyl; each of which may have 1 or 2 substituents selected from the group consisting of a halogen atom (preferably fluorine, chlorine and bromine, etc.); nitro; $C_{1-3}$ alkylenedioxy (preferably methylenedioxy, etc.); optionally halogenated $C_{1-6}$ alkyl (preferably, methyl, ethyl, propyl, trifluoromethyl, tert-butyl, etc.); hydroxy-$C_{1-6}$ alkyl (preferably hydroxymethyl, etc.); optionally halogenated $C_{3-6}$ cycloalkyl (preferably cyclohexyl, etc.); optionally halogenated $C_{1-6}$ alkoxy (preferably methoxy, ethoxy, etc.); optionally halogenated $C_{1-6}$ alkylthio (preferably methylthio, etc.); hydroxy; $C_{7-19}$ aralkyloxy which may be substituted (preferably benzyloxy, 4-methoxybenzyloxy, 3-methoxybenzyloxy, 4-fluorobenzyloxy, 4-methylthiobenzyloxy, 4-ethylbenzyloxy, etc.); $C_{6-14}$ aryloxy which may be substituted (preferably phenyloxy, etc.); amino; mono-$C_{1-6}$ alkylamino (preferably methylamino, etc.); di-$C_{1-6}$ alkylamino (preferably dimethylamino, etc.); 5- to 7-membered saturated cyclic amino which may be substituted and may be condensed with a benzene ring (preferably 1,3-dioxo-1,3-dihydro-2H-isoindol-2-yl, etc.); 5- to 7-membered non-aromatic heterocyclic groups which may be substituted (preferably 4,5-dihydro-1,3-oxazol-2-yl, etc.); formyl; carboxy; $C_{6-14}$ aryl-carbonyl which may be substituted (preferably benzoyl, etc.); $C_{6-4}$ aryl-carbamoyl which may be substituted (preferably, phenylcarbamoyl, 4-methoxyphenylcarbamoyl, 3,4-dimethoxyphenylcarbamoyl, etc.); aromatic heterocyclic ring-carbamoyl which may be substituted (preferably 2-pyridinylcarbamoyl, 2-quinolinylcarbamoyl, etc.); $C_{1-6}$ alkoxy-carbonyl (preferably methoxycarbonyl, ethoxycarbonyl, etc.); optionally halogenated $C_{1-6}$ alkyl-carboxamide (preferably methylcarboxamide, trifluoromethylcarboxamide, etc.); $C_{6-14}$ aryl-carboxamide which may be substituted (preferably phenylcarboxamide, 2-methoxyphenylcarboxamide, 4-methoxyphenylcarboxamide, etc.); $C_{7-19}$ aralkyl-carboxamide which may be substituted (preferably benzyl-carboxamide, etc.); aromatic heterocyclic ring-carboxamide which may be substituted (preferably benzothiophen-2-yl-carboxamide, etc.); N—($C_{6-14}$ aryl-carbonyl which may be substituted)-N—$C_{1-6}$ alkylamino (preferably N-4-methoxybenzoyl-N-methylamino, etc.); $C_{6-14}$ arylamino-carbonylamino which may be substituted (preferably phenylaminocarbonylamino, etc.); $C_{6-14}$ arylsulfonylamino which may be substituted (preferably 4-methoxyphenylsulfonylamino, etc.); $C_{6-14}$ aryl-carbonyloxy which may be substituted (preferably 4-methoxybenzoyloxy, etc.); oxo; etc.

Further, preferred examples of R and $Ar^1$ include piperidino, piperazinyl, pyrrolidinyl, etc.; each of which may have 1 or 2 substituents selected from the group consisting of oxo and $C_{6-14}$ aryl which may be substituted (preferably phenyl).

Examples of the halogen atom represented by R include fluorine, chlorine, bromine, iodine, etc. Among them, fluorine is preferred.

The "spacer having a main chain of 1 to 10 atoms" represented by X means a space in which 1 to 10 atoms are linked. Here, the "number of atoms in the main chain" is counted so that the number of atoms in the main chain is minimum. For example, the number of atoms of 1,2-cyclopentylene is counted as 2, and the number of atoms of 1,3-cyclopentylene is counted as 3.

Examples of the "spacer having a main chain of 1 to 10 atoms" include a bivalent group consisting of 1 to 5 members selected from —O—, —S—, —CO—, —SO—, —$SO_2$—, —$NR^8$— ($R^8$ is hydrogen atom, optionally halogenated $C_{1-6}$ alkyl, optionally halogenated $C_{1-6}$ alkyl-carbonyl, optionally halogenated $C_{1-6}$ alkylsulfonyl), bivalent $C_{1-6}$ non-cyclic hydrocarbon groups which may be substituted, and bivalent $C_{5-8}$ monocyclic non-aromatic hydrocarbon groups, and the like.

Here, as the "optionally halogenated $C_{1-6}$ alkyl", those exemplified as the "substituents" in the above "cyclic group which may be substituted" can be used.

As the "optionally halogenated $C_{1-6}$ alkyl-carbonyl" and "optionally halogenated $C_{1-6}$ alkylsulfonyl", those exemplified as the "substituents" in the above "$C_{7-19}$ aralkyl which may be substituted" can be used, respectively.

Examples of the "bivalent $C_{1-6}$ non-cyclic hydrocarbon groups" in the "bivalent $C_{1-6}$ non-cyclic hydrocarbon groups which may be substituted" include (1) $C_{1-6}$ alkylene (e.g. —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$CH_2$—$CH(CH_3)$—, —$(CH(CH_3))_2$—, —$(CH_2)_2C(CH_3)_2$—, —$(CH_2)_3C(CH_3)_2$, etc.);

(2) $C_{2-6}$ alkenylene (e.g. —CH=CH—, —CH$_2$—CH=CH—, —CH=CH—CH$_2$—, —CH=CH—CH$_2$—CH$_2$—, —CH$_2$—CF=CH—, —C(CH$_3$)$_2$—CH=CH—, —CH$_2$—CH=CH—CH$_2$—, —CH$_2$—CH$_2$—CH=CH—, —CH=CH—CH=CH—, —CH=CH—CH$_2$—CH$_2$—CH$_2$—, —etc.);

(3) $C_{2-6}$ alkynylene (e.g. —C≡C—, —CH$_2$—C≡C—, —C≡C—CH$_2$—, —CH$_2$—C≡C—CH$_2$—CH$_2$—, etc.); etc.

Examples of the "substituent" in the "bivalent $C_{1-6}$ non-cyclic hydrocarbon groups which may be substituted" include halogen atom (e.g., fluorine, chlorine, bromine, iodine, etc.), hydroxy, nitro, cyano, optionally halogenated $C_{1-6}$ alkoxy, optionally halogenated $C_{1-6}$ alkylthio, amino, mono-$C_{1-6}$ alkylamino (e.g., methylamino, ethylamino, propylamino, isopropylamino, butylamino, etc.), di-$C_{1-6}$ alkylamino (e.g., dimethylamino, diethylamino, dipropylamino, dibutylamino, ethylmethylamino, etc.), formyl, carboxy, carbamoyl, thiocarbamoyl, optionally halogenated $C_{1-6}$ alkyl-carbonyl, $C_{1-6}$ alkoxy-carbonyl (e.g., methoxycarbonyl, ethoxycarbonyl, propoxycarbonyl, tert-butoxycarbonyl, etc.), optionally halogenated $C_{1-6}$ alkylsulfonyl, etc. The number of substituents is, for example, 1 to 5, preferably 1 to 3.

Here, as the "optionally halogenated $C_{1-6}$ alkoxy" and "optionally halogenated $C_{1-6}$ alkylthio", those exemplified as the "substituent" in the above "cyclic group which may be substituted" can be used, respectively.

As the "optionally halogenated $C_{1-6}$ alkyl-carbonyl" and "optionally halogenated $C_{1-6}$ alkylsulfonyl", those exemplified as the "substituent" in the above "$C_{7-19}$ aralkyl which may be substituted" can be used.

Preferably, the "substituent" in the "bivalent $C_{1-6}$ non-aromatic hydrocarbon group which may be substituted" is a halogen atom (e.g., fluorine, chlorine, bromine, iodine, etc.), hydroxy, etc.

As the "bivalent $C_{5-8}$ monocyclic non-aromatic hydrocarbon groups", for example, bivalent groups formed by removing an optional two hydrogen atoms from $C_{5-8}$ cycloalkane or $C_{5-8}$ cycloalkene, can be mentioned. Specific examples include 1,2-cyclopentylene; 1,3-cyclopentylene; 1,2-cyclohexylene; 1,3-cyclohexylene; 1,4-cyclohexylene; 1,2-cycloheptylene; 1,3-cycloheptylene; 1,4-cycloheptylene; 3-cyclohexen-1,4-ylene; 3-cyclohexen-1,2-ylene; 2,5-cyclohexadien-1,4-ylene, etc. Especially, $C_{5-8}$ cycloalkylene is preferable.

As the "spacer having a main chain of 1 to 6 atoms" represented by Y, among the above "spacer having a main chain of 1 to 10 atoms" represented by X, that whose main chain has 1 to 6 atoms can be mentioned.

The "spacer" represented by X and Y is preferably the "spacer having a main chain of 1 to 6 atoms", more preferably a bivalent group consisting of 1 to 3 members selected from —O—, —S—, —CO—, —SO—, —SO$_2$—, —NR$^8$— (R$^8$ is as defined above) and bivalent $C_{1-6}$ non-cyclic hydrocarbon group which may be substituted.

Preferred examples of the "spacer having a main chain of 1 to 6 atoms" include (1) $C_{1-6}$ alkylene (e.g. —CH$_2$—, —(CH$_2$)$_2$—, —(CH$_2$)$_3$—, —CH(OH)—(CH$_2$)$_2$—, —(CH$_2$)$_4$—, —(CH$_2$)$_5$—, —(CH$_2$)$_6$—, —CHCH$_3$—, —C(CH$_3$)$_2$—, —CH$_2$—CH(CH$_3$)—, —CH(CF$_3$)—, —(CH(CH$_3$))$_2$—, —(CF$_2$)$_2$—, —(CH$_2$)$_2$C(CH$_3$)$_2$—, —(CH$_2$)$_3$C(CH$_3$)$_2$—, etc.) which may be substituted (preferably with halogen atom, hydroxy, etc.);

(2) $C_{2-6}$ alkenylene (e.g. —CH=CH—, —CH$_2$—CH=CH—, —CH=CH—CH$_2$—, —CH=CH—CH$_2$—CH$_2$—, —CH$_2$—CF=CH—, —C(CH$_3$)$_2$—CH=CH—, —CH$_2$—CH=CH—CH$_2$—, —CH$_2$—CH$_2$—CH=CH—, —CH=CH—CH=CH—, —CH=CH—CH$_2$—CH$_2$—CH$_2$—, etc.) which may be substituted (preferably with halogen atom, hydroxy, etc.);

(3) $C_{2-6}$ alkynylene (e.g. —C≡C—, —CH$_2$—C≡C—, —C≡C—CH$_2$—, —CH$_2$—C≡C—CH$_2$—CH$_2$—, etc.) which may be substituted (preferably with halogen atom, hydroxy, etc.);

(4) —(CH$_2$)$_{w1}$O(CH$_2$)$_{w2}$—, —(CH$_2$)$_{w1}$S(CH$_2$)$_{w2}$—, —(CH$_2$)$_{w1}$CO(CH$_2$)$_{w2}$—, —(CH$_2$)$_{w1}$SO(CH$_2$)$_{w2}$—, —(CH$_2$)$_{w1}$SO$_2$(CH$_2$)$_{w2}$—, —(CH$_2$)$_{w1}$NR$^8$(CH$_2$)$_{w2}$—;

(5) —(CH$_2$)$_{w3}$CO—, —(CH$_2$)$_{w3}$CONR$^8$(CH$_2$)$_{w4}$—, —(CH$_2$)$_{w3}$NR$^8$CO(CH$_2$)$_{w4}$—, —(CH$_2$)$_{w3}$SO$_2$NR$^8$(CH$_2$)$_{w4}$—, —(CH$_2$)$_{w3}$NR$^8$SO$_2$(CH$_2$)$_{w4}$—, —(CH$_2$)$_{w3}$COO(CH$_2$)$_{w4}$—;

(6) —(CH$_2$)$_{w5}$NR$^8$CO—, —(CH$_2$)$_{w5}$NR$^8$CONR$^{8b}$(CH$_2$)$_{w6}$—, —(CH$_2$)$_{w5}$CH=CH(CH$_2$)$_{w6}$CO—;

(7) —O(CH$_2$)$_{w7}$CO—, —CO(CH$_2$)$_{w7}$CO—, —S(CH$_2$)$_{w7}$CO—, —SO(CH$_2$)$_{w7}$CO—, —SO$_2$(CH$_2$)$_{w7}$CO—, —NR$^8$(CH$_2$)$_{w7}$CO—, —COCH=CHCO—;

(8) —NR$^8$CO(CH$_2$)$_{w8}$CO—, —CONR$^8$(CH$_2$)$_{w8}$CO—;

wherein R$^8$ is as defined above; R$^{8b}$ is as defined with respect to R$^8$; w1 and w2 is an integer of 0 to 5, and w1+w2 is 0 to 5; w3 and w4 is an integer of 0 to 4, and w3+w4 is 0 to 4; w5 and w6 is an integer of 0 to 3, and w5+w6 is 0 to 3; w7 is an integer of 0 to 4; and w8 is an integer of 0 to 3, etc.

The "spacer having a main chain of 1 to 10 atoms" represented by X is more preferably —(CH$_2$)$_{w1}$O(CH$_2$)$_{w2}$—, —CONR$^8$—, —NR$^8$CO—, —(CH$_2$)$_{w3}$CO—, —(CH$_2$)$_{w5}$NR$^8$CO—, —CO—, —(CH$_2$)$_{w1}$CO(CH$_2$)$_{w2}$—, (the symbols are as defined above), $C_{1-3}$ alkylene (e.g., —CH$_2$—, —(CH$_2$)$_2$—, —(CH$_2$)$_3$—, —CH$_2$—CH(CH$_3$)—, etc.) which may be substituted (preferably with halogen atom, hydroxy, etc.), $C_{2-6}$ alkenylene (preferably —CH=CH—CH$_2$—, etc.) which may be substituted (preferably with halogen atom, hydroxy, etc.), $C_{2-6}$ alkynylene (preferably —C≡C—CH$_2$—, etc.) which may be substituted (preferably with halogen atom, hydroxy, etc.), —(CH$_2$)$_{w1}$SO$_2$(CH$_2$)$_{w2}$— (the symbols are as defined above), etc., in particular, —CO—.

More preferably, the "spacer having a main chain of 1 to 6 atoms" represented by Y is —(CH$_2$)$_{w1}$O(CH$_2$)$_{w2}$— (the symbols are as defined above) (preferably —O(CH$_2$)$_{w2}$—) (e.g., —O(CH$_2$)$_3$—, etc.), $C_{1-3}$ alkylene (e.g., —CH$_2$—, —(CH$_2$)$_2$—, —(CH$_2$)$_3$—, —CH(OH)—(CH$_2$)$_2$—, etc.) which may be substituted (preferably with halogen atom, hydroxy, etc.), $C_{2-6}$ alkenylene (e.g., —CH=CH—, —CH$_2$—CH=CH—, —CH=CH—CH$_2$—, —CH=CH—CH$_2$—CH$_2$—, etc.) which may be substituted (preferably with halogen atom, hydroxy, etc.), —(CH$_2$)$_{w3}$CONH(CH$_2$)$_{w4}$—, —(CH$_2$)$_{w3}$COO(CH$_2$)$_{w4}$— (the symbols are as defined above), —(CH$_2$)$_{w1}$CO(CH$_2$)$_{w2}$— (the symbols are as defined above), (e.g., —CO(CH$_2$)$_2$—, —CO(CH$_2$)$_3$—, —(CH$_2$)$_2$CO—, —(CH$_2$)$_3$CO—, etc.), —CO(CH$_2$)$_{w7}$CO— (the symbols are as defined above) (e.g., —CO(CH$_2$)$_2$CO—, —CO(CH$_2$)$_3$CO—, etc.), —COCH=CHCO—, —O(CH$_2$)$_{w7}$CO— (the symbols are as defined above) (e.g., —O(CH$_2$)$_2$CO—, etc.), —CONR$^8$(CH$_2$)$_{w8}$CO— (the symbols are as defined above) (e.g., —CONHCH$_2$CO—), etc.

In the formula (I″), as the "spacer having a main chain of 1 to 5 atoms" represented by Ya, among the above "spacer having a main chain of 1 to 10 atoms" represented by X, that whose main chain has 1 to 5 atoms can be mentioned. Ya is preferably —(CH$_2$)$_{w1}$O(CH$_2$)$_{w2}$— (the symbols are as defined above) (preferably —CO(CH$_2$)$_2$—), etc.

In the formula (I'''), the "spacer having a main chain of 1 to 6 atoms" is the same as the above Y.

The particularly preferred X is a bond, —(CH$_2$)$_{w1}$CO (CH$_2$)$_2$— (the symbols are as defined above), C$_{1-3}$ alkylene (preferably —CH$_2$—, —(CH$_2$)$_2$—, —(CH$_2$)$_3$—, —CH$_2$—CH(CH$_3$)—, etc.), C$_{2-6}$ alkenylene (preferably —CH=CH—CH$_2$—, etc.), C$_{2-6}$ alkynylene (e.g., —C≡C—CH$_2$—, etc.), etc.

The particularly preferred Y is —(CH$_2$)$_{w1}$O(CH$_2$)$_{w2}$— (the symbols are as defined above) (preferably —O(CH$_2$)$_{w2}$—, more preferably —O(CH$_2$)$_3$—, etc.), C$_{1-3}$ alkylene which may be substituted with hydroxy group (preferably —(CH$_2$)$_3$—, —CH(OH)—(CH$_2$)$_2$—, etc.), C$_{2-6}$ alkenylene (preferably —CH=CH—CH$_2$—, —CH=CH—CH$_2$—CH$_2$—, etc.), —(CH$_2$)$_{w1}$CO(CH$_2$)$_{w2}$— (the symbols are as defined above) (preferably —CO(CH$_2$)$_3$—, etc.), —CO(CH$_2$)$_{w7}$CO— (the symbols are as defined above) (preferably —CO(CH$_2$)$_2$CO—, etc.), etc.

The group represented by the formula:

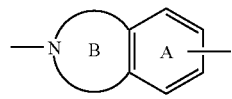

wherein the symbols are as defined above, and the group represented by the formula:

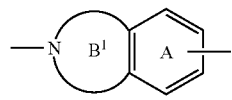

wherein the symbols are as defined above, are preferably

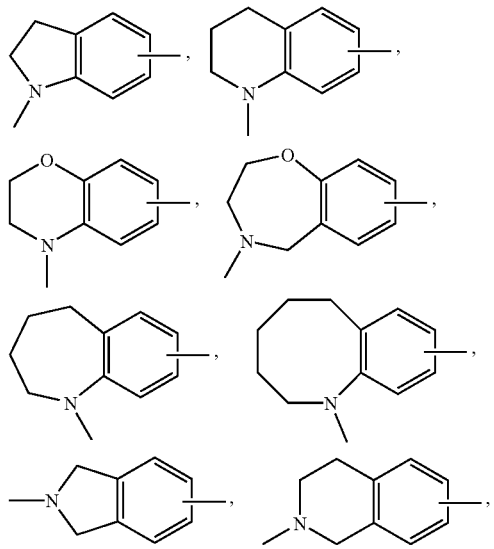

-continued

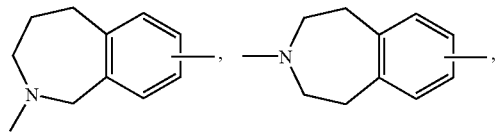

and the like. Among them,

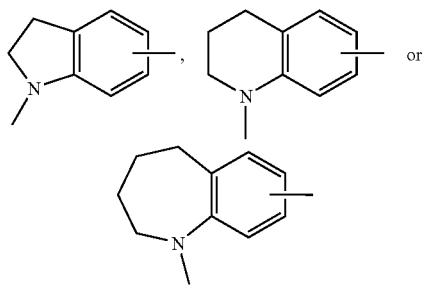

etc., is preferred. Further,

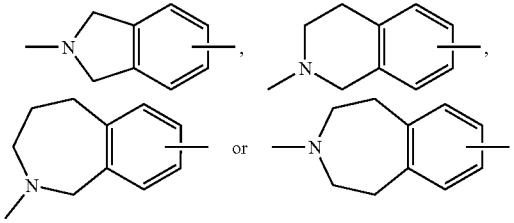

etc., is also preferred.

As the "substituents" in the "benzene ring" represented by ring A and the "5- to 9-membered nitrogen-containing non-aromatic heterocyclic ring" represented by ring B, those exemplified as the "substituents" in the "cyclic group which may be substituted" represented by the above R and Ar$^1$ can be used.

The number of substituents is, for example, 1 to 5, preferably 1 to 3. When the number of substituents is 2 or more, each substituents can be the same or different.

The substituents on ring A and ring B are preferably oxo, C$_{6-14}$aryl which may be substituted (preferably with C$_{1-6}$ alkoxy), etc.

As the "hydrocarbon groups which may be substituted" represented by R$^1$ and R$^2$, those exemplified as the above R$^3$ can be used.

The "hydrocarbon groups which may be substituted" are preferably "C$_{1-6}$ alkyl which may be substituted", C$_{2-6}$ alkynyl (e.g., ethynyl, etc.), C$_{3-6}$ cycloalkyl (e.g., cyclopropyl, cyclohexyl, etc.), C$_{6-14}$ aryl (e.g., phenyl, naphthyl, etc.), dihydroindene, etc. Among them, "C$_{1-6}$ alkyl which may be substituted" is preferred, in particular, "C$_{1-6}$ alkyl" is preferred.

Here, examples of the "C$_{1-6}$ alkyl" in the "C$_{1-6}$ alkyl which may be substituted" include methyl, ethyl, propyl, isopropyl, butyl, isobutyl, sec-butyl, tert-butyl, pentyl, hexyl, etc. Especially, methyl, ethyl, propyl, etc. are preferred.

Examples of the "substituents" in the "$C_{1-6}$ alkyl which may be substituted" include halogen atom (e.g. fluorine, chlorine, bromine, iodine, etc.), $C_{1-3}$ alkylenedioxy (e.g. methylenedioxy, ethylenedioxy etc.), nitro, cyano, optionally halogenated $C_{3-6}$ cycloalkyl (e.g., cyclohexyl, etc.), optionally halogenated $C_{1-6}$ alkoxy (e.g., methoxy, isopropoxy, etc.), optionally halogenated $C_{1-6}$ alkylthio (e.g., methylthio, etc.), hydroxy, amino, mono-$C_{1-6}$ alkylamino (e.g. methylamino, ethylamino, propylamino, isopropylamino, butylamino, etc.), di-($C_{1-6}$ alkyl which may be substituted with hydroxy)amino (e.g. dimethylamino, diethylamino, dipropylamino, diisopropylamino, dibutylamino, ethylmethylamino, di(hydroxyethyl)amino, etc.), $C_{6-14}$ aryl-amino which may be substituted with one to three $C_{1-6}$ alkyl (e.g., phenylamino, 2,6-dimethylphenylamino, etc.), N—$C_{1-6}$ alkyl-N-($C_{6-14}$ aryl which may be substituted with $C_{1-6}$ alkyl)amino (e.g., N-methyl-N-phenylamino, N-ethyl-N-(methylphenyl)amino, etc.), 5- or 6-membered monocyclic aromatic heterocyclic ring amino which may be substituted with nitro (e.g., nitropyridylamino, etc.), 5- to 8-membered monocyclic non-aromatic heterocyclic group (e.g., tetrahydrofuryl, pyrrolidinyl, oxopyrrolidinyl, piperidinyl, methylpiperidinyl, morpholinyl, methylpiperazinyl, etc.), formyl, carboxy, carbamoyl, thiocarbamoyl, optionally halogenated $C_{1-6}$ alkyl-carbonyl, $C_{1-6}$ alkoxy-carbonyl (e.g. methoxycarbonyl, ethoxycarbonyl, propoxycarbonyl, tert-butoxycarbonyl, etc.), mono-$C_{1-6}$ alkyl-carbamoyl (e.g. methylcarbamoyl, ethylcarbamoyl, etc.), di-$C_{1-6}$ alkyl-carbamoyl (e.g. dimethylcarbamoyl, diethylcarbamoyl, ethylmethylcarbamoyl etc.), optionally halogenated $C_{1-6}$ alkylsulfonyl, formylamino, optionally halogenated $C_{1-6}$ alkyl-carboxamide, $C_{1-6}$ alkoxy-carboxamide (e.g. methoxycarboxamide, ethoxycarboxamide, propoxycarboxamide, butoxycarboxamide, etc.), $C_{1-6}$ alkylsulfonylamino (e.g. methylsulfonylamino, ethylsulfonylamino, etc.), $C_{1-6}$ alkyl-carbonyloxy (e.g. acetoxy, propanoyloxy, etc.), $C_{1-6}$ alkoxy-carbonyloxy (e.g. methoxycarbonyloxy, ethoxycarbonyloxy, propoxycarbonyloxy, butoxycarbonyloxy, etc.), mono-$C_{1-6}$ alkyl-carbamoyloxy (e.g. methylcarbamoyloxy, ethylcarbamoyloxy, etc.), di-$C_{1-6}$ alkyl-carbamoyloxy (e.g. dimethylcarbamoyloxy, diethylcarbamoyloxy, etc.), aromatic groups which may be substituted, optionally halogenated $C_{8-19}$ aryloxy (e.g., phenoxy, chlorophenyloxy, etc.), etc. The number of substituents is, for example, 1 to 5, preferably 1 to 3. When the number of substituents is 2 or more, each substituents can be the same or different.

Here, as the "optionally halogenated $C_{3-6}$ cycloalkyl", "optionally halogenated $C_{1-6}$ alkoxy" and "optionally halogenated $C_{1-6}$ alkylthio", those exemplified as the "substituents" in the above "cyclic group which may be substituted" can be used.

As the "optionally halogenated $C_{1-6}$ alkyl-carbonyl", "optionally halogenated $C_{1-6}$ alkylsulfonyl" and "optionally halogenated $C_{1-6}$ alkyl-carboxamide", those exemplified as the "substituents" in the above "$C_{7-19}$ aralkyl which may be substituted" can be used.

As the "substituents" and "aromatic groups" in the "aromatic groups which may be substituted", those exemplified as the "substituents" and "aromatic groups" in the "cyclic group which may be substituted" represented by the above R can be used. The number of substituents is, for example, 1 to 5, preferably 1 to 3. When the number of substituents is 2 or more, each substituents can be the same or different.

The "aromatic groups" are preferably phenyl, naphthyl, furyl, pyridyl, imidazoly, indolyl, etc. And, the "substituents" are preferably $C_{1-3}$ alkylenedioxy (e.g., methylenedioxy, etc.), optionally halogenated $C_{1-6}$ alkyl (e.g., trifluoromethyl, etc.), optionally halogenated $C_{1-6}$ alkoxy (e.g., methoxy, etc.), a halogen atom (e.g., chlorine, etc.), etc.

As the "heterocyclic group which may be substituted" represented by $R^1$ and $R^2$, those exemplified as the above $R^3$ can be used.

The "heterocyclic group" in the "heterocyclic group which may be substituted" is preferably a 5- to 10-membered non-aromatic heterocyclic group, more preferably pyrrolidinyl, piperidinyl, etc. Further, the "substituent" in the "heterocyclic group which may be substituted" is preferably optionally halogenated $C_{1-6}$ alkyl (e.g., methyl, etc.), $C_{7-19}$ aralkyl (e.g., benzyl, etc.), etc. The number of the substituents is, for example, 1 to 5.

Examples of the "nitrogen-containing heterocyclic rings" in the "nitrogen-containing heterocyclic rings which may be substituted" formed by $R^1$ and $R^2$ together with the adjacent nitrogen atom include 3- to 10-membered (preferably 3- to 8-membered) nitrogen-containing heterocyclic rings which contain at least one nitrogen atom in addition to carbon atoms, and which may further contain 1 to 3 hetero atoms selected from nitrogen, sulfur and oxygen atoms. Specific examples include aziridine, azetidine, morpholine, thiomorpholine, piperidine, piperazine, pyrrolidine, hexamethyleneimine, heptamethyleneimine, hexahydropyrimidine, 1,4-diazepan, dihydroisoquinoline, and their unsaturated cyclic amines (e.g. 1,2,5,6-tetrahydropyridine, 1,4-diazepin, octahydroisoquinoline, etc.), etc. can be mentioned. Especially, morpholine, piperidine, piperazine, pyrrolidine, etc., are preferred.

As the "substituents" in the "nitrogen-containing heterocyclic rings which may be substituted", for example, those exemplified as the "substituents" in the above "5- to 7-membered saturated cyclic amino which may be substituted" can be used. The number of substituents is, for example, 1 to 5, preferably 1 to 3. When the number of substituents is 2 or more, each substituents can be the same or different.

The "substituents" are preferably hydroxy; optionally halogenated $C_{1-6}$ alkyl (preferably methyl, ethyl, etc.); $C_{6-14}$ aryl (e.g., phenyl, naphthyl, etc.) which may have 1 to 3 substituents selected from halogen atom, optionally halogenated $C_{1-6}$ alkyl and optionally substituted $C_{1-6}$ alkoxy; carbamoyl; hydroxy-$C_{1-6}$ alkyl; $C_{1-6}$ alkoxy-carbonyl-$C_{1-6}$ alkyl (e.g., ethoxycarbonylmethyl, etc.); $C_{7-19}$ aralkyl (e.g., benzyl, diphenylmethyl, etc.) which may be substituted with $C_{1-3}$ alkylenedioxy (e.g., methylenedioxy, etc.); 5- to 10-membered aromatic heterocyclic group (preferably pyridyl, pyrimidinyl, etc.); 5- to 8-monocyclic non-aromatic heterocyclic group (e.g., pyrrolidinyl, piperidinyl, etc.); $C_{8-19}$ aryl-alkenyl (e.g., 3-phenyl-2-prop-2-enyl, etc.); $C_{1-6}$ alkyl-carboxamide (e.g., methylcarboxamide, etc.); (N—$C_{1-6}$ alkyl)-$C_{1-6}$ alkyl-carboxamide (e.g., (N-ethyl)methylcarboxamide, etc.); di-$C_{1-6}$ alkylamino (e.g., dimethylamino, etc.), 5- to 8-membered monocyclic non-aromatic heterocyclic group-$C_{1-6}$ alkyl (e.g., pyrrolidinylmethyl, etc.); $C_{6-14}$ aryl-amino-$C_{1-6}$ alkyl (e.g., 2,6-dimethylphenylaminomethyl, etc.) substituted with 1 to 3 $C_{1-6}$ alkyl; etc.

Preferably, $R^1$ and $R^2$, together with the adjacent nitrogen atom, form a nitrogen-containing heterocyclic ring which may be substituted.

In particular, $R^1$ and $R^2$, together with the adjacent nitrogen atom, form piperidino, pyrrolidin-1-yl, etc.

The "nitrogen-containing heterocyclic rings which may be substituted" formed by $R^1$ and $R^2$ together with the adjacent nitrogen atom is preferably

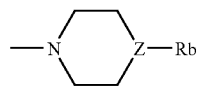

wherein the symbols are as defined above.

Here, as the "hydrocarbon group which may be substituted" represented by Rb, those exemplified as the above $R^3$ can be mentioned. Preferably, Rb is a hydrocarbon group which may be substituted and specific examples thereof include optionally halogenated $C_{1-6}$ alkyl (preferably methyl, ethyl, etc.); $C_{6-14}$ aryl (e.g., phenyl, naphthyl, etc.) which may have 1 to 3 substituents selected from halogen atom (e.g., fluorine, chlorine, etc.), optionally halogenated $C_{1-6}$ alkyl (e.g., methyl, etc.) and optionally substituted $C_{1-6}$ alkoxy (e.g., methoxy, etc.); hydroxy-$C_{1-6}$ alkyl; $C_{1-6}$ alkoxy-carbonyl-$C_{1-6}$ alkyl (e.g., ethoxycarbonylmethyl, etc.); $C_{7-19}$ aralkyl (e.g., benzyl, diphenylmethyl, etc.) which may be substituted with $C_{1-3}$ alkylenedioxy (e.g., methylenedioxy, etc.); $C_{8-19}$ arylalkenyl (e.g., 3-phenyl-2-prop-2-enyl, etc.); 5- to 8-monocyclic non-aromatic heterocyclic group-$C_{1-6}$ alkyl (e.g., pyrrolidinylmethyl etc.); $C_{6-14}$ arylamino-$C_{1-6}$ alkyl (e.g., 2,6-dimethylphenylaminomethyl, etc.) which may be substituted with 1 to 3 $C_{1-6}$ alkyl; etc. More preferably, Rb is $C_{6-14}$ aryl which may be substituted.

Z is preferably CH.

In the formula (I''''), as the "hydrocarbon group which may be substituted" represented by Rc, those exemplified as the above Rb can be mentioned. Preferably, Rc is $C_{6-14}$ aryl which may be substituted.

As the "nitrogen-containing heterocyclic ring which may be substituted" formed by $R^2$ together with the adjacent nitrogen atom and Y, those exemplified as the "nitrogen-containing heterocyclic ring which may be substituted" formed by $R^1$ and $R^2$ together with the adjacent nitrogen atom can be mentioned.

Suitable examples of the compounds represented by the formula (I) include those represented by the formulas (I'), (I''), (I'''), (I''''), (I'''''), etc.

Among the compounds represented by the formula (I), those represented by the formulas (I'), (I''), (I'''') or (I''''') are novel compounds.

Suitable examples of the compounds represented by the formula (I') include the following compounds:

(E)-3-[1-[4-[(4-methoxybenzyl)oxy]benzoyl]-2,3-dihydro-1H-indol-5-yl]-N,N-dimethyl-2-propene-1-amine;
(E)-3-[1-[4-[(4-methylbenzyl)oxy]benzoyl]-2,3-dihydro-1H-indol-5-yl]-N,N-dimethyl-2-propene-1-amine;
(E)-3-[1-[4-[(4-chlorobenzyl)oxy]benzoyl]-2,3-dihydro-1H-indol-5-yl]-N,N-dimethyl-2-propene-1-amine;
1-[[6-(4-chlorophenyl)-3-pyridinyl]carbonyl]-6-[(E)-3-(1-pyrrolidinyl)-1-propenyl]-1,2,3,4-tetrahydroquinoline;
1-[[6-(4-fluorophenyl)-3-pyridinyl]carbonyl]-6-[(E)-3-(1-pyrrolidinyl)-1-propenyl]-1,2,3,4-tetrahydroquinoline;
1-[[6-(4-methylphenyl)-3-pyridinyl]carbonyl]-6-[(E)-3-(1-pyrrolidinyl)-1-propenyl]-1,2,3,4-tetrahydroquinoline;
1-[[6-(4-chlorophenyl)-3-pyridinyl]carbonyl]-6-[(E)-3-dimethylamino-1-propenyl]-1,2,3,4-tetrahydroquinoline;
1-[[6-(4-fluorophenyl)-3-pyridinyl]carbonyl]-6-[(E)-3-dimethylamino-1-propenyl]-1,2,3,4-tetrahydroquinoline;
1-[[6-(4-methylphenyl)-3-pyridinyl]carbonyl]-6-[(E)-3-dimethylamino-1-propenyl]-1,2,3,4-tetrahydroquinoline;
1-[[6-(4-chlorophenyl)-3-pyridinyl]carbonyl]-6-[(E)-4-(1-pyrrolidinyl)-1-butenyl]-1,2,3,4-tetrahydroquinoline;
1-[[6-(4-fluorophenyl)-3-pyridinyl]carbonyl]-6-[(E)-4-(1-pyrrolidinyl)-1-butenyl]-1,2,3,4-tetrahydroquinoline;
1-[[6-(4-methylphenyl)-3-pyridinyl]carbonyl]-6-[(E)-4-(1-pyrrolidinyl)-1-butenyl]-1,2,3,4-tetrahydroquinoline;
1-[[6-(4-chlorophenyl)-3-pyridinyl]carbonyl]-6-[(E)-4-dimethylamino-1-butenyl]-1,2,3,4-tetrahydroquinoline;
1-[[6-(4-fluorophenyl)-3-pyridinyl]carbonyl]-6-[(E)-4-dimethylamino-1-butenyl]-1,2,3,4-tetrahydroquinoline;
1-[[6-(4-methylphenyl)-3-pyridinyl]carbonyl]-6-[(E)-4-dimethylamino-1-butenyl]-1,2,3,4-tetrahydroquinoline;
(E)-N,N-dimethyl-3-[1-[[4-(4-methylphenyl)-1-piperidinyl]carbonyl]-1,2,3,4-tetrhydro-6-quinolinyl]-2-propen-1-amine;
(E)-N,N-dimethyl-3-[1-[[4-(4-fluorophenyl)-1-piperidinyl]carbonyl]-1,2,3,4-tetrhydro-6-quinolinyl]-2-propen-1-amine;
(E)-N,N-dimethyl-3-[1-[[4-(4-chlorophenyl)-1-piperidinyl]carbonyl]-1,2,3,4-tetrhydro-6-quinolinyl]-2-propen-1-amine;
1-[[4-(4-methylphenyl)-1-piperidinyl]carbonyl]-6-[(E)-3-(1-pyrrolidinyl)-1-propenyl]-1,2,3,4-tetrahydroquinoline;
1-[[4-(4-fluorophenyl)-1-piperidinyl]carbonyl]-6-[(E)-3-(1-pyrrolidinyl)-1-propenyl]-1,2,3,4-tetrahydroquinoline;
1-[[4-(4-chlorophenyl)-1-piperidinyl]carbonyl]-6-[(E)-3-(1-pyrrolidinyl)-1-propenyl]-1,2,3,4-tetrahydroquinoline;
(E)-3-[1-[[4-(4-chlorophenyl)-1-piperazinyl]carbonyl]-1,2,3,4-tetrahydro-6-quinolinyl]-N,N-dimethyl-2-propen-1-amine;
(E)-3-[1-[[4-(4-methylphenyl)-1-piperazinyl]carbonyl]-1,2,3,4-tetrahydro-6-quinolinyl]-N,N-dimethyl-2-propen-1-amine;
(E)-3-[1-[[4-(4-fluorophenyl)-1-piperazinyl]carbonyl]-1,2,3,4-tetrahydro-6-quinolinyl]-N,N-dimethyl-2-propen-1-amine;
1-[[5-(4-fluorophenyl)-2-pyridinyl]carbonyl]-6-[(E)-3-(1-pyrrolidinyl)-1-propenyl]-1,2,3,4-tetrahydroquinoline;
1-[[5-(4-methylphenyl)-2-pyridinyl]carbonyl]-6-[(E)-3-(1-pyrrolidinyl)-1-propenyl]-1,2,3,4-tetrahydroquinoline;
1-[[6-(4-chlorophenyl)-3-pyridinyl]carbonyl]-6-[1-methyl-3-piperidinylidene)methyl-1,2,3,4-tetrahydroquinoline;
1-[[5-(4-chlorophenyl)-2-furoyl]-6-[(E)-3-(4-phenyl-1-piperidinyl)-1-propenyl]-1,2,3,4-tetrahydroquinoline.

Suitable examples of the compounds represented by the formula (I'') include the following compounds:

4-[4-(4-chlorophenyl)-1-piperidinyl]-4-oxo-1-(1,2,3,4-tetrahydro-7-isoquinolinyl)-1-butanone;
4-[4-(4-chlorophenyl)-1-piperidinyl]-4-oxo-1-(2,3,4,5-tetrahydro-1H-3-benzazepin-7-yl)-1-butanone;
4-[4-(4-chlorophenyl)-1-piperidinyl]-4-oxo-1-(3-methyl 2,3,4,5-tetrahydro-1H-3-benzazepin-7-yl)-1-butanone;
4-[4-(4-chlorophenyl)-1-piperidinyl]-1-(3-ethyl-2,3,4,5-tetrahydro-1H-3-benzazepin-7-yl)-4-oxo-1-butanone;
4-[4-(4-chlorophenyl)-1-piperidinyl]-4-oxo-1-(3-propyl-2,3,4,5-tetrahydro-1H-3-benzazepin-7-yl)-1-butanone;
1-(3-benzyl-2,3,4,5-tetrahydro-1H-3-benzazepin-7-yl)-4-[4-(4-chlorophenyl)-1-piperidinyl]-4-oxo-1-butanone;
1-(3-acetyl-2,3,4,5-tetrahydro-1H-3-benzazepin-7-yl)-4-[4-(4-chlorophenyl)-1-piperidinyl]-4-oxo-1-butanone;
4-[4-(4-chlorophenyl)piperidin-1-yl]-1-(3-isopropyl-2,3,4,5-tetrahydro-1H-3-benzazepin-7-yl)-4-oxobutan-1-one;
4-[4-(4-chlorophenyl)-1-piperidinyl]-4-oxo-1-(2,3,4,5-tetrahydro-1H-2-benzazepin-8-yl)-1-butanone;
4-[4-(4-chlorophenyl)-1-piperidinyl]-1-(2-methyl-2,3,4,5-tetrahydro-1H-2-benzazepin-8-yl)-4-oxo-1-butanone;
4-[4-(4-chlorophenyl)-1-piperidinyl]-1-(2,3-dihydro-1H-isoindol-5-yl)-4-oxo-1-butanone.

In addition to the above compounds represented by the formula (I') or (I"), suitable examples of the compound represented by the formula (I) include the following compounds:

(E)-3-[1-[(4'-chloro[1,1'-biphenyl]-4-yl)carbonyl]-1,2,3,4-tetrahydro-6-quinolinyl]-N,N-dimethyl-2-propen-1-amine;
1-[(4'-chloro[1,1'-biphenyl]-4-yl)carbonyl]-6-[(E)-3-piperidino-1-propenyl]-1,2,3,4-tetrahydroquinoline;
(E)-3-[1-[([1,1'-biphenyl]-4-yl)carbonyl]-2,3-dihydro-1H-indol-5-yl]-N,N-dimethyl-2-propen-1-amine;
(E)-3-[1-[(4'-chloro[1,1'-biphenyl]-4-yl)carbonyl]-2,3-dihydro-1H-indol-5-yl]-N,N-dimethyl-2-propen-1-amine;
(E)-4-[1-[(4'-chloro[1,1'-biphenyl]-4-yl)carbonyl]-1,2,3,4-tetrahydro-6-quinolinyl]-N,N-dimethyl-3-buten-1-amine;
1-(3-acetyl-2,3,4,5-tetrahydro-1H-3-benzazepin-7-yl)-4-[4-(4-chlorophenyl)-1-piperidinyl]-1-butanone;
4-[4-(4-chlorophenyl)-1-piperidinyl]-1-(2,3,4,5-tetrahydro-1H-3-benzazepin-7-yl)-1-butanone;
4-[4-(4-chlorophenyl)-1-piperidinyl]-1-(3-methyl-2,3,4,5-tetrahydro-1H-3-benzazepin-7-yl)-1-butanone;
4-oxo-N-(2-phenethyl)-4-(2,3,4,5-tetrahydro-1H-3-benzazepin-7-yl)butanamide;
4-oxo-N-(3-phenylpropyl)-4-(2,3,4,5-tetrahydro-1H-3-benzazepin-7-yl)butanamide;
N-[2-(1H-indol-3-yl)ethyl]-4-oxo-4-(2,3,4,5-tetrahydro-1H-3-benzazepin-7-yl)butanamide.

Further, suitable examples of the compounds represented by the formula (I) include the following compounds:
7-[3-[4-(4-chlorophenyl)piperidin-1-yl]propoxy]-2,3,4,5-tetrahydro-1H-3-benzazepine;
7-[3-[4-(4-chlorophenyl)-1-piperidinyl]propoxy]-3-methyl-2,3,4,5-tetrahydro-1H-3-benzazepine;
7-[3-[4-(4-chlorophenyl)-1-piperidinyl]propoxy]-3-isopropyl-2,3,4,5-tetrahydro-1H-3-benzazepine;
7-[3-[4-(4-chlorophenyl)-1-piperidinyl]propoxy]-3-cyclopentyl-2,3,4,5-tetrahydro-1H-3-benzazepine;
3-benzyl-7-[3-[4-(4-chlorophenyl)-1-piperidinyl]propoxy]-2,3,4,5-tetrahydro-1H-3-benzazepine;
3-acetyl-7-[3-[4-(4-chlorophenyl)-1-piperidinyl]propoxy]-2,3,4,5-tetrahydro-1H-3-benzazepine;
7-[3-[4-(4-chlorophenyl)-1-piperidinyl]propoxy]-3-isobutyryl-2,3,4,5-tetrahydro-1H-3-benzazepine;
3-benzoyl-7-[3-[4-(4-chlorophenyl)-1-piperidinyl]propoxy]-2,3,4,5-tetrahydro-1H-3-benzazepine;
tert-butyl 7-[3-[4-(4-chlorophenyl)-1-piperidinyl]propoxy]-1,2,4,5-tetrahydro-1H-3-benzazepine-3-carboxylate;
7-[3-[4-(4-chlorophenyl)-1-piperidinyl]propoxy]-3-(methylsulfonyl)-2,3,4,5-tetrahydro-1H-3-benzazepine;
7-[3-[4-(4-chlorophenyl)-1-piperidinyl]propoxy]-N-ethyl-1,2,4,5-tetrahydro-3H-3-benzazepine-3-carboxamide;
7-[3-[4-(4-fluorophenyl)-1-piperidinyl]propoxy]-3-isopropyl-2,3,4,5-tetrahydro-1H-3-benzazepine;
7-[3-[4-(2,4-difluorophenyl)-1-piperidinyl]propoxy]-3-isopropyl-2,3,4,5-tetrahydro-1H-3-benzazepine;
7-[3-[4-(4-methylphenyl)-1-piperidinyl]propoxy]-3-isopropyl-2,3,4,5-tetrahydro-1H-3-benzazepine;
3-isopropyl-7-[3-[4-(3-methylphenyl)-1-piperidinyl]propoxy]-2,3,4,5-tetrahydro-1H-3-benzazepine;
3-isopropyl-7-[3-[4-(2-methylphenyl)-1-piperidinyl]propoxy]-2,3,4,5-tetrahydro-1H-3-benzazepine;
3-isopropyl-7-[3-[4-(4-methoxyphenyl)-1-piperidinyl]propoxy]-2,3,4,5-tetrahydro-1H-3-benzazepine;
3-isopropyl-7-[3-[4-(3-trifluoromethylphenyl)-1-piperidinyl]propoxy]-2,3,4,5-tetrahydro-1H-3-benzazepine;
3-acetyl-7-[3-[4-(4-methylphenyl)-1-piperidinyl]propoxy]-2,3,4,5-tetrahydro-1H-3-benzazepine;
3-acetyl-7-[3-[4-(4-methoxyphenyl)-1-piperidinyl]propoxy]-2,3,4,5-tetrahydro-1H-3-benzazepine;
3-isobutyryl-7-[3-[4-(4-methylphenyl)-1-piperidinyl]propoxy]-2,3,4,5-tetrahydro-1H-3-benzazepine;
3-isobutyryl-7-[3-[4-(4-methoxyphenyl)-1-piperidinyl]propoxy]-2,3,4,5-tetrahydro-1H-3-benzazepine;
7-[3-[4-(4-methylphenyl)-1-piperidinyl]propoxy]-3-(methylsulfonyl)-2,3,4,5-tetrahydro-1H-3-benzazepine;
7-[3-[4-(4-methoxyphenyl)-1-piperidinyl]propoxy]-3-(methylsulfonyl)-2,3,4,5-tetrahydro-1H-3-benzazepine;
3-acetyl-7-[3-[4-(4-fluorophenyl)-1-piperidinyl]propoxy]-2,3,4,5-tetrahydro-1H-3-benzazepine;
3-acetyl-7-[3-[4-(3-fluorophenyl)-1-piperidinyl]propoxy]-2,3,4,5-tetrahydro-1H-3-benzazepine;
3-acetyl-7-[3-[4-(2,4-difluorophenyl)-1-piperidinyl]propoxy]-2,3,4,5-tetrahydro-1H-3-benzazepine;
3-acetyl-7-[3-[4-(4-methylphenyl)-1-piperidinyl]propoxy]-2,3,4,5-tetrahydro-1H-3-benzazepine;
3-acetyl-7-[3-[4-(3-methylphenyl)-1-piperidinyl]propoxy]-2,3,4,5-tetrahydro-1H-3-benzazepine;
3-acetyl-7-[3-[4-(2-methylphenyl)-1-piperidinyl]propoxy]-2,3,4,5-tetrahydro-1H-3-benzazepine;
3-acetyl-7-[3-[4-(4-methoxyphenyl)-1-piperidinyl]propoxy]-2,3,4,5-tetrahydro-1H-3-benzazepine;
3-[(3-isopropyl-2,3,4,5-tetrahydro-1H-3-benzazepin-7-yl)oxy]-N-[3-(4-methylphenyl)propyl]propanamide;
N-[3-(4-chlorophenyl)propyl]-3-[(3-isopropyl-2,3,4,5-tetrahydro-1H-3-benzazepin-7-yl)oxy]propanamide;
N-[3-(3-chlorophenyl)propyl]-3-[(3-isopropyl-2,3,4,5-tetrahydro-1H-3-benzazepin-7-yl)oxy]propanamide;
N-[3-(2-chlorophenyl)propyl]-3-[(3-isopropyl-2,3,4,5-tetrahydro-1H-3-benzazepin-7-yl)oxy]propanamide;
3-(4-chlorophenyl)-N-[3-[(3-isopropyl-2,3,4,5-tetrahydro-1H-3-benzazepin-7-yl)oxy]propyl]-1-propanamine;
(E)-4-[4-(4-chlorophenyl)-1-piperidinyl]-4-oxo-1-[3-(trifluoroacetyl)-2,3,4,5-tetrahydro-1H-3-benzazepin-7-yl]-2-buten-1-one;
(E)-4-[4-(4-chlorophenyl)-1-piperidinyl]-4-oxo-1-(2,3,4,5-tetrahydro-1H-3-benzazepin-7-yl)-2-buten-1-one;
(E)-4-[4-(4-chlorophenyl)-1-piperidinyl]-1-(3-isopropyl-2,3,4,5-tetrahydro-1H-3-benzazepin-7-yl)-4-oxo-2-buten-1-one;
8-[3-[4-(4-chlorophenyl)-1-piperidinyl]propoxy]-3-isopropyl-2,3,4,5-tetrahydro-1H-2-benzazepine;
8-[3-[4-(4-chlorophenyl)-1-piperidinyl]propoxy]-3-cyclopentyl-2,3,4,5-tetrahydro-1H-2-benzazepine;
2-benzyl-8-[3-[4-(4-chlorophenyl)-1-piperidinyl]propoxy]-2,3,4,5-tetrahydro-1H-2-benzazepine;
8-[3-[4-(4-chlorophenyl)-1-piperidinyl]propoxy]-2-isobutyryl-2,3,4,5-tetrahydro-1H-2-benzazepine;
2-benzoyl-8-[3-[4-(4-chlorophenyl)-1-piperidinyl]propoxy]-2,3,4,5-tetrahydro-1H-2-benzazepine;
8-[3-[4-(4-chlorophenyl)-1-piperidinyl]propoxy]-2-(methylsulfonyl)-2,3,4,5-tetrahydro-1H-2-benzazepine;
8-[3-[4-(4-chlorophenyl)-1-piperidinyl]propoxy]-N-ethyl-1,3,4,5-tetrahydro-2H-2-benzazepine-2-carboxamide;
8-[3-[4-(4-fluorophenyl)-1-piperidinyl]propoxy]-2-isopropyl-2,3,4,5-tetrahydro-1H-2-benzazepine;
8-[3-[4-(2,4-difluorophenyl)-1-piperidinyl]propoxy]-2-isopropyl-2,3,4,5-tetrahydro-1H-2-benzazepine;
8-[3-[4-(4-methylphenyl)-1-piperidinyl]propoxy]-2-isopropyl-2,3,4,5-tetrahydro-1H-2-benzazepine;
2-isopropyl-8-[3-[4-(3-methylphenyl)-1-piperidinyl]propoxy]-2,3,4,5-tetrahydro-1H-2-benzazepine;
2-isopropyl-8-[3-[4-(2-methylphenyl)-1-piperidinyl]propoxy]-2,3,4,5-tetrahydro-1H-2-benzazepine;

2-isopropyl-8-[3-[4-(4-methoxyphenyl)-1-piperidinyl]propoxy]-2,3,4,5-tetrahydro-1H-2-benzazepine;
2-isopropyl-8-[3-[4-(3-trifluoromethylphenyl)-1-piperidinyl]propoxy]-2,3,4,5-tetrahydro-1H-2-benzazepine;
2-acetyl-8-[3-[4-(4-methylphenyl)-1-piperidinyl]propoxy]-2,3,4,5-tetrahydro-1H-2-benzazepine;
2-acetyl-8-[3-[4-(4-methoxyphenyl)-1-piperidinyl]propoxy]-2,3,4,5-tetrahydro-1H-2-benzazepine;
2-isobutyryl-8-[3-[4-(4-methylphenyl)-1-piperidinyl]propoxy]-2,3,4,5-tetrahydro-1H-2-benzazepine;
2-isobutyryl-8-[3-[4-(4-methoxyphenyl)-1-piperidinyl]propoxy]-2,3,4,5-tetrahydro-1H-2-benzazepine;
8-[3-[4-(4-methylphenyl)-1-piperidinyl]propoxy]-2-(methylsulfonyl)-2,3,4,5-tetrahydro-1H-2-benzazepine;
8-[3-[4-(4-methoxyphenyl)-1-piperidinyl]propoxy]-2-(methylsulfonyl)-2,3,4,5-tetrahydro-1H-2-benzazepine;
2-acetyl-8-[3-[4-(4-fluorophenyl)-1-piperidinyl]propoxy]-2,3,4,5-tetrahydro-1H-2-benzazepine;
2-acetyl-8-[3-[4-(3-fluorophenyl)-1-piperidinyl]propoxy]-2,3,4,5-tetrahydro-1H-2-benzazepine;
2-acetyl-8-[3-[4-(2,4-difluorophenyl)-1-piperidinyl]propoxy]-2,3,4,5-tetrahydro-1H-2-benzazepine;
2-acetyl-8-[3-[4-(4-methylphenyl)-1-piperidinyl]propoxy]-2,3,4,5-tetrahydro-1H-2-benzazepine;
2-acetyl-8-[3-[4-(3-methylphenyl)-1-piperidinyl]propoxy]-2,3,4,5-tetrahydro-1H-2-benzazepine;
2-acetyl-8-[3-[4-(2-methylphenyl)-1-piperidinyl]propoxy]-2,3,4,5-tetrahydro-1H-2-benzazepine;
2-acetyl-8-[3-[4-(4-methoxyphenyl)-1-piperidinyl]propoxy]-2,3,4,5-tetrahydro-1H-2-benzazepine;
3-[(2-isopropyl-2,3,4,5-tetrahydro-1H-2-benzazepin-8-yl)oxy]-N-[3-(4-methylphenyl)propyl]propanamide;
N-[3-(4-chlorophenyl)propyl]-3-[(2-isopropyl-2,3,4,5-tetrahydro-1H-2-benzazepin-8-yl)oxy]propanamide;
N-[3-(3-chlorophenyl)propyl]-3-[(2-isopropyl-2,3,4,5-tetrahydro-1H-2-benzazepin-8-yl)oxy]propanamide;
N-[3-(2-chlorophenyl)propyl]-3-[(2-isopropyl-2,3,4,5-tetrahydro-1H-2-benzazepin-8-yl)oxy]propanamide;
3-(4-chlorophenyl)-N-[3-[(2-isopropyl-2,3,4,5-tetrahydro-1H-2-benzazepin-8-yl)oxy]-1-propanamine.

Examples of salts of compound (I), (I'), (I''), (I'''), (I'''') or (I''''') include salts with inorganic bases, ammonium salts, salts with organic bases, salts with inorganic acids, salts with organic acids, salts with basic or acidic amino acids, and the like.

Preferred examples of salts with inorganic bases include alkali metal salts such as sodium salts, potassium salts, etc.; alkaline earth metal salts such as calcium salts, magnesium salts, barium salts, etc.; aluminum salts; etc.

Preferred examples of salts with organic bases include salts with trimethylamine, triethylamine, pyridine, picoline, ethanolamine, diethanolamine, triethanolamine, dicyclohexylamine, N,N-dibenzylethylenediamine, etc.

Preferred examples of salts with inorganic acids include salts with hydrochloric acid, hydrobromic acid, nitric acid, sulfuric acid, phosphoric acid, etc.

Preferred examples of salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

Preferred examples of salts with basic amino acids include salts with arginine, lysine, ornithine, etc. Preferred examples of salts with acidic amino acids include salts with aspartic acid, glutamic acid, etc.

Among these salts, pharmaceutically acceptable salts are preferred. For example, when compound (I), (I'), (I''), (I'''), (I'''') or (I''''') possesses an acidic functional group, it can form an inorganic salt such as an alkali metal salt (e.g., sodium salt, potassium salt, etc.), an alkaline earth metal salt (e.g. calcium salt, magnesium salt, barium salt, etc.), etc., an ammonium salt, etc. When compound (I), (I'), (I''), (I'''), (I'''') or (I''''') possesses a basic functional group, it can form an inorganic salt such as hydrochloride, sulfate, phosphate, hydrobromate, etc.; or an organic salt such as acetate, maleate, fumarate, succinate, methanesulfonate, p-toluenesulfonate, citrate, tartrate, etc.

Compounds (I), (I'), (I''), (I'''), (I'''') and (I''''') (hereinafter also abbreviated as the compound of the present invention) can be either anhydrides or hydrates. A hydrate may have 0.5 to 3 water molecules.

In addition, the compounds of the invention can be labeled using isotopes (e.g. $^3H$, $^{14}C$, and $^{35}S$, etc.).

When the compound of the present invention contain optical isomers, stereoisomers, regio isomers, rotational isomers, these are also included as the compound of the present invention, and each of them can be obtained as a single substance by per se known synthesis methods and separation methods. For example, when optical isomers exist in the compound of the present invention, the optical isomers resolved from the compound are included in the compound of the present invention.

The optical isomers can be produced using per se known methods. Specifically, the optical isomer can be obtained by using an optically active synthetic intermediate, or subjecting a racemic mixture of the final product to optical resolution in accordance with common method.

Examples of optical resolution methods include per se known methods such as the fractional recrystallization method, chiral column method, diastereomer method, etc., which are described in detail below.

1) Fractional Recrystallization Method

The method which comprises allowing a racemate to form a salt with an optically active compound (e.g. (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.), separating the salt using a fractional recrystallization method, followed by, if desired, neutralizing process to obtain a free optical isomer.

2) Chiral Column Method

This method comprises subjecting a racemate or its salt to a column for separating an optical isomer (chiral column) for separation. For example, in the case of liquid chromatography, an optical isomer mixture is added to the chiral column such as ENANTIO-OVM [produced by Toso] or CHIRAL series [produced by Daicel], which is developed using water, various buffer solutions (e.g. phosphate buffer), organic solvents (e.g. ethanol, methanol, isopropanol, acetonitrile, trifluoroacetic acid, diethylamine, etc.) as single or mixed solutions, and the optical isomers are separated. Also, in the case of gas chromatography, for example, separation is conducted using a chiral column such as CP-Chirasil-DeX CB (produced by G.L.Science Co.).

3) Diastereomer Method

In this method, a racemic mixture is subjected to a chemical reaction with an optically active reagent to give a diastereomer mixture, which is separated into a single substance by an ordinary separation means (e.g. fractional recrystallization, chromatography method, etc.). This single substance is subjecting to removal of the optically active reagent part using chemical processing such as a hydrolysis reaction. For example, when a compound of the invention possesses hydroxy or primary or secondary amino in its molecule, this compound is subjected to a condensation reaction with an optically active organic acid (e.g. MTPA [α-methoxy-α-(trifluoromethyl)phenylacetic acid], (–)-menthoxyacetic acid, etc.), to give the diastereomer in an ester form or an amide form, respectively. On the other hand, when a compound of the invention possesses carboxylic acid group, this compound is subjected to a condensation reaction with an optically active amine or alcohol reagent, to give the diastereomer in an amide form or an ester form, respectively. The separated diastereomer can be converted to an optical isomer of the original compound, by applying acidic hydrolysis or basic hydrolysis.

A prodrug of compound (I') or (I") is a compound which is converted to compound (I') or (I") by reactions involving enzymes and gastric acid, etc. under physiological conditions in the living body; in other words, a compound that is changed into compound (I') or (I") by enzymatically-caused oxidation, reduction and hydrolysis, and a compound that is changed into compound (I') or (I") by hydrolysis caused by gastric acid. Examples of the prodrugs of compound (I') or (I") include compounds in which amino groups of compound (I') or (I") have been acylated, alkylated, or phosphorylated [e.g. compounds in which amino groups of compound (I') or (I") have been eicosanoylated, aranylated, pentylaminocarbonylated, (5-methyl-2-oxo-1,3-dioxolen-4-yl)methoxycarbonylated, tetrahydrofuranylated, pyrrolidyl-methylated, pivaloyloxymethylated, tert-butylated, etc.]; compounds in which hydroxyl groups of compound (I') or (I") have been acylated, alkylated, phosphorylated, borated (e.g. compounds in which hydroxyl groups of compound (I') or (I") have been acetylated, palmitoylated, propanoylated, pivaloylated, succinylated, fumarilated, alanilated, dimethylaminomethylcarbonylated, etc.); compounds in which carboxyl groups of compound (I') or (I") have been esterified or amidated [e.g. compounds in which carboxyl groups of compound (I') or (I") have been ethylesterified, phenylesterified, carboxylmethylesterified, dimethylaminomethylesterified, pivaloyloxymethylesterified, ethoxycarbonyloxyethylesterified, phthalidylesterified, (5-methyl-2-oxo-1,3-dioxolen-4-yl)methylesterified, cyclohexyloxycarbonylethylesterified, or methylamidated, etc.]. These compounds can be produced from compound (I') or (I") using per se known methods.

Also, a prodrug of compound (I') or (I") can be a compound which is changed to compound (I') or (I") by physiological conditions, as described in pages 163 to 198 of Molecular Design, Volume 7, "Development of Drugs", published in 1990 by Hirokawa Shoten.

Prodrugs of compounds (I), (I'''), (I"") and (I""') may also be used. As prodrugs of these compounds, those exemplified as prodrugs of the above compound (I') or (I") can be mentioned.

The compound of the present invention can be produced by [Production method 1] to [Production method 10] which are described in detail below, or analogous methods thereto.

Compound (II), compound (III), compound (V), compound (VI), compound (IIa), compound (IIb), compound (IIIa), compound (IIIaa), compound (IIIab), compound (IIIac), compound (IIIb), compound (IIIc), compound (IVa), compound (IVb), compound (IVc), compound (IVd), compound (Va), compound (VIa), compound (VIaa), compound (VIIa), compound (VIId), compound (VIIg), compound (VIIIe), compound (IXa), compound (IXb), compound (IXe), compound (IXg), compound (Xa), compound (Xb), compound (Xf), compound (XIa), compound (XIf) and compound (XIg) used as raw materials can be used in the form of salts, respectively. As such salts, those exemplified as salts of the above compound (I), etc. can be used.

In the following [Production method 1] to [Production method 10], when an alkylation reaction, a hydrolysis reaction, an amination reaction, an esterification reaction, an amidation reaction, an esterification reaction, an etherification reaction, an oxidation reaction, a reducing reaction, etc. are carried out, these reactions are carried out in accordance with per se known methods. Examples of such methods include the methods described in Organic Functional Group Preparations, Second Edition, Academic Press, Inc., published in 1989; Comprehensive Organic Transformations, VCH Publishers Inc., published in 1989, etc.

[Production Method 1]

Compound (Ia) having —(CH$_2$)$_{w3}$CO— (w3 is as defined above) for X in the formula (I) is produced, for example, by the following amidation reaction.

(Amidation Reaction)

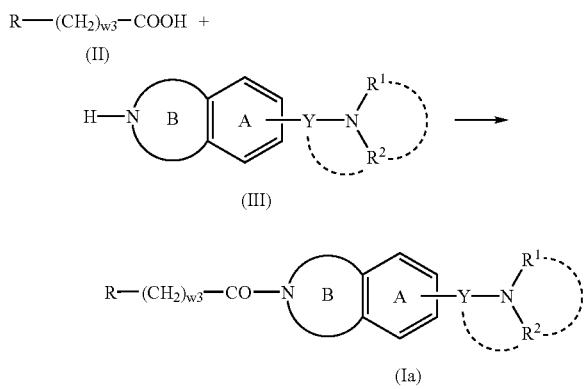

wherein the symbols are as defined above.

The "amidation reaction" includes the following "method using a dehydration and condensation agent" and "method using a reactive derivative of carboxylic acid".

i) Method Using a Dehydration And Condensation Agent

Compound (III), 1 to 5 equivalents of compound (II), and 1 to 2 equivalents of a dehydration and condensation agent are reacted in an inert solvent. If necessary, the reaction can be carried out with the coexistence of 1 to 1.5 equivalents of 1-hydroxybenzotriazole (HOBT) and/or catalytic quantity to 5 equivalents of a base.

Examples of the "dehydrating and condensation agent" include dicyclohexylcarbodimide (DCC), 1-ethyl-3-(3-dimethylaminopropyl)carbodimide hydrochloride (WSC). WSC is particularly preferable.

Examples of the "inert solvent" include nitrile solvents (preferably acetonitrile), amide solvents (preferably DMF), halogenated hydrocarbon solvents (preferably dichloromethane), ether solvents (preferably THF). Two or more kinds of these can be mixed in an appropriate ratio for use.

Examples of the "base" include
1) for example, strong bases such as hydrides of alkali metals or alkaline earth metals (e.g. lithium hydride, sodium hydride, potassium hydride, calcium hydride, etc.), amides of alkali metals or alkaline earth metals (e.g. lithium amide, sodium amide, lithium diisopropylamide, lithium dicyclohexylamide, lithium hexamethyldisilazide, sodium hexamethyldisilazide, potassium hexamethyldisilazide, etc.), lower alkoxides of alkali metals or alkaline earth metals (e.g. sodium methoxide, sodium ethoxide, potassium tert-butoxide, etc.), etc.;
2) for example, inorganic bases such as hydroxides of alkali metals or alkaline earth metals (e.g. sodium hydroxide, potassium hydroxide, lithium hydroxide, barium hydroxide, etc.), carbonates of alkali metals or alkaline earth metals (e.g. sodium carbonate, potassium carbonate, cesium carbonate, etc.) and hydrogencarbonates of alkali metals or alkaline earth metals (e.g. sodium hydrogencarbonate, potassium hydrogencarbonate, etc.), etc.; and
3) for example, organic bases exemplified by amines such as triethylamine, diisopropylethylamine, N-methylmorpholine, dimethylaminopyridine, DBU (1,8-diazabicyclo[5.4.0]undec-7-en), DBN (1,5-diazabicyclo[4.3.0]non-5-en), ect.; basic heterocyclic compounds such as pyridine, imidazole, 2,6-lutidine, etc.; and the like.

Among the above bases, triethylamine, 4-dimethylaminopyridine, etc., are preferable.

Reaction temperature is usually room temperature (0° C. to 30° C., hereafter the same). Reaction time is, for example, 10 to 24 hours.

ii) Method Using a Reactive Derivative of Carboxylic Acid

A reactive derivative of compound (II) and 1 to 5 equivalents (preferably 1 to 3 equivalents) of compound (III) are reacted in an inert solvent. If necessary, the reaction can be carried out with the coexistence of 1 to 10 equivalents, preferably 1 to 3 equivalents of a base. Examples of the "reactive derivative" of compound (II) include acid halides (e.g., acid chloride, acid bromide, etc.), mixed acid anhydrides (e.g. acid anhydrides with $C_{1-6}$ alkyl-carboxylic acid, $C_{6-10}$ aryl-carboxylic acid or $C_{1-6}$ alkylcarbonate), active esters (e.g. esters with phenol which may be substituted, 1-hydroxybenzotriazole or N-hydroxysuccinimide, etc.), etc.

Examples of the "substituents" in the "phenol which may be substituted" include halogen atom (e.g. fluorine, chlorine, bromine, iodine, etc.), nitro, optionally halogenated $C_{1-6}$ alkyl, optionally halogenated $C_{1-6}$ alkoxy. The number of substituents is, for example, 1 to 5.

As the "optionally halogenated $C_{1-6}$ alkyl" and "optionally halogenated $C_{1-6}$ alkoxy", those exemplified as "substituents" in the above "cyclic group which may be substituted" can be used.

Specific examples of "phenol which may be substituted" include phenol, pentachlorophenol, pentafluorophenol, p-nitrophenol, etc. The reactive derivative is, preferably, an acid halide.

Examples of the "inert solvent" include ether solvents, halogenated hydrocarbon solvents, aromatic solvents, nitrile solvents, amide solvents, ketone solvents, sulfoxide solvents, and water. Two or more kinds of these can be mixed in an appropriate ratio for use. Especially, acetonitrile, THF, dichloromethane, chloroform, etc. are preferable.

As the "base", the same as above are used. The base is preferably sodium hydride, potassium carbonate, sodium carbonate, sodium hydroxide, potassium hydroxide, sodium hydrogencarbonate, potassium hydrogencarbonate, triethylamine, pyridine, etc.

Reaction temperature is usually −20° C. to 50° C., preferably room temperature. Reaction time is usually 5 minutes to 40 hours, preferably 1 to 18 hours.

Further, the compound of the formula (I) wherein X is —(CH$_2$)$_{w3}$SO$_2$— or —(CH$_2$)$_{w3}$SO— (the symbols are as defined above) can be produced by subjecting a sulfonic acid of the formula R—(CH$_2$)$_{w3}$—SO$_2$OH (the symbols are as defined above) or a sulfinic acid of the formula R—(CH$_2$)$_{w3}$—SOOH (the symbols are as defined above) to the same method as the above "method using a reactive derivative of carboxylic acid".

Compound (II) can be produced by per se known methods or analogous methods thereto.

Compound (III) can be produced by per se known methods, for example, the methods described in Chem. Pharm. Bull., 36, 4377 (1988), JP 9-506885 A, JP 10-504315 A, etc. or analogous methods thereto.

For example, compound (III) can be produced by subjecting the compound of the formula:

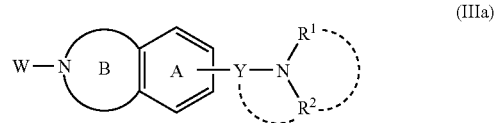

(IIIa)

wherein W is a protecting group for amino; and the other symbols are as defined above, to a deprotection reaction to remove W.

Examples of the protecting group for amino represented by W include formyl, $C_{1-6}$ alkyl-carbonyl (e.g. acetyl, propionyl, etc.), $C_{1-6}$ alkoxy-carbonyl (e.g. methoxycarbonyl, ethoxycarbonyl, tert-butoxycarbonyl, etc.), benzoyl, $C_{7-10}$ aralkyl-carbonyl (e.g. benzylcarbonyl, etc.), $C_{7-14}$ aralkyloxy-carbonyl (e.g. benzyloxycarbonyl, 9-fluorenylmethoxycarbonyl, etc.), trityl, phthaloyl, N,N-dimethylaminomethylene, silyl (e.g. trimethylsilyl, triethylsilyl, dimethylphenylsilyl, tert-butyldimethylsilyl, tert-butyldiethylsilyl, etc.), $C_{2-6}$ alkenyl (e.g. 1-allyl, etc.), etc. These groups may be substituted by 1 to 3 of halogen atom (e.g. fluorine, chlorine, bromine, iodine, etc.), $C_{1-6}$ alkoxy (e.g. methoxy, ethoxy, propoxy, etc.) or nitro, etc.

The deprotection reaction is carried out, for example, by maintaining compound (IIIa), preferably at 20° C. to 140° C., in an aqueous solution of an acid such as a mineral acid (e.g., hydrochloric acid, sulfuric acid, hydrobromic acid, iodic acid, periodic acid, etc.) etc., or a base such as an alkali metal hydroxide (e.g., sodium hydroxide, potassium hydroxide, lithium hydroxide, etc.) etc. The acid or base is usually used in an amount of 1 to 100 equivalents, preferably 1 to 40 equivalents based on compound (IIIa). Strength of the acid or base is usually 0.1 N to 18 N, preferably 1 N to 12 N. Reaction time is usually 0.5 hour to 48 hours, preferably 1 hour to 24 hours.

Further, when W is t-butoxycarbonyl group, etc., the deprotection reaction can also be carried out by dissolving compound (IIIa) in an organic acid (e.g., trifluoroacetic acid, formic acid, acetic acid, methanesulfonic acid, benzenesulfonic acid, trifluoromethanesulfonic acid, etc.) and maintaining the solution usually at −20° C. to 200° C., preferably 0° C. to 100° C. The organic acid is used in an amount of 1 to 100 equivalents, preferably 1 to 40 equivalents based on compound (IIIa).

The deprotection reaction can also be carried out by subjecting compound (IIIa) to catalytic reduction in an alcoholic solvent, for example, ethanol, etc., or a solvent such as acetic acid, etc., with a catalyst such as palladium, palladium-carbon, Raney nickel, Raney cobalt, platinum oxide, etc. at normal pressure or, if necessary, under pressure.

Compound (IIIa) can be produced by per se known methods or analogous methods thereto. For example, compound (IIIa) wherein Y is $C_{2-6}$ alkenylene [e.g., —CH=CH—(CH$_2$)$_{w4}$— (w4 is as defined above)], i.e., compound (IIIaa), can be produced, for example, according to the following [Reaction scheme 1-1].

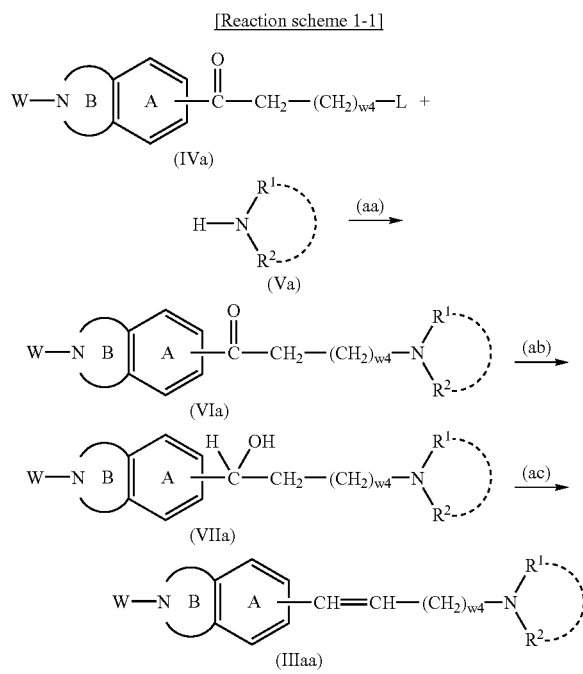

wherein L is a leaving group and the other symbols are as defined above.

In the step (aa), compound (VIa) is produced by a condensation reaction of compound (IVa) and compound (Va).

Examples of the "leaving group" represented by L include halogen atom (e.g. chlorine, bromine, iodine, etc.), optionally halogenated C$_{1-6}$ alkylsulfonyloxy (e.g. methanesulfonyloxy, ethanesulfonyloxy, trifluoromethanesulfonyloxy, etc.), C$_{6-10}$ arylsulfonyloxy which may be substituted, hydroxy, etc.

Examples of the "substituents" in the "C$_{6-10}$ arylsulfonyloxy which may be substituted" include halogen atom (e.g. chlorine, bromine, iodine, etc.), optionally halogenated C$_{1-6}$ alkyl, C$_{1-6}$ alkoxy, etc. The number of substituents is, for example, 1 to 3. Specific examples of the C$_{6-10}$ arylsulfonyloxy which may be substituted" include benzenesulfonyloxy, p-toluenesulfonyloxy, 1-naphthalenesulfonyloxy, 2-naphthalenesulfonyloxy, etc.

The "leaving group" is preferably halogen atom (e.g. chlorine, bromine, iodine, etc.), methanesulfonyloxy, trifluoromethanesulfonyloxy, p-toluenesulfonyloxy, etc.

This reaction is usually carried out in an inert solvent.

Examples of the "inert solvent" include alcohol solvents, ether solvents, halogenated hydrocarbon solvents, aromatic solvents, nitrite solvents, amide solvents, ketone solvents, sulfoxide solvents, water, etc. Two or more kinds of these can be mixed in an appropriate ratio for use. Especially, acetonitrile, N,N-dimethylformamide (DMF), acetone, ethanol, pyridine, etc., are preferred.

Compound (Va) is used in an amount of 1 equivalent to 100 equivalents based on compound (IVa). Further, compound (Va) can be used in an amount corresponding to a reaction solvent.

Reaction temperature is about −20° C. to 200° C., preferably room temperature to 100° C. Reaction time is, for example, 0.5 hour to 1 day.

This condensation reaction may be carried out in the presence of a base. The base is preferably sodium hydride, potassium carbonate, sodium carbonate, sodium hydroxide, potassium hydroxide, sodium hydrogencarbonate, potassium hydrogencarbonate, triethylamine, pyridine, etc. The amount of the base is 0.1 to 100 equivalents, preferably 1 to 10 equivalents based on compound (IVa).

Compound (IVa) can be produced by a per se known method or an analogous method thereto. For example, compound (IVa) can be produced by the method described in JP 6-166676 A, etc. or an analogous method thereto.

Further, compound (Va) can be produced by a per se known method or an analogous method thereto.

In the step (ab), compound (VIIa) is produced by subjecting compound (VIa) to a reducing reaction.

This reducing reaction can be carried out by using a reducing agent such as sodium borohydride, lithium aluminum hydride, triethylsilane, etc.

The reducing reaction can be carried out, for example, according to the methods described in Reduction with Complex Metal Hydrides, Interscience, New York (1956); Chem. Soc. Rev., 5, 23 (1976); Synthesis, 633 (1974); J. Am. Chem. Soc., 91, 2967 (1969); J. Org. Chem., 29, 121 (1964); Org. Reactions, 1, 15 (1942); Angew. Chem., 71, 726 (1956); Synthesis, 633 (1974); J. Am. Chem. Soc., 80, 2896 (1958); Org. Reactions, 4, 378 (1948); J. Am. Chem. Soc., 108, 3385 (1986); etc., or analogous methods thereto.

In the step (ac), compound (IIIaa) is produced by subjecting compound (VIIa) to dehydration reaction.

This dehydration reaction can be carried out with heating or at room temperature, if necessary, by using an acid catalyst (e.g., sulfuric acid, phosphoric acid, potassium hydrogen sulfate, p-toluenesulfonic acid, boron trifluoride-ether complex, iodine, etc.). Further, the dehydration reaction can also be carried out by using an activating agent such as thionyl chloride-pyridine, phosphorus oxychloride-pyridine, etc.

The dehydration reaction can be carried out, for example, according to the methods described in Org. Synth., I, 183 (1941); Org. Synth., I, 430 (1941); Org. Synth., III, 204 (1955); Org. Synth., VI, 307 (1988); Synthesis, III, 1159 (1980); J. Am. Chem. Soc., 106, 6690 (1984); Tetrahedron Lett., 599 (1871); etc., or analogous methods thereto.

Further, compound (VIa) used in [Reaction scheme 1-1] wherein w4 is 1, i.e., compound (VIaa), can be produced, for example, by subjecting compound (IXa), compound (Va) and formaldehyde to Mannich reaction according to the following [Reaction scheme 1-2].

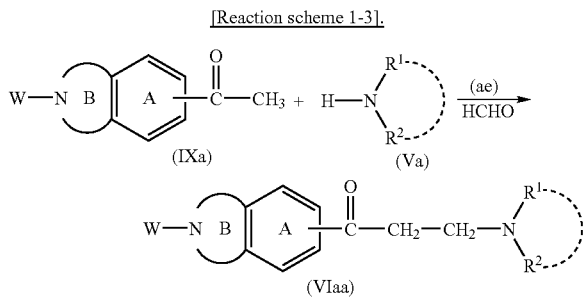

wherein the symbols are as defined above.

Mannich reaction in the step (ae) can be carried out, for example, according to the methods described in Org. Reactions, 1, 303 (1942); Tetrahedron Lett., 18, 1299 (1977); etc., or analogous methods thereto.

Compound (IXa) can be produced by a per se known method or an analogous method thereto. For example, compound (IXa) can be produced according to the method described in J. Chem. Soc., Perkin Trans. 1, 2993 (1994), etc., or an analogous method thereto.

Compound (VIaa) can also be produced by the following

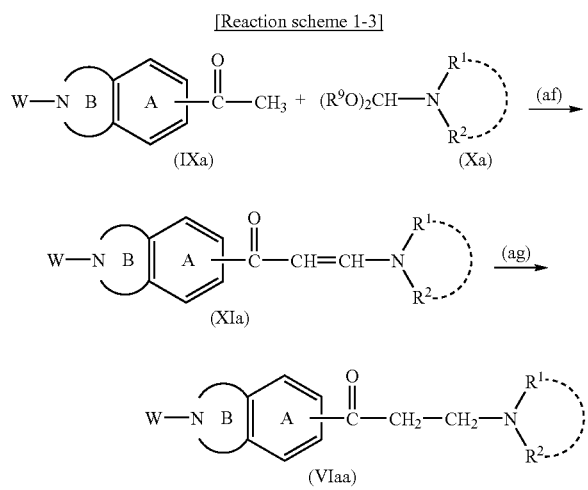

wherein $R^9$ is $C_{1-6}$ alkyl and the other symbols are as defined above.

As the "$C_{1-6}$ alkyl" represented by $R^9$, the same as the "$C_{1-6}$ alkyl" represented by the above $R^4$ can be mentioned.

That is, compound (VIaa) can be produced by carrying out in turn the step (af): the condensation reaction of compound (IXa) and (Xa); and the step (ag): the reducing reaction of compound (XIa).

The step (af) can be carried out by using a per se known condensation reaction. The condensation reaction can be carried out, for example, by the methods described in J. Heterocyclic Chem., 30, 23 (1993); Heterocycles, 22, 195 (1984); etc., or analogous methods thereto.

Compound (Xa) can be produced by a per se known method or an analogous method thereto.

The step (ag) can be carried out by using a per se known reducing reaction (e.g., catalytic reduction using a transition metal catalyst such as Pd/C, etc.; reducing reaction using a metal hydride such as $Et_3SiH$, etc.; reducing reaction using a metal hydrogen complex such as $NaBH(OAc)_3$, etc.). For example, the reducing reaction can be carried out by the methods described in J. Am. Chem. Soc., 76, 5014 (1954); Bull. Chem. Soc. Jpn., 45, 3506 (1972); etc., or analogous methods thereto.

Compound (IIIa) wherein Y is —O—$(CH_2)_{w2}$— (w2 is as defined above), i.e., compound (IIIab), can be produced by subjecting compound (IXb) and compound (Xb) to a dehydration reaction, for example, under the conditions of Mitsunobu reaction according to the following [Reaction scheme 2-1].

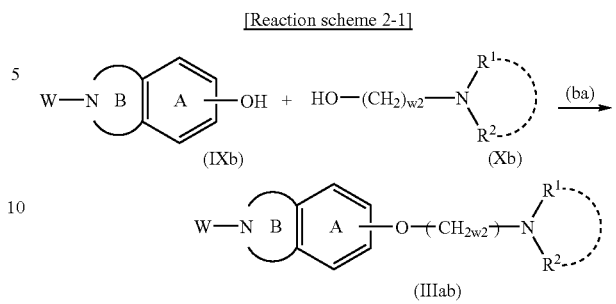

wherein the symbols are as defined above.

The dehydration reaction in the step (ba) can be carried out, for example, according to the methods described in Synthesis, 1 (1981); Bull. Chem. Soc. Jpn., 49, 510 (1976); etc., or analogous methods thereto.

Compound (IXb) can be produced by a per se known method or an analogous method thereto.

Compound (Xb) can be produced by a per se known method or an analogous method thereto.

Compound (IIIa) wherein Y is —CO—$(CH_2)_{w7}$—CO— (w7 is as defined above), i.e., compound (IIIac) can be synthesized by subjecting compound (IVd) and compound (Va) to the above "amidation reaction" according to the following [Reaction scheme 2-2].

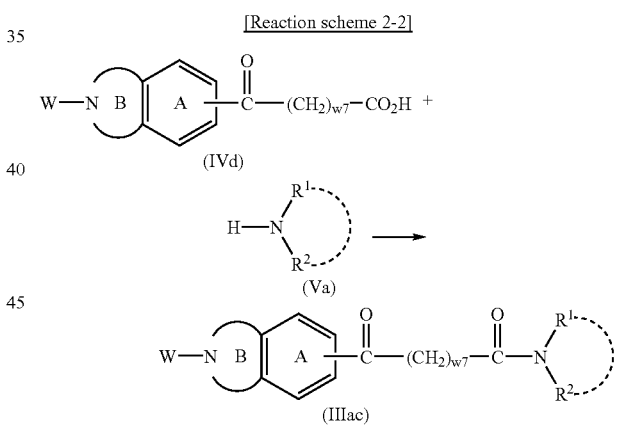

wherein the symbols are as defined above.

Compound (IVd) can be produced according to a per se known method or an analogous method thereto.

[Production Method 2]

Compound (I) wherein X is —$(CH_2)_{w3}$—COO$(CH_2)_{w4}$— (the symbols are as defined above), i.e., compound (Ib), can be produced by the following esterification reaction.

[Esterification reaction]

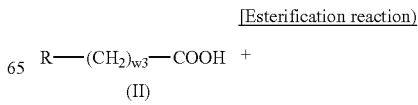

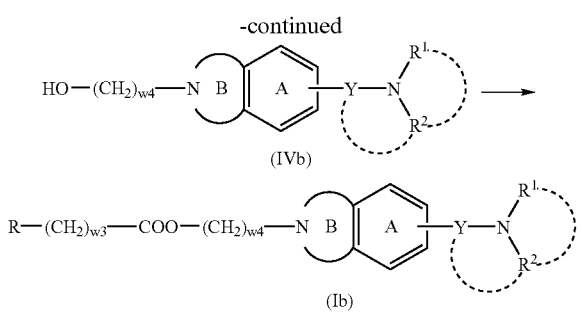

wherein the symbols are as defined above.

In this reaction, a reactive derivative of compound (II) and 1 to 5 equivalents (preferably 1 to 3 equivalents) of compound (IVb) is reacted in an inert solvent, usually, in the presence of 1 to 10 equivalents, preferably 1 to 3 equivalents of a base.

As the reactive derivative of compound (II), that exemplified in the above [Production method 1] is used. Especially, an acid halide is preferable.

Examples of the "inert solvent" include ether solvents, halogenated hydrocarbon solvents, aromatic solvents, nitrile solvents, amide solvents, ketone solvents, sulfoxide solvents. Two or more kinds of these can be mixed in an appropriate ratio for use. Especially, acetonitrile, dichloromethane, chloroform, etc. are preferable.

As the "base", that exemplified in the above [Production method 1] can be used. The base is preferably sodium hydride, potassium carbonate, sodium carbonate, sodium hydroxide, potassium hydroxide, sodium hydrogencarbonate, potassium hydrogencarbonate, triethylamine, pyridine, etc.

Reaction temperature is usually −20° C. to 50° C., preferably room temperature. Reaction time is usually 5 minutes to 40 hours, preferably 1 to 18 hours.

[Production Method 3]

Compound (I) wherein X is —(CH$_2$)$_{w1}$O(CH$_2$)$_{w2}$— (the symbols are as defined above), i.e., compound (Ic), can be produced by, for example, the following etherification reaction.

(Etherification reaction)

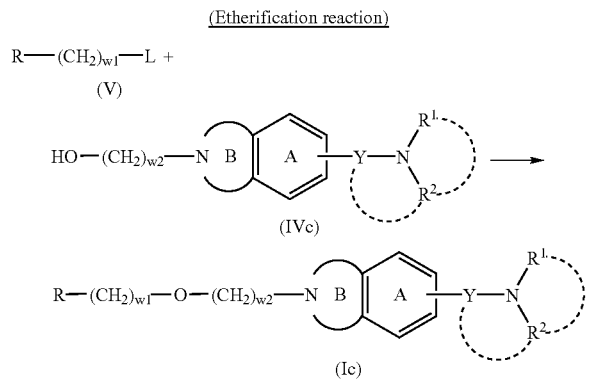

wherein the symbols are as defined above.

In this reaction, compound (IVc) and about 1 to 5 equivalents (preferably 1 to 2 equivalents) of compound (V) are reacted in inert solvent in the presence of base.

As the "base", that exemplified in the above [Production method 1] can be used. The base is preferably potassium carbonate, sodium hydrogencarbonate, triethylamine, N-methylmorpholine, pyridine, etc.

The amount of the base used is usually about 1 to 5 equivalents based on compound (V).

Examples of the "inert solvent" include alcohol solvents, ether solvents, halogenated hydrocarbon solvents, aromatic solvents, nitrile solvents, amide solvents, ketone solvents, sulfoxide solvents, water. Two or more kinds of these can be mixed in an appropriate ratio for use. Especially, acetonitrile, N,N-dimethylformamide (DMF), acetone, ethanol, pyridine, etc., are preferable.

Reaction temperature is about −20° C. to 100° C., preferably room temperature to 80° C. Reaction time is, for example, about 0.5 hour to 1 day.

When the leaving group for L in compound (V) is hydroxy, compound (Ic) can be produced by using Mitsunobu reaction.

The Mitsunobu reaction is carried out by reacting compound (V) and 0.5 to 5 equivalents (preferably 1 to 1.5 equivalents) of compound (IVc) in inert solvent in the coexistence of 0.5 to 5 equivalents (preferably 1 to 1.5 equivalents) of ethyl acetyldicarboxylate.

Examples of the inert solvent include ether solvents, halogenated hydrocarbon solvents, aromatic solvents, nitrile solvents, amide solvents, ketone solvents, sulfoxide solvents. Two or more kinds of these can be mixed in an appropriate ratio for use. Especially, acetonitrile, dichloromethane, chloroform, etc. are preferable.

Reaction temperature is usually −20° C. to 50° C., preferably room temperature. Reaction time is usually 5 minutes to 40 hours, preferably 1 to 18 hours.

Compound (IVc) can be produced by a per se known method.

[Production Method 4]

Compound (I) wherein X is —(CH$_2$)$_{w3}$NR$^{8a}$CO(CH$_2$)$_{w4}$— (the symbols are as defined above), i.e., compound (Id), can be produced, for example, by the following amidation reaction.

(Amidation reaction)

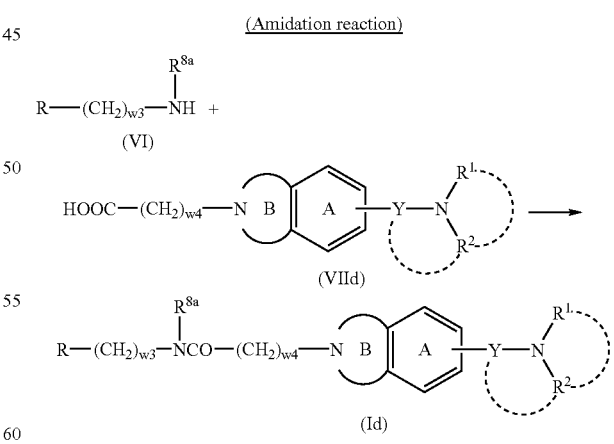

wherein R$^{8a}$ is hydrogen atom or optionally halogenated C$_{1-6}$ alkyl and the other symbols are as defined above.

As the "optionally halogenated C$_{1-6}$ alkyl" represented by R$^{8a}$, that exemplified with respect to the above R$^8$ can be mentioned.

This reaction is carried out in accordance with the above [Production method 1].

Compound (VI) can be produced by a per se known method.

Compound (VIId) can be produced by a per se known method.

[Production Method 5]

Compound (I) wherein X is —$(CH_2)_{w5}NHCONR^{8a}(CH_2)_{w6}$— (the symbols are as defined above), i.e., compound (Ie), can be produced, for example, by the following urea reaction.

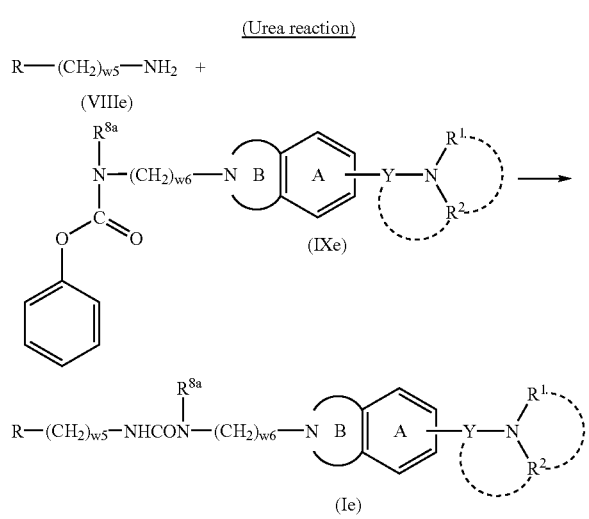

wherein the symbols are as defined above.

In this reaction, compound (IXe) and 1 to 5 equivalents (preferably 1 to 1.5 equivalents) of compound (VIIIe) is reacted in an inert solvent in the coexistence of a base.

As the "base", that exemplified in the above {Production method 1] can be used. The base is preferably potassium carbonate, sodium carbonate, sodium hydroxide, potassium hydroxide, sodium hydrogencarbonate, potassium hydrogencarbonate, triethylamine, pyridine, etc.

Examples of the "inert solvent" include alcohol solvents, ether solvents, halogenated hydrocarbon solvents, aromatic solvents, nitrile solvents, amide solvents, ketone solvents, sulfoxide solvents, water. Two or more kinds of these can be mixed in an appropriate ratio for use. Especially, acetonitrile, DMF, acetone, ethanol, pyridine, etc. are preferable.

Reaction temperature is usually −20° C. to 100° C., preferably room temperature to 80° C. Reaction time is, for example, 0.5 hour to 1 day.

Compound (VIIIe) can be produced by a per se known method.

Compound (IXe) can be produced by a per se known method.

[Production Method 6]

Compound (I) wherein R is a ring assembly aromatic group ($Ar^2$—$Ar^3$) which may be substituted, i.e., compound (If), can be produced by, for example, the following aryl-coupling reaction.

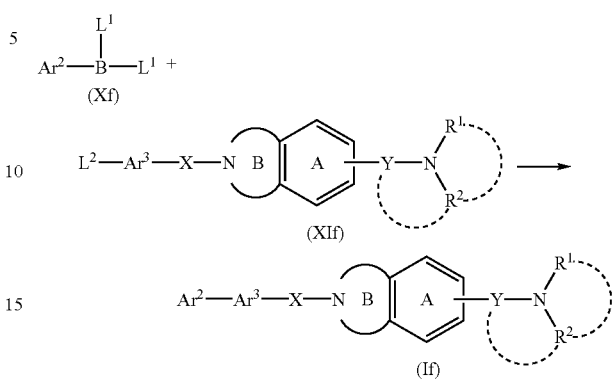

wherein $Ar^2$ and $Ar^3$ are monocyclic aromatic groups or condensed aromatic groups, each of which may be substituted; $L^1$ is hydroxy or $C_{1-6}$ alkyl; $L^2$ is halogen (preferably chlorine, bromine) or trifluoromethanesulfonyloxy; the other symbols are as defined above.

As "substituents", "monocyclic aromatic groups" and "condensed aromatic groups" in the "monocyclic aromatic groups or condensed aromatic groups, each of which may be substituted" represented by $Ar^2$ and $Ar^3$, those exemplified as the above R and $Ar^1$ can be used. Especially, it is preferable that both of $Ar^2$ and $Ar^3$ are phenyl groups which may be substituted, and $Ar^2$—$Ar^3$ is biphenylyl which may be substituted.

The aryl-coupling reaction can be carried out in accordance with per se known methods such as the method described in Acta. Chemica Scandinavia, pp. 221–230, 1993, or methods analogous thereto.

In this reaction, compound (Xf) and 1 to 3 equivalents (preferably 1 to 1.5 equivalents) of compound (XIf) are reacted in an inert solvent in the presence of a base and a transition metal catalyst.

As the base, that exemplified in the above [Production method 1] can be used. The base is preferably sodium carbonate, sodium hydrogencarbonate, etc.

The amount of the "base" used is, for example, about 1 to 10 equivalents based on compound (XIf).

Examples of the "transition metal catalyst" include palladium catalyst, nickel catalyst. Examples of the "palladium catalyst" include tetrakis(triphenylphosphine)palladium (O), palladium acetate, bis (triphenylphosphine) palladium (II) chloride, palladium-carbon, etc. Examples of the "nickel catalyst" include tetrakis(triphenylphosphine) nickel (O), etc.

The amount of the "transition metal catalyst" used is about 0.01 to 1 equivalent, preferably about 0.01 to 0.5 equivalent, based on compound (XIf).

Reaction temperature is room temperature to 150° C., preferably about 80° C. to 150° C. Reaction time is, for example, about 1 to 48 hours.

Examples of the "inert solvent" include water, alcohol solvents, aromatic solvents. Two or more kinds of these can be mixed in an appropriate ratio for use. Especially, a single solvent such as water, ethanol and toluene; or a mixed solvent of two or more kinds of these is preferred.

Compound (Xf) can be produced by a per se known method.

Compound (XIf) can be produced by a per se known method.

[Production Method 7]

Compound (I) wherein Y is $C_{2-6}$ alkenylene (e.g., $CH=CHCH_2$), i.e., compound (Ig) can be produced by the following [Reaction scheme 3-1].

That is, compound (Ig) can be produced by carrying out in turn the step (Aa): a condensation reaction of compound (IXg) and compound (Xa); the step (Ab): a reducing reaction of compound (XIg); and the step (Ac): a dehydration reaction of compound (VIIg).

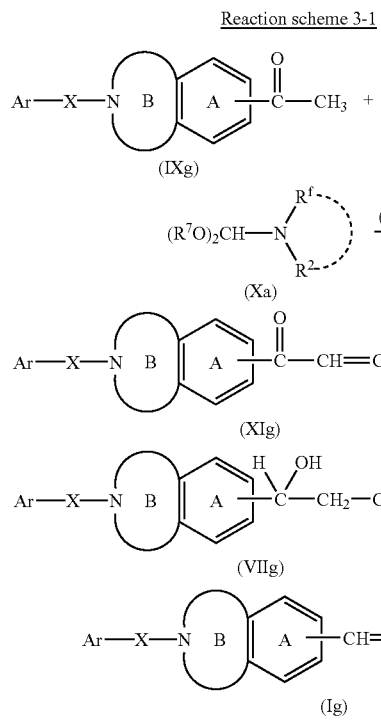

wherein the symbols are as defined above.

The condensation reaction of the step (Aa) can be carried out, for example, according to the same manner as that in the above step (af).

The reducing reaction of the step (Ab) can be carried out, for example, by a per se known method (e.g., catalytic reduction using a transition metal catalyst such as Pd/C, etc.; reducing reaction using a metal hydride such as $Et_3SiH$, etc.; reducing reaction using a metal hydrogen complex such as $NaBH_4$, etc.).

Further, this reaction can be carried out by a two-stage reaction, for example, by reducing the double bond under the same conditions as those of the above reducing reaction of the step (ag), followed by reducing the carbonyl group with a metal hydrogen complex such as $NaBH_4$, etc.

The dehydration reaction of the step (Ac) can be carried out by the same manner as that in the above step (ac).

Compound (IXg) can be produced by a per se known method.

Compound (I) can also be produced by subjecting compound (IIa) and compound (III) to a condensation reaction according to the following [Production method 8]. The "condensation reaction" can be carried out according to the same manner as the condensation reaction in the above step (aa).

[Production Method 8]

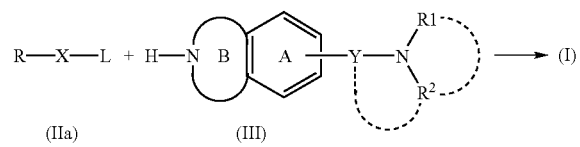

wherein the symbols are as defined above.

Compound (IIa) can be produced by a per se known method or an analogous method thereto.

Compound (I') can be produced by subjecting compound (IIb) and compound (IIIb) to a condensation reaction, for example, according to the following [Production method 9]. The "condensation reaction" can be carried out according to the same manner as the condensation reaction in the above step (aa).

[Production Method 9]

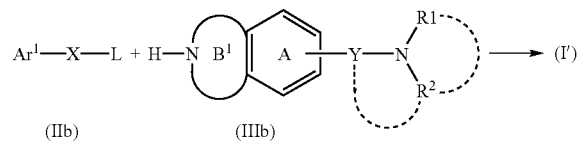

wherein the symbols are as defined above.

Compound (IIb) can be produced by a per se known method or an analogous method thereto.

Compound (IIIb) can be produced according to the same manner as that for the above compound (III).

Compound (I'') can be produced by subjecting compound (IIa) and compound (IIIc) to a condensation reaction according to, for example, the following [Production method 10]. The "condensation reaction" can be carried out according to the same manner as the condensation reaction in the above step (aa).

[Production Method 10]

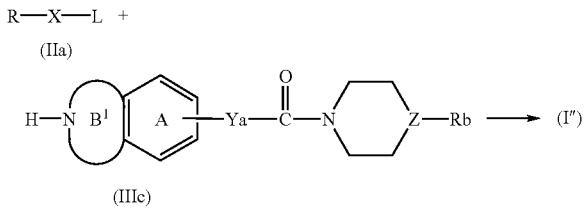

wherein the symbols are as defined above.

Compound (IIIc) can be produced according to the same manner as the above compound (III).

Examples of the above "alcohol solvents" include methanol, ethanol, isopropanol, tert-butanol, etc.

Examples of the above "ether solvents" include diethylether, tetrahydrofuran (THF), 1,4-dioxane, 1,2-dimethoxyethane, etc.

Examples of the above "halogenated hydrocarbon solvents" include dichloromethane, chloroform, 1,2-dichloroethane, carbon tetrachloride, etc.

Examples of the above "aromatic solvents" include benzene, toluene, xylene, pyridine, etc.

Examples of the above "hydrocarbon solvents" include hexane, pentane, cyclohexane, etc.

Examples of the above "amide solvents" include N,N-dimethylformamide (DMF), N,N-dimethylacetamide, N-methylpyrrolidone, etc.

Examples of the above "ketone solvent" include acetone, methylethylketone, etc.

Examples of the above "sulfoxide solvents" include dimethylsulfoxide (DMSO), etc.

Examples of the above "nitrile solvents" include acetonitrile, propionitrile, etc.

In a compound of the invention thus obtained, the intramolecular functional group can be converted to a desired functional group by combining per se known chemical reactions. Examples of the chemical reactions include oxidation reaction, reducing reaction, alkylation reaction, hydrolysis reaction, amination reaction, esterification reaction, aryl-coupling reaction, deprotection reaction.

In each of the above reactions, when the starting material compounds possess amino, carboxy, hydroxy, and/or carbonyl as substituents, protecting groups which are generally used in peptide chemicals, etc., can be introduced into these groups, and the desired compound can be obtained by removing the protecting groups after the reaction if necessary.

Examples of the protecting group for amino include those exemplified with respect to the above W.

Examples of the protecting group for carboxy include $C_{1-6}$ alkyl (e.g. methyl, ethyl, propyl, isopropyl, butyl, tert-butyl, etc.), $C_{7-11}$ aralkyl (e.g. benzyl, etc.), phenyl, trityl, silyl (e.g. trimethylsilyl, triethylsilyl, dimethylphenylsilyl, tert-butyldimethylsilyl, tert-butyldiethylsilyl, etc.), $C_{2-6}$ alkenyl (e.g. 1-allyl, etc.). These groups may be substituted by 1 to 3 of halogen atom (e.g. fluorine, chlorine, bromine, iodine, etc.), $C_{1-6}$ alkoxy (e.g. methoxy, ethoxy, propoxy, etc.) or nitro.

Examples of the protective group for hydroxy include $C_{1-6}$ alkyl (e.g. methyl, ethyl, propyl, isopropyl, butyl, tert-butyl, etc.), phenyl, trityl, $C_{7-10}$ aralkyl (e.g. benzyl, etc.), formyl, $C_{1-6}$ alkyl-carbonyl (e.g. acetyl, propionyl, etc.), benzoyl, $C_{7-10}$ aralkyl-carbonyl (e.g. benzylcarbonyl, etc.), 2-tetrahydropyranyl, 2-tetrahydrofuranyl, silyl (e.g. trimethylsilyl, triethylsilyl, dimethylphenylsilyl, tert-butyldimethylsilyl, tert-butyldiethylsilyl, etc.), $C_{2-6}$ alkenyl (e.g. 1-allyl, etc.). These groups may be substituted by 1 to 3 of halogen atom (e.g. fluorine, chlorine, bromine, iodine, etc.), $C_{1-6}$ alkyl (e.g. methyl, ethyl, n-propyl, etc.), $C_{1-6}$ alkoxy (e.g. methoxy, ethoxy, propoxy, etc.) or nitro, etc.

Examples of the protecting group for carbonyl include cyclic acetal (e.g. 1,3-dioxane, etc.), and non-cyclic acetal (e.g. di-$C_{1-6}$ alkylacetal, etc.).

Removal of the above protecting groups can be carried out in accordance with per se known methods such as those described in Protective Groups in Organic Synthesis, published by John Wiley and Sons (1980). For instance, the methods using acid, base, ultraviolet light, hydrazine, phenylhydrazine, sodium N-methyldithiocarbamate, tetrabutylammonium fluoride, palladium acetate, trialkylsilyl halide (e.g. trimethylsilyl iodide, trimethylsilyl bromide, etc.), and a reduction method, etc. can be used.

The compound of the present invention can be isolated and purified by per se known methods such as solvent extraction, changing of liquid properties, transdissolution, crystallization, recrystallization, chromatography, etc. It is also possible to isolate and purify the starting material compounds of the compound of the present invention, or their salts using the same known methods as above, but they can also be used as raw materials in the next process as a reaction mixture without being isolated.

The compound of the present invention possesses an excellent MCH receptor antagonistic action, therefore, it is useful as an agent for preventing or treating diseases caused by MCH. Also, the compound of the present invention is low in toxicity, and is excellent in oral absorbency and intracerebral transitivity.

Therefore, a melanin-concentrating hormone antagonist comprising a compound of the invention can be safely administered to mammals (e.g. rats, mice, guinea pigs, rabbits, sheep, horses, swine, cattle, monkeys, humans, etc.) as an agent for preventing or treating diseases caused by MCH.

Here, examples of the diseases caused by MCH include obesity (e.g. malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], hyperphagia, emotional disorders, reproductive function disorders, etc.

The compound of the present invention is also useful as an agent for preventing or treating lifestyle diseases such as diabetes, diabetic complications (e.g. diabetic retinopathy, diabetic neuropathy, diabetic nephropathy, etc.), arteriosclerosis, gonitis, etc.

Further, the compound of the present invention is useful as an anorectic agent.

The MCH antagonist and the pharmaceutical composition of the present invention can be used in combination with an alimentary therapy (e.g., alimentary therapy for diabetes) and exercise.

The MCH antagonist and the pharmaceutical composition of the present invention can be produced by subjecting the compound of the present invention, as it is, or together with a pharmacologically acceptable carrier, to pharmaceutical manufacturing process in accordance with a per se known means.

Here, examples of the pharmacologically acceptable carriers include various organic or inorganic carrier substances which are commonly used as materials for pharmaceutical preparations, such as excipients, lubricants, binders, and disintegrators in solid preparations; solvents, solubilizing agents, suspending agents, isotonizing agents, buffering agents, soothing agents, in liquid preparations; and the like. Also, in the pharmaceutical manufacturing process, additives such as antiseptics, antioxidants, coloring agents, sweeteners, absorbents, moistening agents, etc., can be used, if necessary.

Examples of the excipients include lactose, sucrose, D-mannitol, starch, cornstarch, crystalline cellulose, light anhydrous silicic acid, etc.

Examples of the lubricants include magnesium stearate, calcium stearate, talc, colloidal silica, etc.

Examples of the binders include crystalline cellulose, sucrose, D-mannitol, dextrin, hydroxypropylcellulose, hydroxypropylmethylcellulose, polyvinylpyrrolidone, starch, saccharose, gelatin, methylcellulose, carboxymethylcellulose sodium, etc.

Examples of the disintegrators include starch, carboxymethylcellulose, carboxymethylcellulose calcium, crosscarmellose sodium, carboxymethylstarch sodium, low-substituted hydroxypropylcellulose (L-HPC), etc.

Examples of the solvents include distilled water for injection, alcohol, propylene glycol, macrogol, sesame oil, corn oil, etc.

Examples of the solubilizing agents include polyethylene glycol, propylene glycol, D-mannitol, benzyl benzoate, ethanol, trisaminomethane, cholesterol, triethanolamine, sodium carbonate, sodium citrate, etc.

Examples of the suspending agents include surfactants such as stearyltriethanolamine, sodium lauryl sulfate, lauryl amino propionic acid, lecithin, benzalkonium chloride, benzethonium chloride, glyceryl monostearate; or hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose, etc.

Examples of the isotonizing agents include glucose, D-sorbitol, sodium chloride, glycerin, D-mannitol, etc.

Examples of the buffering agents include buffer solutions of phosphate, acetate, carbonate, citrate, etc.

Examples of the soothing agents include benzyl alcohol, etc.

Examples of the antiseptics include paraoxybenzoates, chlorobutanol, benzyl alcohol, phenethylalcohol, dehydroacetic acid, sorbic acid, etc.

Examples of the antioxidants include sulfite, ascorbic acid, etc.

The MCH antagonist and the pharmaceutical composition of the present invention can be safely administered orally or parenterally (e.g. by local, rectal and intravenous administration) in various dosage forms, for example, as oral drugs such as tablets (including sugar-coated tablets and film-coated tablets), powders, granules, capsules (including soft capsules), solutions; and parenteral preparations such as injectable preparations (e.g. preparations for subcutaneous injections, intravenous injections, intramuscular injections, intraperitoneal injections, etc.), external preparations (e.g. nasal preparations, percutaneous preparations, ointments, etc.), suppositories (e.g. rectal suppositories, vaginal suppositories, etc.), sustained-release preparations (e.g. sustained-release microcapsules, etc.), pellets, drip infusions, etc.

The content of the compound of the present invention in the MCH antagonist of the present invention and the content of the compound of the present invention in the pharmaceutical composition of the present invention are, for example, about 0.1 to 100% by weight based on the total weight of the MCH antagonist or pharmaceutical composition, respectively.

The dose of the MCH antagonist and the pharmaceutical composition of the present invention can be appropriately selected depending on the subject of administration, route of administration, disease, etc.

For example, the dose per day when the MCH antagonist or the pharmaceutical composition of the present invention is orally administered to an adult obesity patient (body weight: about 60 kg), is about 0.1 to about 500 mg, preferably about 1 to about 100 mg, more preferably about 5 to about 100 mg, in terms of the compound of the present invention which is an active ingredient. This amount can be divided into one to several doses per day for administration.

The MCH antagonist and pharmaceutical composition of the present invention can be used in combination with other concomitant drugs which do not interfere with the MCH antagonist and pharmaceutical composition of the present invention, for the purpose of "strengthening of therapeutic effect against obesity", "reduction of dose of MCH antagonist", etc. Examples of the concomitant drugs include a "agents for treating diabetes", "agents for treating diabetic complications", "agents for treating obesity other than MCH antagonists", "agents for treating hypertension", "agents for treating hyperlipidemia", "agents for treating arthritis", "antianxiety agents", "antidepressant", etc. Two or more kinds of these concomitant drugs can be combined in an appropriate ratio for use.

Examples of the above "agents for treating diabetes" include insulin sensitizers, insulin secretion enhancers, biguamides, insulins, $\alpha$-glucosidase inhibitors, $\beta 3$ adrenaline receptor agonists, etc.

Examples of the insulin sensitizers include pioglitazone or its salt (preferably hydrochloride), troglitazone, rosiglitazone or its salt (preferably maleate), JTT-501, GI-262570, MCC-555, YM-440, DRF-2593, BM-13-1258, KRP-297, R-119702, etc.

Examples of the insulin secretion enhancers include sulfonylureas. Specific examples of the sulfonylureas include tolbutamide, chlorpropamide, tolazamide, acetohexamide, glyclopyramide and its ammonium salt, glibenclamide, gliclazide, glimepiride, etc.

Other than the above, examples of insulin secretion enhancers include repaglinide, nateglinide, mitiglinide (KAD-1229), JTT-608, etc.

Examples of biguamides include metformin, buformin, phenformin, etc.

Examples of insulins include animal insulins extracted from bovine or porcine pancreas; semi-synthetic human insulin which is enzymatically synthesized from insulin extracted from porcine pancreas; human insulin synthesized by genetic engineering, using *Escherichia coli* and yeast; etc. As insulin, also employed are insulin-zinc containing 0.45 to 0.9 (w/w) % of zinc; protamine-insulin-zinc produced from zinc chloride, protamine sulfate and insulin; etc. In addition, insulin can be an insulin fragment or derivative (e.g. INS-1, etc.).

Insulin can also include various types such as ultra immediate action type, immediate action type, two-phase type, intermediate type, prolonged action type, etc., and these can be selected depending on the pathological conditions of patients.

Examples of $\alpha$-glucosidase inhibitors include acarbose, voglibose, miglitol, emiglitate, etc.

Examples of $\beta 3$ adrenaline receptor agonists include AJ-9677, BMS-196085, SB-226552, AZ40140, etc.

Other than the above, examples of the "agents for treating diabetes" include ergoset, pramlintide, leptin, BAY-27-9955, etc.

Examples of the above "agents for treating diabetic complications" include aldose reductase inhibitors, glycation inhibitors, protein kinase C inhibitors, etc.

Examples of aldose reductase inhibitors include torlestat; eparlestat; imirestat; zenarestat; SNK-860; zopolrestat; ARI-509; AS-3201, etc.

Examples of glycation inhibitors include pimagedine.

Examples of protein kinase C inhibitors include NGF, LY-333531, etc.

Other than the above, examples of "agents for treating diabetic complications" include alprostadil, thiapride hydrochloride, cilostazol, mexiletine hydrochloride, ethyl eicosapentate, memantine, pimagedline (ALT-711), etc.

Examples of the above "agents for treating obesity other than MCH antagonists" include lipase inhibitors and anorectics, etc.

Examples of lipase inhibitors include orlistat, etc.

Examples of anorectics include mazindol, dexfenfluramine, fluoxetine, sibutramine, baiamine, etc.

Other than the above, examples of "agents for treating obesity other than MCH antagonists" include lipstatin, etc.

Examples of the above "agents for treating hypertension" include angiotensin converting enzyme inhibitors, calcium antagonists, potassium channel openers, angiotensin II antagonists, etc.

Examples of angiotensin converting enzyme inhibitors include captopril, enarapril, alacepril, delapril (hydrochloride), lisinopril, imidapril, benazepril, cilazapril, temocapril, trandolapril, manidipine (hydrochloride), etc.

Examples of calcium antagonists include nifedipine, amlodipine, efonidipine, nicardipine, etc.

Examples of potassium channel openers include levcromakalim, L-27152, AL0671, NIP-121, etc.

Examples of angiotensin II antagonists include losartan, candesartan cilexetil, valsartan, irbesartan, CS-866, E4177, etc.

Examples of the above "agents for treating hyperlipidemia (agents for treating arteriosclerosis)" include HMG-CoA reductase inhibitors, fibrate compounds, etc.

Examples of HMG-CoA reductase inhibitors include pravastatin, simvastatin, lovastatin, atorvastatin, fluvastatin, lipantil, cerivastatin, itavastatin, ZD-4522, or their salts (e.g. sodium salts, etc.), etc.

Examples of fibrate compounds include bezafibrate, clinofibrate, clofibrate, simfibrate, etc.

Examples of the above "agents for treating arthritis" include ibuprofen, etc.

Examples of the above "antianxiety agents" include chlordiazepoxide, diazepam, oxazolam, medazepam, cloxazolam, bromazepam, lorazepam, alprazolam, fludiazepam, etc.

Examples of the above "antidepressants" include fluoxetine, fluvoxamine, imipramine, paroxetine, sertraline, etc.

The timing of administration of the above concomitant drugs is not limited. The MCH antagonist or pharmaceutical composition and the concomitant drugs can be administrated to the subject simultaneously or at staggered times.

The dosages of the concomitant drugs can be determined in accordance with clinically used dosages, and can be appropriately selected according to the subject of administration, route of administration, diseases and combinations of drugs, etc.

The administration forms for the concomitant drugs are not particularly limited as long as the MCH antagonist or the pharmaceutical composition are used in combination with a concomitant drugs at the time of administration. Examples of such administration forms includes 1) administration of a single preparation obtained by simultaneous preparation of MCH antagonist or pharmaceutical composition together with concomitant drugs, 2) simultaneous administration of two kinds of preparations obtained by separate preparation of MCH antagonist or pharmaceutical composition, and concomitant drugs, through the same route of administration, 3) staggered administration of two kinds of preparations obtained by separate preparation of MCH antagonist or pharmaceutical composition, and concomitant drugs, through the same route of administration, 4) simultaneous administration of two kinds of preparations obtained by separate preparation of MCH antagonist or pharmaceutical composition, and concomitant drugs, through different routes of administration, 5) staggered administration of two kinds of preparations obtained by separate preparation of MCH antagonist or pharmaceutical composition, and concomitant drugs, through different routes of administration (for example, administration of MCH antagonist or pharmaceutical composition; and concomitant drugs in this order; or administration in reverse order).

The ratio of combination of MCH antagonist or pharmaceutical composition with concomitant drugs can be appropriately selected in accordance with the subject of administration, route of administration and diseases, etc.

BEST MODE FOR CARRYING OUT THE INVENTION

The present invention will be explained further in detail by the following Reference Examples, Examples, Preparation Examples, and Experimental Examples. However, these do not limit the present invention, and they can be changed within the scope that does not deviate from the scope of the present invention.

In the following Reference Examples and Examples, "room temperature" means 0 to 30° C. Anhydrous magnesium sulfate or anhydrous sodium sulfate was used to dry the organic layer. "%" means percent by weight, unless otherwise specified.

Infrared absorption spectra were determined by the diffuse reflectance method, using fourier transform type infrared spectrophotometer.

FABMS (pos) is mass spectrum determined by the (+) method, in Fast Atom Bombardment Mass Spectrometry.

MS (APCI) and MS (ESI) are mass spectra determined by Atmospheric Pressure Chemical Inonization (APCI) or Electron Spray Ionization (ESI), respectively.

Other symbols used in the description have the following meanings.

| | |
|---|---|
| s | singlet |
| d | doublet |
| t | triplet |
| q | quartet |
| m | multiplet |
| br | broad |
| J | coupling constant |
| Hz | Hertz |
| $CDCl_3$ | heavy chloroform |
| $DMSO-d_6$ | heavy dimethylsulfoxide |
| THF | tetrahydrofuran |
| DMF | N,N-dimethylformamide |
| DMSO | dimethylsulfoxide |
| WSCD | 1-ethyl-3-(3-dimethylaminopropyl) carbodimide |
| WSC | 1-ethyl-3-(3-dimethylaminopropyl) carbodimide hydrochloride |
| $^1$H-NMR | proton nuclear resonance (Free substances were usually measured in $CDCl_3$.) |
| IR | infrared absorption spectrum |
| Me | methyl |
| Et | ethyl |
| HOBt | 1-hydroxy-1H-benzotriazole |
| IPE | diisopropyl ether |
| DMAP | 4-dimethylaminopyridine |

In this specification and drawings, when bases and amino acids are shown by codes, these codes are based on those by the IUPAC-IUB Commission on Biochemical Nomenclature or common codes in the concerned fields. Examples of these codes are shown below. Also, where some optical isomers of amino acids can exist, the L form is shown unless otherwise specified.

DNA: deoxyribonucleic acid
cDNA: complimentary deoxyribonucleic acid

| A | adenine |
|---|---|
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediamine tetraacetic acid |
| SDS | sodium dodecyl sulfate |
| EIA | enzyme immunoassay |
| Gly | glycine |
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Tro | tryptophan |
| Pro | proline |
| Asn | asparagine |
| Gln | glutamine |
| pGl | pyroglutamine |
| Me | methyl group |
| Et | ethyl group |
| Bu | butyl group |
| Ph | phenyl group |
| TC | thiazolidine-4(R)-carboxamide group |

Substituents, protecting groups and reagents frequently used in this specification, are shown by the following symbols.

| Tos | p-toluenesulfonyl |
|---|---|
| CHO | formyl |
| Bzl | benzyl |
| Cl$_2$Bzl | 2,6-dichlorobenzyl |
| Bom | benxyloxymethyl |
| Z | benxyloxycarbonyl |
| Cl-Z | 2-chlorobenzyloxycarbonyl |
| Br-Z | 2-bromobenzyloxycarbonyl |
| Boc | t-butoxycarbonyl |
| DNP | dinitrophenol |
| Trt | trityl |
| Bum | t-butoxymethyl |
| Fmoc | N-9-fluorenylmethoxycarbonyl |
| HOOBt | 3,4-dihydro-3-hydroxy-4-oxo-1,2,3-benzotriazine |
| HONB | 1-hydroxy-5-norbornene-2,3-dicarbodiimide |
| DCC | N,N'-dicyclohexylcarbodiimide |

SEQ ID NO in the SEQUENCE LISTING in the specification of the present application shows the following sequences.

[SEQ ID NO: 1] shows a synthetic DNA used for screening of cDNA coding rat SLC-1.

[SEQ ID NO: 2] shows a synthetic DNA used for screening of cDNA coding rat SLC-1.

[SEQ ID NO: 3] shows an entire amino acid sequence of rat SLC-1.

[SEQ ID NO: 4] shows an entire base sequence of rat SLC-1cDNA wherein Sal I recognition sequence was added to the 5' side, and Spe I recognition sequence was added to the 3' side.

[SEQ ID NO: 5] shows riboprobe used to determine the quantity of SLC-1mRNA expressed in each clone of rat SLC-1 expression CHO cells.

[SEQ ID NO: 6] shows a synthetic DNA used to obtain cDNA for coding of human SLC-1.

[SEQ ID NO: 7] shows a primer used to make double-strand cDNA for coding human SLC-1.

[SEQ ID NO: 8] shows an entire base sequence of cDNA for coding human SLC-1.

[SEQ ID NO: 9] shows an entire amino acid sequence of human SLC-1.

[SEQ ID NO: 10] shows a synthetic DNA used for screening of cDNA for coding human SLC-1(S).

[SEQ ID NO: 11] shows a synthetic DNA used for screening of cDNA for coding human SLC-1(S).

[SEQ ID NO: 12] shows a synthetic DNA used for screening of cDNA for coding human SLC-1(L).

[SEQ ID NO: 13] shows a synthetic DNA used for screening of cDNA for coding human SLC-1(L).

[SEQ ID NO: 14] shows an entire base sequence of human SLC-1(S) cDNA wherein Sal I recognition sequence was added to the 5' side, and Spe I recognition sequence was added to the 3' side.

[SEQ ID NO: 15] shows an entire base sequence of human SLC-1(L) cDNA wherein Sal I recognition sequence was added to the 5' side, and Spe I recognition sequence was added to the 3' side.

[SEQ ID NO: 16] shows riboprobe used to determine the quantity of SLC-lmRNA expressed in each clone of human SLC-1(S) expression CHO cells and SLC-1(L) expression CHO cells.

Transformant *Escherichia coli* DH10B/phSLC1L8 transformed by plasmid containing DNA which codes the base sequence shown by SEQ ID NO: 9, obtained in Reference Example 1–6, has been deposited with National Institute of Bioscience and Human-Technology (NIBH), Agency of Industrial Science and Technology, Ministry of International Trade and Industry, under accession of number FERM BP-6632 since Feb. 1, 1999; and with the Institute for Fermentation, Osaka, Japan (IFO), under accession number of IFO 16254 since Jan. 21, 1999.

EXAMPLES

Reference Example 1

Ethyl 6-(3-chloropropanoyl)-3,4-dihydro-1(2H)-quinoline carboxylate

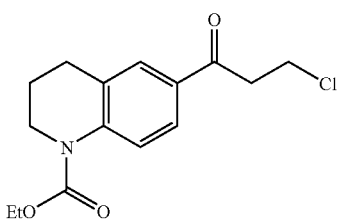

Aluminum chloride (23.5 g, 176 mmol) was added to a solution of ethyl 3,4-dihydro-1(2H)-quinoline carboxylate (14.5 g, 70.4 mmol) and 3-chloropropionyl chloride (7.39 ml, 77.4 mmol) in dichloromethane under cooling with water-bath, and the mixture was stirred at room temperature for 14 hours. The reaction solution was poured into iced water and extracted with dichloromethane. The extract was washed with a saturated saline solution and dried over anhydrous sodium sulfate, and the solvent was distilled away under reduced pressure. The resulting residues were purified by silica gel column chromatography (developing solvent; hexane:ethyl acetate=3:1) and crystallized from hexane, whereby the title compound (15.6 g) was obtained as colorless powder with a mp. of 78 to 79° C.

$^1$H NMR (CDCl$_3$) δ 1.35 (3H, t, J=7.0 Hz), 1.93 (2H, m), 2.83 (2H, t, J=6.2 Hz), 3.42 (2H, t, J=7.0 Hz), 3.81 (2H, t, J=6.2 Hz), 3.92 (2H, t, J=7.0 Hz), 4.28 (2H, q, J=7.0 Hz), 7.74 (2H, m), 7.92 (1H, d, J=8.8 Hz). Elemental analysis for C$_{15}$H$_{18}$ClNO$_3$ Calcd.: C, 60.91; H, 6.13; N, 4.74. Found: C, 61.20; H, 6.05; N, 4.74.

Reference Example 2

Ethyl 6-[3-(dimethylamino)propanoyl]-3,4-dihydro-1(2H)-quinoline carboxylate

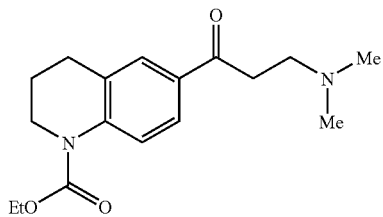

50% Aqueous dimethylamine (51 mL) was added to a solution of ethyl 6-(3-chloropropanoyl)-3,4-dihydro-1(2H)-quinoline carboxylate (15.0 g, 50.7 mmol) obtained in Reference Example 1 in dichloromethane at room temperature and then stirred for 2 hours. The reaction solution was separated, and the organic layer was washed with a saturated saline solution and dried over anhydrous sodium sulfate, and the solvent was distilled away under reduced pressure. The resultant residues were purified by alumina column chromatography (developing solvent; hexane:ethyl acetate=1:1), whereby the title compound (16.3 g) was obtained as pale yellow matter.

$^1$H NMR (CDCl$_3$) δ: 1.34 (3H, t, J=7.0 Hz), 1.96 (2H, m), 2.29 (6H, s), 2.79 (4H, m), 3.11 (2H, m), 3.79 (2H, m), 4.24 (2H, q, J=7.0 Hz), 7.72–7.78 (2H, m), 7.78 (1H, d, J=8.4 Hz).

Reference Example 3

Ethyl 6-[3-(dimethylamino)propyl]-3,4-dihydro-1(2H)-quinoline carboxylate hydrochloride

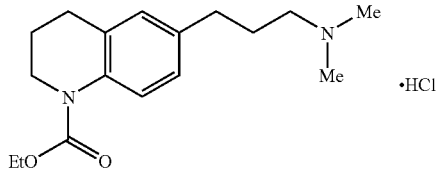

Triethyl silane (64.8 ml, 406 mmol) was added under a nitrogen atmosphere to a solution of ethyl 6-[3-(dimethylamino)propanoyl]-3,4-dihydro-1(2H)-quinoline carboxylate (15.4 g, 50.7 mmol) obtained in Reference Example 2 in trifluoroacetic acid and then stirred at room temperature for 5 days. The solvent was distilled away under reduced pressure, and ether was added to the residues which were then extracted with water. The aqueous layer was made basic with 8 N aqueous sodium hydroxide and then extracted with ethyl acetate. The extract was washed with a saturated saline solution and dried over anhydrous sodium sulfate, and the solvent was distilled away under reduced pressure. The resultant residues were purified by alumina column chromatography (developing solvent; hexane:ethyl acetate=3:1). 4 N hydrogen chloride-ethyl acetate was added to a solution of the resultant oily matter in ether, and the formed solids were washed with diethyl ether, whereby the title compound (14.8 g) was obtained as hygroscopic colorless powder.

$^1$H NMR (CDCl$_3$, free base) δ: 1.32 (3H, t, J=7.0 Hz), 1.78 (2H, m), 1.83 (2H, m), 2.22 (6H, s), 2.29 (2H, m), 2.56 (2H, m), 2.75 (2H, t, J=6.6 Hz), 3.74 (2H, m), 4.24 (2H, q, J=7.0 Hz), 6.98 (2H, m), 7.59 (1H, d, J=8.4 Hz).

Reference Example 4

N,N-Dimethyl-3-(1,2,3,4-tetrahydro-6-quinolinyl)-1-propan amine dihydrochloride

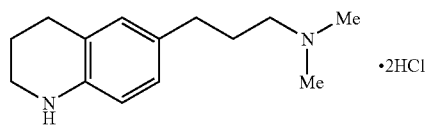

A solution of ethyl 6-[3-(dimethylamino)propyl]-3,4-dihydro-1(2H)-quinoline carboxylate hydrochloride (14.5 g, 44.4 mmol) obtained in Reference Example 3 in concd. hydrochloric acid (200 mL) was stirred at 120° C. for 16 hours, and the solvent was distilled away under reduced pressure and dried under reduced pressure, whereby the title compound (12.8 g) was obtained as hygroscopic powder with a mp. of 250° C. (decomp.).

$^1$H NMR (D$_2$O) δ 1.78 (4H, m), 2.41 (2H, t-like), 2.54 (6H, s), 2.60 (2H, t-like), 2.81 (2H, m), 3.22 (2H, m), 6.93 (3H, m). Elemental analysis for C$_{14}$H$_{22}$N$_2$.2HCl Calcd.: C, 57.73; H, 8.31; N, 9.62. Found: C, 57.44; H, 8.22; N, 9.47.

Reference Example 5

1-[1-[(4'-Chloro[1,1'-biphenyl]-4-yl)carbonyl]-1,2,3,4-tetrahydro-6-quinolinyl]ethanone

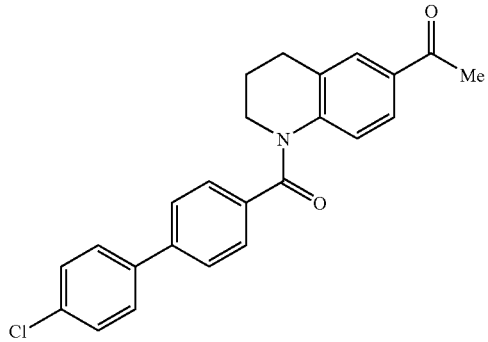

Oxalyl chloride (0.39 mL) and N,N-dimethylformamide (1 drop) were added in this order to a suspension of 4-(4-chlorophenyl)benzoic acid (1.05 g) in tetrahydrofuran (15 mL). After the mixture was stirred at room temperature for 1 hour, the solvent was distilled away under reduced pressure. The resultant residues were dissolved in tetrahydrofuran (10 mL) and then added to a suspension of 6-acetyl-1,2,3,4-tetrahydroquinoline (0.7 g), sodium hydroxide powder (0.31 g) and tetrabutyl ammonium hydrogensulfate (12 mg) in tetrahydrofuran (15 mL). After the mixture was stirred at room temperature for 3 hours, water was added to the reaction solution which was then extracted with ethyl acetate. The extract was washed with a saturated saline solution and dried over anhydrous magnesium sulfate, and the solvent was distilled away under reduced pressure. The resultant residues were crystallized from diethyl ether, whereby the title compound (1.1 g) was obtained as colorless crystals with a mp of 149 to 151° C.

$^1$H NMR (CDCl$_3$) δ: 2.03–2.15 (2H, m), 2.53 (3H, s), 2.94 (2H, t, J=6.4 Hz), 3.95 (2H, t, J=6.3 Hz), 6.87 (1H, d, J=8.6 Hz), 7.38–7.61 (9H, m) 7.79 (1H, s). Elemental analysis for C$_{24}$H$_{20}$ClNO$_2$ Calcd.: C, 73.94; H, 5.17; N, 3.59. Found: C, 73.79; H, 5.13; N, 3.57.

Reference Example 6

(E)-1-[1-[(4'-Chloro[1,1'-biphenyl]-4-yl)carbonyl]-1,2,3,4-tetrahydro-6-quinolinyl]-3-(dimethylamino)-2-propen-1-one

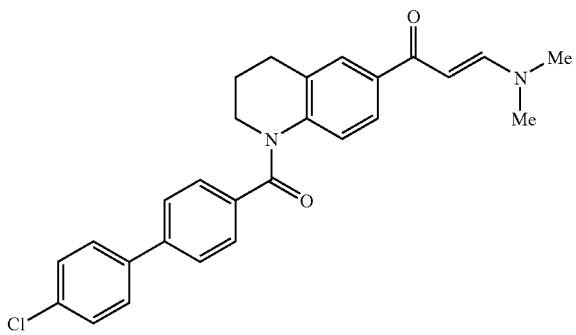

A mixture of 1-[1-[(4'-chloro[1,1'-biphenyl]-4-yl)carbonyl]-1,2,3,4-tetrahydro-1-quinolinyl]ethanone (0.65 g) obtained in Reference Example 5 and N,N-dimethylformamide dimethylacetal (8 ml) was stirred at 110° C. for 16 hours. The reaction solution was cooled to room temperature, then concentrated under reduced pressure and purified by alumina column chromatography (developing solvent; ethyl acetate). The resultant residues were crystallized from diethyl ether, whereby the title compound (1.1 g) was obtained as colorless crystals with a mp of 168 to 170° C.

$^1$H NMR (CDCl$_3$) δ: 2.00–2.15 (2H, m), 2.75–3.20 (8H, m), 3.95 (2H, t, J=6.4 Hz), 5.64 (1H, d, J=12.3 Hz), 6.76 (1H, d, J=8.4 Hz), 7.37–7.53 (9H, m) 7.75–7.82 (2H, m). Elemental analysis for C$_{27}$H$_{25}$ClN$_2$O$_2$ Calcd.: C, 72.88; H, 5.66; N, 6.30. Found: C, 72.58; H, 5.84; N, 6.20.

Reference Example 7

1-(1-Acetyl-2,3,4,5-tetrahydro-1H-1-benzazepin-8-yl)-3-chloro-1-propanone

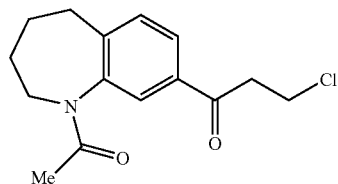

Aluminum chloride (30.8 g, 231 mmol) was added to a solution of 1-acetyl-2,3,4,5-tetrahydro-1H-1-benzazepine (17.5 g, 92.5 mmol) and 3-chloropropionyl chloride (13.2 ml, 139 mmol) in dichloroethane under cooling with water-bath, and then the mixture was stirred at 50° C. for 1 day. The reaction solution was poured into iced water and extracted with dichloromethane. The extract was washed with a saturated saline solution and dried over anhydrous sodium sulfate, and the solvent was distilled away under reduced pressure. The resultant residues were purified by silica gel column chromatography (developing solvent; hexane:ethyl acetate=1:1) and crystallized from hexane, whereby the title compound (8.47 g) was obtained as colorless powder with a mp. of 106 to 107° C.

$^1$H NMR (CDCl$_3$) δ: 1.41 (1H, m), 1.87 (3H, s), 1.87–2.08 (3H, m), 2.54–2.83 (3H, m), 3.44 (2H, m), 3.93 (2H, m), 4.74 (1H, m), 7.38 (1H, d, J=8.0 Hz), 7.76 (1H, s), 7.84 (1H, d, J=8.0 Hz).

Reference Example 8

1-(1-Acetyl-2,3,4,5-tetrahydro-1H-1-benzazepin-8-yl)-3-(dimethylamino)-1-propanone

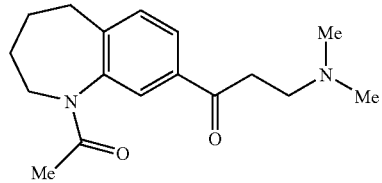

50% aqueous dimethylamine (27 ml) was added to a solution of 1-(1-acetyl-2,3,4,5-tetrahydro-1H-1-benzazepin-8-yl)-3-chloro-1-propanone (7.10 g, 25.4 mmol) obtained in Reference Example 7 in dichloromethane at room temperature, and then stirred for 4 hours. After the reaction solution was separated, the organic layer was washed with a saturated saline solution and dried over anhydrous sodium sulfate, and the solvent was distilled away under reduced pressure. The resultant residues were purified by alumina column chromatography (developing solvent; hexane:ethyl acetate=1:1) and crystallized from hexane, whereby the title compound (5.38 g) was obtained as colorless powder with a mp. of 68 to 70° C.

$^1$H NMR (CDCl$_3$) δ: 1.40 (1H, m), 1.86 (3H, s), 1.81–2.07 (3H, m), 2.29 (6H, s), 2.59 (1H, m), 2.77 (4H, m), 3.13 (2H, m), 4.69 (1H, m), 7.36 (1H, d, J=8.0 Hz), 7.75 (1H, d, J=1.8 Hz), 7.83 (1H, dd, J=1.8, 8.0 Hz). Elemental analysis for C$_{17}$H$_{24}$N$_2$O$_2$ Calcd.: C, 70.80; H, 8.39; N, 9.71. Found: C, 70.87; H, 8.16; N, 9.44.

Reference Example 9

(E)-3-(1-Acetyl-2,3,4,5-tetrahydro-1H-1-benzazepin-8-yl)-N,N-dimethyl-2-propen-1-amine

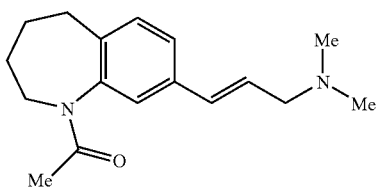

Triethyl silane (22.2 ml, 139 mmol) was added under a nitrogen atmosphere to a solution of 1-(1-acetyl-2,3,4,5-tetrahydro-1H-1-benzazepin-8-yl)-3-(dimethylamino)-1-propanone (5.00 g, 17.3 mmol) obtained in Reference Example 8 in trifluoroacetic acid, and then the mixture was stirred at room temperature for 5 days. After the solvent was distilled away under reduced pressure, ether was added to the residues which were then extracted with water. The aqueous layer was made basic with 8 N aqueous sodium hydroxide and then extracted with ethyl acetate. The extract was washed with a saturated saline solution and dried over anhydrous sodium sulfate, and the solvent was distilled away under reduced pressure. The resultant residues were purified by alumina column chromatography (developing solvent; hexane:ethyl acetate=1:1), whereby the title compound (2.74 g) was obtained as oily matter.

$^1$H NMR (CDCl$_3$) δ: 1.39 (1H, m), 1.73–2.05 (5H, m), 2.28 (6H, s), 2.53–2.75 (4H, m), 3.08 (2H, dd, J=0.8, 6.6 Hz), 4.69 (1H, m), 6.24 (1H, dt, J=6.6, 16.0 Hz), 6.48 (1H, d, J=16.0 Hz), 7.12–7.27 (3H, m).

Reference Example 10

(E)-N,N-Dimethyl-3-(2,3,4,5-tetrahydro-1H-1-benzazepin-8-yl)-2-propen-1-amine

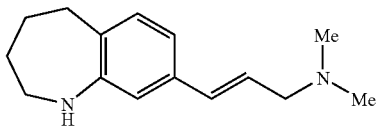

A solution of (E)-3-(1-acetyl-2,3,4,5-tetrahydro-1H-1-benzazepin-8-yl)-N,N-dimethyl-2-propene-1-amine (2.73 g, 9.95 mmol) obtained in Reference Example 9 in concd. hydrochloric acid was stirred at 120° C. for 12 hours. After the solvent was distilled away under reduced pressure, the residues were made basic with 8 N aqueous sodium hydroxide and extracted with ethyl acetate. After the extract was washed with a saturated saline solution and dried over anhydrous sodium sulfate, the solvent was distilled away under reduced pressure, and the residues were crystallized from hexane, whereby the title compound (1.49 g) was obtained as colorless powder with a mp. of 87 to 88° C.

$^1$H NMR (CDCl$_3$) δ: 1.63 (2H, m), 1.78 (2H, m), 2.26 (6H, s), 2.74 (2H, m), 3.04 (4H, m), 3.78 (1H, br), 6.18 (1H, dt, J=6.6, 16.0 Hz), 6.42 (1H, d, J=16.0 Hz), 6.75 (1H, d, J=1.6 Hz), 6.85 (1H, dd, J=1.6, 7.8 Hz), 7.04 (1H, d, J=7.8 Hz). Elemental analysis for C$_{15}$H$_{22}$N$_2$ Calcd.: C, 78.21; H, 9.63; N, 12.16. Found: C, 78.15; H, 9.73; N, 12.23.

Reference Example 11

(E)-1-[1-[(4'-Chloro[1,1'-biphenyl]-4-yl)carbonyl]-1,2,3,4-tetrahydro-6-quinolinyl]-3-piperidino-2-propen-1-one

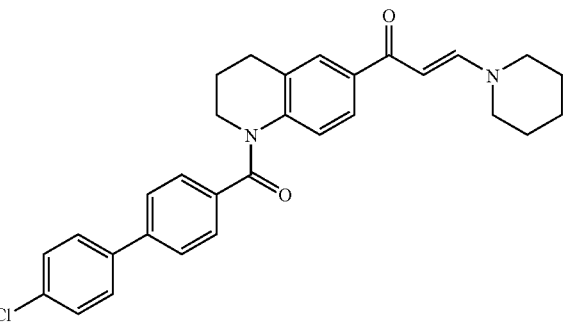

A mixture of (E)-[1-[(4'-chloro[1,1'-biphenyl]-4-yl)carbonyl]-1,2,3,4-tetrahydro-6-quinolinyl]-3-(dimethylamino)-2-propen-1-one (0.29 g) obtained in Reference Example 6 and piperidine (3 ml) was stirred at 110° C. for 2 hours. The reaction solution was cooled to room temperature, concentrated under reduced pressure and purified by alumina column chromatography (developing solvent; ethyl acetate). The resultant residues were crystallized from diethyl ether, whereby the title compound (0.28 g) was obtained as colorless crystals with a mp of 167 to 170° C.

$^1$H NMR (CDCl$_3$) δ: 1.57–1.70 (6H, m), 2.03–2.15 (2H, m), 2.92 (2H, t, J=6.6 Hz), 3.25–3.45 (4H, m), 3.95 (2H, t, J=6.4 Hz), 5.74 (1H, d, J=12.5 Hz), 6.74 (1H, d, J=8.4 Hz), 7.37–7.61 (9H, m) 7.72–7.78 (2H, m).

Reference Example 12

1-(1-Acetyl-2,3-dihydro-1H-indol-5-yl)-3-(dimethylamino)-1-propanone

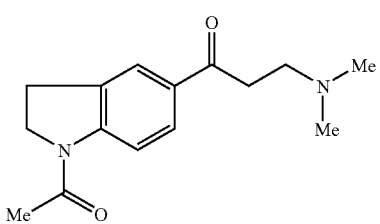

Using 1-acetyl indoline, the title compound was obtained as viscous oily matter by the same procedures as in Reference Examples 1 and 2.

$^1$H NMR (CDCl$_3$) δ: 2.21–2.33 (9H, m), 2.74 (2H, t, J=7.2 Hz), 3.11 (2H, t, J=7.2 Hz), 3.23 (2H, t, J=8.6 Hz), 4.12 (2H, t, J=8.6 Hz), 7.78–7.97 (2H, m) 8.24 (1H, d, J=8.4 Hz).

Reference Example 13

(E)-3-[2,3-Dihydro-1H-indol-5-yl]-N,N-dimethyl-2-propene-1-amine

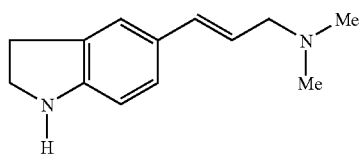

1) Sodium borohydride (0.75 g) was added to a solution of 1-(1-acetyl-2,3-dihydro-1H-indol-5-yl)-3-(dimethylamino)-1-propanone (4.3 g) obtained in Reference Example 12 in methanol (40 ml) under cooling with ice-bath, and the mixture was stirred at 0 to 5° C. for 30 minutes. After iced water was added to the reaction solution, the solvent was distilled away under reduced pressure, and the residues were extracted with ethyl acetate. The extract was washed with a saturated saline solution and dried over anhydrous magnesium sulfate, and the solvent was distilled away under reduced pressure. The resultant residues were purified by alumina column chromatography (developing solvent; ethyl acetate), whereby 3-[1-acetyl-2,3-dihydro-1H-indol-5-yl]-3-hydroxy-N,N-dimethyl-1-propanamine (3.3 g) was obtained as colorless powder.

2) A mixture of 3-[1-acetyl-2,3-dihydro-1H-indol-5-yl]-3-hydroxy-N,N-dimethyl-1-propanamine (3.3 g) obtained in 1) above and concd. hydrochloric acid (20 ml) was heated for 16 hours under reflux. The reaction solution was cooled to room temperature, then concentrated under reduced pressure, diluted with water, made basic with 2 N aqueous sodium hydroxide and extracted with ethyl acetate. The extract was washed with a saturated saline solution and dried over anhydrous magnesium sulfate, and the solvent was distilled away under reduced pressure, whereby the title compound (2.3 g) was obtained as oily matter.

$^1$H NMR (CDCl$_3$) δ: 2.25 (6H, s), 2.97–3.04 (4H, m), 3.55 (2H, t, J=8.2 Hz), ca. 3.8 (1H, br.s, NH), 5.98–6.09 (1H, m), 6.41 (1H, d, J=16.2 Hz), 6.56 (1H, d, J=8.1 Hz), 7.02 (1H, dd, J=1.5, 8.1 Hz), 7.19 (1H, s).

Reference Example 14

1-(1,2,3,4-Tetrahydro-6-quinolinyl)-4-(dimethylamino)-1-butanone

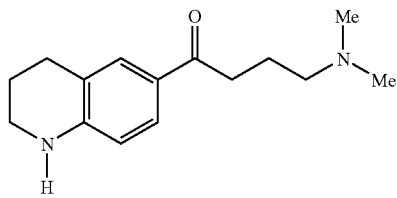

Using ethyl 3,4-dihydro-1(2H)-quinoline carboxylate, the title compound was obtained as viscous oily matter by the same procedures as in Reference Examples 1, 2 and 4.

$^1$H NMR (CDCl$_3$) δ: 1.87–2.00 (4H, m), 2.33 (6H, s), 2.48 (2H, t, J=7.4 Hz), 2.78 (2H, t, J=6.3 Hz), 2.91 (2H, t, J=7.2 Hz), 3.37 (2H, t, J=5.6 Hz), 4.4 (1H, br, NH), 6.39 (1H, d, J=9.2 Hz), 7.60–7.64 (2H, m).

Reference Example 15

4-Oxo-4-[2-(trifluoroacetyl)-1,2,3,4-- tetrahydro-7-isoquinolinyl]butanoic acid

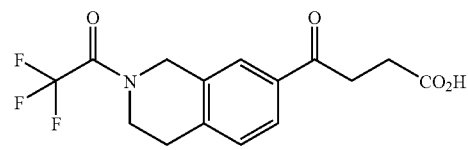

1) Trifluoroacetic anhydride (47.5 ml, 336 mmol) was added dropwise to a solution of 1,2,3,4-tetrahydroisoquinoline (25 g, 188 mmol) in THF (100 ml) at 0° C. and stirred for 2 hours at room temperature, and then the solvent was distilled away under reduced pressure. Water was poured into the residues which were then extracted with ethyl acetate, washed with 1 N hydrochloric acid, and dried over anhydrous magnesium sulfate. The solvent was distilled away under reduced pressure, whereby 43.5 g of 2-(trifluoroacetyl)-1,2,3,4-tetrahydroisoquinoline was obtained as oily matter.

$^1$H-NMR (CDCl$_3$) δ: 3.00–2.93 (2H, m), 3.92–3.80 (2H, m), 4.77 (2H, m), 7.28–7.13 (4H, m).

2) Aluminum chloride (26 g, 200 mmol) was added little by little to a mixture of 2-(trifluoroacetyl)-1,2,3,4-tetrahydroisoquinoline (10 g, 43.6 mmol) obtained in 1) above and succinic anhydride (4.8 g, 48 mmol) in dichloroethane at room temperature, and the mixture was stirred at 45° C. for 1 hour. The reaction solution was poured into iced water, extracted with ethyl acetate, washed with a saturated saline solution and dried over anhydrous magnesium sulfate. The solvent was distilled away under reduced pressure, and the residues were purified by silica gel column chromatography (developing solvent; hexane:ethyl acetate=1:1), whereby 7.5 g of the title compound was obtained as colorless powder.

$^1$H-NMR (DMSO-d$_6$) δ: 2.58 (2H, m), 3.00 (2H, m), 3.23 (2H, m), 3.83 (2H, m), 4.84 (2H, m), 7.38 (1H, m), 7.84 (1H, m), 7.93 (1H, m), 12.17 (1H, s).

Reference Example 16

4-Oxo-4-[3-(trifluoroacetyl)-2,3,4,5-tetrahydro-1H-3-benzazepin-7-yl]butanoic acid

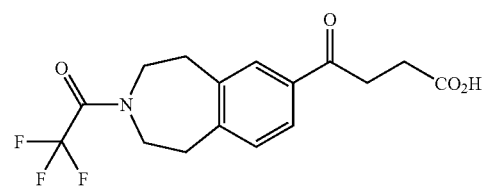

Using 2,3,4,5-tetrahydro-1H-3-benzazepine, the title compound was obtained as colorless powder by the same procedure as in Reference Example 15.

$^1$H-NMR (CDCl$_3$) δ: 2.81 (2H, t, J=6.4 Hz), 2.90–3.15 (4H, m), 3.29 (2H, t, J=6.4 Hz), 3.65–3.85 (4H, m), 7.20–7.33 (1H, m), 7.75–7.85 (2H, m), ca. 10 (1H, br).

Reference Example 17

N,N-Dipropyl-(4-ethoxycarbonylmethoxy-3-nitrophenyl) Acetamide

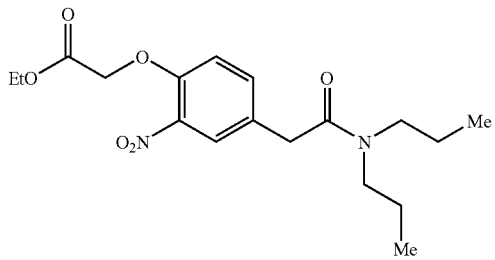

1) A solution of nitric acid (24.5 ml, 398 mmol) in acetic acid (20 ml) was slowly added dropwise under cooling with ice-bath to a solution of (4-hydroxyphenyl)acetic acid (50.4 g, 330 mmol) in acetic acid (230 ml) such that the temperature of the reaction solution did not exceed 10° C. After the reaction solution was stirred for 2 hours, water (1 L) was added dropwise thereto and the precipitated crystals were collected by filtration. The resultant crystals were washed with water and dried, whereby (4-hydroxy-3-nitrophenyl) acetic acid (49 g) was obtained as crystals with a mp of 144 to 146° C.

$^1$H-NMR (CDCl$_3$) δ: 3.76 (2H, s), 7.16 (1H, d, J=8.8 Hz), 7.53 (1H, dd, J=8.8, 2.2 Hz), 8.04 (1H, d, J=2.2 Hz).

2) Thionyl chloride (50 ml, 680 mmol) was added dropwise to a solution of (4-hydroxy-3-nitrophenyl)acetic acid (25 g, 127 mmol) obtained in 1) in THF (100 ml) at room temperature, and the mixture was heated under reflux for 2 hours. The reaction solution was concentrated, and the resultant residues were dissolved in chloroform (250 ml) and added dropwise over 1 hour to a solution of dipropylamine (35 ml, 255 mmol) in chloroform (300 ml) under cooling with ice-bath. After this addition, the reaction solution was washed with water and aqueous saturated sodium bicarbonate, and the organic layer was dried over anhydrous sodium sulfate and concentrated. The residues were crystallized from ethyl acetate-hexane, whereby N,N-dipropyl-(4-hydroxy-3-nitrophenyl) acetamide (26.5 g) was obtained as crystals with a mp of 55 to 57° C.

$^1$H-NMR (CDCl$_3$) δ: 0.8–1.0 (6H, m), 1.4–1.7 (4H, m), 3.2–3.4 (4H, m), 3.67 (2H, s), 7.12 (1H, d, J=8.6 Hz), 7.53 (1H, dd, J=8.6, 2.2 Hz), 7.96 (1H, d, J=2.2 Hz).

3) Potassium carbonate (7.4 g, 53 mmol) was added to a solution of N,N-dipropyl-(4-hydroxy-3-nitrophenyl) acetamide (3.5 g, 17.8 mmol) obtained in 2) above and ethyl bromoacetate (3.0 ml, 26.7 mmol) in DMF (40 ml). After the reaction solution was stirred overnight at room temperature, water was added to the reaction solution which was then extracted with ethyl acetate. The extract was washed with water, dried over anhydrous sodium sulfate and concentrated. The residues were recrystallized from ethyl acetate-hexane, whereby the title compound (4.9 g, 75%) was obtained as crystals with a mp of 79 to 80° C.

$^1$H-NMR (CDCl$_3$) δ: 0.8–1.0 (6H, m), 1.29 (3H, t, J=7.0 Hz), 1.4–1.7 (4H, m), 3.1–3.4 (4H, m), 3.68 (2H, s), 4.27 (2H, q, J=7.0 Hz), 4.76 (2H, s), 6.96 (1H, d, J=8.6 Hz), 7.38 (1H, dd, J=8.6, 2.2 Hz), 7.77 (1H, d, J=2.2 Hz). Elemental analysis for C$_{18}$H$_{26}$N$_2$O$_6$ Calcd.: C, 59.00; H, 7.15; N, 7.65. Found: C, 58.92; H, 7.15; N, 7.85.

Reference Example 18

Methyl 3-(4-ethoxycarbonylmethoxy-3-nitrophenyl) propionate

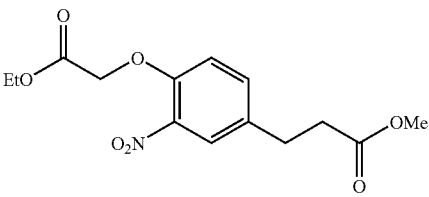

1) Using 3-(4-hydroxyphenyl)propionic acid, 3-(4-hydroxy-3-nitrophenyl)propionic acid was obtained as powder by the same procedure as in 1) in Reference Example 17.

$^1$H-NMR (CDCl$_3$) δ: 2.70 (2H, t, J=7.4 Hz), 2.95 (2H, t, J=7.4 Hz), 7.10 (1H, d, J=8.8 Hz), 7.46 (1H, dd, J=8.8, 2.0 Hz), 7.96 (1H, d, J=2.0 Hz). Melting point: 80–82° C. (crystallizing solvent: ethyl acetate-hexane)

2) Thionyl chloride (15 ml) was added dropwise to a solution of 3-(4-hydroxy-3-nitrophenyl)propionic acid (49 g, 232 mmol) obtained in 1) above in methanol (500 ml), and the mixture was stirred overnight at room temperature. After, the reaction solution was concentrated, water (500 ml) was added to the reaction solution which was then extracted with ethyl acetate. The extract was washed with water and aqueous saturated sodium bicarbonate, dried over magnesium sulfate and concentrated, whereby methyl 3-(4-hydroxy-3-nitrophenyl)propionate (47 g) was obtained as powder.

$^1$H-NMR (CDCl$_3$) δ: 2.64 (2H, t, J=7.4 Hz), 2.95 (2H, t, J=7.4 Hz), 3.68 (3H, s), 7.10 (1H, d, J=8.6 Hz), 7.46 (1H, dd, J=8.6, 2.2 Hz), 7.95 (1H, d, J=2.2 Hz). Melting point: 60–62° C. (crystallizing solvent: ethyl acetate-hexane)

3) Using methyl 3-(4-hydroxy-3-nitrophenyl)propionate obtained in 2) above, the title compound was obtained as powder by the same procedure as in 3) in Reference Example 17.

$^1$H-NMR (CDCl$_3$) δ: 1.28 (3H, t, J=7.0 Hz), 2.64 (2H, t, J=7.4 Hz), 2.95 (2H, t, J=7.4 Hz), 3.67 (3H, s), 4.26 (2H, q, J=7.0 Hz), 4.75 (2H, s), 6.93 (1H, d, J=8.6 Hz), 7.38 (1H, dd, J=8.6, 2.2 Hz), 7.72 (1H, d, J=2.2 Hz). Melting point: 70–72° C. (crystallizing solvent: ethyl acetate-hexane)

Reference Example 19

3,4-Dihydro-6-(3-iodopropyl)-4-(2-naphthalenesulfonyl)-2H-1,4-benzoxazine

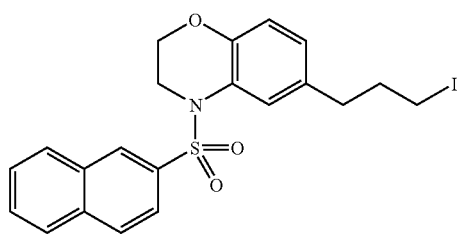

1) Using methyl 3-(4-ethoxycarbonylmethoxy-3-nitrophenyl)propionate obtained in Reference Example 18, methyl 3-(3,4-dihydro-2H-1,4-benzoxazine-3-oxo-6-yl)propionate was obtained as powder by the same procedure as in Example 133.

¹H-NMR (CDCl₃) δ: 2.60 (2H, t, J=7.4 Hz), 2.88 (2H, t, J=7.4 Hz), 3.68 (3H, s), 4.59 (2H, s), 6.7–7.0 (3H, m). Melting point: 131–132° C. (crystallizing solvent: ethyl acetate-hexane)

2) 1 N borane/THF solution (150 ml, 150 mmol) was added to a solution of methyl 3-(3,4-dihydro-2H-1,4-benzoxazine-3-oxo-6-yl)propionate (24 g, 102 mmol) obtained in 1) above in THF (400 ml) under cooling with ice-bath. The reaction solution was stirred overnight at room temperature, then 6 N hydrochloric acid (50 ml, 300 mmol) was added to the reaction solution which was then stirred for 2 hours, neutralized with 6 N aqueous sodium hydroxide and extracted with ethyl acetate. The extract was washed with water and a saturated saline solution, dried over magnesium sulfate, and concentrated. After triethylamine (25 g, 250 mmol) was added to a solution of the residues in acetonitrile (300 ml), a solution of 2-naphthalene sulfonyl chloride (56 g, 250 mmol) in acetonitrile (100 ml) was added thereto under cooling with ice-bath and stirred at room temperature for 4 hours. The reaction solution was concentrated, and water was added to the residues which were then extracted with ethyl acetate. The extract was washed with water and a saturated saline solution, dried over magnesium sulfate and concentrated. Sodium iodide (37.5 g, 250 mmol) was added to a solution of the residues in acetone (500 ml), and the mixture was stirred overnight at room temperature. The reaction solution was concentrated, and water (500 ml) was added to the concentrate which was then extracted with ethyl acetate. The extract was washed with water and a saturated saline solution, dried over magnesium sulfate and concentrated, whereby the title compound (22 g) was obtained as powder.

¹H-NMR (CDCl₃) δ: 2.0–2.2 (2H, m), 2.71 (2H, t, J=7.4 Hz), 3.18 (2H, t, J=7.2 Hz), 3.72 (2H, t, J=4.6 Hz), 3.93 (2H, t, J=4.6 Hz), 6.70 (1H, d, J=8.0 Hz), 6.90 (1H, dd, J=8.0, 1.8 Hz), 7.5–7.8 (4H, m), 7.8–8.0 (3H, m), 8.30 (1H, s). Melting point: 87–88° C. (crystallizing solvent: ethyl acetate-hexane)

Reference Example 20

N,N-Dipropyl-[4-(4-methoxyphenyl)carbonylmethoxy-3-nitrophenyl]acetamide

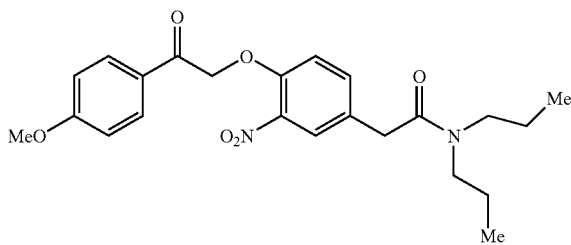

Using N,N-dipropyl-(4-hydroxy-3-nitrophenyl)acetamide obtained in 2) in Reference Example 17, the title compound was obtained as powder by the same procedure as in 3) in Reference Example 17.

¹H-NMR (CDCl₃) δ: 0.8–1.0 (6H, m), 1.4–1.7 (4H, m), 3.1–3.4 (4H, m), 3.65 (2H, s), 3.89 (3H, s), 5.34 (2H, s), 6.9–7.1 (3H, m), 7.40 (1H, dd, J=8.6, 2.2 Hz), 7.76 (1H, d, J=2.2 Hz), 8.00 (2H, d, J=9.0 Hz). Melting point: 95–97° C. (crystallizing solvent: ethyl acetate-hexane)

Reference Example 21

3-(4-Chlorophenyl)propylamine

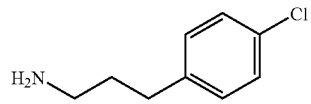

1) After a mixture of 3-(4-chlorophenyl)propionic acid (5.00 g, 27.0 mmol) and thionyl chloride (3 ml) was refluxed for 2 hours, an excess of the thionyl chloride was distilled away under reduced pressure. The resultant residues were dissolved in tetrahydrofuran (200 ml), dropped slowly to a suspension of LiAlH₄ in tetrahydrofuran at 0° C. and stirred at room temperature for 1 hour. Water and 1 N aqueous sodium hydroxide were added to the reaction mixture, and after insolubles were filtered off, the filtrate was dried over anhydrous magnesium sulfate. The solvent was distilled away under reduced pressure, whereby 4.6 g 3-(4-chlorophenyl)propyl alcohol was obtained as oily matter.

¹H-NMR (CDCl₃) δ: 1.86 (2H, tt, J=7.4, 7.4 Hz), 2.68 (2H, t, J=7.4 Hz), 3.67 (2H, t, J=7.4 Hz), 7.12 (2H, d, J=8.4 Hz), 7.27 (2H, d, J=8.4 Hz).

2) Mesyl chloride (2.10 ml, 27.1 mmol) was added to a solution of 3-(4-chlorophenyl)propyl alcohol (4.6 g, 27 mmol) obtained in 1) above and triethylamine (3.78 ml, 27.1 mmol) in tetrahydrofuran (100 ml) at 0° C. and stirred at room temperature for 30 minutes. Water was added to the reaction mixture which was then extracted with ethyl acetate. The extract was washed with an aqueous saturated NaCl solution and dried over anhydrous magnesium sulfate. After the solvent was distilled away under reduced pressure, the reaction mixture and potassium phthalimide (5.02 g, 27.1 mmol) were dissolved in dimethylformamide and heated at 80° C. for 10 hours under stirring. 8 N aqueous sodium hydroxide was added to the resultant solution which was then extracted with ethyl acetate. The extract was washed with an aqueous saturated NaCl solution and dried over anhydrous magnesium sulfate. The solvent was distilled away under reduced pressure, whereby 7.47 g 2-[3-(4-chlorophenyl)propyl]-1H-isoindole-1,3(2H)-dione was obtained as solid.

¹H-NMR (CDCl₃) δ: 2.00 (2H, tt, J=7.4, 7.4 Hz), 2.69 (2H, t, J=7.4 Hz), 3.73 (2H, t, J=7.4 Hz), 7.10–7.82 (4H, m), 7.69–7.89 (4H, m).

3) A solution of 2-[3-(4-chlorophenyl)propyl]-1H-isoindole-1,3(2H)-dione (7.47 g, 24.8 mmol) obtained in 2) above and hydrazine monohydrate (2.4 ml, 49.7 mmol) in ethanol was heated for 10 hours under reflux. After the solvent was distilled away, water was added to the residues which were then extracted with ethyl acetate. The extract was washed with an aqueous saturated NaCl solution and dried over anhydrous magnesium sulfate. The solvent was distilled away under reduced pressure, whereby 3.66 g of the title compound was obtained as oily matter.

¹H-NMR (CDCl₃) δ: 1.80 (2H, tt, J=7.4, 7.4 Hz), 2.63 (2H, t, J=7.4 Hz), 2.76 (2H, t, J=7.4 Hz), 3.08 (2H, s), 7.08–7.29 (4H, m).

Reference Example 22

2-[4-(4-Chlorophenyl)-1-piperidinyl]-2-oxoethylamine hydrochloride

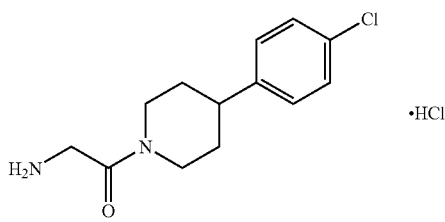

1) Diethyl cyanophosphate (1.29 ml) was added to a solution of 4-(4-chlorophenyl)-1-piperidine hydrochloride (1.80 g), N-(tert-butoxycarbonyl) glycine (1.49 g) and triethylamine (2.38 ml) in DMF (80 ml). The reaction mixture was stirred at room temperature for 4 hours, diluted with water and extracted with ether. The extract was washed with a saturated saline solution and dried over anhydrous magnesium sulfate, and the solvent was distilled away under reduced pressure. The residues were purified by silica gel column chromatography (n-hexane/ethyl acetate=1/1), whereby tert-butyl-2-[4-(4-chlorophenyl)-1-piperidinyl]-2-oxoethyl carbamate (2.48 g) was obtained.

$^1$H-NMR (CDCl$_3$) δ: 1.46 (9H, s), 1.50–1.70 (2H, m), 1.80–2.00 (2H, m), 2.60–2.90 (2H, m), 3.00–3.20 (1H, m), 3.75–3.90 (1H, m), 3.99 (2H, m), 4.70–4.80 (1H, m), 5.56 (1H, m), 7.11 (2H, d, J=8.4 Hz), 7.29 (2H, d, J=8.4 Hz).

2) tert-Butyl-2-[4-(4-chlorophenyl)-1-piperidinyl]-2-oxoethyl carbamate (2.48 g) obtained in 1) above was dissolved in 4 N hydrogen chloride in ethyl acetate (50 ml) and stirred at room temperature for 4 hours. The solvent was distilled away under reduced pressure, whereby the title compound (2.16 g) was obtained.

MS(ESI) (M+H): 253. $^1$H-NMR (CDCl$_3$) δ: 1.40–2.00 (4H, m), 2.65–3.00 (2H, m), 3.05–3.20 (1H, m), 3.75–4.00 (3H, m), 4.40–4.60 (1H, m), 7.27 (2H, d, J=8.8 Hz), 7.37 (2H, d, J=8.5 Hz), 8.25 (2H, m).

Reference Example 23

2-[4-(2-Methylphenyl)-1-piperidinyl]-2-oxoethylamine hydrochloride

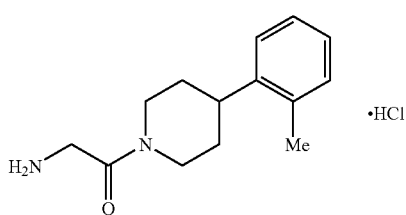

1) Using 4-(2-methylphenyl)-1-piperidine hydrochloride, tert-butyl-2-[4-(2-methylphenyl)-1-piperidinyl]-2-oxoethyl carbamate was obtained by the same procedure as in 1) in Reference Example 22.

$^1$H-NMR (CDCl$_3$) δ: 1.46 (9H, s), 1.55–1.75 (2H, m), 1.80–1.90 (2H, m), 2.36 (3H, s), 2.60–2.80 (1H, m), 2.90–3.20 (2H, m), 3.75–3.90 (1H, m), 4.01 (2H, m), 4.70–4.85 (1H, m), 5.58 (1H, m), 7.00–7.20 (4H, m).

2) Using tert-butyl-2-[4-(2-methylphenyl)-1-piperidinyl]-2-oxoethyl carbamate obtained in 1) above, the title compound was obtained by the same procedure as in 2) in Reference Example 22.

MS(ESI) (M+H): 233. $^1$H-NMR (CDCl$_3$) δ: 1.40–2.00 (4H, m), 2.32 (3H, s), 2.70–2.91 (1H, m), 2.95–3.30 (2H, m), 3.75–4.00 (3H, m), 4.40–4.60 (1H, m), 7.10–7.30 (4H, m), 8.25 (2H, m).

Reference Example 24

2-[4-(4-Fluorophenyl)-1-piperazinyl]-2-oxoethylamine dihydrochloride

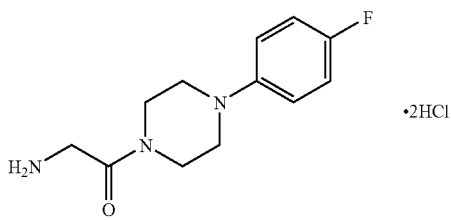

1) Using 1-(4-fluorophenyl) piperazine, tert-butyl-2-[4-(4-fluorophenyl)-1-piperazinyl]-2-oxoethyl carbamate was obtained by the same procedure as in 1) in Reference Example 22.

$^1$H-NMR (CDCl$_3$) δ: 1.46 (9H, s), 3.05–3.15 (4H, m), 3.55 (2H, t, J=5.1 Hz), 3.79 (2H, t, J=5.1 Hz), 4.01 (2H, d, J=4.5 Hz), 5.52 (1H, m), 6.85–7.05 (4H, m).

2) Using tert-butyl-2-[4-(4-fluorophenyl)-1-piperazinyl]-2-oxoethyl carbamate obtained in 1) above, the title compound was obtained by the same procedure as in 2) in Reference Example 22.

MS(ESI) (M+H): 238. $^1$H-NMR (CDCl$_3$) δ: 3.25–3.60 (4H, m), 3.70–4.00 (6H, m), 7.15–7.30 (3H, m), 7.30–7.50 (1H, m).

Reference Example 25

2-[4-(2-Methoxyphenyl)-1-piperazinyl]-2-oxoethylamine dihydrochloride

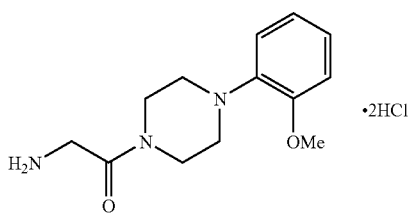

1) Using 1-(2-methoxyphenyl) piperazine, tert-butyl-2-[4-(2-methoxyphenyl)-1-piperazinyl]-2-oxoethyl carbamate was obtained by the same procedure as in 1) in Reference Example 22.

$^1$H-NMR (CDCl$_3$) δ: 1.46 (9H, s), 3.00–3.07 (4H, m), 3.56 (2H, t, J=5.4 Hz), 3.82 (2H, t, J=5.4 Hz), 3.88 (3H, s), 4.01 (2H, d, J=4.5 Hz), 5.56 (1H, m), 6.85–7.05 (4H, m).

2) Using tert-butyl-2-[4-(2-methoxyphenyl)-1-piperazinyl]-2-oxoethyl carbamate obtained in 1) above, the title compound was obtained by the same procedure as in 2) in Reference Example 22.

MS(ESI) (M+H): 250. ¹H-NMR (CDCl₃) δ: 3.20–3.50 (4H, m), 3.75–4.10 (6H, m), 3.87 (3H, s), 7.01 (1H, t, J=8.0 Hz), 7.15 (1H, d, J=8.0 Hz), 7.27 (1H, t, J=8.0 Hz), 7.49 (1H, d, J=8.0 Hz).

Reference Example 26

2-(4-Chlorophenoxy)ethylamine

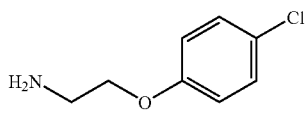

1) Sodium hydride (60% in oil, 640 mg, 16 mmol) was added to a solution of 4-chlorophenol (2 g, 15.6 mmol) in dimethylformamide (20 ml) and stirred at room temperature for 30 minutes, and then N-(2-bromoethyl) phthalimide (4 g, 15.6 mmol) was added thereto and heated at 50° C. for 2 hours under stirring. After the solvent was distilled away under reduced pressure, water was added to the residues which were then extracted with ethyl acetate. The extract was washed with an aqueous saturated NaCl solution and dried over anhydrous magnesium sulfate. The solvent was distilled away under reduced pressure, whereby 1.00 g of 2-[3-(4-chlorophenoxy)ethyl]-1H-isoindole-1,3(2H)-dione was obtained as powder.

¹H-NMR (CDCl₃) δ: 4.10 (2H, t, J=5.7 Hz), 4.18 (2H, t, J=5.7 Hz), 7.10–7.82 (4H, m), 7.69–7.89 (4H, m).

2) Using 2-[3-(4-chlorophenoxy)ethyl]-1H-isoindole-1,3(2H)-dione obtained in 1) above, the title compound was obtained by the same procedure as in 3) in Reference Example 21.

¹H-NMR (CDCl₃) δ: 3.10 (2H, t, J=5.4 Hz), 3.40 (2H, s), 3.98 (2H, t, J=5.4 Hz), 6.82 (2H, d, J=9.2 Hz), 7.24 (2H, d, J=9.2 Hz).

Reference Example 27 tert-Butyl 8-hydroxy-1,3,4,5-tetrahydro-2H-2-benzazepine-2-carboxylate

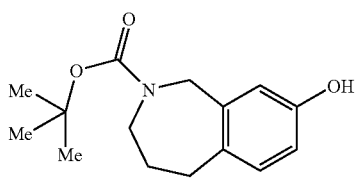

2 N sodium hydroxide (40 ml) and t-butyl dicarbonate were added at 0° C. to a solution of 2,3,4,5-tetrahydro-1H-2-benzazepin-8-ol hydrobromate (12.0 g, 49.2 mm) in chloroform (40 ml) and water (40 ml), and the mixture was stirred at room temperature for 16 hours. Ethyl acetate was added to the resulting mixture which was then washed with a saturated saline solution and dried over anhydrous sodium sulfate. The solvent was concentrated under reduced pressure, and the resultant residues were formed into powder with ethyl acetate-isopropyl ether, to give the title compound (7.99 g).

¹H NMR (CDCl₃) δ: 1.40 (9H, s), 1.73 (2H, m), 2.86 (2H, m), 3.67 (2H, m), 4.30–4.36 (2H, m), 6.61–6.70 (2H, m), 6.98 (1H, m).

Reference Example 28

1-[(4-Phenyl-1-piperidinyl)carbonyl]-1,2,3,4-tetrahydroquinoline

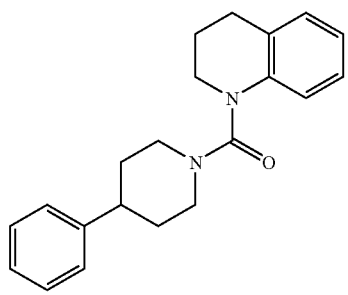

1) 1,2,3,4-Tetrahydroquinoline (1 ml, 7.97 mmol) was dissolved in THF (20 ml), and pyridine (1.58 ml, 15.93 mmol) was added thereto and cooled on ice. p-Nitrophenyl chloroformate (1.61 g, 7.97 mmol) was added to the reaction solution and stirred at room temperature for 4 hours, then water and a saturated saline solution were added, and the reaction solution was extracted with ethyl acetate. The extract was dried over magnesium sulfate and concentrated under reduced pressure, whereby 2.57 g 4-nitrophenyl 3,4-dihydroquinoline-1(2H)-carboxylate was obtained as pale yellow solution.

2) 4-Nitrophenyl 3,4-dihydroquinoline-1(2H)-carboxylate obtained in 1) above was dissolved in DMSO (10 ml), and 4-phenylpiperidine hydrochloride (1.58 g, 7.97 mmol) and 4 N aqueous sodium hydroxide (2.09 ml, 8.36 mmol) were added thereto and stirred at room temperature for 22.5 hours. 60 ml ethyl acetate was added to the reaction solution which was then washed with an aqueous potassium carbonate solution and a saturated saline solution. The organic layer was dried over magnesium sulfate and concentrated under reduced pressure, and the resultant residues were purified by silica gel column chromatography (developing solvent; hexane:ethyl acetate=2:1), whereby 2.10 g of the title compound was obtained as pale yellow liquid.

¹H-NMR (CDCl₃) δ: 1.68 (2H, m), 1.80 (2H, m), 1.98 (2H, m), 2.65 (1H, m), 2.78 (2H, dd, J=6.6 and 6.9 Hz), 2.85 (2H, m), 3.62 (2H, t, J=6.1 Hz), 3.95 (2H, m), 6.90 (1H, m), 7.04–7.32 (8H, m).

Example 1

3-[1-([1,1'-Biphenyl]-4-ylcarbonyl)-1,2,3,4-tetrahydro-6-quinolinyl]-N,N-dimethyl-1-propanamine

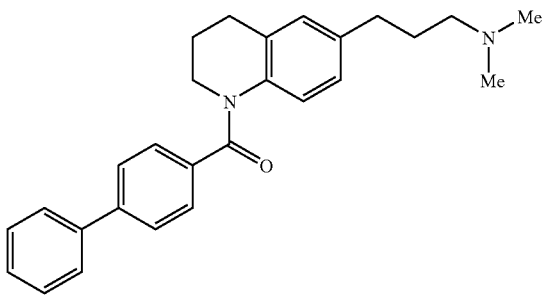

Biphenylcarbonyl chloride (327 mg, 1.51 mmol) was added to a solution of N,N-dimethyl-3-(1,2,3,4-tetrahydro-6-quinolinyl)-1-propanamine dihydrochloride (400 mg, 1.37 mmol) obtained in Reference Example 4 and triethylamine (669 ml, 4.81 mmol) in dimethylformamide under cooling with ice-bath, and the mixture was stirred at room temperature for 3 days. Ethyl acetate was added to the reaction solution which was then washed with an aqueous saturated sodium bicarbonate solution and a saturated saline solution and dried over anhydrous sodium sulfate, and the solvent was distilled away under reduced pressure. The resultant residues were purified by alumina column chromatography (developing solvent; hexane:ethyl acetate=3:1) and crystallized from hexane, whereby the title compound (113 mg) was obtained as colorless powder with a mp. of 100 to 101° C.

$^1$H NMR (CDCl$_3$) δ: 1.73 (2H, m), 2.06 (2H, m), 2.20 (6H, s), 2.26 (2H, m), 2.54 (2H, m), 2.83 (2H, m), 3.92 (2H, t-like), 6.72 (2H, m), 6.99 (1H, s), 7.35–7.60 (9H, m). Elemental analysis for C$_{27}$H$_{30}$N$_2$O Calcd.: C, 81.37; H, 7.59; N, 7.03. Found: C, 81.26; H, 7.46; N, 7.05.

Example 2

(E)-3-[1-([1,1'-Biphenyl]-4-ylcarbonyl)-2,3,4,5-tetrahydro-1H-1-benzazepin-8-yl]-N,N-dimethyl-2-propen-1-amine hydrochloride

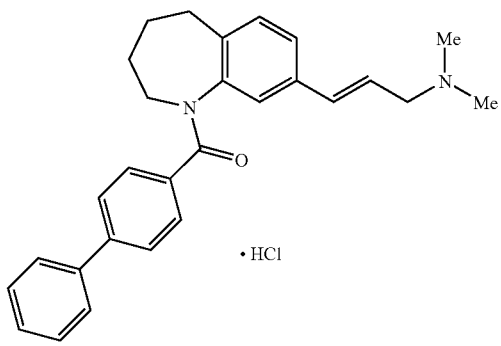

Biphenylcarbonyl chloride (423 mg, 1.95 mmol) was added to a solution of (E)-N,N-dimethyl-3-(2,3,4,5-tetrahydro-1H-1-benzazepin-8-yl)-2-propene-1-amine (300 mg, 1.30 mmol) obtained in Reference Example 10, sodium hydroxide (130 mg, 3.26 mmol) and tetrabutylammonium hydrogensulfate (4.4 mg, 13.0 mmol) in tetrahydrofuran under cooling with ice-bath, and the mixture was stirred at room temperature for 5 hours. Ethyl acetate was added to the reaction solution which was then washed with a saturated saline solution and dried over anhydrous sodium sulfate, and the solvent was distilled away under reduced pressure. The resultant residues were purified by alumina column chromatography (developing solvent; hexane:ethyl acetate=3:1). 4 N hydrogen chloride in ethyl acetate was added to the resultant oily matter, and the formed crystals were washed with diethyl ether, whereby the title compound (124 mg) was obtained as colorless powder with a mp. of 112 to 113° C.

$^1$H NMR (CDCl$_3$, free base) δ: 1.53 (1H, m), 1.96 (2H, m), 2.15 (6H, s), 2.77–3.07 (6H, m), 5.04 (1H, m), 5.93 (1H, dt, J=6.6, 15.8 Hz), 6.20 (1H, d, J=15.8 Hz), 6.68 (1H, s), 7.02–7.51 (11H, m). Elemental analysis for C$_{28}$H$_{30}$N$_2$O.HCl.1.5H$_2$O Calcd.: C, 70.94; H, 7.23; N, 5.91. Found: C, 71.40; H, 7.31; N, 6.11.

Example 3

3-[1-([1,1'-Biphenyl]-4-ylcarbonyl)-2,3,4,5-tetrahydro-1H-1-benzazepin-8-yl]-N,N-dimethyl-1-propanamine hydrochloride

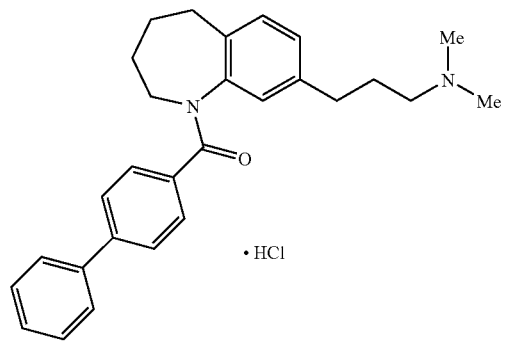

Palladium-carbon (200 mg) was added to a solution of (E)-3-[1-([1,1'-biphenyl]-4-ylcarbonyl)-2,3,4,5-tetrahydro-1H-1-benzazepin-8-yl]-N,N-dimethyl-2-propen-1-amine (238 mg, 0.580 mmol) obtained in Example 2 in tetrahydrofuran, and the mixture was stirred in a hydrogen atmosphere for 1.5 days. The catalyst was filtered off, and the solvent was distilled away under reduced pressure. The resultant residues were purified by alumina column chromatography (developing solvent; hexane:ethyl acetate=3:1). 4 N hydrogen chloride in ethyl acetate was added to the resultant oily matter, and the formed crystals were washed with diethyl ether, whereby the title compound (97.9 mg) was obtained as colorless powder with a mp. of 84 to 86° C.

$^1$H NMR (CDCl$_3$, free base) δ 1.35–1.52 (3H, m), 1.93–2.00 (10H, m), 2.33 (2H, m), 2.79–3.02 (4H, m), 5.04 (1H, m), 6.49 (1H, s), 6.89 (1H, m), 7.12 (1H, d, J=7.8 Hz), 7.22–7.52 (9H, m). Elemental analysis for C$_{28}$H$_{32}$N$_2$O.HCl.H$_2$O Calcd.: C, 72.01; H, 7.55; N, 6.00. Found: C, 71.88; H, 7.56; N, 5.99.

Example 4

3-[1-([4'-Chloro[1,1-biphenyl]-4-yl)carbonyl)-1,2,3,4-tetrahydro-6-quinolinyl]-3-hydroxy-N,N-dimethyl-1-propanamine

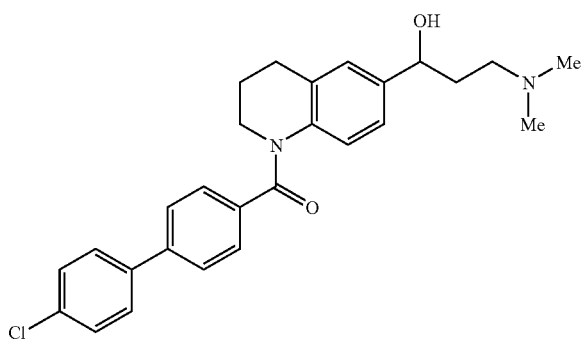

Sodium borohydride (0.6 g) was added to a solution of (E)-1-[(4'-chloro[1,1'-biphenyl]-4-yl)carbonyl]-1,2,3,4-tetrahydro-6-quinolinyl]-3-(dimethylamino)-2-propen-1-one (0.3 g) obtained in Reference Example 6 in methanol (30 ml), and the mixture was heated for 3 hours under reflux. After the solvent was distilled away under reduced pressure, the residues were dissolved in water-ethyl acetate and extracted with ethyl acetate. The extract was washed with water and dried over anhydrous magnesium sulfate, and the solvent was distilled away under reduced pressure. The resultant residues were purified by alumina column chromatography (developing solvent; ethyl acetate), whereby the title compound (0.1 g) was obtained as amorphous powder.

$^1$H NMR (CDCl$_3$) δ: 1.72–1.80 (2H, m), 2.00–2.12 (2H, m), 2.28 (6H, s), 2.40–2.50 (1H, m), 2.60–2.70 (1H, m), 2.87 (2H, t, J=6.7 Hz), 3.04 (2H, d, J=6.6 Hz), 4.83 (1H, t, J=5.9 Hz), 6.70–6.75 (1H, m), 6.87 (1H, d, J=8.4 Hz), 7.22 (1H, s), 7.37–7.52 (8H, m).

Example 5

(E)-3-[1-[(4'-Chloro[1,1-biphenyl]-4-yl)carbonyl]-1,2,3,4-tetrahydro-6-quinolinyl]-N,N-dimethyl-2-propen-1-amine

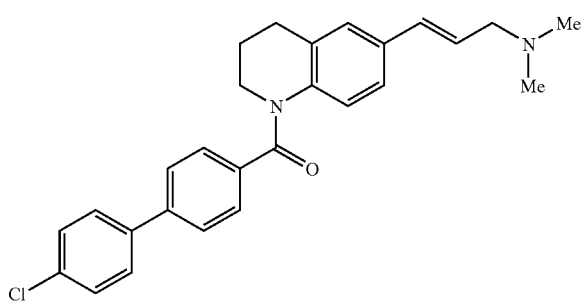

Concd. sulfuric acid (4 drops) was added to a solution of 3-[1-[(4'-chloro[1,1-biphenyl]-4-yl)carbonyl]-1,2,3,4-tetrahydro-6-quinolinyl]-3-hydroxy-N,N-dimethyl-1-propanamine (0.1 g) obtained in Example 4 in acetic acid (1 mL), and the mixture was stirred at 50 to 55° C. for 3 hours. After the solvent was distilled away under reduced pressure, the residues were made basic with 2 N aqueous sodium hydroxide and then extracted with ethyl acetate. The extract was washed with water and dried over anhydrous magnesium sulfate, and the solvent was distilled away under reduced pressure. The resultant residues were purified by alumina column chromatography (developing solvent; ethyl acetate) and crystallized from diethyl ether, whereby the title compound (75 mg) was obtained as colorless powder with a mp of 162 to 164° C.

$^1$H NMR (CDCl$_3$) δ: 2.02–2.13 (2H, m), 2.26 (6H, s), 2.85 (2H, t, J=6.6 Hz), 3.04 (2H, d, J=6.4 Hz), 3.93 (2H, t, J=6.4 Hz), 6.16 (1H, dt, J=6.4, 15.9 Hz), 6.40 (1H, d, J=15.9 Hz), 6.68 (1H, d, J=8.5 Hz), 6.91 (1H, d, J=8.5 Hz), 7.19 (1H, s), 7.37–7.53 (8H, m). Elemental analysis for C$_{27}$H$_{27}$ClN$_2$O Calcd.: C, 75.25; H, 6.31; N, 6.50. Found: C, 74.90; H, 6.52; N, 6.35.

Example 6

1-[(4'-Chloro[1,1-biphenyl]-4-yl)carbonyl]-6-[(E)-3-piperidino-1-propenyl]-1,2,3,4-tetrahydroquinoline

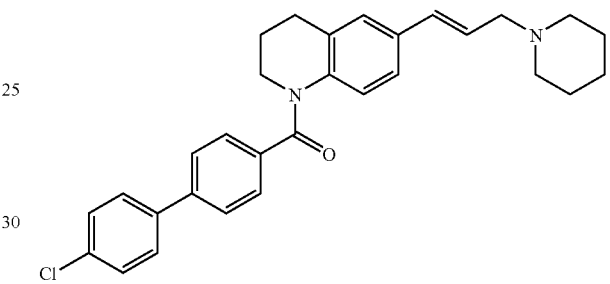

Using (E)-1-[1-[(4'-chloro[1,1'-biphenyl]-4-yl) carbonyl]-1,2,3,4-tetrahydro-6-quinolinyl]-3-piperidino-2-propen-1-one obtained in Reference Example 11, the title compound was obtained as colorless crystals with a mp of 141 to 143° C. by the same procedures as in Examples 4 and 5.

$^1$H NMR (CDCl$_3$) δ: 1.42–1.65 (6H, m), 2.00–2.09 (2H, m), 2.35–2.48 (4H, m), 2.84 (2H, t, J=6.4 Hz), 3.08 (2H, d, J=6.7 Hz), 3.92 (2H, t, J=6.4 Hz), 6.20 (1H, dt, J=6.7, 15.6 Hz), 6.38 (1H, d, J=15.6 Hz), 6.66 (1H, d, J=8.5 Hz), 6.89 (1H, d, J=8.5 Hz), 7.18 (1H, s), 7.38–7.52 (8H, m). Elemental analysis for C$_{30}$H$_{31}$ClN$_2$O Calcd.: C, 76.50; H, 6.63; N, 5.95. Found: C, 76.40; H, 6.64; N, 5.65.

Example 7

(E)-3-[1-[([1,1'-Biphenyl]-4-yl)carbonyl]-2,3-dihydro-1H-indol-5-yl]-N,N-dimethyl-2-propen-1-amine

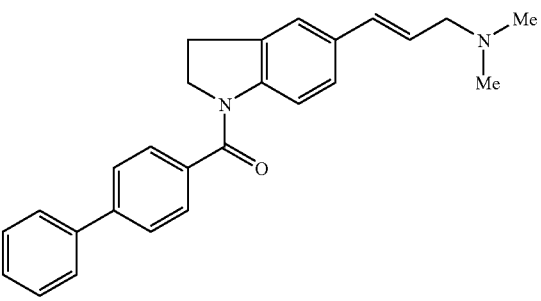

Using (E)-3-[2,3-dihydro-1H-indol-5-yl]-N,N-dimethyl-2-propen-1-amine obtained in Reference Example 13, the title compound was obtained as colorless crystals with a mp of 174 to 176° C. by the same procedure as in Example 2.

¹H NMR (CDCl₃) δ: 2.27 (6H, s), 3.06 (2H, d, J=6.0 Hz), 3.13 (2H, t, J=8.1 Hz), 4.15 (2H, br), 6.11–6.23 (1H,m), 6.46 (1H, d, J=15.9 Hz), 7.06–7.28 (2H, m), 7.36–7.51 (3H, m), 7.61–7.70 (7H, m). Elemental analysis for $C_{26}H_{26}N_2O$ Calcd.: C, 81.64; H, 6.85; N, 7.32. Found: C, 81.31; H, 6.84; N, 7.29.

Example 8

(E)-3-[1-[(4'-Chloro[1,1'-biphenyl]-4-yl)carbonyl]-2,3-dihydro-1H-indol-5-yl]-N,N-dimethyl-2-propen-1-amine

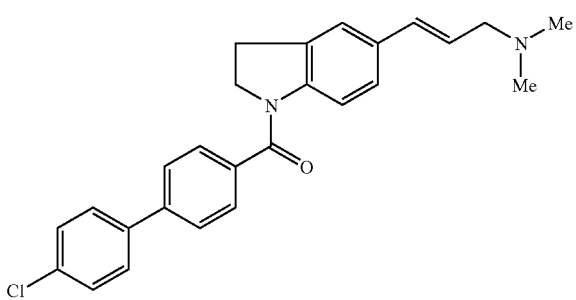

Using (E)-3-[2,3-dihydro-1H-indol-5-yl]-N,N-dimethyl-2-propen-1-amine obtained in Reference Example 13, the title compound was obtained as colorless crystals with a mp of 208 to 211° C. by the same procedure as in Example 2.

¹H NMR (CDCl₃) δ: 2.27 (6H, s), 3.06 (2H, d, J=6.6 Hz), 3.12 (2H, t, J=8.2 Hz), 4.14 (2H, br), 6.12–6.23 (1H, m), 6.46 (1H, d, J=15.3 Hz), 7.06–7.28 (2H, m), 7.44 (2H, d, J=6.6 Hz), 7.56 (2H, d, J=6.6 Hz), 7.63 (5H, s).

Example 9

(E)-3-[1-[4-[(4-Methoxybenzyl)oxy]benzoyl]-2,3-dihydro-1H-indol-5-yl]-N,N-dimethyl-2-propen-1-amine

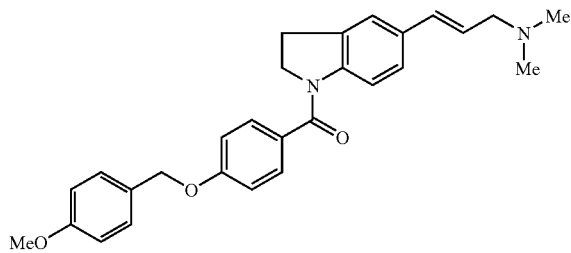

Using (E)-3-[2,3-dihydro-1H-indol-5-yl]-N,N-dimethyl-2-propen-1-amine obtained in Reference Example 13, the title compound was obtained as colorless crystals with a mp of 164 to 166° C. by the same procedure as in Example 2.

¹H NMR (CDCl₃) δ: 2.27 (6H, s), 3.04–3.12 (4H, m), 3.83 (3H, s), 4.12 (2H, t, J=8.2 Hz), 5.04 (2H, s), 6.10–6.21 (1H, m), 6.45 (1H, d, J=15.9 Hz), 6.90–7.30 (7H, m), 7.37 (2H, d, J=8.7 Hz), 7.54 (2H, d, J=8.4 Hz). Elemental analysis for $C_{28}H_{30}N_2O_3$ Calcd.: C, 75.99; H, 6.83; N, 6.33. Found: C, 75.77; H, 6.86; N, 6.21.

Example 10

1-[1-[(4'-Chloro[1,1'-biphenyl]-4-yl)carbonyl]-1,2,3,4-tetrahydro-6-quinolinyl]-4-(dimethylamino)-1-butanone

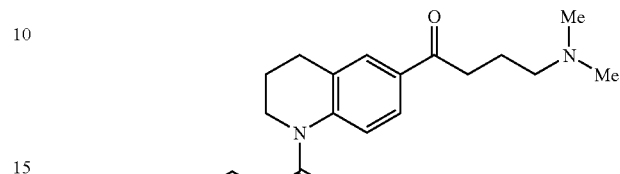

Using 1-(1,2,3,4-tetrahydro-6-quinolinyl)-4-(dimethylamino)-1-butanone obtained in Reference Example 14, the title compound was obtained as oily matter by the same procedure as in Reference Example 5.

¹H NMR (CDCl₃) δ: 1.84–1.96 (2H, m), 2.04–2.13 (2H, m), 2.21 (6H, s), 2.33 (2H, t, J=7.1 Hz), 2.90–3.20 (4H, m), 3.95 (2H, t, J=6.4 Hz), 6.85 (1H, d, J=8.6 Hz), 7.38–7.62 (9H, m), 7.82 (1H, s).

Example 11

(E)-4-[1-[(4'-Chloro[1,1'-biphenyl]-4-yl)carbonyl]-1,2,3,4-tetrahydro-6-quinolinyl]-N,N-dimethyl-3-buten-1-amine

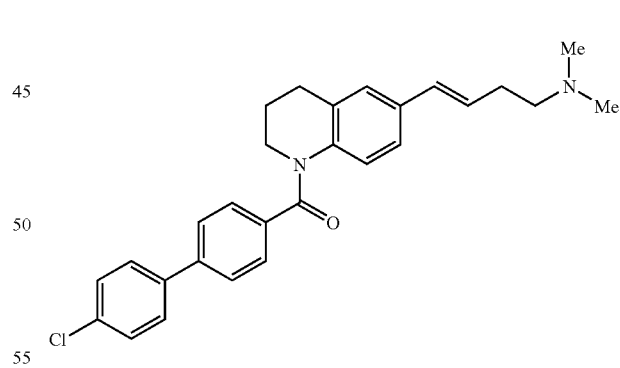

Using 1-[1-[(4'-chloro[1,1'-biphenyl]-4-yl)carbonyl]-1,2,3,4-tetrahydro-6-quinolinyl]-4-(dimethylamino)-1-butanone obtained in Example 10, the title compound was obtained as colorless crystals with a mp of 142 to 144° C. by the same procedures as in Examples 4 and 5.

¹H NMR (CDCl₃) δ: 2.01–2.11 (2H, m), 2.25 (6H, s), 2.28–2.43 (4H, m), 2.84 (2H, t, J=6.6 Hz), 3.92 (2H, t, J=6.4 Hz), 6.06–6.18 (1H, m), 6.32 (1H, d, J=15.6 Hz), 6.63 (1H, brd, J=8.1 Hz), 6.86 (1H, d, J=8.4 Hz), 7.15 (1H, s), 7.37–7.52 (8H, m).

Example 12

4-[4-(4-Chlorophenyl)-1-piperidinyl]-4-oxo-1-[2-(trifluoroacetyl)-1,2,3,4-tetrahydro-7-isoquinolinyl]-1-butanone

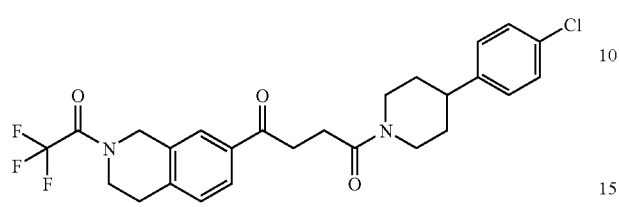

A solution of 4-oxo-4-[2-(trifluoroacetyl)-1,2,3,4-tetrahydro-7-isoquinolinyl]butanoic acid (1.0 g, 3.04 mmol) obtained in Reference Example 15, 4-chlorophenyl piperidine hydrochloride (708 mg, 3.05 mmol) and triethylamine (0.85 ml, 6.1 mmol) in dimethylformamide (8 ml) was stirred at room temperature for 20 minutes and then cooled to 0° C. Diethyl cyanophosphate (0.463 ml, 3.05 mmol) was added to the reaction mixture, stirred at 0° C. for 30 minutes, poured into water and extracted with ethyl acetate. The extract was washed with a saturated saline solution and dried over anhydrous magnesium sulfate. The solvent was distilled away under reduced pressure and purified by silica gel column chromatography (developing solvent; ethyl acetate), whereby 1.1 g of the title compound was obtained as colorless crystals.

$^1$H-NMR (CDCl$_3$) δ: 1.57 (2H, m), 1.90 (2H, m), 2.68 (2H, m), 2.85 (2H, m), 3.00 (2H, m), 3.13 (1H, m), 3.33 (2H, m), 3.88 (2H, m), 4.13 (1H, m), 4.74 (1H, m), 4.81 (2H, m), 7.31–7.12 (5H, m), 7.93–7.79 (2H, m). Melting point: 142° C. (dec.) (crystallizing solvent: ethanol-diisopropyl ether).

Example 13

4-[4-(4-Chlorophenyl)-1-piperidinyl]-4-oxo-1-(1,2,3,4-tetrahydro-7-isoquinolinyl]-1-butanone

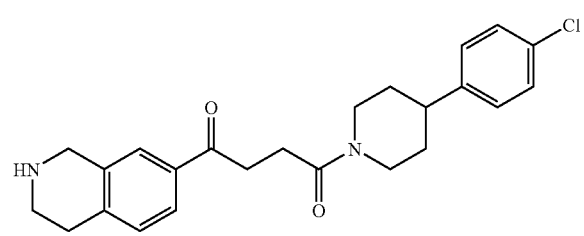

A solution of 4-[4-(4-chlorophenyl)-1-piperidinyl]-4-oxo-1-[2-(trifluoroacetyl)-1,2,3,4-tetrahydro-7-isoquinolinyl]-1-butanone (1.1 g, 2.17 mmol) and potassium carbonate (900 mg, 6.5 mmol) in a mixed solvent of water (10 ml) and methanol (40 ml) was stirred at room temperature for 2 hours and then extracted with ethyl acetate. The extract was washed with a saturated saline solution and dried over anhydrous magnesium sulfate. The solvent was distilled away under reduced pressure, whereby 810 mg of the title compound was obtained as colorless powder.

$^1$H-NMR (CDCl$_3$) δ: 1.60 (2H, m), 1.89 (2H, m), 2.91–2.61 (6H, m), 3.19 (2H, m), 3.33 (2H, t, J=6.6 Hz), 3.70 (2H, q, J=6.9 Hz), 4.10 (2H, s), 4.14 (1H, d, J=13.2 Hz), 4.75 (1H, d, J=13.2 Hz), 7.28–7.12 (5H, m), 7.70 (1H, s), 7.80 (1H, d, J=8.1 Hz). Melting point: 121–122° C. (crystallizing solvent: ethanol-diisopropyl ether)

Example 14

4-[4-(4-Chlorophenyl)-1-piperidinyl]-4-oxo-1-[3-(trifluoroacetyl)-2,3,4,5-tetrahydro-1H-3-benzazepin-7-yl]-1-butanone

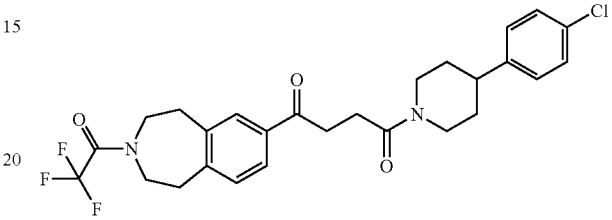

Using 4-oxo-4-[3-(trifluoroacetyl)-2,3,4,5-tetrahydro-1H-3-benzazepin-7-yl]butanoic acid obtained in Reference Example 16, the title compound was obtained as colorless powder by the same procedure as in Example 12.

$^1$H-NMR (CDCl$_3$) δ: 1.45–2.00 (4H, m), 2.55–2.90 (4H, m), 2.97–3.28 (5H, m), 3.34 (2H, t, J=6.4 Hz), 3.64–3.84 (4H, m), 4.04–4.21 (1H, m), 4.68–4.84 (1H, m), 7.14 (2H, d, J=8.4 Hz), 7.20–7.34 (3H, m), 7.80–7.90 (2H, m). Elemental analysis for C$_{27}$H$_{28}$ClF$_3$N$_2$O$_3$ Calcd.: C, 62.25; H, 5.42; N, 5.38. Found: C, 62.23; H, 5.44; N, 5.29. Melting point: 131–132° C. (crystallizing solvent: isopropanol-diisopropyl ether)

Example 15

4-[4-(4-Chlorophenyl)-1-piperidinyl]-4-oxo-1-(2,3,4,5-tetrahydro-1H-3-benzazepin-7-yl)-1-butanone

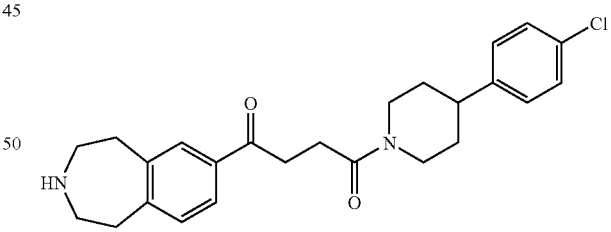

Using 4-[4-(4-chlorophenyl)-1-piperidinyl]-4-oxo-1-[3-(trifluoroacetyl)-2,3,4,5-tetrahydro-1H-3-benzazepin-7-yl]-1-butanone obtained in Example 14, the title compound was obtained as colorless powder by the same procedure as in Example 13.

$^1$H-NMR (CDCl$_3$) δ: 1.47–2.00 (4H, m), 2.57–2.88 (5H, m), 2.98 (8H, br), 3.07–3.27 (1H, m), 3.50 (2H, t, J=6.6 Hz), 4.05–4.21 (1H, m), 4.72–4.84 (1H, m), 7.10–7.34 (5H, m), 7.74–7.83 (2H, m). Elemental analysis for C$_{25}$H$_{29}$ClN$_2$O$_2$ Calcd.: C, 70.66; H, 6.88; N, 6.59. Found: C, 70.22; H, 7.13; N, 6.51. Melting point: 148–149° C. (crystallizing solvent: ethanol)

Example 16

4-[4-(4-Chlorophenyl)-1-piperidinyl]-4-oxo-1-(3-methyl-2,3,4,5-tetrahydro-1H-3-benzazepin-7-yl)-1-butanone

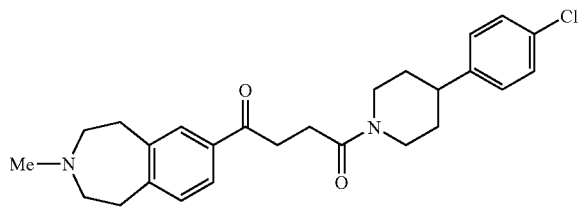

A mixture of 4-[4-(4-chlorophenyl)-1-piperidinyl]-4-oxo-1-(2,3,4,5-tetrahydro-1H-3-benzazepin-7-yl)-1-butanone (0.3 g, 0.70 mmol) obtained in Example 15, formaldehyde (0.086 ml, 1.06 mmol) and formic acid (0.9 ml) was heated at 100° C. for 4 hours, then poured into water, made basic with 8 N aqueous sodium hydroxide and extracted with ethyl acetate. The extract was washed with water and then with a saturated saline solution, and dried over anhydrous magnesium sulfate. After the solvent was distilled away under reduced pressure, the residues were purified by alumina column chromatography (developing solvent; ethyl acetate-methanol=10:1), whereby 0.15 g of the title compound was obtained as colorless powder.

$^1$H-NMR (CDCl$_3$) δ: 1.47–2.00 (4H, m), 2.38 (3H, s), 2.47–2.88 (8H, m), 2.95–3.06 (4H, m), 3.08–3.28 (1H, m), 3.35 (2H, t, J=6.8 Hz), 4.07–4.21 (1H, m)., 4.71–4.86 (1H, m), 7.08–7.34 (5H, m), 7.75–7.85 (2H, m). Elemental analysis for C$_{26}$H$_{31}$ClN$_2$O$_2$ Calcd.: C, 71.14; H, 7.12; N, 6.38. Found: C, 70.92; H, 7.35; N, 6.41. Melting point: 143–145° C. (crystallizing solvent: ethyl acetate-diethyl ether)

Example 17

4-[4-(4-Chlorophenyl)-1-piperidinyl]-1-(3-ethyl-2,3,4,5-tetrahydro-1H-3-benzazepin-7-yl)-4-oxo-1-butanone

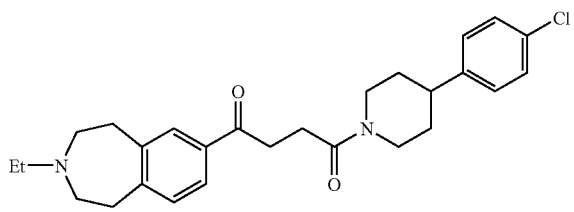

A solution of 4-[4-(4-chlorophenyl)-1-piperidinyl]-4-oxo-1-(2,3,4,5-tetrahydro-1H-3-benzazepin-7-yl)-1-butanone (200 mg, 0.47 mmol) obtained in Example 15, iodoethane (0.0376 ml, 0.47 mmol) and potassium carbonate (138 mg, 1.0 mmol) in acetonitrile (5 ml) was stirred at room temperature for 12 hours, then poured into water and extracted with ethyl acetate. The extract was washed with a saturated saline solution and dried over anhydrous magnesium sulfate. The solvent was distilled away under reduced pressure, and the residues were purified by alumina silica gel column chromatography (developing solvent; ethyl acetate), whereby 101 mg of the title compound was obtained as colorless powder.

$^1$H-NMR (CDCl$_3$) δ: 1.10 (3H, t, J=7.0 Hz), 1.62 (2H, m), 1.94 (2H, m), 2.72–2.52 (8H, m), 2.79 (2H, t, J=6.4 Hz), 2.97 (4H, m), 3.23 (1H, m), 3.35 (2H, t, J=6.6 Hz), 4.13 (1H, d, J=15.6 Hz), 4.76 (1H, d, J=12 Hz), 7.35–7.11 (5H, m), 7.79 (2H, m). Melting point: 156–157° C. (crystallizing solvent: ethanol-diisopropyl ether)

Example 18

4-[4-(4-Chlorophenyl)-1-piperidinyl]-4-oxo-1-(3-propyl-2,3,4,5-tetrahydro-1H-3-benzazepin-7-yl)-1-butanone

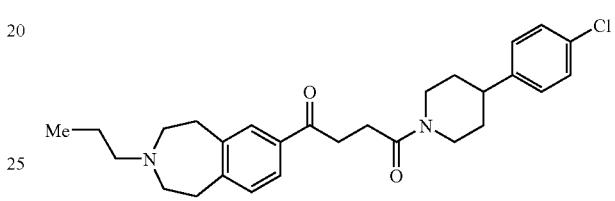

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^1$H-NMR (CDCl$_3$) δ: 0.91 (3H, t, J=7.2 Hz), 1.62 (4H, m), 1.89 (2H, m), 2.45 (2H, t, J=8.0 Hz), 2.72–2.66 (6H, m), 2.79 (2H, t, J=6.4 Hz), 2.97 (4H, m), 3.23 (1H, m), 3.35 (2H, t, J=6.6 Hz), 4.13 (1H, d, J=15.6 Hz), 4.76 (1H, d, J=12 Hz), 7.35–7.11 (5H, m), 7.79 (2H, m). Melting point: 151–152° C. (crystallizing solvent: ethanol-diisopropyl ether)

Example 19

1-(3-Benzyl-2,3,4,5-tetrahydro-1H-3-benzazepin-7-yl)-4-[4-(4-chlorophenyl)-1-piperidinyl]-4-oxo-1-butanone

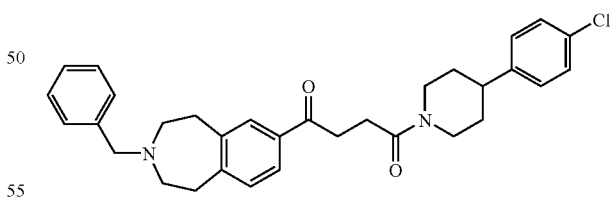

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^1$H-NMR (CDCl$_3$) δ: 1.64 (2H, m), 1.89 (2H, m), 2.72–2.65 (6H, m), 2.85 (2H, t, J=6.4 Hz), 2.97 (4H, m), 3.23 (1H, m), 3.34 (2H, t, J=6.6 Hz), 3.64 (2H, s), 4.13 (1H, d, J=15.6 Hz), 4.76 (1H, d, J=12 Hz), 7.35–7.11 (10H, m), 7.79 (2H, m). Melting point: 133–134° C. (crystallizing solvent: ethanol-diisopropyl ether)

Example 20

1-(3-Benzoyl-2,3,4,5-tetrahydro-1H-3-benzazepin-7-yl)-4-[4-(4-chlorophenyl)-1-piperidinyl]-4-oxo-1-butanone

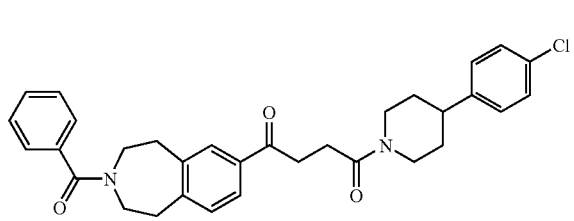

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^1$H-NMR (CDCl$_3$) δ: 1.64 (2H, m), 1.89 (2H, m), 3.17–2.59 (9H, m), 3.34 (2H, t, J=6.6 Hz), 3.53 (2H, m), 3.87 (2H, m), 4.13 (1H, d, J=15.6 Hz), 4.76 (1H, d, J=12 Hz), 7.35–7.11 (10H, m), 7.79 (2H, m). Melting point: 158–160° C. (crystallizing solvent: ethanol-diisopropyl ether)

Example 21

4-[4-(4-Chlorophenyl)-1-piperidinyl]-4-oxo-1-[3-(2-oxo-2-phenylethyl)-2,3,4,5-tetrahydro-1H-3-benzazepin-7-yl]-1-butanone

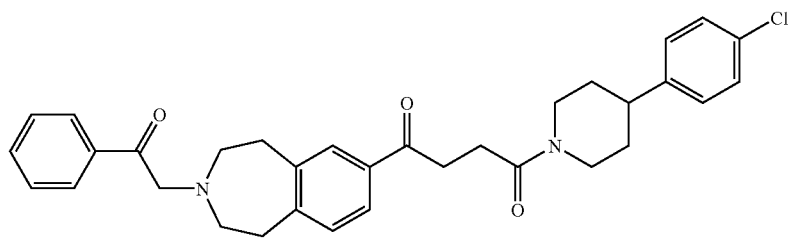

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^1$H-NMR (CDCl$_3$) δ: 1.64 (2H, m), 1.89 (2H, m), 2.86–2.58 (8H, m), 3.03 (4H, m), 3.17 (1H, m), 3.35 (2H, t, J=6.6 Hz), 3.96 (2H, s), 4.13 (1H, d, J=15.6 Hz), 4.76 (1H, d, J=12 Hz), 7.31–7.11 (5H, m), 7.55–7.43 (3H, m), 7.79 (2H, m), 8.05 (2H, m). Melting point: 108–109° C. (crystallizing solvent: ethanol-diisopropyl ether)

Example 22

1-(3-Acetyl-2,3,4,5-tetrahydro-1H-3-benzazepin-7-yl)-4-[4-(4-chlorophenyl)-1-piperidinyl]-4-oxo-1-butanone

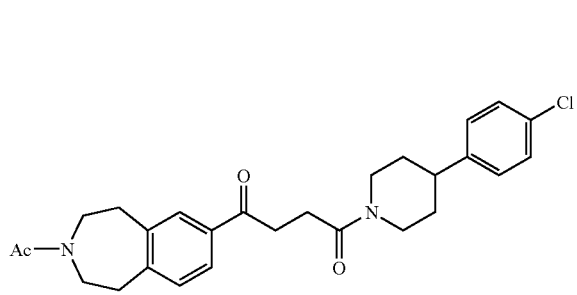

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^1$H-NMR (CDCl$_3$) δ: 1.64 (2H, m), 1.89 (2H, m), 2.66 (3H, s), 2.58 (4H, m), 2.87 (2H, t, J=6.6 Hz), 3.11 (4H, m), 3.17 (1H, m), 3.34 (2H, t, J=6.6 Hz), 3.76–3.58 (4H, m), 4.13 (1H, d, J=15.6 Hz), 4.73 (1H, d, J=12 Hz), 7.31–7.11 (5H, m), 7.81 (2H, m). Melting point: 110–112° C. (crystallizing solvent: ethanol-diisopropyl ether)

Example 23

4-[4-(4-Chlorophenyl)-1-piperidinyl]-4-oxo-1-[3-(2-oxopropyl)-2,3,4,5-tetrahydro-1H-3-benzazepin-7-yl]-1-butanone

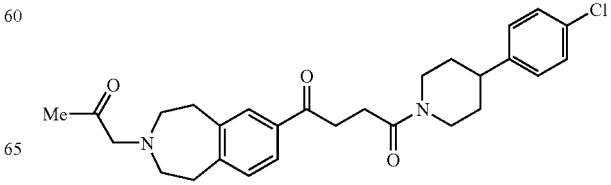

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^1$H-NMR (CDCl$_3$) δ: 1.64 (2H, m), 1.89 (2H, m), 2.22 (3H, s), 2.67 (4H, m), 2.87 (2H, t, J=6.6 Hz), 3.00 (4H, m), 3.17 (1H, m), 3.78–3.32 (4H, m), 4.13 (1H, d, J=15.6 Hz), 4.73 (1H, d, J=12 Hz), 7.31–7.11 (5H, m), 7.81 (2H, m). Melting point: 119–120° C. (crystallizing solvent: ethanol-diisopropyl ether)

Example 24

4-[4-(4-Chlorophenyl)-1-piperidinyl]-4-oxo-1-[3-[2-(1H-pyrrol-1-yl)ethyl]-2,3,4,5-tetrahydro-1H-3-benzazepin-7-yl]-1-butanone

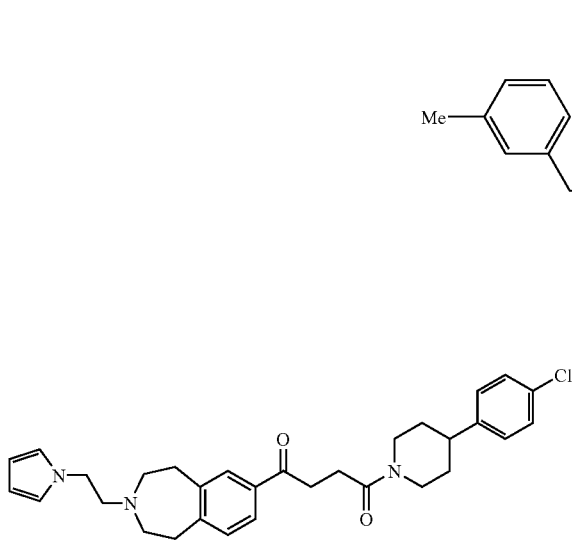

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^1$H-NMR (CDCl$_3$) δ: 1.64 (2H, m), 1.89 (2H, m), 2.95–2.59 (14H, m), 3.17 (1H, m), 3.34 (2H, t, J=6.2 Hz), 4.18–4.00 (3H, m), 4.75 (1H, m), 6.15 (2H, m), 6.70 (2H, m), 7.31–7.11 (5H, m), 7.81 (2H, m). Melting point: 96–97° C. (crystallizing solvent: ethanol-diisopropyl ether)

Example 25

4-[4-(4-Chlorophenyl)-1-piperidinyl]-1-[3-(2-methylbenzyl)-2,3,4,5-tetrahydro-1H-3-benzazepin-7-yl]-4-oxo-1-butanone

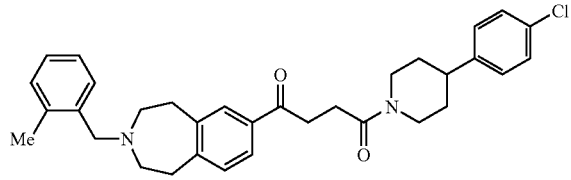

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^1$H-NMR (CDCl$_3$) δ: 1.64 (2H, m), 1.89 (2H, m), 2.40 (3H, s), 2.72–2.65 (6H, m), 2.82 (2H, t, J=6.4 Hz), 2.94 (4H, m), 3.23 (1H, m), 3.35 (2H, t, J=6.6 Hz), 3.54 (2H, s), 4.13 (1H, d, J=15.6 Hz), 4.76 (1H, d, J=12 Hz), 7.35–7.11 (9H, m), 7.79 (2H, m). Melting point: 108–109° C. (crystallizing solvent: ethanol-diisopropyl ether)

Example 26

4-[4-(4-Chlorophenyl)-1-piperidinyl]-1-[3-(3-methylbenzyl)-2,3,4,5-tetrahydro-1H-3-benzazepin-7-yl]-4-oxo-1-butanone

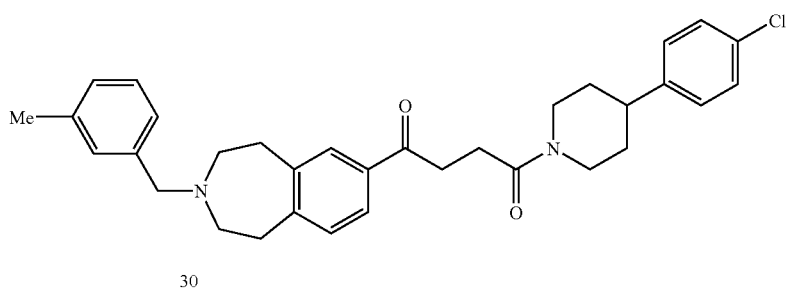

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^1$H-NMR (CDCl$_3$) δ: 1.64 (2H, m), 1.89 (2H, m), 2.36 (3H, s), 2.72–2.65 (6H, m), 2.82 (2H, t, J=6.4 Hz), 2.94 (4H, m), 3.23 (1H, m), 3.35 (2H, t, J=6.6 Hz), 3.60 (2H, s), 4.13 (1H, d, J=15.6 Hz), 4.76 (1H, d, J=12 Hz), 7.35–7.11 (9H, m), 7.79 (2H, m) Melting point: 127–128° C. (crystallizing solvent: ethanol-diisopropyl ether)

Example 27

4-[4-(4-Chlorophenyl)piperidin-1-yl]-1-[3-(4-methylbenzyl)-2,3,4,5-tetrahydro-1H-3-benzazepin-7-yl]-4-oxobutan-1-one

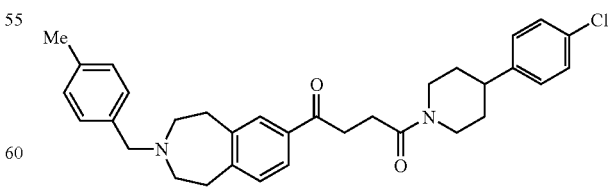

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^1$H-NMR (CDCl$_3$) δ: 1.63 (2H, m), 1.88 (2H, m), 2.35 (3H, s), 2.64 (6H, m), 2.78 (2H, t, J=6.4 Hz), 2.95 (4H, m), 3.23 (1H, m), 3.34 (2H, t, J=6.6 Hz), 3.60 (2H, s), 4.13 (1H, m), 4.76 (1H, m), 7.35–7.11 (9H, m), 7.79 (2H, m) Melting point: 137–138° C. (crystallizing solvent: ethanol-diisopropyl ether)

Example 28

1-(3-Allyl-2,3,4,5-tetrahydro-1H-3-benzazepin-7-yl)-4-[4-(4-chlorophenyl) piperidin-1-yl]-4-oxobutan-1-one

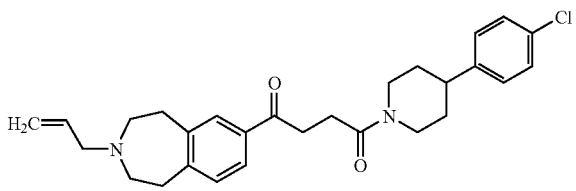

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^1$H-NMR (CDCl$_3$) δ: 1.63 (2H, m), 1.88 (2H, m), 2.65 (7H, m), 2.78 (2H, t, J=6.4 Hz), 2.97 (4H, m), 3.23 (2H, m), 3.35 (2H, t, J=6.6 Hz), 4.13 (1H, m), 4.76 (1H, m), 5.23–5.15 (2H, m), 5.90 (1H, m), 7.31–7.11 (5H, m), 7.79 (2H, m). Melting point: 136–137° C. (crystallizing solvent: ethanol-diisopropyl ether)

Example 29

4-[4-(4-Chlorophenyl)piperidin-1-yl]-4-oxo-1-(2-propynyl-2,3,4,5-tetrahydro-1H-3-benzazepin-7-yl)butan-1-one

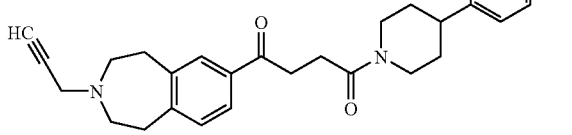

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^1$H-NMR (CDCl$_3$) δ: 1.63 (2H, m), 1.88 (2H, m), 2.21 (1H, s), 3.43–2.58 (15H, m), 4.13 (2H, m), 4.76 (1H, m), 5.07 (1H, m), 5.84 (1H, m), 7.31–7.11 (5H, m), 7.79 (2H, m). Melting point: 132–134° C. (crystallizing solvent: ethanol-diisopropyl ether)

Example 30

4-[4-(4-Chlorophenyl)piperidin-1-yl]-1-(3-isopropyl-2,3,4,5-tetrahydro-1H-3-benzazepin-7-yl)-4-oxobutan-1-one

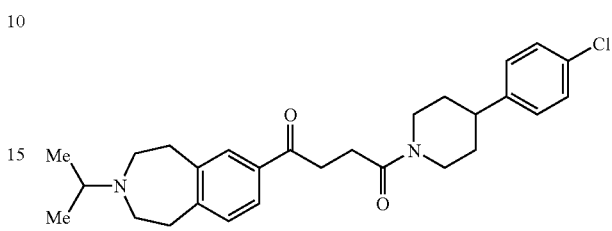

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^1$H-NMR (CDCl$_3$) δ: 1.00 (6H, d, J=6.6 Hz), 1.62 (4H, m), 1.89 (2H, m), 2.64 (7H, m), 2.82 (2H, t, J=6.4 Hz), 2.95 (4H, m), 3.23 (1H, m), 3.35 (2H, t, J=6.6 Hz), 4.13 (1H, m), 4.76 (1H, m), 7.35–7.11 (5H, m), 7.79 (2H, m). Melting point: 139–140° C. (crystallizing solvent: ethanol-diisopropyl ether)

Example 31

4-Oxo-4-(phenyl-1-piperidinyl)-1-[3-(trifluoroacetyl)-2,3,4,5-tetrahydro-1H-3-benzazepin-7-yl]-1-butanone

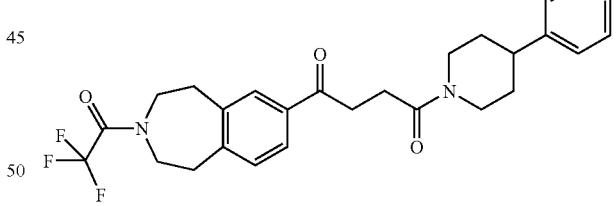

Using 4-oxo-4-[3-(trifluoroacetyl)-2,3,4,5-tetrahydro-1H-3-benzazepin-7-yl]butanoic acid obtained in Reference Example 16, the title compound was obtained as colorless powder by the same procedure as in Example 12.

$^1$H-NMR (CDCl$_3$) δ: 1.48–1.78 (2H, m), 1.82–2.00 (2H, m), 2.60–2.88 (4H, m), 2.98–3.10 (4H, m), 3.13–3.26 (1H, m), 3.34 (2H, t, J=6.5 Hz), 3.67–3.83 (4H, m), 4.07–4.18 (1H, m), 4.72–4.82 (1H, m), 7.16–7.37 (6H, m), 7.80–7.90 (2H, m). Elemental analysis for C$_{27}$H$_{29}$F$_3$N$_2$O$_3$. Calcd.: C, 66.65; H, 6.01; N, 5.76. Found: C, 66.45; H, 6.09; N, 5.56. Melting point: 132–133° C. (crystallizing solvent: isopropanol).

Example 32

4-Oxo-4-(phenyl-1-piperidinyl)-1-(2,3,4,5-tetrahydro-1H-3-benzazepin-7-yl)-1-butanone

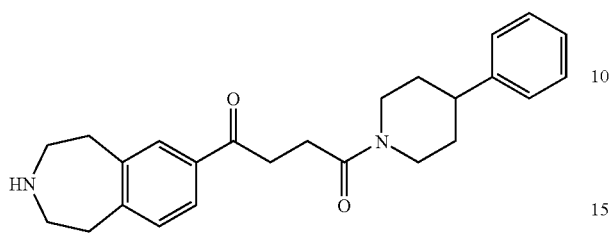

Using 4-oxo-4-(phenyl-1-piperidinyl)-1-[3-(trifluoroacetyl)-2,3,4,5-tetrahydro-1H-3-benzazepin-7-yl]-1-butanone obtained in Example 31, the title compound was obtained as colorless powder by the same procedure as in Example 13.

$^1$H-NMR (CDCl$_3$) δ: 1.54–2.00 (5H, m), 2.60–2.87 (4H, m), 2.97 (8H, br), 3.12–3.24 (1H, m), 3.35 (2H, t, J=16.7 Hz), 4.08–4.20 (1H, m), 4.73–4.83 (1H, m), 7.16–7.37 (6H, m), 7.77–7.82 (2H, m). Elemental analysis for C$_{25}$H$_{30}$N$_2$O$_2$. Calcd.: C, 76.89; H, 7.74; N, 7.17. Found: C, 76.44; H, 7.68; N, 7.02. Melting point: 114° C. (crystallizing solvent: isopropanol-diisopropyl ether).

Example 33

4-(3-Acetyl-2,3,4,5-tetrahydro-1H-3-benzazepin-7-yl)-4-[4-(chlorophenyl)-1-piperidinyl]-1-butanone

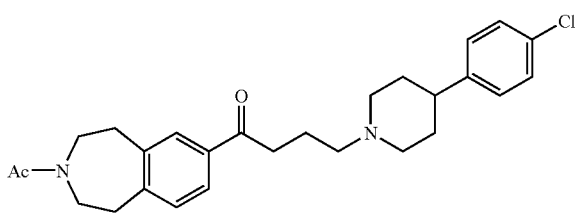

1) Aluminum chloride (2.9 g, 21.7 mmol) was added little by little to a mixture of 3-acetyl-2,3,4,5-tetrahydro-1H-3-benzazepine (2 g, 10.5 mmol) and 4-chlorobutyryl chloride (1.56 g, 11 mmol) in nitromethane (5 ml) at room temperature and stirred for 2 hours at room temperature. The reaction solution was poured into ice water which was then extracted with ethyl acetate, washed with a saturated saline solution and dried over anhydrous magnesium sulfate. The solvent was distilled away under reduced pressure, whereby 1-(3-acetyl-2,3,4,5-tetrahydro-1H-3-benzazepin-7-yl)-4-chloro-1-butanone (2.9 g) was obtained.

2) A mixture of 1-(3-acetyl-2,3,4,5-tetrahydro-1H-3-benzazepin-7-yl)-4-chloro-1-butanone (0.75 g, 2.55 mmol) obtained in 1) above, 4-chlorophenyl piperidine (5.1 g, 5.1 mmol) and potassium iodide (0.05 g) in toluene (15 ml) was heated under reflux for 16 hours. The reaction solution was poured into water, made basic with 1 N aqueous sodium hydroxide and extracted with ethyl acetate. The extract was washed with a saturated saline solution and dried over anhydrous magnesium sulfate. The solvent was distilled away under reduced pressure, and the residues were purified by silica gel column chromatography (developing solvent; ethyl acetate:methanol=1:1), whereby 0.6 g of the title compound was obtained as colorless powder.

$^1$H-NMR (CDCl$_3$) δ: 1.54–2.25 (11H, m), 2.37–2.56 (3H, m), 2.90–3.12 (8H, m), 3.53–3.64 (2H, m), 3.66–3.79 (2H, m), 7.07–7.31 (5H, m), 7.72–7.82 (2H, m). Melting point: 131–132° C. (crystallizing solvent: isopropanol-diisopropyl ether).

Example 34

4-[4-(4-Chlorophenyl)-1-piperidinyl]-1(2,3,4,5-tetrahydro-1H-3-benzazepin-7-yl)-1-butanone

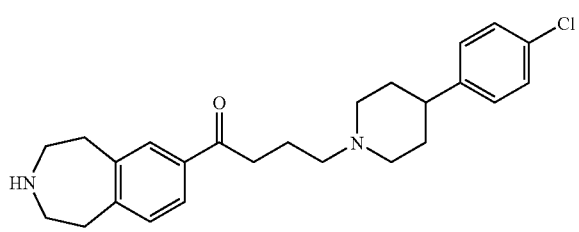

Using 1-(3-acetyl-2,3,4,5-tetrahydro-1H-3-benzazepin-7-yl)-4-[4-(4-chlorophenyl)-1-piperidinyl]-1-butanone obtained in Example 33, the title compound was obtained as colorless powder by the same procedure as in Reference Example 10.

$^1$H-NMR (CDCl$_3$, free base) δ: 1.53–2.13 (9H, m), 2.35–2.55 (3H, m), 2.90–3.10 (12H, m), 7.07–7.30 (5H, m), 7.68–7.80 (2H, m). Elemental analysis for C$_{25}$H$_{31}$ClN$_2$O·2HCl. Calcd.: C, 62.05; H, 6.87; N, 5.79. Found: C, 61.93; H, 6.78; N, 5.48. Melting point: 243–247° C. (dec.) (crystallizing solvent: isopropanol-diisopropyl ether).

Example 35

4-[4-(4-Chlorophenyl)-1-piperidinyl]-1-(3-methyl-2,3,4,5-tetrahydro-1H-3-benzazepin-7-yl)-1-butanone

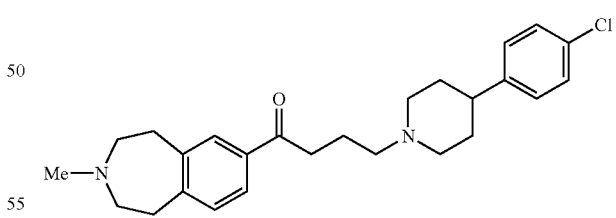

Using 4-[4-(4-chlorophenyl)-1-piperidinyl]-1-(2,3,4,5-tetrahydro-1 H-3-benzazepin-7-yl)-1-butanone obtained in Example 34, the title compound was obtained as colorless powder by the same procedure as in Example 16.

$^1$H-NMR (CDCl$_3$, free base) δ: 1.62–2.20 (8H, m), 2.36–2.67 (10H, m), 2.93–3.15 (8H, m), 7.07–7.30 (5H, m), 7.70–7.80 (2H, m). Elemental analysis for C$_{26}$H$_{33}$ClN$_2$O·2HCl·0.5H$_2$O·Calcd.: C, 61.60; H, 7.16; N, 5.53. Found: C, 61.73; H, 7.32; N, 5.48. Melting point: 248–252° C. (dec.) (crystallizing solvent: isopropanol).

Example 36

N-Butyl-4-oxo-4-(2,3,4,5-tetrahydro-1H-3-benzazepin-7-yl) butanamide trifluoroacetate

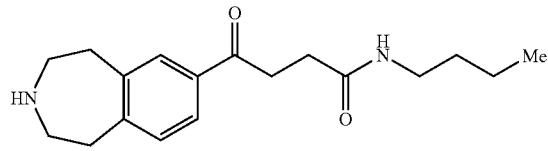

4-Oxo-4-[3-(trifluoroacetyl)-2,3,4,5-tetrahydro-1H-3-benzazepin-7-yl] butanoic acid (30.2 mg, 0.088 mmol) obtained in Reference Example 16, n-butylamine (5.9 mg, 0.08 mol) and carbodiimide resin (136 mg, 0.12 mmol, 0.88 mmol/g) were stirred in dichloromethane (1 ml) at room temperature for 12 hours. The reaction mixture was filtered, the filtrate was concentrated, and an aqueous solution (0.5 ml) of methanol (500 µl) and potassium carbonate (331 mg, 2.4 mmol) was added to the reaction mixture and then stirred at room temperature for 12 hours. The solvent was distilled away, and the residues were purified by preparative liquid chromatography (developing solvent: 0.1% aqueous trifluoroacetic acid/0.1% trifluoroacetic acid in acetonitrile=90/10 to 10/90), whereby 10.2 mg of the title compound was obtained as colorless powder.
MS(ESI)(M+1): 303

Example 37

N-(Cyclohexylmethyl)-4-oxo-4-(2,3,4,5-tetrahydro-1H-3-benzazepin-7-yl)butanamide trifluoroacetate

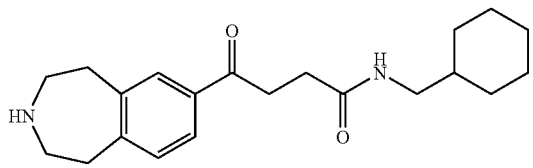

The title compound was obtained in the same manner as in Example 36.
MS(ESI)(M+1): 343

Example 38

N-Cyclohexyl-4-oxo-4-(2,3,4,5-tetrahydro-1H-3-benzazepin-7-yl)butanamide trifluoroacetate

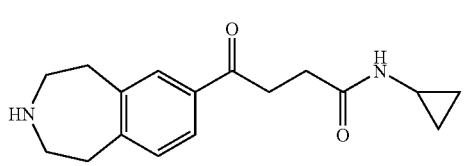

The title compound was obtained in the same manner as in Example 36.
MS(APCI)(M+1): 287

Example 39

N-Benzyl-4-oxo-4-(2,3,4,5-tetrahydro-1H-3-benzazepin-7-yl)butanamide trifluoroacetate

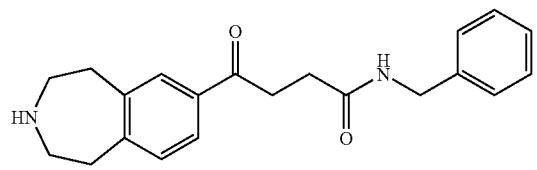

The title compound was obtained in the same manner as in Example 36.
MS(ESI)(M+1): 337

Example 40

N-(1,3-Benzodioxol-5-ylmethyl)-4-oxo-4-(2,3,4,5-tetrahydro-1H-3-benzazepin-7-yl)butanamide trifluoroacetate

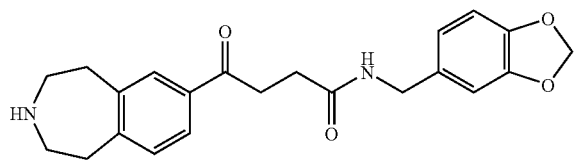

The title compound was obtained in the same manner as in Example 36.
MS(ESI)(M+1): 381

Example 41

4-Oxo-N-(2-phenetyl)-4-(2,3,4,5-tetrahydro-1H-3-benzazepin-7-yl)butanamide trifluoroacetate

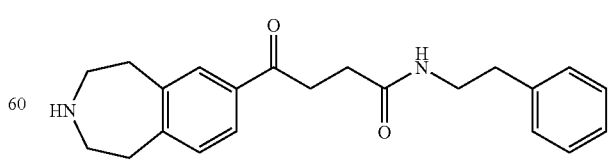

The title compound was obtained in the same manner as in Example 36.
MS(ESI)(M+1): 351

Example 42

4-Oxo-N-(3-phenylpropyl)-4-(2,3,4,5-tetrahydro-1H-3-benzazepin-7-yl)butanamide trifluoroacetate

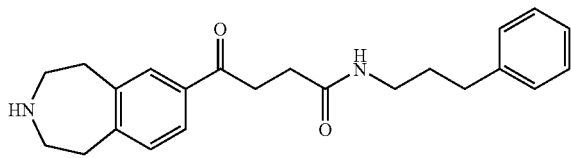

The title compound was obtained in the same manner as in Example 36.
MS(ESI)(M+1): 365

Example 43

N-Benzhydryl-4-oxo-4-(2,3,4,5-tetrahydro-1H-3-benzazepin-7-yl)butanamide trifluoroacetate

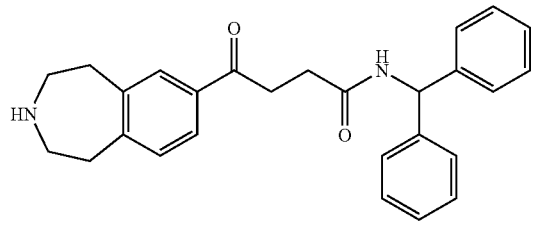

The title compound was obtained in the same manner as in Example 36.
MS(ESI)(M+1): 413

Example 44

N-(2-Methoxyethyl)-4-oxo-4-(2,3,4,5-tetrahydro-1H-3-benzazepin-7-yl)butanamide trifluoroacetate

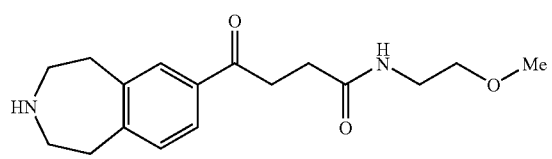

The title compound was obtained in the same manner as in Example 36.
MS(APCI)(M+1): 305

Example 45

N-[3-(Methylthio)propyl]-4-oxo-4-(2,3,4,5-tetrahydro-1H-3-benzazepin-7-yl)butanamide trifluoroacetate

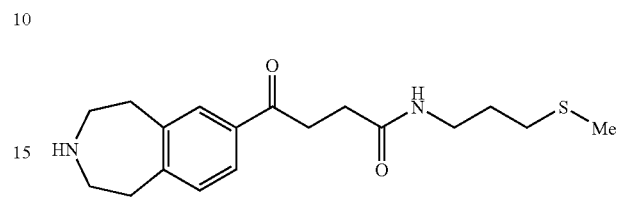

The title compound was obtained in the same manner as in Example 36.
MS(ESI)(M+1): 335

Example 46

4-Oxo-4-(2,3,4,5-tetrahydro-1H-3-benzazepin-7-yl)-N-(tetrahydrofuran-2-ylmethyl)butanamide trifluoroacetate

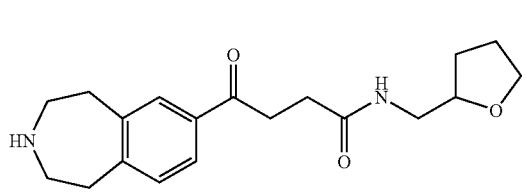

The title compound was obtained in the same manner as in Example 36.
MS(APCI)(M+1): 331

Example 47

N-[2-(1H-Indol-3-yl)ethyl]-4-oxo-4-(2,3,4,5-tetrahydro-1H-3-benzazepin-7-yl)butanamide trifluoroacetate

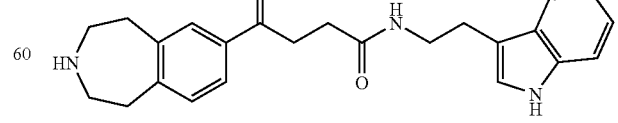

The title compound was obtained in the same manner as in Example 36.
MS(ESI)(M+1): 390

Example 48

N-(1-Ethylpropyl)-4-oxo-4-(2,3,4,5-tetrahydro-1H-3-benzazepin-7-yl)butanamide trifluoroacetate

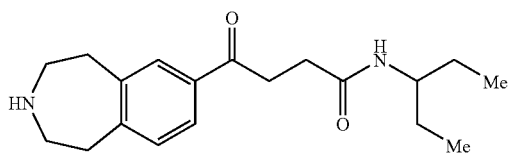

The title compound was obtained in the same manner as in Example 36.
MS(ESI)(M+1): 317

Example 49

N-(tert-Butyl)-4-oxo-4-(2,3,4,5-tetrahydro-1H-3-benzazepin-7-yl)butanamide trifluoroacetate

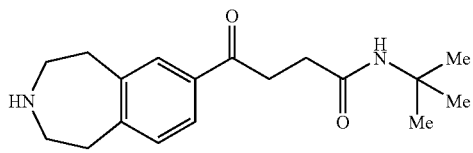

The title compound was obtained in the same manner as in Example 36.
MS(ESI)(M+1): 303

Example 50

N-(Cyclohexyl)-4-oxo-4-(2,3,4,5-tetrahydro-1H-3-benzazepin-7-yl)butanamide trifluoroacetate

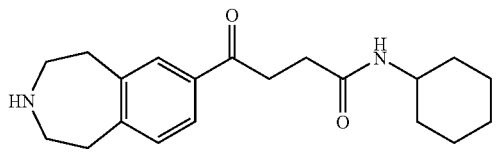

The title compound was obtained in the same manner as in Example 36.
MS(ESI)(M+1): 329

Example 51

4-Oxo-N-prop-2-ynyl-4-(2,3,4,5-tetrahydro-1H-3-benzazepin-7-yl)butanamide trifluoroacetate

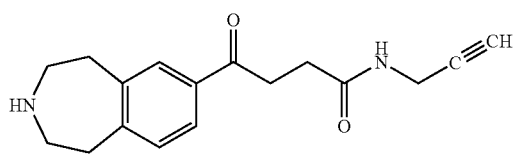

The title compound was obtained in the same manner as in Example 36.
MS(APCI)(M+1): 285

Example 52

4-Oxo-4-(2,3,4,5-tetrahydro-1H-3-benzazepin-7-yl)-N-[4-(trifluoromethyl)benzyl]butanamide trifluoroacetate

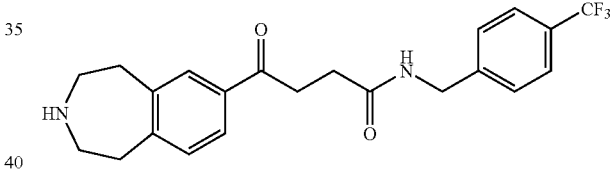

The title compound was obtained in the same manner as in Example 36.
MS(ESI)(M+1): 405

Example 53

N-[2-(3,4-Dimethoxyphenyl)ethyl]-4-oxo-4-(2,3,4,5-tetrahydro-1H-3-benzazepin-7-yl)butanamide trifluoroacetate

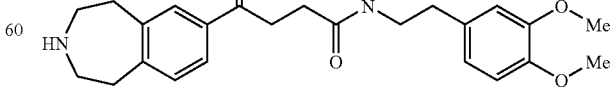

The title compound was obtained in the same manner as in Example 36.
MS(ESI)(M+1): 411

Example 54

N-(3,3-Diphenylpropyl)-4-oxo-4-(2,3,4,5-tetrahydro-1H-3-benzazepin-7-yl)butanamide trifluoroacetate

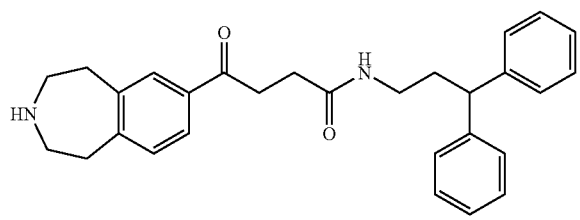

The title compound was obtained in the same manner as in Example 36.

MS(ESI)(M+1): 441

Example 55

N-(2,3-Dihydro-1H-inden-2-yl)-4-oxo-4-(2,3,4,5-tetrahydro-1H-3-benzazepin-7-yl)butanamide trifluoroacetate

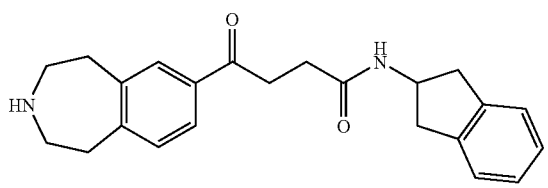

The title compound was obtained in the same manner as in Example 36.

MS(ESI)(M+1): 363

Example 56

N-(3-Isopropoxypropyl)-4-oxo-4-(2,3,4,5-tetrahydro-1H-3-benzazepin-7-yl)butanamide trifluoroacetate

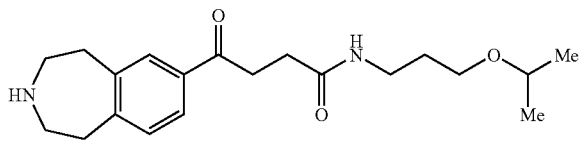

The title compound was obtained in the same manner as in Example 36.

MS(ESI)(M+1): 347

Example 57

N-(3-Furylmethyl)-4-oxo-4-(2,3,4,5-tetrahydro-1H-3-benzazepin-7-yl)butanamide trifluoroacetate

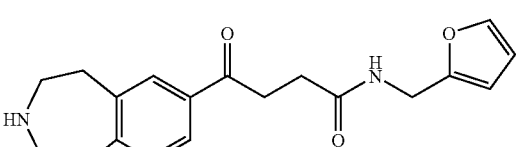

The title compound was obtained in the same manner as in Example 36.

MS(ESI)(M+1): 327

Example 58

4-Oxo-N-[3-(2-oxopyrrolidin-1-yl)propyl]-4-(2,3,4,5-tetrahydro-1H-3-benzazepin-7-yl)butanamide trifluoroacetate

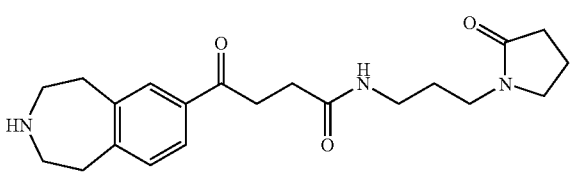

The title compound was obtained in the same manner as in Example 36.

MS(APCI)(M+1): 372

Example 59

4-Oxo-N,N-dipropyl-4-(2,3,4,5-tetrahydro-1H-3-benzazepin-7-yl)butanamide trifluoroacetate

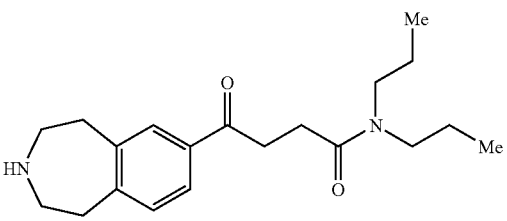

The title compound was obtained in the same manner as in Example 36.

MS(ESI)(M+1): 331

Example 60

N-Methyl-N-(1-naphthylmethyl)-4-oxo-4-(2,3,4,5-tetrahydro-1H-3-benzazepin-7-yl)butanamide trifluoroacetate

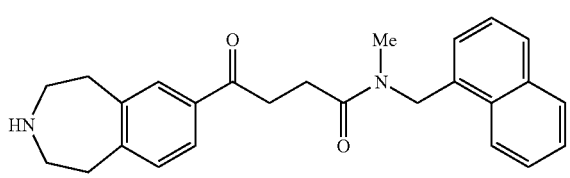

The title compound was obtained in the same manner as in Example 36.
MS(ESI)(M+1): 401

Example 61

N-[2-(3,4-Dimethoxyphenyl)ethyl]-N-methyl-4-oxo-4-(2,3,4,5-tetrahydro-1H-3-benzazepin-7-yl)butanamide trifluoroacetate

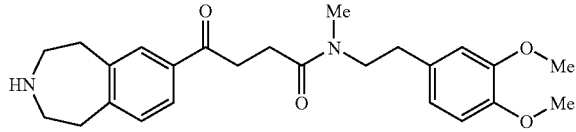

The title compound was obtained in the same manner as in Example 36.
MS(ESI)(M+1): 425

Example 62

N,N-bis(2-Methoxyethyl)-4-oxo-4-(2,3,4,5-tetrahydro-1H-3-benzazepin-7-yl)butanamide trifluoroacetate

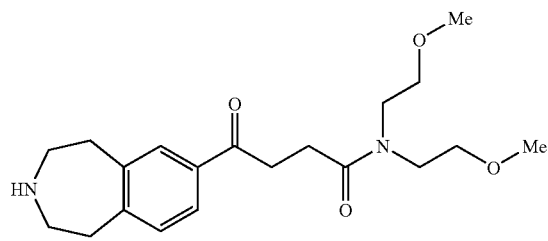

The title compound was obtained in the same manner as in Example 36.
MS(ESI)(M+1): 363

Example 63

4-Oxo-4-piperidin-1-yl-1-(2,3,4,5-tetrahydro-1H-3-benzazepin-7-yl)butan-1-one trifluoroacetate

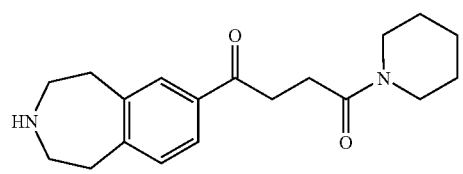

The title compound was obtained in the same manner as in Example 36.
MS(ESI)(M+1): 315

Example 64

4-(2,6-Dimethylmorpholin-4-yl)-4-oxo-1-(2,3,4,5-tetrahydro-1H-3-benzazepin-7-yl)butan-1-one trifluoroacetate

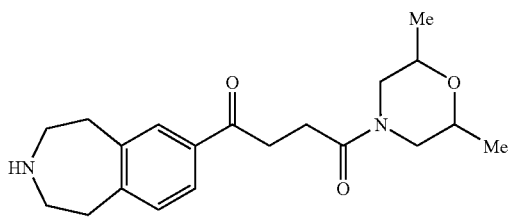

The title compound was obtained in the same manner as in Example 36.
MS(ESI)(M+1): 345

Example 65

4-(3,4-Dihydroisoquinolin-2(1H)-yl)-4-oxo-1-(2,3,4,5-tetrahydro-1H-3-benzazepin-7-yl)butan-1-one trifluoroacetate

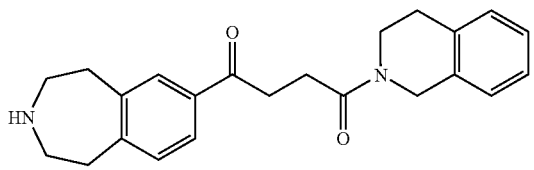

The title compound was obtained in the same manner as in Example 36.
MS(ESI)(M+1): 363

Example 66

1-[4-Oxo-4-(2,3,4,5-tetrahydro-1H-3-benzazepin-7-yl)butanoyl]piperidine-4-carboxamide trifluoroacetate

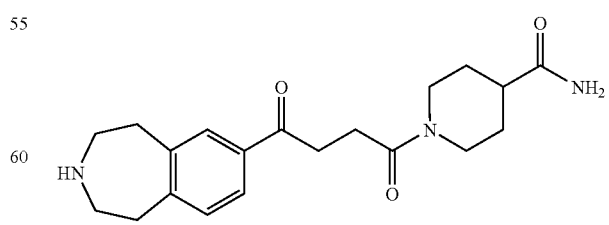

The title compound was obtained in the same manner as in Example 36.
MS(APCI)(M+1): 358

Example 67

4-[4-(2-Hydroxyethyl)piperidin-1-yl]-4-oxo-1-(2,3,4,5-tetrahydro-1H-3-benzazepin-7-yl)butan-1-one trifluoroacetate

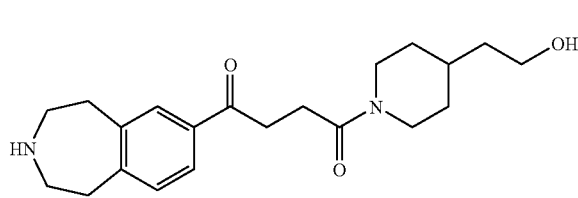

The title compound was obtained in the same manner as in Example 36.
MS(ESI)(M+1): 359

Example 68

4-Oxo-1-(2,3,4,5-tetrahydro-1H-3-benzazepin-7-yl)-4-thiomorphin-4-ylbutan-1-one trifluoroacetate

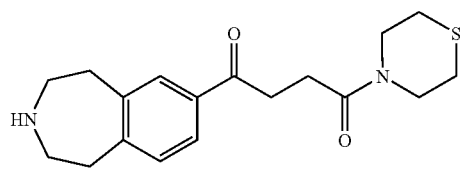

The title compound was obtained in the same manner as in Example 36.
MS(ESI)(M+1): 333

Example 69

4-(4-Benzylpiperidin-1-yl)-4-oxo-1-(2,3,4,5-tetrahydro-1H-3-benzazepin-7-yl)butan-1-one trifluoroacetate

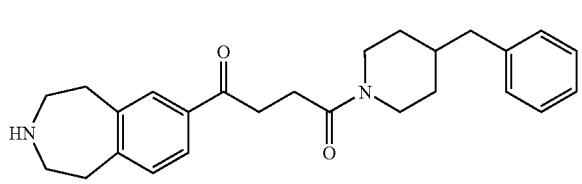

The title compound was obtained in the same manner as in Example 36.
MS(ESI)(M+1): 405

Example 70

N-[1-[4-Oxo-4-(2,3,4,5-tetrahydro-1H-3-benzazepin-7-yl)butanoyl]pyrrolidin-3-yl]acetamide trifluoroacetate

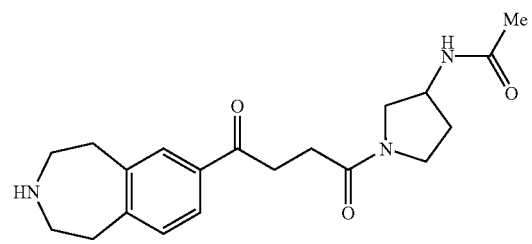

The title compound was obtained in the same manner as in Example 36.
MS(APCI)(M+1): 358

Example 71

N-Cyclohexyl-N-methyl-4-oxo-4-(2,3,4,5-tetrahydro-1H-3-benzazepin-7-yl)butanamide trifluoroacetate

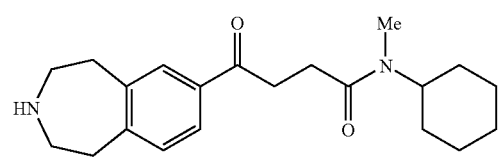

The title compound was obtained in the same manner as in Example 36.
MS(ESI)(M+1): 343

Example 72

N-Benzyl-N-methyl-4-oxo-4-(2,3,4,5-tetrahydro-1H-3-benzazepin-7-yl)butanamide trifluoroacetate

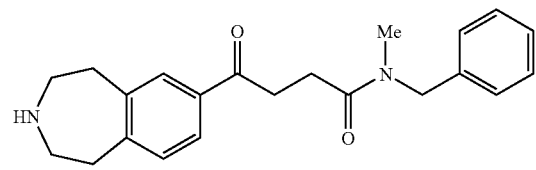

The title compound was obtained in the same manner as in Example 36.
MS(ESI)(M+1): 351

Example 73

N-Ethyl-N-(2-methoxyethyl)-4-oxo-4-(2,3,4,5-tetrahydro-1H-3-benzazepin-7-yl)butanamide trifluoroacetate

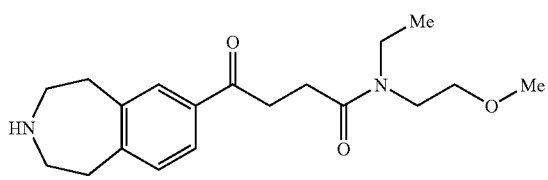

The title compound was obtained in the same manner as in Example 36.
MS(ESI)(M+1): 333

Example 74

4-Morpholin-4-yl-4-oxo-1-(2,3,4,5-tetrahydro-1H-3-benzazepin-7-yl)butan-1-one trifluoroacetate

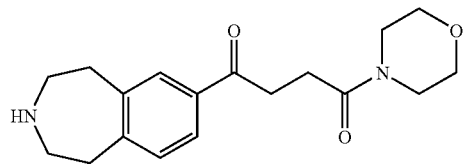

The title compound was obtained in the same manner as in Example 36.
MS(APCI)(M+1): 317

Example 75

4-(3,5-Dimethylpiperidin-1-yl)-4-oxo-1-(2,3,4,5-tetrahydro-1H-3-benzazepin-7-yl)butan-1-one trifluoroacetate

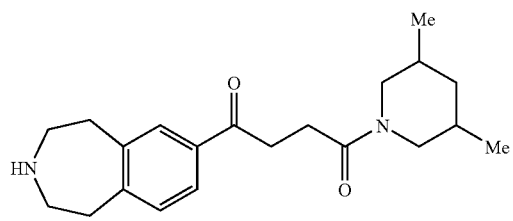

The title compound was obtained in the same manner as in Example 36.
MS(ESI)(M+1): 343

Example 76

4-octahydroisoquinolin-2(1H)-yl-4-oxo-1-(2,3,4,5-tetrahydro-1H-3-benzazepin-7-yl)butan-1-one trifluoroacetate

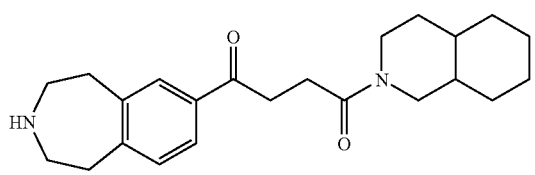

The title compound was obtained in the same manner as in Example 36.
MS(ESI)(M+1): 369

Example 77

4-(4-Hydroxypiperidin-1-yl)-4-oxo-1-(2,3,4,5-tetrahydro-1H-3-benzazepin-7-yl)butan-1-one trifluoroacetate

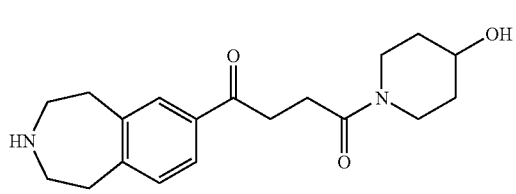

The title compound was obtained in the same manner as in Example 36.
MS(APCI)(M+1): 331

Example 78

4-((2S)-2-[[(2,6-Dimethylphenyl)amino]methyl]pyrrolidin-1-yl)-4-oxo-1-(2,3,4,5-tetrahydro-1H-3-benzazepin-7-yl)butan-1-one trifluoroacetate

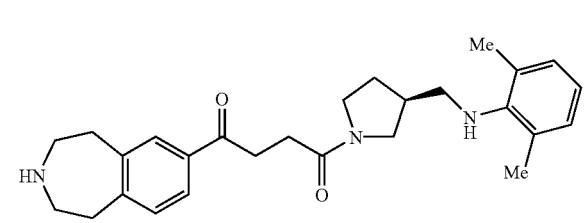

The title compound was obtained in the same manner as in Example 36.
MS(ESI)(M+1): 434

Example 79

4-[4-(4-Chlorophenyl)-4-hydroxypiperidin-1-yl]-4-oxo-1-(2,3,4,5-tetrahydro-1H-3-benzazepin-7-yl)butan-1-one trifluoroacetate

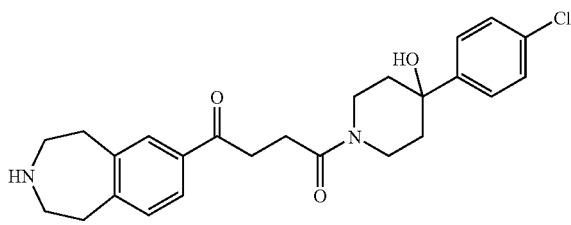

The title compound was obtained in the same manner as in Example 36.
MS(ESI)(M+1): 441

Example 80

N-Ethyl-N-[1-[4-oxo-4-(2,3,4,5-tetrahydro-1H-3-benzazepin-7-yl) butanoyl]pyrrolidin-3-yl]acetamide trifluoroacetate

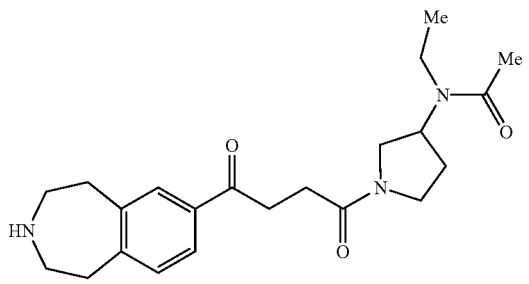

The title compound was obtained in the same manner as in Example 36.
MS(ESI)(M+1): 386

Example 81

N-[2-(Dimethylamino)ethyl]-4-oxo-4-(2,3,4,5-tetrahydro-1H-3-benzazepin-7-yl)butanamide trifluoroacetate

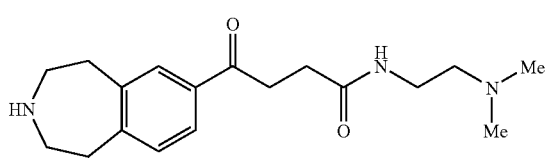

The title compound was obtained in the same manner as in Example 36.
MS(APCI)(M+1): 318

Example 82

N-[3-(Dimethylamino)propyl]-4-oxo-4-(2,3,4,5-tetrahydro-1H-3-benzazepin-7-yl)butanamide trifluoroacetate

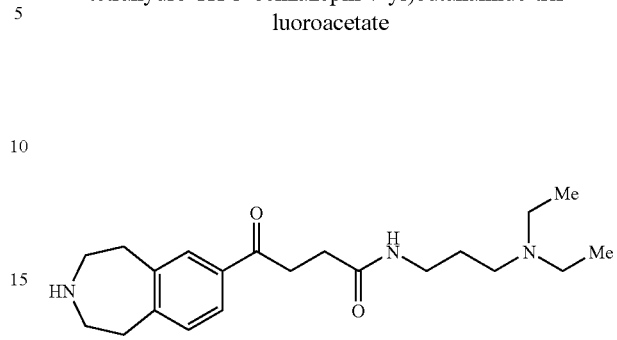

The title compound was obtained in the same manner as in Example 36.
MS(APCI)(M+1): 360

Example 83

4-Oxo-N-(2-piperidin-1-ylethyl)-4-(2,3,4,5-tetrahydro-1H-3-benzazepin-7-yl)butanamide trifluoroacetate

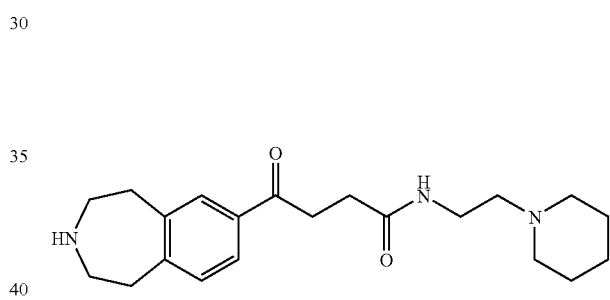

The title compound was obtained in the same manner as in Example 36.
MS(APCI)(M+1): 358

Example 84

N-(2-Morpholin-4-ylethyl)-4-oxo-4-(2,3,4,5-tetrahydro-1H-3-benzazepin-7-yl)butanamide trifluoroacetate

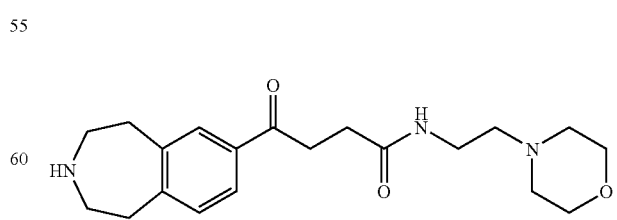

The title compound was obtained in the same manner as in Example 36.
MS(APCI)(M+1): 360

Example 85

N-[3-(4-Methylpiperazin-1-yl)propyl]-4-oxo-4-(2,3,4,5-tetrahydro-1H-3-benzazepin-7-yl)butanamide trifluoroacetate

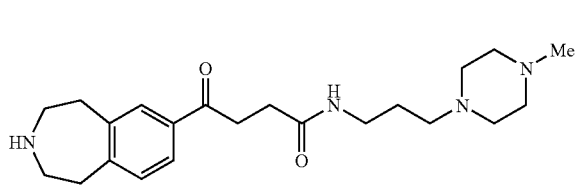

The title compound was obtained in the same manner as in Example 36.
MS(APCI)(M+1): 387

Example 86

N-[3-[Methyl(phenyl)amino]propyl]-4-oxo-4-(2,3,4,5-tetrahydro-1H-3-benzazepin-7-yl)butanamide trifluoroacetate

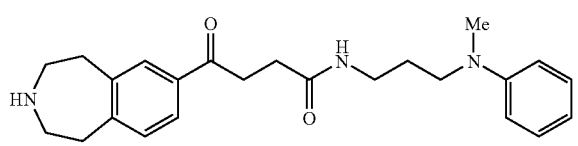

The title compound was obtained in the same manner as in Example 36.
MS(APCI)(M+1): 394

Example 87

N-(1-Benzylpiperidin-4-yl)-4-oxo-4-(2,3,4,5-tetrahydro-1H-3-benzazepin-7-yl)butanamide trifluoroacetate

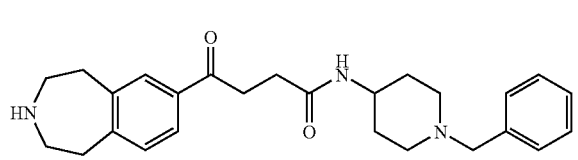

The title compound was obtained in the same manner as in Example 36.
MS(APCI)(M+1): 420

Example 88

4-Oxo-4-(2,3,4,5-tetrahydro-1H-3-benzazepin-7-yl)-N-(2,2,6,6-tetramethylpiperidin-4-yl)butanamide trifluoroacetate

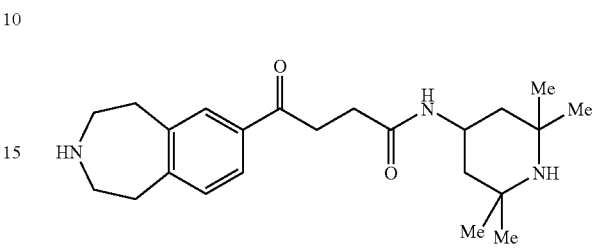

The title compound was obtained in the same manner as in Example 36.
MS(APCI)(M+1): 386

Example 89

N-(2-Anilinoethyl)-4-oxo-4-(2,3,4,5-tetrahydro-1H-3-benzazepin-7-yl)butanamide trifluoroacetate

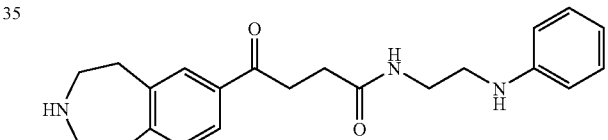

The title compound was obtained in the same manner as in Example 36.
MS(APCI)(M+1): 366

Example 90

4-Oxo-N-(pyridin-2-ylmethyl)-4-(2,3,4,5-tetrahydro-1H-3-benzazepin-7-yl)butanamide trifluoroacetate

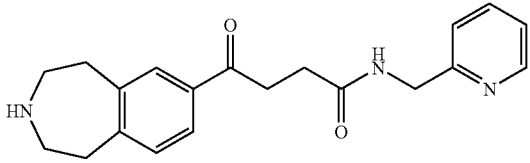

The title compound was obtained in the same manner as in Example 36.
MS(APCI)(M+1): 338

Example 91

4-Oxo-N-(pyridin-4-ylmethyl)-4-(2,3,4,5-tetrahydro-1H-3-benzazepin-7-yl)butanamide trifluoroacetate

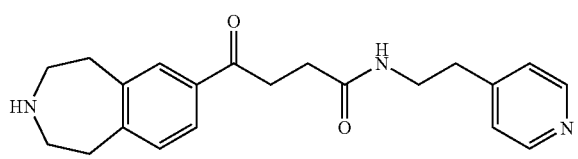

The title compound was obtained in the same manner as in Example 36.
MS(APCI)(M+1): 352

Example 92

N-[3-(1H-Imidazol-1-yl)propyl]-4-oxo-4-(2,3,4,5-tetrahydro-1H-3-benzazepin-7-yl)butanamide trifluoroacetate

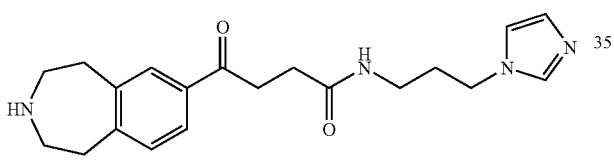

The title compound was obtained in the same manner as in Example 36.
MS(APCI)(M+1): 355

Example 93

N-[3-(Diisopropylamino)ethyl]-4-oxo-4-(2,3,4,5-tetrahydro-1H-3-benzazepin-7-yl)butanamide trifluoroacetate

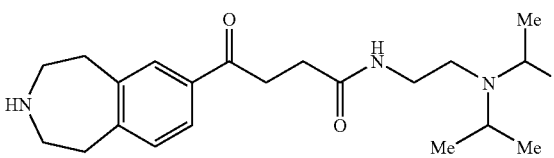

The title compound was obtained in the same manner as in Example 36.
MS(APCI)(M+1): 374

Example 94

N-[3-(Dimethylamino)-2,2-dimethylpropyl]-4-oxo-4-(2,3,4,5-tetrahydro-1H-3-benzazepin-7-yl)butanamide trifluoroacetate

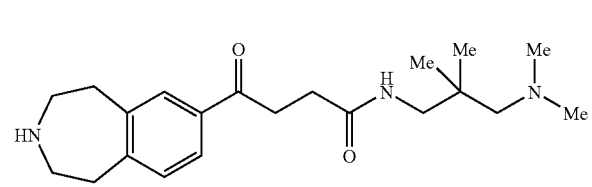

The title compound was obtained in the same manner as in Example 36.
MS(APCI)(M+1): 360

Example 95

N-[3-(2-Methylpiperidin-1-yl)propyl]-4-oxo-4-(2,3,4,5-tetrahydro-1H-3-benzazepin-7-yl)butanamide trifluoroacetate

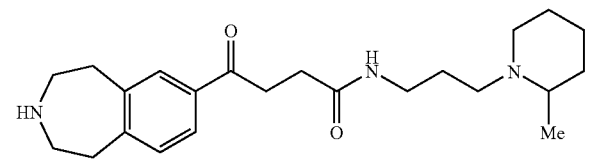

The title compound was obtained in the same manner as in Example 36.
MS(APCI)(M+1): 386

Example 96

N-(3-Morpholin-4-ylpropyl)-4-oxo-4-(2,3,4,5-tetrahydro-1H-3-benzazepin-7-yl)butanamide trifluoroacetate

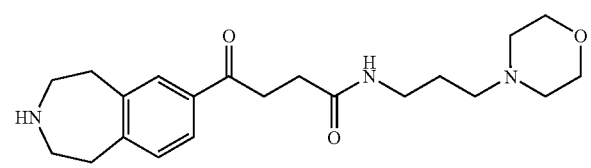

The title compound was obtained in the same manner as in Example 36.
MS(APCI)(M+1): 374

Example 97

4-Oxo-N-(2-pyrrolidin-1-ylethyl)-4-(2,3,4,5-tetrahydro-1H-3-benzazepin-7-yl)butanamide trifluoroacetate

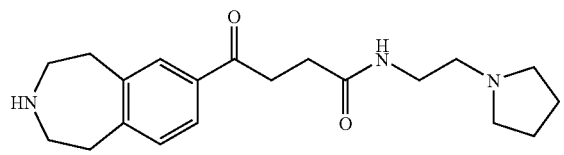

The title compound was obtained in the same manner as in Example 36.
MS(APCI)(M+1): 344

Example 98

N-[2-[Ethyl(2-methylphenyl)amino]ethyl]-4-oxo-4-(2,3,4,5-tetrahydro-1H-3-benzazepin-7-yl)butanamide trifluoroacetate

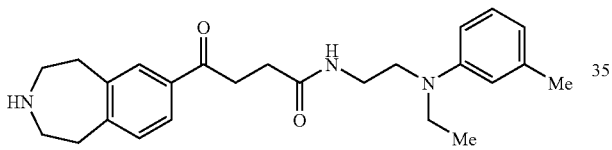

The title compound was obtained in the same manner as in Example 36.
MS(APCI)(M+1): 408

Example 99

N-(1-Benzylpyrrolidin-3-yl)-4-oxo-4-(2,3,4,5-tetrahydro-1H-3-benzazepin-7-yl)butanamide trifluoroacetate

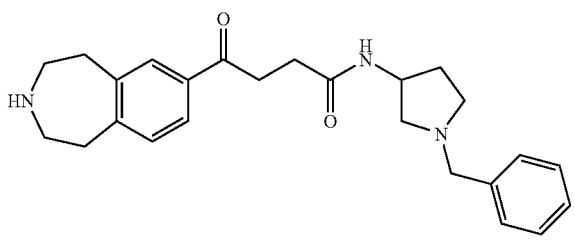

The title compound was obtained in the same manner as in Example 36.
MS(APCI)(M+1): 406

Example 100

N-[3-[bis(2-Hydroxyethyl)amino]propyl]-4-oxo-4-(2,3,4,5-tetrahydro-1H-3-benzazepin-7-yl)butanamide trifluoroacetate

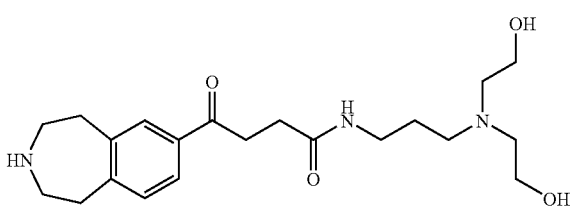

The title compound was obtained in the same manner as in Example 36.
MS(APCI)(M+1): 392

Example 101

N-[3-[(5-Nitropyridine)amino]ethyl]-4-oxo-4-(2,3,4,5-tetrahydro-1H-3-benzazepin-7-yl)butanamide trifluoroacetate

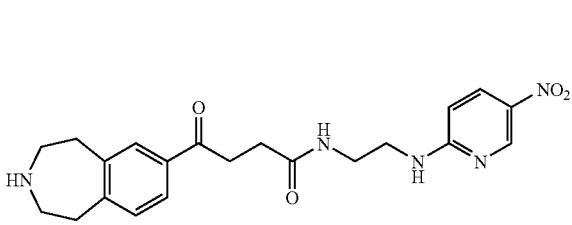

The title compound was obtained in the same manner as in Example 36.
MS(APCI)(M+1): 412

Example 102

4-Oxo-N-(pyridin-4-ylmethyl)-4-(2,3,4,5-tetrahydro-1H-3-benzazepin-7-yl)butanamide trifluoroacetate

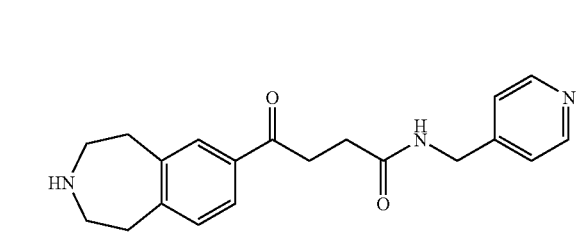

The title compound was obtained in the same manner as in Example 36.
MS(APCI)(M+1): 338

Example 103

4-Oxo-N-(pyridin-3-ylmethyl)-4-(2,3,4,5-tetrahydro-1H-3-benzazepin-7-yl)butanamide trifluoroacetate

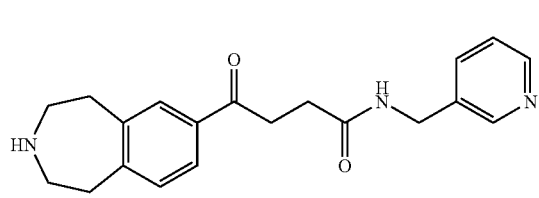

The title compound was obtained in the same manner as in Example 36.
MS(APCI)(M+1): 338

Example 104

4-Oxo-N-(2-pyridin-3-ylethyl)-4-(2,3,4,5-tetrahydro-1H-3-benzazepin-7-yl)butanamide trifluoroacetate

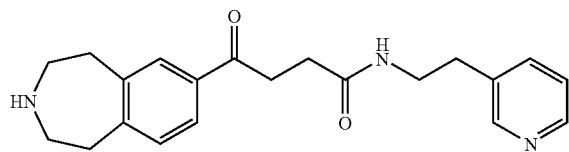

The title compound was obtained in the same manner as in Example 36.
MS(APCI)(M+1) 352

Example 105

N-[2-(Dimethylamino)ethyl]-N-methyl-4-oxo-4-(2,3,4,5-tetrahydro-1H-3-benzazepin-7-yl)butanehydrazide trifluoroacetate

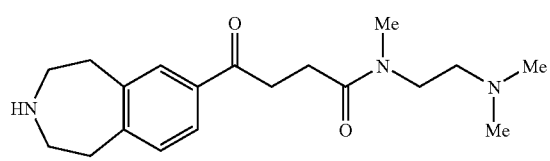

The title compound was obtained in the same manner as in Example 36.
MS(APCI)(M+1): 332

Example 106

N-(1-Benzylpyrrolidin-3-yl)-N-methyl-4-oxo-4-(2,3,4,5-tetrahydro-1H-3-benzazepin-7-yl)butanamide trifluoroacetate

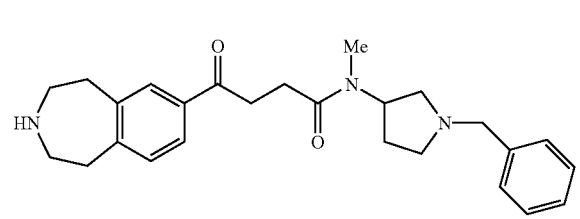

The title compound was obtained in the same manner as in Example 36.
MS(APCI)(M+1): 420

Example 107

N-Ethyl-4-oxo-N-(pyridin-4-ylmethyl)-4-(2,3,4,5-tetrahydro-1H-3-benzazepin-7-yl)butanamide trifluoroacetate

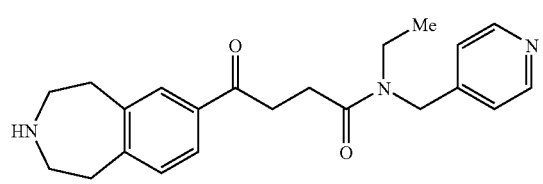

The title compound was obtained in the same manner as in Example 36.
MS(APCI)(M+1): 366

Example 108

4-Oxo-N,N-bis(pyridin-3-ylmethyl)-4-(2,3,4,5-tetrahydro-1H-3-benzazepin-7-yl)butanamide trifluoroacetate

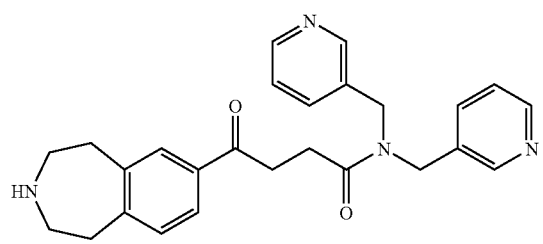

The title compound was obtained in the same manner as in Example 36.
MS(APCI)(M+1): 429

Example 109

4-(4-Ethylpiperazin-1-yl)-4-oxo-1-(2,3,4,5-tetrahydro-1H-3-benzazepin-7-yl)butan-1-one trifluoroacetate

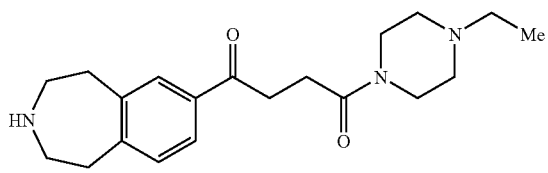

The title compound was obtained in the same manner as in Example 36.
MS(APCI)(M+1): 344

Example 110

Ethyl [4-[4-oxo-4-(2,3,4,5-tetrahydro-1H-benzazepin-7-yl)butanoyl]piperazin-1-yl]acetate trifluoroacetate

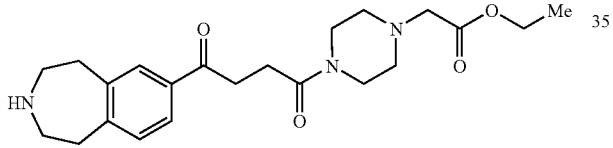

The title compound was obtained in the same manner as in Example 36.
MS(APCI)(M+1): 401

Example 111

4-(4-Benzylpiperazin-1-yl)-4-oxo-1-(2,3,4,5-tetrahydro-1H-3-benzazepin-7-yl)butan-1-one trifluoroacetate

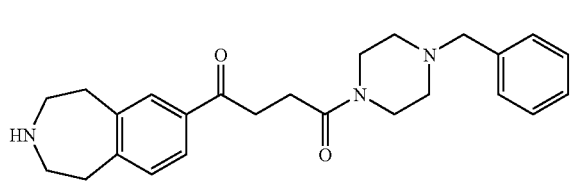

The title compound was obtained in the same manner as in Example 36.
MS(APCI)(M+1): 406

Example 112

4-Oxo-4-[4-(pyridin-2-yl)piperazin-1-yl]-1-(2,3,4,5-tetrahydro-1H-3-benzazepin-7-yl)butan-1-one trifluoroacetate

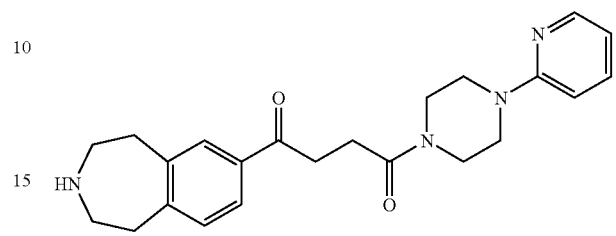

The title compound was obtained in the same manner as in Example 36.
MS(APCI)(M+1): 393

Example 113

4-(4-Benzhydrylpiperazin-1-yl)-4-oxo-1-(2,3,4,5-tetrahydro-1H-3-benzazepin-7-yl)butan-1-one trifluoroacetate

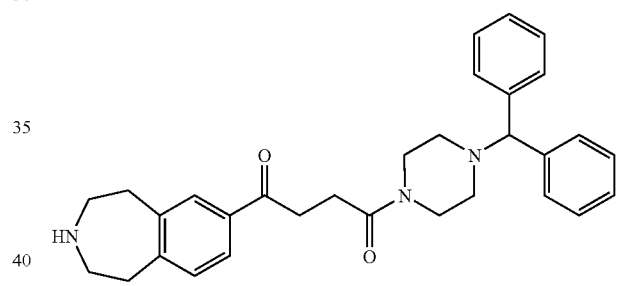

The title compound was obtained in the same manner as in Example 36.
MS(ESI)(M+1): 482

Example 114

4-Oxo-4-(4-phenylpiperazin-1-yl)-1-(2,3,4,5-tetrahydro-1H-3-benzazepin-7-yl)butan-1-one trifluoroacetate

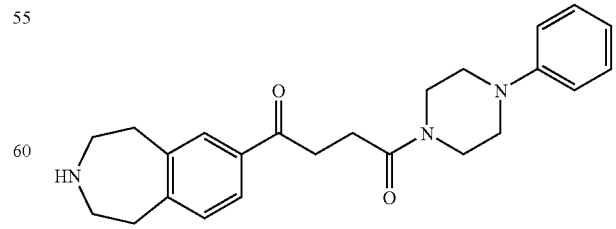

The title compound was obtained in the same manner as in Example 36.
MS(ESI)(M+1): 392

Example 115

4-[4-(2-Methoxyphenyl)piperazin-1-yl]-4-oxo-1-(2,3,4,5-tetrahydro-1H-3-benzazepin-7-yl)butan-1-one trifluoroacetate

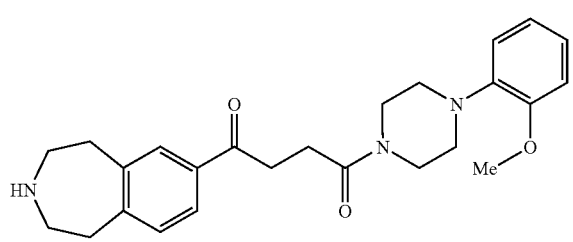

The title compound was obtained in the same manner as in Example 36.
MS(ESI)(M+1): 432

Example 116

4-(1,4'-Bipiperidin-1'-yl)-4-oxo-1-(2,3,4,5-tetrahydro-1H-3-benzazepin-7-yl)butan-1-one trifluoroacetate

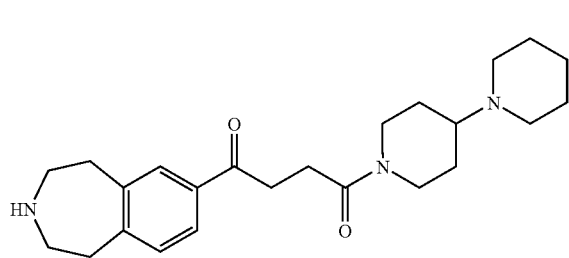

The title compound was obtained in the same manner as in Example 36.
MS(APCI)(M+1): 398

Example 117

4-[3-(Dimethylamino)pyrrolidin-1-yl]-4-oxo-1-(2,3,4,5-tetrahydro-1H-3-benzazepin-7-yl)butan-1-one trifluoroacetate

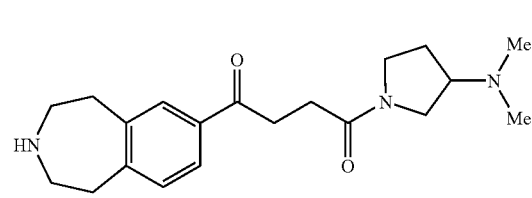

The title compound was obtained in the same manner as in Example 36.
MS(APCI)(M+1): 344

Example 118

N-Benzyl-N-(1-benzylpyrrolidin-3-yl)-4-oxo-4-(2,3,4,5-tetrahydro-1H-3-benzazepin-7-yl)butanamide trifluoroacetate

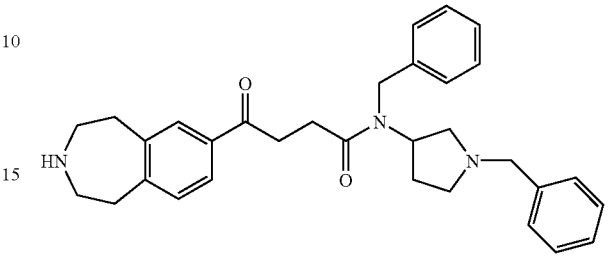

The title compound was obtained in the same manner as in Example 36.
MS(ESI)(M+1): 496

Example 119

4-Oxo-N,N-bis(pyridin-2-ylmethyl)-4-(2,3,4,5-tetrahydro-1H-3-benzazepin-7-yl)butanamide trifluoroacetate

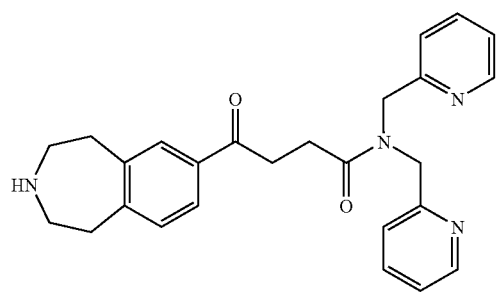

The title compound was obtained in the same manner as in Example 36.
MS(APCI)(M+1) 429

Example 120

4-(4-Methyl-1,4-diazepin-1-yl)-4-oxo-1-(2,3,4,5-tetrahydro-1H-3-benzazepin-7-yl)butan-1-one trifluoroacetate

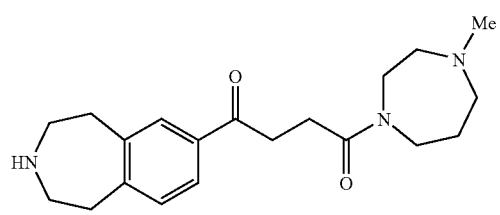

The title compound was obtained in the same manner as in Example 36.
MS(APCI)(M+1): 344

Example 121

4-[4-(2-Hydroxyethyl)pyrazin-1-yl]-4-oxo-1-(2,3,4,5-tetrahydro-1H-3-benzazepin-7-yl)butan-1-one trifluoroacetate

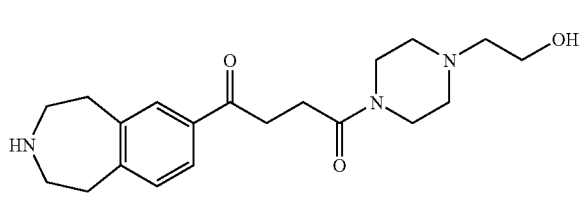

The title compound was obtained in the same manner as in Example 36.
MS(APCI)(M+1): 360

Example 122

4-[4-(1,3-Benzodioxol-5-ylmethyl)pyrazin-1-yl]-4-oxo-1-(2,3,4,5-tetrahydro-1H-3-benzazepin-7-yl)butan-1-one trifluoroacetate

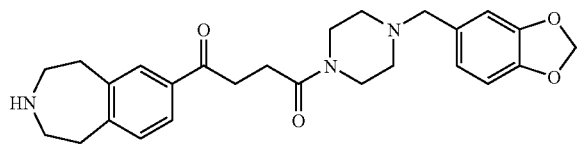

The title compound was obtained in the same manner as in Example 36.
MS(APCI)(M+1): 450

Example 123

4-Oxo-4-[4-(pyrimidin-2-yl)piperazin-1-yl]-1(2,3,4,5-tetrahydro-1H-3-benzazepin-7-yl)butan-1-one trifluoroacetate

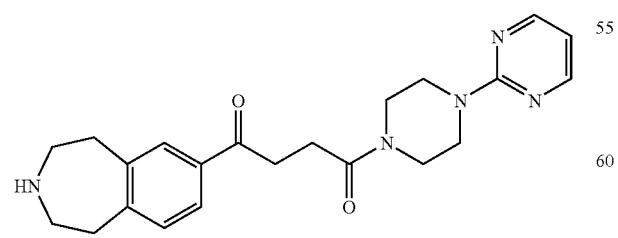

The title compound was obtained in the same manner as in Example 36.
MS(ESI)(M+1): 394

Example 124

4-Oxo-4-[4-[(2E)-3-phenyl-2-propenyl]piperazin-1-yl]-1-(2,3,4,5-tetrahydro-1H-3-benzazepin-7-yl)butan-1-one trifluoroacetate

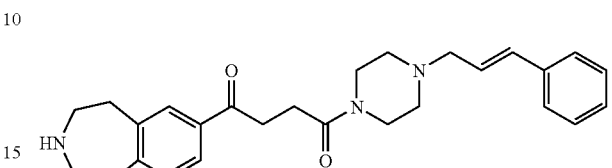

The title compound was obtained in the same manner as in Example 36.
MS(ESI)(M+1): 432

Example 125

N-Benzyl-N-[2-(dimethylamino)ethyl]-4-oxo-4-(2,3,4,5-tetrahydro-1H-3-benzazepin-7-yl)butanamide trifluoroacetate

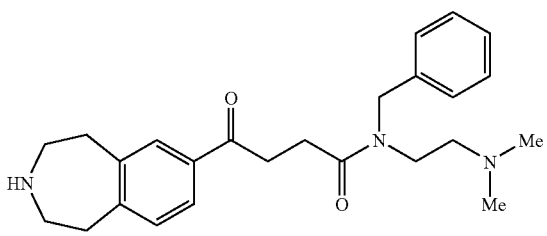

The title compound was obtained in the same manner as in Example 36.
MS(APCI)(M+1): 408

Example 126

N-Methyl-N-(1-methylpiperazin-4-yl)-4-oxo-4-(2,3,4,5-tetrahydro-1H-3-benzazepin-7-yl)butanamide trifluoroacetate

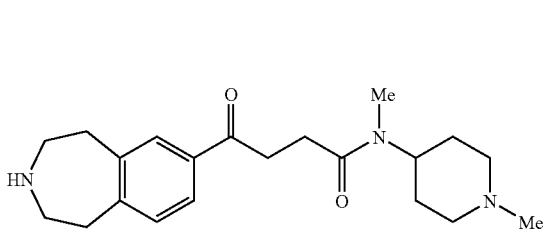

The title compound was obtained in the same manner as in Example 36.
MS(APCI)(M+1): 358

Example 127

4-Oxo-4-[2-(pyrrolidin-1-ylmethyl)pyrrolidin-1-yl]-1-(2,3,4,5-tetrahydro-1H-3-benzazepin-7-yl)butan-1-one trifluoroacetate

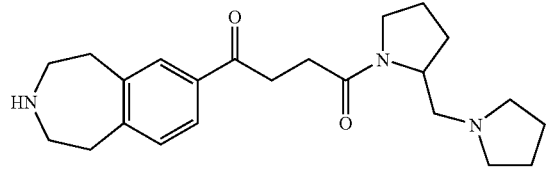

The title compound was obtained in the same manner as in Example 36.
MS(APCI)(M+1): 384

Example 128

4-Oxo-4-[4-(pyrrolidin-1-yl)piperidin-1-yl]-1(2,3,4,5-tetrahydro-1H-3-benzazepin-7-yl)butan-1-one trifluoroacetate

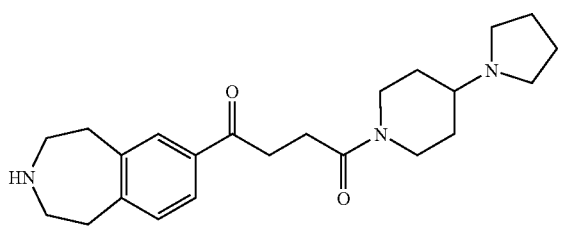

The title compound was obtained in the same manner as in Example 36.
MS(APCI)(M+1): 384

Example 129

N-Benzyl-N-(2-carboxyethyl)-4-oxo-4-(2,3,4,5-tetrahydro-1H-3-benzazepin-7-yl)butanamide trifluoroacetate

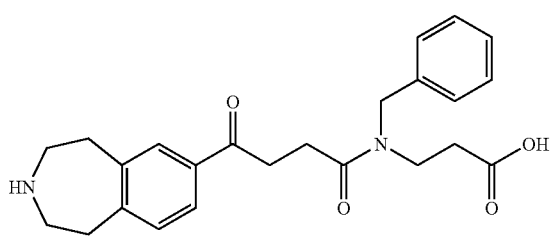

The title compound was obtained in the same manner as in Example 36.
MS(ESI)(M+1): 409

Example 130

4-[4-(4-Chlorophenyl)-1-piperidinyl]-4-oxo-1-(2,3,4,5-tetrahydro-1H-2-benzazepin-8-yl)-1-butanone

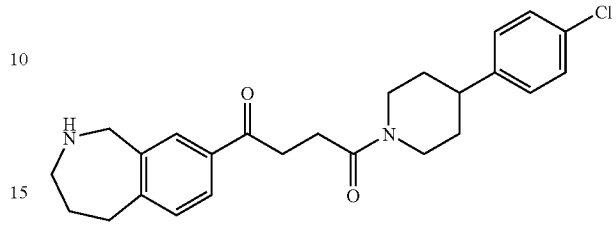

1) Using 2-(trifluoroacetyl)-2,3,4,5-tetrahydro-1H-2-benzazepine, 4-oxo-4-[2-(trifluoroacetyl)-2,3,4,5-tetrahydro-1H-2-benzazepin-8-yl]butanoic acid was obtained by the same procedure as in Reference Example 15.

$^1$H-NMR (DMSO-$d_6$) δ: 1.82 (2H, m), 2.58 (2H, t, J=6.2 Hz), 3.08 (2H, m), 3.23 (2H, t, J=6.0 Hz), 3.89 (2H, m), 4.73 (2H, m), 7.37–7.41 (1H, m), 7.84–7.88 (2H, m), 12.16 (1H, s).

2) Using 4-oxo-4-[2-(trifluoroacetyl)-2,3,4,5-tetrahydro-1H-2-benzazepin-8-yl]butanoic acid obtained in 1) above, the title compound was obtained as colorless powder by the same procedures as in Examples 12 and 13.

$^1$H-NMR (CDCl$_3$) δ: 1.57–1.90 (6H, m), 2.60–2.74 (3H, m), 2.82 (2H, t, J=6.6 Hz), 2.99 (2H, m), 3.12–3.24 (3H, m), 3.34 (2H, t, J=6.6 Hz), 4.01 (2H, s), 4.13 (1H, d, J=15.6 Hz), 4.76 (1H, d, J=12 Hz), 7.12–7.30 (5H, m), 7.79 (2H, m). Melting point: 122–124° C. (crystallizing solvent: ethanol-diisopropyl ether).

Example 131

4-[4-(4-Chlorophenyl)-1-piperidinyl]-1-(2-methyl-2,3,4,5-tetrahydro-1H-2-benzazepin-8-yl)-4-oxo-1-butanone

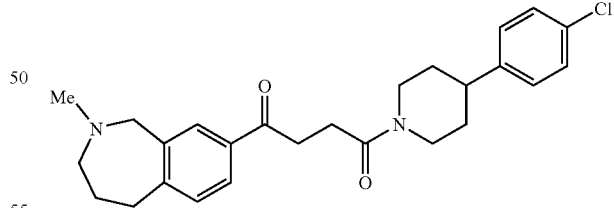

Using 4-[4-(4-chlorophenyl)-1-piperidinyl]-4-oxo-1-(2,3,4,5-tetrahydro-1H-2-benzazepin-8-yl)-1-butanone obtained in Example 130, the title compound was obtained as colorless powder by the same procedure as in Example 16.

$^1$H-NMR (CDCl$_3$) δ: 1.57–1.94 (6H, m), 2.33 (3H, s), 2.61–2.70 (2H, m), 2.84 (2H, t, J=6.6 Hz), 3.00 (2H, m), 3.02 (2H, t, J=5.1 Hz), 3.18 (1H, m), 3.36 (2H, t, J=6.6 Hz), 3.85 (2H, s), 4.14 (1H, d, J=15.6 Hz), 4.76 (1H, d, J=12 Hz), 7.12–7.30 (5H, m), 7.83 (2H, m). Melting point: 133–134° C. (crystallizing solvent: ethanol-diisopropyl ether).

Example 132

4-[4-(4-Chlorophenyl)-1-piperidinyl]-1(2,3-dihydro-1H-isoindol-5-yl)-4-oxo-1-butanone

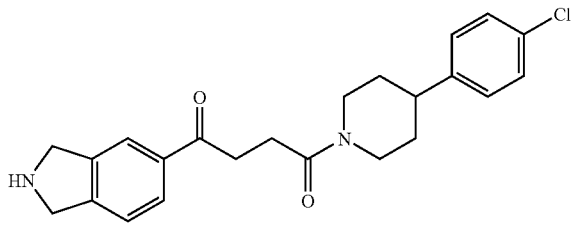

1) Using 2-(trifluoroacetyl) isoindole, 4-oxo-4-[2-(trifluoroacetyl)-2,3-dihydro-1H-isoindol-5-yl]butanoic acid was obtained by the same procedure as in Reference Example 15.
$^1$H-NMR (DMSO-$d_6$) δ: 2.59 (2H, t, J=6.2 Hz), 3.25 (2H, t, J=6.0 Hz), 4.90 (2H, m), 5.12 (2H, m), 7.55 (1H, m), 7.96–8.05 (2H, m), 12.16 (1H, s).

2) Using 4-oxo-4-[2-(trifluoroacetyl)-2,3-dihydro-1H-isoindol-5-yl]butanoic acid obtained in 1) above, the title compound was obtained as colorless powder by the same procedures as in Examples 12 and 13.
$^1$H-NMR (CDCl$_3$) δ: 1.56–1.68 (2H, m), 1.82–1.96 (2H, m), 2.58–2.74 (2H, s), 2.84 (2H, t, J=6.6 Hz), 3.04 (1H, s), 3.17 (1H, m), 3.36 (2H, t, J=6.6 Hz), 4.15 (1H, d, J=15.6 Hz), 4.31 (4H, s), 4.76 (1H, d, J=12 Hz), 7.11–7.36 (5H, m), 7.92 (2H, m). Melting point: 133–134° C. (crystallizing solvent: ethanol-diisopropyl ether).

Example 133

N,N-Dipropyl-(3,4-dihydro-2H-1,4-benzoxazine-3-oxo-6-yl) acetamide

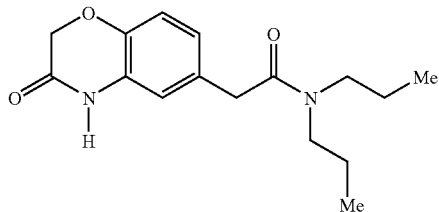

10% palladium-carbon (2.5 g) was added to a solution of N,N-dipropyl-(4-ethoxycarbonylmethoxy-3-nitrophenyl) acetamide (11 g, 30.0 mmol) obtained in Reference Example 17 in ethanol (500 ml) and then subjected to catalytic hydrogenation reaction at normal pressure at room temperature. After the reaction was finished, the catalyst was filtered off, and the resultant filtrate was concentrated. The residues were dissolved in toluene (500 ml) and heated overnight under reflux. The reaction solution was concentrated and then recrystallized from ethyl acetate-hexane, whereby the title compound (8.4 g) was obtained as crystals with a mp of 121 to 122° C.
$^1$H-NMR (CDCl$_3$) δ: 0.8–1.0 (6H, m), 1.4–1.7 (4H, m), 3.15–3.4 (4H, m), 3.62 (2H, s), 4.53 (2H, s), 6.7–6.9 (3H, m), 9.1–9.4 (1H, br) Elemental analysis for C$_{16}$H$_{22}$N$_2$O$_3$. Calcd.: C, 66.18; H, 7.64; N, 9.65. Found: C, 66.07; H, 7.37; N, 9.59.

Example 134

3,4-Dihydro-6-[2-(N,N-dipropylamino)ethyl]-2H-1,4-benzoxazine hydrochloride

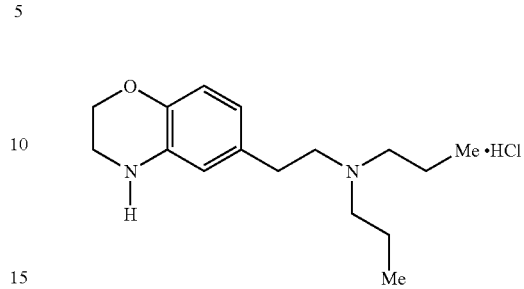

1 N borane/THF solution (140 ml, 140 mmol) was added to a solution of N,N-dipropyl-(3,4-dihydro-2H-1,4-benzoxazine-3-oxo-6-yl)acetamide (10 g, 34.4 mmol) obtained in Example 133 in THF (200 ml), and the mixture was stirred at room temperature for 4 hours, and then 6 N hydrochloric acid (30 ml, 180 mmol) was added dropwise to the reaction solution under cooling with ice-bath. The reaction solution was neutralized with 6 N aqueous sodium hydroxide and extracted with ethyl acetate. The reaction solution was washed with water, dried over anhydrous magnesium sulfate and concentrated. The residues were purified by silica gel column chromatography (developing solvent; hexane:ethyl acetate=4:1), then 4 N hydrochloric acid in ethyl acetate was added thereto, and the solution was concentrated, whereby the title compound (6.8 g) was obtained as amorphous powder.
$^1$H-NMR (CDCl$_3$, free base) δ: 0.91 (6H, t, J=7.2 Hz), 1.6–1.8 (4H, m), 2.6–2.8 (4H, m), 2.84 (4H, brs), 3.41 (2H, t, J=4.4 Hz), 3.6–4.0 (1H, br), 4.22 (2H, t, J=4.4 Hz), 6.4–6.6 (2H, m), 6.65–6.75 (1H, m).

Example 135

3,4-Dihydro-6-[2-(N,N-dipropylamino)ethyl]-4-(1-naphthalenesulfonyl)-2H-1,4-benzoxazine succinate

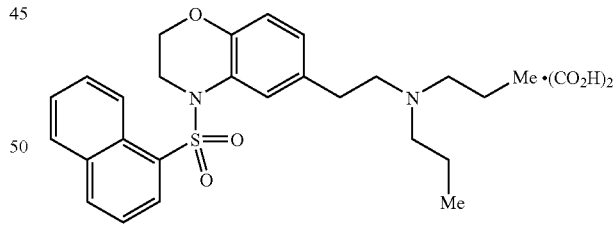

A solution of 1-naphthalenesulfonyl chloride (388 mg, 1.72 mmol) in acetonitrile (5 ml) was added to a solution of 3,4-dihydro-6-[2-(N,N-propylamino)ethyl]-2H-1,4-benzoxazine hydrochloride (300 mg, 1.14 mmol) obtained in Example 134, 4-dimethylaminopyridine (140 mg, 1.14 mmol) and triethylamine (0.48 ml, 3.43 mmol) in acetonitrile (15 ml) under cooling with ice-bath, and the mixture was stirred at room temperature for 4 hours. Water (50 ml) was added to the reaction solution which was then extracted with ethyl acetate. The extract was washed with 10% aqueous potassium carbonate and a saturated saline solution, dried over anhydrous sodium sulfate and concentrated. The residues were purified by silica gel column chromatography (developing solvent; ethyl acetate), and succinic acid (1 equivalent) was added thereto, and the product was recrystallized from ethyl acetate-diisopropyl ether, whereby the title compound (220 mg) was obtained as crystals with a mp of 144 to 145° C.

$^1$H-NMR (CDCl$_3$, free base) δ: 0.89 (6H, t, J=7.2 Hz), 1.4–1.6 (4H, m), 2.4–2.6 (4H, m), 2.66 (4H, brs), 3.65 (2H, t, J=4.6 Hz), 3.89 (2H, t, J=4.6 Hz), 6.64 (1H, d, J=8.4 Hz), 6.89 (1H, dd, J=8.4, 1.8 Hz), 7.3–7.6 (4H, m), 7.90 (1H, d, J=7.8 Hz), 8.08 (1H, d, J=8.4 Hz), 8.2–8.4 (2H, m).

Example 136

3,4-Dihydro-6-[2-(N,N-dipropylamino)ethyl]-4-(2-naphthalenesulfonyl)-2H-1,4-benzoxazine succinate

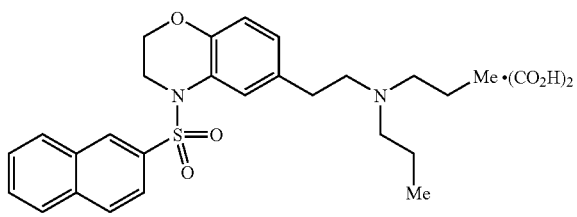

Using 3,4-dihydro-6-[2-(N,N-dipropylamino)ethyl]-2H-1,4-benzoxazine hydrochloride obtained in Example 134, the title compound was obtained as colorless amorphous powder by the same procedure as in Example 135.

$^1$H-NMR (CDCl$_3$, free base) δ: 0.90 (6H, t, J=7.2 Hz), 1.4–1.6 (4H, m), 2.4–2.6 (4H, m), 2.71 (4H, brs), 3.68 (2H, t, J=4.6 Hz), 3.93 (2H, t, J=4.6 Hz), 6.68 (1H, d, J=8.4 Hz), 6.90 (1H, dd, J=8.4, 1.8 Hz), 7.5–7.8 (4H, m), 7.8–8.0 (3H, m), 8.29 (1H, brs).

Example 137

4-(4-Chlorobenzenesulfonyl)-3,4-dihydro-6-[2-(N,N-dipropylamino)ethyl]-2H-1,4-benzoxazine succinate

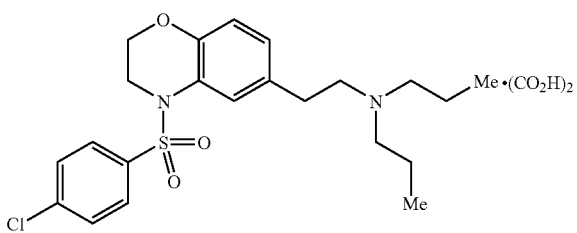

Using 3,4-dihydro-6-[2-(N,N-dipropylamino)ethyl]-2H-1,4-benzoxazine hydrochloride obtained in Example 134, the title compound was obtained as powder by the same procedure as in Example 135.

$^1$H-NMR (CDCl$_3$, free base) δ: 0.89 (6H, t, J=7.2 Hz), 1.4–1.6 (4H, m), 2.4–2.6 (4H, m), 2.69 (4H, brs), 3.72 (2H, t, J=4.6 Hz), 3.88 (2H, t, J=4.6 Hz), 6.72 (1H, d, J=8.4 Hz), 6.92 (1H, dd, J=8.6, 2.0 Hz), 7.41 (2H, d, J=8.8 Hz), 7.56 (2H, d, J=8.8 Hz), 7.64 (1H, d, J=2.0 Hz). Elemental analysis for C$_{24}$H$_{31}$ClN$_2$O$_7$S. Calcd.: C, 54.70; H, 5.93; N, 5.32. Found: C, 54.46; H, 5.88; N, 5.29. Melting point: 130–133° C. (crystallizing solvent: acetone)

Example 138

3,4-Dihydro-6-[2-(N,N-dipropylamino)ethyl]-4-(2,4,6-trimethylbenzenesulfonyl)-2H-1,4-benzoxazine succinate

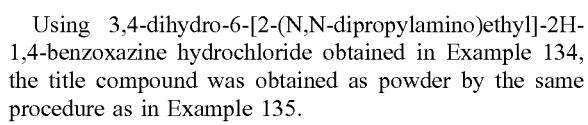

Using 3,4-dihydro-6-[2-(N,N-dipropylamino)ethyl]-2H-1,4-benzoxazine hydrochloride obtained in Example 134, the title compound was obtained as powder by the same procedure as in Example 135.

$^1$H-NMR (CDCl$_3$, free base) δ: 0.88 (6H, t, J=7.4 Hz), 1.3–1.6 (4H, m), 2.3–2.6 (4H, m), 2.33 (3H, s), 2.48 (4H, brs), 2.57 (6H, s), 3.83 (2H, t, J=4.6 Hz), 4.23 (2H, t, J=4.6 Hz), 6.61 (1H, brs), 6.8–6.85 (2H, m), 7.00 (2H, s). Melting point: 157–158° C. (crystallizing solvent: ethyl acetate-diisopropyl ether)

Example 139

4-(4-t-Butylbenzenesulfonyl)-3,4-dihydro-6-[2-(N,N-dipropylamino)ethyl]-2H-1,4-benzoxazine succinate Using 3,4-dihydro-6-[2-(N,N-dipropylamino)ethyl]-2H-1,4-benzoxazine hydrochloride obtained in Example 134, the title compound was obtained as amorphous powder by the same procedure as in Example 135.

$^1$H-NMR (CDCl$_3$, free base) δ: 0.90 (6H, t, J=7.2 Hz), 1.30 (9H, s), 1.3–1.6 (4H, m), 2.4–2.55 (4H, m), 2.69 (4H, s), 3.71 (2H, t, J=4.0 Hz), 3.85 (2H, t, J=4.0 Hz), 6.72 (1H, d, J=8.2 Hz), 6.90 (1H, dd, J=8.2, 2.0 Hz), 7.44 (2H, d, J=8.8 Hz), 7.57 (2H, d, J=8.8 Hz), 7.68 (1H, d, J=2.0 Hz). Elemental analysis for C$_{28}$H$_{40}$N$_2$O$_7$S. Calcd.: C, 61.29; H, 7.35; N, 5.11. Found: C, 61.02; H, 7.57; N, 5.00.

Example 140

4-Benzylsulfonyl-3,4-dihydro-6-[2-(N,N-dipropylamino)ethyl]-2H-1,4-benzoxazine succinate

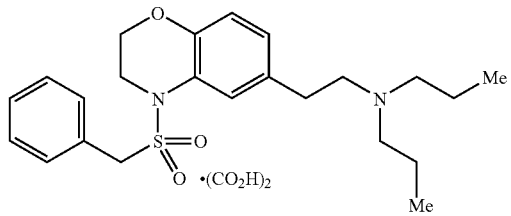

Using 3,4-dihydro-6-[2-(N,N-dipropylamino)ethyl]-2H-1,4-benzoxazine hydrochloride obtained in Example 134, the title compound was obtained as powder by the same procedure as in Example 135.

$^1$H-NMR (CDCl$_3$, free base) δ: 0.89 (6H, t, J=7.2 Hz), 1.4–1.6 (4H, m), 2.4–2.55 (4H, m), 2.66 (4H, brs), 3.53 (2H, t, J=4.2 Hz), 3.73 (2H, t, J=4.2 Hz), 4.44 (2H, s), 6.7–7.0 (2H, m), 7.1–7.4 (6H, m). Melting point: 150–151° C. (crystallizing solvent: ethyl acetate-diisopropyl ether)

Example 141

3,4-Dihydro-6-[2-(N,N-dipropylamino)ethyl]-4-(2-naphthoyl)-2H-1,4-benzoxazine hydrochloride

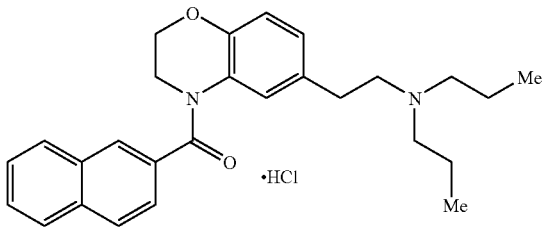

Using 3,4-dihydro-6-[2-(N,N-dipropylamino)ethyl]-2H-1,4-benzoxazine hydrochloride obtained in Example 134, the title compound was obtained as powder by the same procedure as in Example 135.

$^1$H-NMR (CDCl$_3$, free base) δ: 0.75 (6H, t, J=7.2 Hz), 1.0–1.4 (4H, m), 1.9–2.2 (6H, m), 2.2–2.4 (2H, m), 4.06 (2H, t, J=4.2 Hz), 4.39 (2H, t, J=4.2 Hz), 6.5–6.9 (3H, m), 7.4–7.6 (3H, m), 7.7–7.9 (3H, m), 8.04 (1H, s). Melting point: 165–166° C. (crystallizing solvent: methanol-diethyl ether)

Example 142

4-(4-Biphenyl-1-carbonyl)-3,4-dihydro-6-[2-(N,N-dipropylamino)ethyl]-2H-1,4-benzoxazine

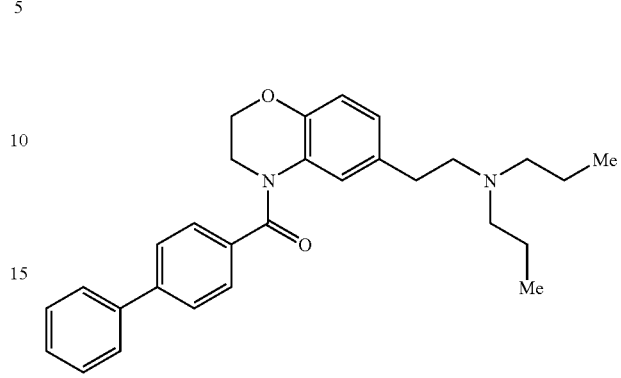

Using 3,4-dihydro-6-[2-(N,N-dipropylamino)ethyl]-2H-1,4-benzoxazine hydrochloride obtained in Example 134, the title compound was obtained as powder by the same procedure as in Example 135.

$^1$H-NMR (CDCl$_3$) δ: 0.75 (6H, t, J=7.2 Hz), 1.1–1.4 (4H, m), 2.1–2.6 (8H, m), 4.04 (2H, t, J=4.6 Hz), 4.38 (2H, t, J=4.6 Hz), 6.6–6.9 (3H, m), 7.3–7.5 (3H, m), 7.5–7.7 (6H, m). Melting point: 95–96° C. (crystallizing solvent: ethyl acetate-diisopropyl ether)

Example 143

3,4-Dihydro-6-[2-(N,N-dipropylamino)ethyl]-4-(1-naphthylmethyl)-2H-1,4-benzoxazine hydrochloride

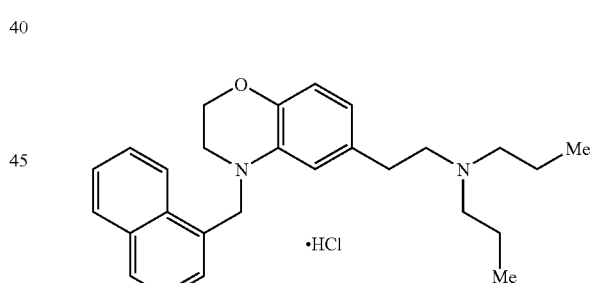

Potassium carbonate (316 mg, 2.29 mmol) was added to a solution of 3,4-dihydro-6-[2-(N,N-dipropylamino)ethyl]-2H-1,4-benzoxazine hydrochloride (200 mg, 0.76 mmol) obtained in Example 134 and 1-chloromethyl naphthalene (400 mg, 2.29 mmol) in DMF (15 ml). After the reaction solution was stirred at room temperature for 2 hours, water was added to the reaction solution which was then extracted with ethyl acetate. The extract was washed with water, dried over anhydrous sodium sulfate and concentrated. The residues were purified by silica gel column chromatography (developing solvent; hexane:ethyl acetate=3:1), treated with 4 N hydrochloric acid in ethyl acetate and crystallized from acetone-pentane, whereby the title compound (80 mg) was obtained as crystals with a mp of 177 to 178° C.

$^1$H-NMR (CDCl$_3$, free base) δ: 0.82 (6H, t, J=7.4 Hz), 1.4–1.7 (4H, m), 2.3–2.5 (4H, m), 2.59 (4H, brs), 3.28 (2H, t, J=4.4 Hz), 4.21 (2H, t, J=4.4 Hz), 4.84 (2H, s), 6.4–6.6 (2H, m), 6.7–6.8 (1H, m), 7.3–7.6 (4H, m), 7.7–8.0 (2H, m), 8.0–8.1 (1H, m). Elemental analysis for C$_{27}$H$_{35}$ClN$_2$O·0.5H$_2$O. Calcd.: C, 72.38; H, 8.10; N, 6.25. Found: C, 72.24; H, 7.91; N, 6.12.

Example 144

3,4-Dihydro-6-[2-(N,N-dipropylamino)ethyl]-4-(2-naphthylmethyl)-2H-1,4-benzoxazine hydrochloride

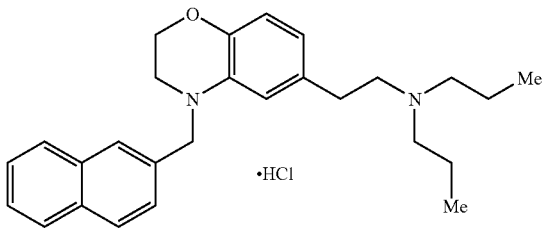

Using 3,4-dihydro-6-[2-(N,N-dipropylamino) ethyl]-2H-1,4-benzoxazine hydrochloride obtained in Example 134, the title compound was obtained as powder by the same procedure as in Example 143.

$^1$H-NMR (CDCl$_3$, free base) δ: 0.82 (6H, t, J=7.4 Hz), 1.4–1.7 (4H, m), 2.4–2.9 (8H, m), 3.3–3.5 (2H, m), 4.2–4.4 (2H, m), 4.59 (2H, brs), 6.4–6.6 (2H, m), 6.7–6.8 (1H, m), 7.3–7.5 (3H, m), 7.7–7.9 (4H, m). Melting point: 169–170° C. (crystallizing solvent: diethyl ether-hexane)

Example 145

3,4-Dihydro-6-[3-(N,N-dipropylamino)propyl]-4-(2-naphthalenesulfonyl)-2H-1,4-benzoxazine succinate

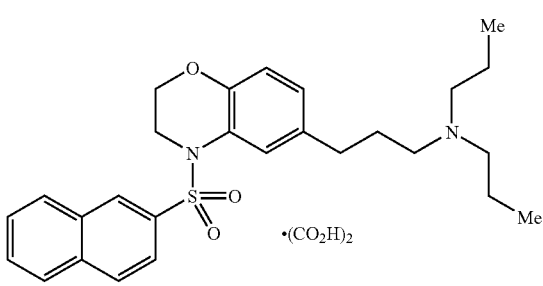

Potassium carbonate (0.9 g, 6.48 mmol) was added to a solution of 3,4-dihydro-6-(3-iodopropyl)-4-(2-naphthalenesulfonyl)-2H-1,4-benzoxazine (1.0 g, 2.16 mmol) obtained in Reference Example 19 and dipropylamine (263 mg, 2.60 mmol) in DMF (20 ml), and the mixture was stirred overnight at room temperature. Water was added to the reaction solution which was then extracted with ethyl acetate. The extract was washed with water and aqueous saturated sodium bicarbonate, dried over anhydrous sodium sulfate and concentrated. The residues were purified by alumina column chromatography (developing solvent; hexane:ethyl acetate=4:1) and then dissolved in ethyl acetate. 1 equivalent of succinic acid was added to the resultant solution, and then the solvent was distilled away, whereby the title compound (1.17 g) was obtained as amorphous powder.

$^1$H-NMR (CDCl$_3$, free base) δ: 0.8–1.0 (6H, m), 1.3–1.6 (4H, m), 1.6–1.9 (2H, m), 2.3–2.6 (8H, m), 3.67 (2H, t, J=4.6 Hz), 3.92 (2H, t, J=4.6 Hz), 6.68 (1H, d, J=8.4 Hz), 6.91 (1H, dd, J=8.4, 2.0 Hz), 7.52 (1H, dd, J=8.4, 2.0 Hz), 7.5–7.5 (2H, m), 7.76 (1H, d, J=2.0 Hz), 7.8–8.0 (3H, m), 8.28 (1H, d, J=1.8 Hz).

Example 146

3,4-Dihydro-4-(2-naphthalenesulfonyl)-6-[3-(N-propylamino)propyl]-2H-1,4-benzoxazine succinate

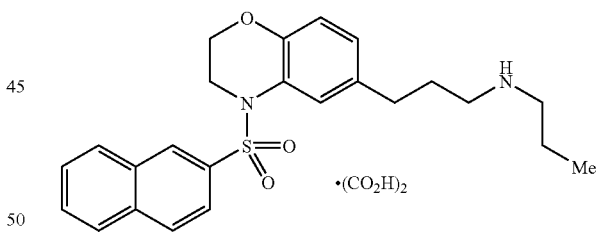

Using 3,4-dihydro-6-(3-iodopropyl)-4-(2-naphthalene sulfonyl)-2H-1,4-benzoxazine obtained in Reference Example 19, the title compound was obtained as powder by the same procedure as in Example 145.

$^1$H-NMR (CDCl$_3$, free base) δ: 0.92 (3H, t, J=7.4 Hz), 1.4–1.7 (2H, m), 1.7–2.0 (4H, m), 2.5–2.8 (4H, m), 3.68 (2H, t, J=4.6 Hz), 3.92 (2H, t, J=4.6 Hz), 6.68 (1H, d, J=8.4 Hz), 6.89 (1H, dd, J=8.4, 2.2 Hz), 7.4–7.7 (3H, m), 7.74 (1H, d, J=1.8 Hz), 7.8–8.0 (3H, m), 8.28 (1H, d, J=1.6 Hz). Melting point: 155–156° C. (crystallizing solvent: methanol-diethyl ether)

Example 147

3,4-Dihydro-4-(2-naphthalenesulfonyl)-6-[3-(4-piperidinopiperidino)propyl]-2H-1,4-benzoxazine dihydrochloride

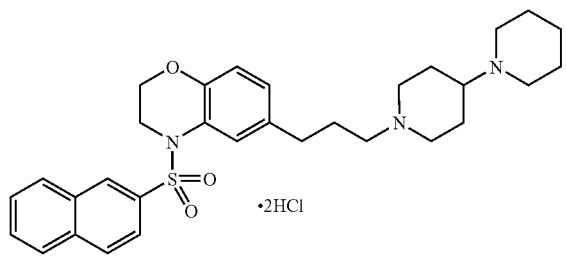

Using 3,4-dihydro-6-(3-iodopropyl)-4-(2-naphthalenesulfonyl)-2H-1,4-benzoxazine obtained in Reference Example 19, the title compound was obtained as powder by the same procedure as in Example 145.

$^1$H-NMR (CDCl$_3$, free base) δ: 1.3–2.0 (13H, m), 2.1–2.4 (4H, m), 2.4–2.7 (6H, m), 2.9–3.1 (2H, m), 3.68 (2H, d, J=4.6 Hz), 3.91 (2H, d, J=4.6 Hz), 6.68 (1H, d, J=8.2 Hz), 6.89 (1H, dd, J=8.2, 2.0 Hz), 7.4–7.7 (3H, m), 7.74 (1H, d, J=2.0 Hz), 7.8–8.0 (3H, m), 8.28 (1H, d, J=1.6 Hz). Melting point: 240–241° C. (crystallizing solvent: methanol-diethyl ether)

Example 148

3,4-Dihydro-4-(2-naphthalenesulfonyl)-6-[3-(4-phenylpiperidino)propyl]-2H-1,4-benzoxazine hydrochloride

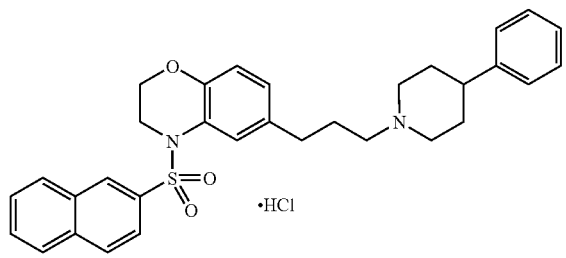

Using 3,4-dihydro-6-(3-iodopropyl)-4-(2-naphthalenesulfonyl)-2H-1,4-benzoxazine obtained in Reference Example 19, the title compound was obtained as powder by the same procedure as in Example 145.

$^1$H-NMR (CDCl$_3$, free base) δ: 1.6–2.2 (8H, m), 2.3–2.6 (3H, m), 2.64 (2H, t, J=7.6 Hz), 3.0–3.2 (2H, m), 3.68 (2H, t, J=4.6 Hz), 3.93 (2H, t, J=4.6 Hz), 6.69 (1H, d, J=8.4 Hz), 6.91 (1H, dd, J=8.4, 2.0 Hz), 7.1–7.4 (5H, m), 7.4–7.7 (3H, m), 7.76 (1H, d, J=2.0 Hz), 7.8–8.0 (3H, m), 8.30 (1H, brs). Melting point: 182–183° C. (crystallizing solvent: methanol-diethyl ether)

Example 149

6-[3-[4-(4-Chlorophenyl)-4-hydroxypiperidino]propyl]-3,4-dihydro-4-(2-naphthalenesulfonyl)-2H-1,4-benzoxazine hydrochloride

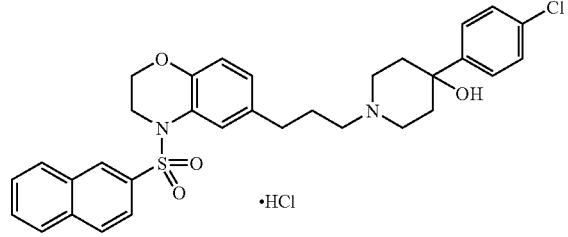

Using 3,4-dihydro-6-(3-iodopropyl)-4-(2-naphthalenesulfonyl)-2H-1,4-benzoxazine obtained in Reference Example 19, the title compound was obtained as powder by the same procedure as in Example 145.

$^1$H-NMR (CDCl$_3$) δ: 1.7–2.0 (4H, m), 2.15 (2H, td, J=13.2, 4.4 Hz), 2.3–2.6 (4H, m), 2.65 (2H, t, J=7.6 Hz), 2.7–2.9 (2H, m), 3.67 (2H, t, J=4.6 Hz), 3.92 (2H, t, J=4.6 Hz), 6.70 (1H, d, J=8.4 Hz), 6.91 (1H, dd, J=8.4, 1.8 Hz), 7.2–7.4 (2H, m), 7.4–7.7 (7H, m), 7.77 (1H, d, J=2.0 Hz), 7.8–8.0 (3H, m), 8.29 (1H, brs). Melting point: 125–126° C. (crystallizing solvent: methanol-diethyl ether)

Example 150

3,4-Dihydro-6-[3-[4-(3,4-methylenedioxybenzyl)piperazino]propyl]-4-(2-naphthalenesulfonyl)-2H-1,4-benzoxazine dihydrochloride

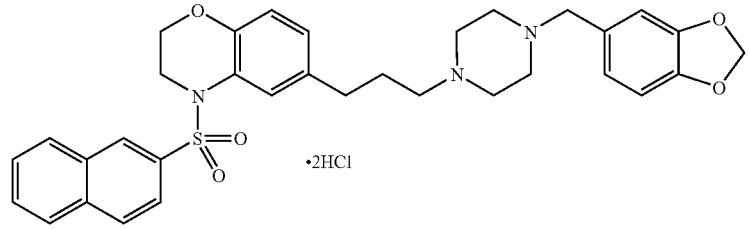

Using 3,4-dihydro-6-(3-iodopropyl)-4-(2-naphthalene sulfonyl)-2H-1,4-benzoxazine obtained in Reference Example 19, the title compound was obtained as powder by the same procedure as in Example 145.

$^1$H-NMR (CDCl$_3$, free base) δ: 1.7–1.9 (2H, m), 2.3–2.7 (12H, m), 3.42 (2H, s), 3.68 (2H, t, J=4.6 Hz), 3.92 (2H, t, J=4.6 Hz), 5.94 (2H, s), 6.68 (1H, d, J=8.4 Hz), 6.75 (2H, brs), 6.8–7.0 (2H, m), 7.4–7.7 (3H, m), 7.74 (1H, d, J=2.0 Hz), 7.8–8.0 (3H, m), 8.28 (1H, d, J=1.6 Hz). Melting point: 212–213° C. (crystallizing solvent: methanol-diethyl ether)

Example 151

3,4-Dihydro-4-[3,4-dihydro-6,7-dimethoxyspiro [naphthalene-2(1H),2'-piperidine]-2'-yl]-4-(2-naphthalenesulfonyl)-2H-1,4-benzoxazine hydrochloride

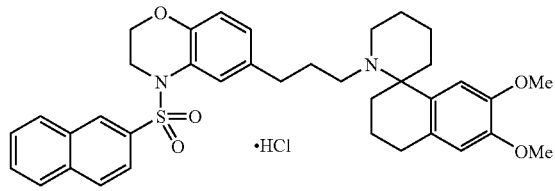

Using 3,4-dihydro-6-(3-iodopropyl)-4-(2-naphthalene sulfonyl)-2H-1,4-benzoxazine obtained in Reference Example 19, the title compound was obtained as amorphous powder by the same procedure as in Example 145.

$^1$H-NMR (CDCl$_3$, free base) δ: 1.3–2.0 (10H, m), 2.3–2.9 (10H, m), 3.66 (2H, t, J=4.4 Hz), 3.82 (6H, s), 3.90 (2H, t, J=4.4 Hz), 6.56 (2H, brs), 6.68 (1H, d, J=8.4 Hz), 6.90 (1H, dd, J=8.4, 2.0 Hz), 7.47 (1H, dd, J=8.6, 2.0 Hz), 7.5–7.7 (2H, m), 7.7–8.0 (4H, m), 8.27 (1H, brs).

Example 152

3,4-Dihydro-4-(2-naphthalenesulfonyl)-6-[3-(4-pyridylmethylamino)propyl]-2H-1,4-benzoxazine dihydrochloride

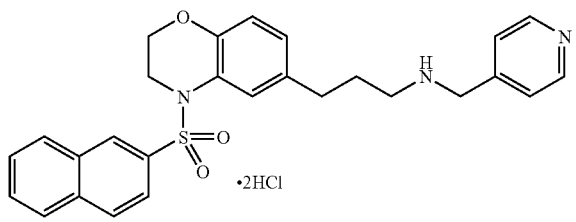

Using 3,4-dihydro-6-(3-iodopropyl)-4-(2-naphthalene sulfonyl)-2H-1,4-benzoxazine obtained in Reference Example 19, the title compound was obtained as amorphous powder by the same procedure as in Example 145.

$^1$H-NMR (CDCl$_3$, free base) δ: 1.7–2.0 (2H, m), 2.67 (4H, t, J=7.0 Hz), 3.68 (2H, t, J=4.4 Hz), 3.81 (2H, s), 3.91 (2H, t, J=4.4 Hz), 6.68 (1H, d, J=8.4 Hz), 6.88 (1H, dd, J=8.4, 2.2 Hz), 7.1–7.3 (2H, m), 7.4–7.7 (3H, m), 7.7–8.0 (4H, m), 8.28 (1H, brs), 8.53 (2H, d, J=6.2 Hz).

Example 153

6-{3-[2-(3-Indolylethyl)amino]propyl}-3,4-dihydro-4-(2-naphthalenesulfonyl)-2H-1,4-benzoxazine hydrochloride

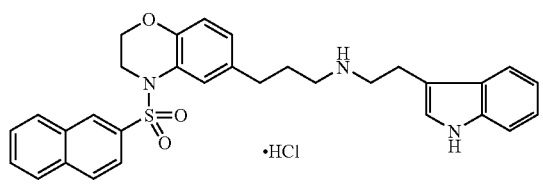

Using 3,4-dihydro-6-(3-iodopropyl)-4-(2-naphthalene sulfonyl)-2H-1,4-benzoxazine obtained in Reference Example 19, the title compound was obtained as amorphous powder by the same procedure as in Example 145.

$^1$H-NMR (CDCl$_3$, free base) δ: 1.7–2.0 (2H, m), 2.58 (2H, t, J=8.0 Hz), 2.69 (2H, t, J=8.0 Hz), 2.8–3.1 (4H, m), 3.67 (2H, t, J=4.4 Hz), 3.90 (2H, t, J=4.4 Hz), 6.64 (1H, d, J=8.4 Hz), 6.82 (1H, dd, J=8.2, 2.0 Hz), 7.0–7.3 (3H, m), 7.3–7.4 (1H, m), 7.4–7.8 (5H, m), 7.8–8.0 (3H, m), 8.18 (1H, brs), 8.27 (1H, brs).

Example 154

N,N-Dipropyl-[3,4-dihydro-3-(4-methoxyphenyl)-2H-1,4-benzoxazin-6-yl]acetamide

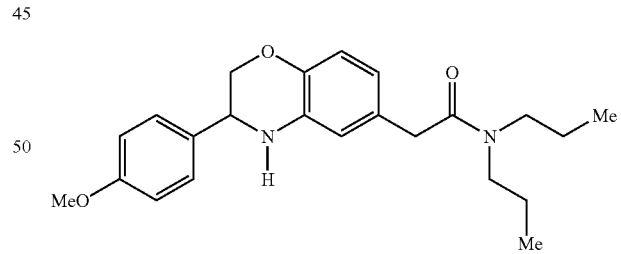

Using N,N-dipropyl-[4-(4-methoxybenzene) carbonylmethoxy-3-nitrophenyl]acetamide obtained in Reference Example 20, the title compound was obtained as oily matter by the same procedure as in Example 133.

$^1$H-NMR (CDCl$_3$) δ: 0.8–1.0 (6H, m), 1.4–1.7 (4H, m), 3.1–3.4 (4H, m), 3.56 (2H, s), 3.82 (3H, s), 3.8–4.0 (2H, m), 4.22 (1H, d, J=10.6 Hz), 4.44 (1H, dd, J=8.8, 3.0 Hz), 6.52 (1H, dd, J=8.2, 2.2 Hz), 6.60 (1H, d, J=2.2 Hz), 6.74 (1H, d, J=8.2 Hz), 6.91 (2H, d, J=8.8 Hz), 7.30 (2H, d, J=8.8 Hz). Elemental analysis for C$_{23}$H$_{30}$N$_2$O$_3$. Calcd.: C, 72.22; H, 7.91; N, 7.32. Found: C, 71.91; H, 8.10; N, 7.35.

Example 155

3,4-Dihydro-6-[2-(N,N-dipropylamino)ethyl]-3-(4-methoxyphenyl)-2H-1,4-benzoxazine hydrochloride

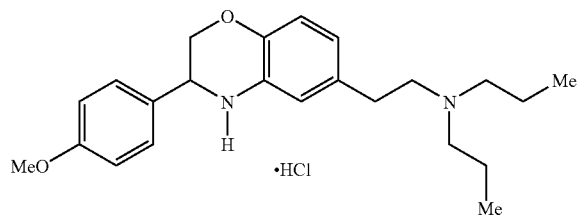

Using N,N-dipropyl-[3,4-dihydro-3-(4-methoxyphenyl)-2H-1,4-benzoxazin-6-yl]acetamide obtained in Example 154, the title compound in the form of a free base was obtained as powder with a mp of 85 to 90° C. by the same procedure as in Example 133. 4 N hydrochloric acid in ethyl acetate was added to the resultant powder which was then concentrated, whereby the title compound was obtained as amorphous powder.

$^1$H-NMR (CDCl$_3$, free base) δ: 0.91 (6H, t, J=7.4 Hz), 1.5–1.8 (4H, m), 1.6–1.8 (4H, m), 2.87 (4H, s), 3.82 (3H, s), 3.8–4.0 (2H, m), 4.23 (1H, dd, J=10.6, 3.0 Hz), 4.43 (1H, dd, J=8.8, 3.0 Hz), 6.4–6.6 (2H, m), 6.77 (1H, d, J=8.8 Hz), 6.91 (2H, d, J=8.8 Hz), 7.30 (2H, d, J=8.8 Hz).

Example 156

4-[4-(4-Chlorophenyl)-1-piperidinyl]-4-oxo-1-[2-(trifluoroacetyl)-2,3,4,5-tetrahydro-1H-2-benzoxazin-8-yl]-1-butanone

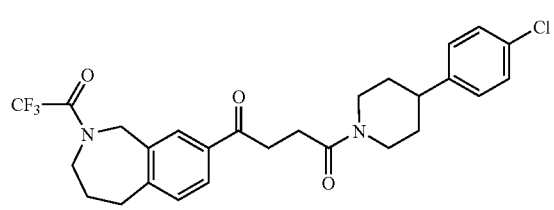

Using 4-oxo-4-[2-(trifluoroacetyl)-2,3,4,5-tetrahydro-1H-2-benzazepin-8-yl]butanoic acid obtained in 1) in Example 130, the title compound was obtained as powder by the same procedure as in Example 12.

$^1$H-NMR (CDCl$_3$) δ: 1.57–1.93 (6H, m), 2.61–2.81 (4H, m), 3.06 (2H, m), 3.22 (1H, m), 3.33 (2H, m), 3.94 (2H, m), 4.13 (1H, m), 4.68–4.79 (3H, m), 7.13 (2H, m), 7.29 (3H, m), 7.88 (1H, m), 8.03 (1H, m). Melting point: 153–155° C. (crystallizing solvent: ethanol-diisopropyl ether)

Example 157

4-[4-(4-Chlorophenyl)piperidin-1-yl]-1-(2-ethyl-2,3,4,5-tetrahydro-1H-2-benzoxazin-8-yl)-4-oxobutan-1-one hydrochloride

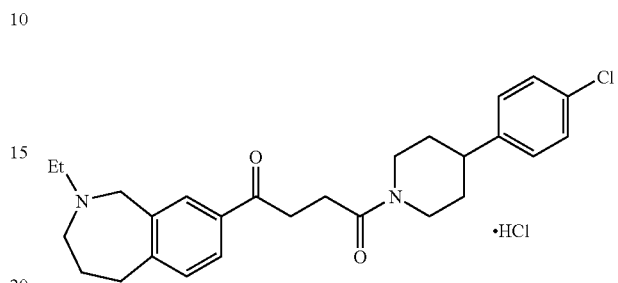

Using 4-[4-(4-chlorophenyl)-1-piperidinyl]-4-oxo-1-(2,3,4,5-tetrahydro-1H-2-benzazepin-8-yl)-1-butanone obtained in Example 130, the title compound was obtained as amorphous powder by the same procedure as in Example 17.

$^1$H-NMR (DMSO-d$_6$) δ: 1.27 (3H, t, J=7.4 Hz), 1.42 (1H, m), 1.63 (1H, m), 1.73–1.96 (4H, m), 2.51–2.89 (5H, m), 3.07 (4H, m), 3.22 (2H, m), 3.49 (2H, m), 4.10 (1H, m), 4.45–4.67 (3H, m), 7.27–7.46 (5H, m), 7.85 (2H, m), 10.47 (1H, m).

Example 158

4-[4-(4-Chlorophenyl)piperidin-1-yl]-1-(2-isopropyl-2,3,4,5-tetrahydro-1H-2-benzoxazin-8-yl)-4-oxobutan-1-one hydrochloride

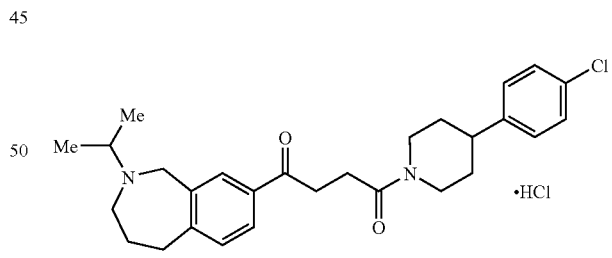

Using 4-[4-(4-chlorophenyl)-1-piperidinyl]-4-oxo-1-(2,3,4,5-tetrahydro-1H-2-benzazepin-8-yl)-1-butanone obtained in Example 130, the title compound was obtained as amorphous powder by the same procedure as in Example 17.

$^1$H-NMR (DMSO-d$_6$) δ: 1.31–1.44 (6H, m), 1.55 (1H, m), 1.81–1.92 (3H, m), 2.07 (1H, m), 2.61 (1H, m), 2.74 (4H, m), 3.04 (1H, m), 3.24–3.30 (4H, m), 3.57 (3H, m), 4.08 (1H, m), 4.47–4.63 (3H, m), 7.24–7.46 (5H, m), 7.96 (2H, m), 9.89 (1H, m).

Example 159

1-(2-Benzyl-2,3,4,5-tetrahydro-1H-2-benzazepin-8-yl)-4-[4-(4-chlorophenyl)piperidin-1-yl]-4-oxobutan-1-one hydrochloride

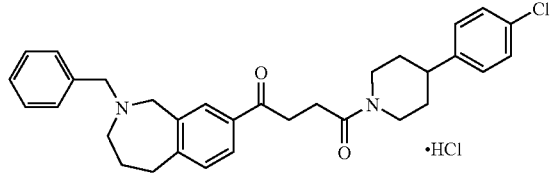

Using 4-[4-(4-chlorophenyl)-1-piperidinyl]-4-oxo-1-(2,3,4,5-tetrahydro-1H-2-benzazepin-8-yl)-1-butanone obtained in Example 130, the title compound was obtained as amorphous powder by the same procedure as in Example 17.

$^1$H-NMR (DMSO-$d_6$) δ: 1.37 (1H, m), 1.58 (1H, m), 1.74–1.85 (3H, m), 2.07 (1H, m), 2.65–2.89 (5H, m), 3.07–3.21 (6H, m), 4.08 (2H, m), 4.40–4.50 (3H, m), 4.73 (1H, m), 7.28–7.61 (10H, m), 7.96 (2H, m), 10.84 (1H, m).

Example 160

4-[4-(4-Chlorophenyl)piperidin-1-yl]-4-oxo-1-[2-(trifluoroacetyl)-2,3-dihydro-1H-isoindol-5-yl]butan-1-one

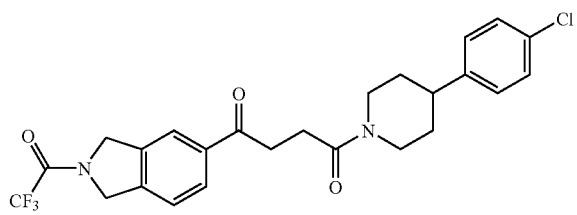

Using 4-oxo-4-[2-(trifluoroacetyl)-2,3-dihydro-1H-isoindol-5-yl]butanoic acid obtained in 1) in Example 132, the title compound was obtained as powder by the same procedure as in Example 12.

$^1$H-NMR (CDCl$_3$) δ: 1.58–1.67 (2H, m), 1.84–1.96 (2H, m), 2.62–2.75 (2H, m), 2.86 (2H, t, J=6.6 Hz), 3.19 (1H, t, J=11.7 Hz), 3.33 (2H, t, J=6.6 Hz), 4.12 (1H, m), 4.75 (1H, m), 4.97 (2H, s), 5.09 (2H, m), 7.13–7.46 (5H, m), 7.96–8.04 (2H, m).

Example 161

4-[4-(4-Chlorophenyl)piperidin-1-yl]-1-(2-methyl-2,3-dihydro-1H-isoindol-5-yl)-4-oxobutan-1-one

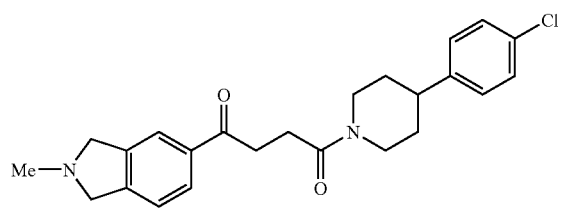

Using 4-[4-(4-chlorophenyl)piperidin-1-yl]-1-(2,3-dihydro-1H-isoindol-5-yl)-4-oxobutan-1-one obtained in Example 132, the title compound was obtained as powder by the same procedure as in Example 16.

$^1$H-NMR (CDCl$_3$) δ: 1.56–1.68 (2H, m), 1.82–1.96 (2H, m), 2.63 (3H, s), 2.74 (2H, m), 2.84 (2H, t, J=6.6 Hz), 3.17 (1H, m), 3.36 (2H, t, J=6.6 Hz), 4.15 (1H, d, J=15.6 Hz), 4.31 (4H, s), 4.76 (1H, d, J=12 Hz), 7.11–7.36 (5H, m), 7.92 (2H, m).

Example 162

4-[4-(4-Chlorophenyl)piperidin-1-yl]-1-(2-ethyl-2,3-dihydro-1H-isoindol-5-yl)-4-oxobutan-1-one

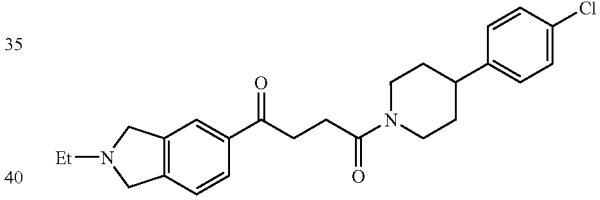

Using 4-[4-(4-chlorophenyl)piperidin-1-yl]-1-(2,3-dihydro-1H-isoindol-5-yl)-4-oxobutan-1-one obtained in Example 132, the title compound was obtained as powder by the same procedure as in Example 17.

$^1$H-NMR (CDCl$_3$) δ: 1.22 (3H, t, J=7.2 Hz), 1.26–1.62 (2H, m), 1.83–1.94 (2H, m), 2.61–2.80 (6H, m), 3.17 (1H, m), 3.36 (2H, t, J=6.6 Hz), 3.96 (4H, s), 4.15 (1H, d, J=15.6 Hz), 4.76 (1H, d, J=12 Hz), 7.11–7.36 (5H, m), 7.88 (2H, m).

Example 163

4-[4-(4-Chlorophenyl)piperidin-1-yl]-1-(2-isopropyl-2,3-dihydro-1H-isoindol-5-yl)-4-oxobutan-1-one

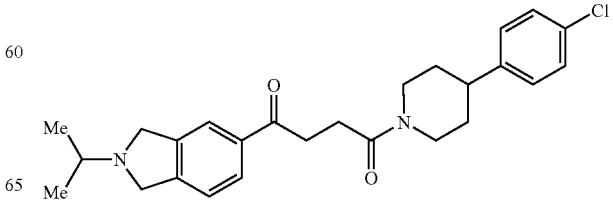

Using 4-[4-(4-chlorophenyl)piperidin-1-yl]-1-(2,3-dihydro-1H-isoindol-5-yl)-4-oxobutan-1-one obtained in Example 132, the title compound was obtained as powder by the same procedure as in Example 17.

¹H-NMR (CDCl₃) δ: 1.21 (6H, d, J=5.4 Hz), 1.62–1.80 (2H, m), 1.83–1.94 (2H, m), 2.61–2.82 (5H, m), 3.17 (1H, m), 3.36 (2H, t, J=6.6 Hz), 4.00 (4H, s), 4.15 (1H, d, J=15.6 Hz), 4.76 (1H, d, J=12 Hz), 7.11–7.36 (5H, m), 7.88 (2H, m).

Example 164

1-(2-Benzyl-2,3-dihydro-1H-isoindol-5-yl)-4-[4-(4-chlorophenyl)piperidin-1-yl]-4-oxobutan-1-one

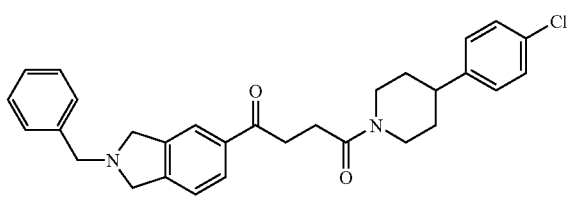

Using 4-[4-(4-chlorophenyl)-1-piperidin-1-yl]-1-(2,3-dihydro-1H-isoindol-5-yl)-4-oxobutan-1-one obtained in Example 132, the title compound was obtained as powder by the same procedure as in Example 17.

¹H-NMR (CDCl₃) δ: 1.62–1.80 (2H, m), 1.83–1.94 (2H, m), 2.59–2.82 (4H, m), 3.17 (1H, m), 3.36 (2H, t, J=6.6 Hz), 3.93 (2H, s), 3.97 (4H, s), 4.15 (1H, d, J=15.6 Hz), 4.76 (1H, d, J=12 Hz), 7.18, (2H, m), 7.29–7.42(8H, m), 7.88 (2H, m).

Example 165

4-(3-Isopropyl-2,3,4,5-tetrahydro-1H-3-benzazepin-7-yl)-4-oxo-N-(3-phenylpropyl)butanamide hydrochloride

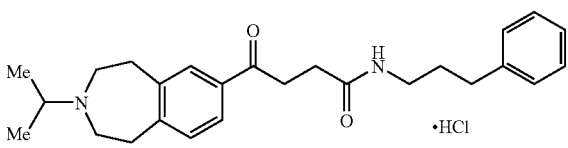

Using 4-oxo-N-(3-phenylpropyl)-4-(2,3,4,5-tetrahydro-1H-3-benzazepin-7-yl)butanamide trifluoroacetate obtained in Example 42, the title compound was obtained as amorphous powder by the same procedure as in Example 17.

¹H-NMR (DMSO-d₆) δ: 1.04 (3H, d, J=6.3 Hz), 1.27 (6H, d, J=6.3 Hz), 1.64 (1H, m), 2.91–3.23 (6H, m), 3.60–3.79 (10H, m), 7.17–7.40 (6H, m), 7.85 (2H, m), 11.0 (1H, m).

Example 166

N-(1-Methyl-3-phenylpropyl)-4-oxo-4-(2,3,4,5-tetrahydro-1H-3-benzazepin-7-yl)-butanamide hydrochloride

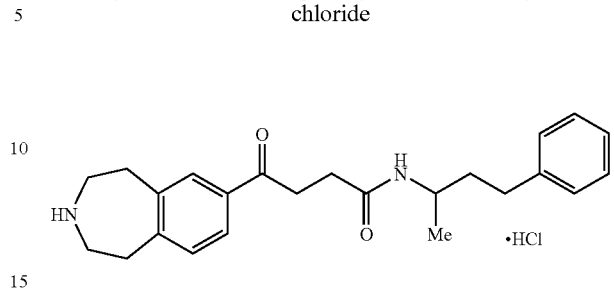

The title compound was obtained as amorphous powder in the same manner as in Example 36.

¹H-NMR (DMSO-d₆) δ: 1.05 (3H, d, J=6.6 Hz), 1.65 (2H, m), 2.50–2.60 (6H, m), 3.19 (8H, m), 3.75 (1H, m), 4.37 (1H, m), 7.17–7.40 (6H, m), 7.86–7.96 (2H, m), 9.53 (1H, m).

Example 167

4-(3-Isopropyl-2,3,4,5-tetrahydro-1H-3-benzazepin-7-yl)-N-(1-methyl-3-phenylpropyl)-4-oxobutanamide hydrochloride

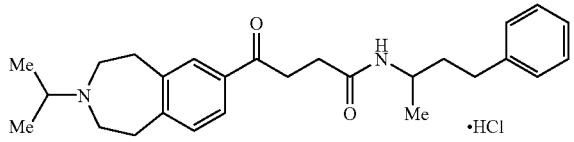

Using N-(1-methyl-3-phenylpropyl)-4-oxo-4-(2,3,4,5-tetrahydro-1H-3-benzazepin-7-yl)-butanamide hydrochloride obtained in Example 166, the title compound was obtained as amorphous powder by the same procedure as in Example 17.

¹H-NMR (DMSO-d₆) δ: 1.05 (3H, d, J=6.3 Hz), 1.27 (6H, d, J=6.3 Hz), 1.67 (2H, m), 2.92–3.23 (6H, m), 3.57–3.79 (5H, m), 3.99–4.05 (5H, m), 7.17–7.40 (6H, m), 7.86–7.96 (2H, m), 10.97 (1H, m).

Example 168

4-Oxo-N-(2-phenoxyethyl)-4-[3-(trifluoroacetyl)-2,3,4,5-tetrahydro-1H-3-benzazepin-7-yl]butanamide

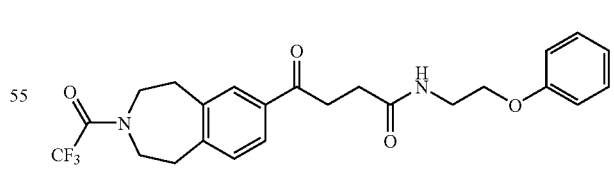

Using 4-oxo-4-[3-(trifluoroacetyl)-2,3,4,5-tetrahydro-1H-3-benzazepin-7-yl]butanoic acid obtained in Reference Example 16, the title compound was obtained as powder by the same procedure as in Example 12.

¹H-NMR (CDCl₃) δ: 2.66 (2H, t, J=6.6 Hz), 3.03 (4H, m), 3.34 (2H, t, J=6.6 Hz), 3.67 (4H, m), 3.78 (2H, m), 4.04 (1H, d, J=4.8 Hz), 6.23 (1H, m), 6.89, (3H, m), 7.24(3H, m), 7.78 (2H, m).

Example 169

4-Oxo-N-(2-phenoxyethyl)-4-(2,3,4,5-tetrahydro-1H-3-benzazepin-7-yl)butanamide

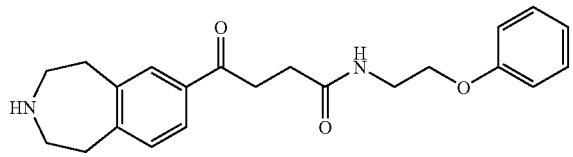

Using 4-oxo-N-(2-phenoxyethyl)-4-[3-(trifluoroacetyl)-2,3,4,5-tetrahydro-1H-3-benzazepin-7-yl]butanamide obtained in Example 168, the title compound was obtained as powder by the same procedure as in Example 13.

$^1$H-NMR (CDCl$_3$) δ: 2.26 (1H, s), 2.65 (2H, t, J=6.6 Hz), 2.98 (8H, m), 3.34 (2H, t, J=6.6 Hz), 3.67 (2H, q, J=5.1 Hz), 4.04 (2H, t, J=4.8 Hz), 6.28 (1H, m), 6.89, (3H, m), 7.24 (3H, m), 7.71 (2H, m).

Example 170

N-[3-(4-Chlorophenyl)propyl]-4-oxo-4-[3-(trifluoroacetyl)-2,3,4,5-tetrahydro-1H-3-benzazepin-7-yl]butanamide

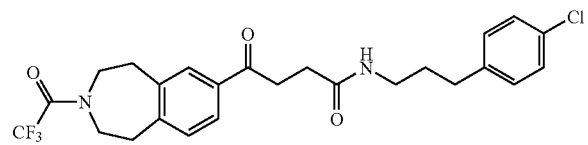

Using 4-oxo-4-[3-(trifluoroacetyl)-2,3,4,5-tetrahydro-1H-3-benzazepin-7-yl]butanoic acid obtained in Reference Example 16 and 3-(4-chlorophenyl)propylamine obtained in Reference Example 23, the title compound was obtained as oily matter by the same procedure as in Example 12.

$^1$H-NMR (CDCl$_3$) δ: 1.73–1.85 (2H, m), 2.60 (4H, m), 3.05 (4H, m), 3.24–3.34 (4H, m), 3.77–3.80 (4H, m), 5.87 (1H, m), 7.09–7.28 (5H, m), 7.77 (2H, m).

Example 171

N-[3-(4-Chlorophenyl)propyl]-4-oxo-4-(2,3,4,5-tetrahydro-1H-3-benzazepin-7-yl)butanamide hydrochloride

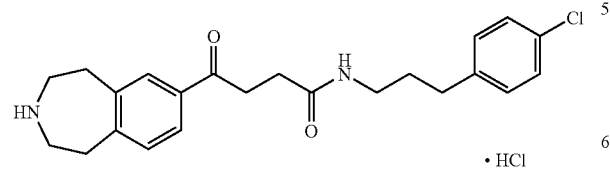

Using N-[3-(4-chlorophenyl) propyl]-4-oxo-4-[3-(trifluoroacetyl)-2,3,4,5-tetrahydro-1H-3-benzazepin-7-yl]butanamide obtained in Example 170, the title compound was obtained as amorphous powder by the same procedure as in Example 13.

$^1$H-NMR (CDCl$_3$) δ: 1.73–1.85 (2H, q, J=7.4 Hz), 2.56–2.72 (6H, m), 2.96 (7H, m), 3.21–3.37 (4H, m), 5.94 (1H, m), 7.07–7.28 (5H, m), 7.75 (2H, m).

Example 172

4-Oxo-N-(4-phenylbutyl)-4-[3-(trifluoroacetyl)-2,3,4,5-tetrahydro-1H-3-benzazepin-7-yl]butanamide

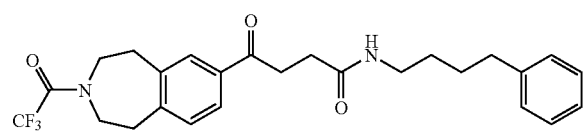

Using 4-oxo-4-[3-(trifluoroacetyl)-2,3,4,5-tetrahydro-1H-3-benzazepin-7-yl]butanoic acid obtained in Reference Example 16, the title compound was obtained as oily matter by the same procedure as in Example 12.

$^1$H-NMR (CDCl$_3$) δ: 1.54–1.70 (4H, m), 2.60 (4H, q, J=6.6 Hz), 3.05 (4H, m), 3.24–3.34 (4H, m), 3.69–3.81 (4H, m), 5.73 (1H, m), 7.15–7.32 (6H, m), 7.78 (2H, m).

Example 173

4-Oxo-N-(4-phenylbutyl)-4-(2,3,4,5-tetrahydro-1H-3-benzazepin-7-yl)butanamide hydrochloride

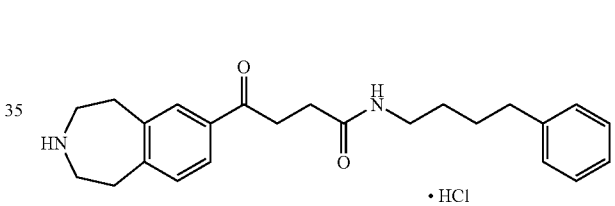

Using 4-oxo-N-(4-phenylbutyl)-4-[3-(trifluoroacetyl)-2, 3,4,5-tetrahydro-1H-3-benzazepin-7-yl] obtained in Example 172, the title compound was obtained as amorphous powder by the same procedure as in Example 13.

$^1$H-NMR (CDCl$_3$) δ: 1.54–1.65 (4H, m), 2.48–2.61 (5H, m), 3.01 (8H, m), 3.26–3.49 (4H, m), 5.79 (1H, m), 7.11–7.28 (6H, m), 7.73 (2H, m).

Example 174

N-[3-(4-Chlorophenyl)propyl]-4-oxo-4-(3-isopropyl-2,3,4,5-tetrahydro-1H-3-benzazepin-7-yl)butanamide

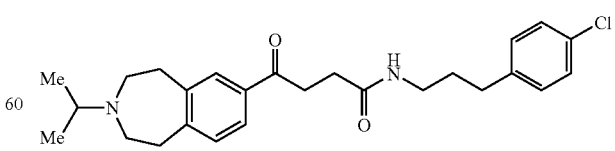

Using N-[3-(4-chlorophenyl)propyl]-4-oxo-4-(2,3,4,5-tetrahydro-1H-3-benzazepin-7-yl)butanamide hydrochloride obtained in Example 171, the title compound was obtained as powder by the same procedure as in Example 17.

¹H-NMR (CDCl₃) δ: 1.03 (6H, d, J=6.6 Hz), 1.77 (2H, m), 2.57–2.66 (9H, m), 2.96 (4H, m), 3.23–3.34 (4H, m), 5.92 (1H, m), 7.07–7.28 (5H, m), 7.75 (2H, m).

Example 175

4-(3-Isopropyl-2,3,4,5-tetrahydro-1H-3-benzazepin-7-yl)-4-oxo-N-(2-phenoxyethyl)-butanamide

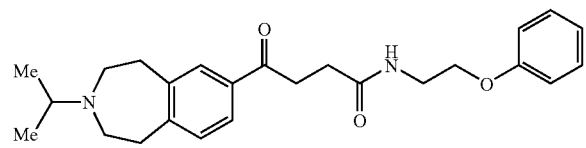

Using 4-oxo-N-(2-phenoxyethyl)-4-(2,3,4,5-tetrahydro-1H-3-benzazepin-7-yl)butanamide obtained in Example 169, the title compound was obtained as powder by the same procedure as in Example 17.

¹H-NMR (CDCl₃) δ: 1.02 (6H, d, J=6.6 Hz), 2.65 (7H, m), 2.95 (4H, m), 3.34 (2H, t, J=6.6 Hz), 3.67 (2H, q, J=5.1 Hz), 4.04 (2H, t, J=4.8 Hz), 6.23 (1H, m), 6.89, (3H, m), 7.24(3H, m), 7.71 (2H, m).

Example 176

N-[2-[4-(4-Chlorophenyl)-1-piperidinyl]-2-oxoethyl]-2,3,4,5-tetrahydro-1H-3-benzazepine-7-carboxamide trifluoroacetate

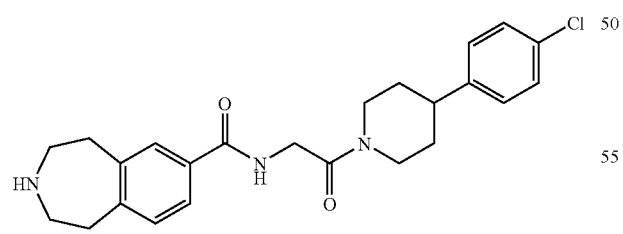

Using 2-[4-(4-chlorophenyl)-1-piperidinyl]-2-oxoethylamine hydrochloride obtained in Reference Example 22, the title compound was obtained in the same manner as in Example 36.

MS(APCI)(M+1):426.

Example 177

N-[2-[4-(2-Methylphenyl)-1-piperidinyl]-2-oxoethyl]-2,3,4,5-tetrahydro-1H-3-benzazepine-7-carboxamide trifluoroacetate

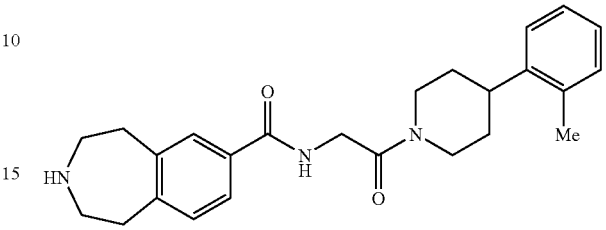

Using 2-[4-(2-methylphenyl)-1-piperidinyl]-2-oxoethylamine hydrochloride obtained in Reference Example 23, the title compound was obtained in the same manner as in Example 36.

MS(APCI)(M+1):406.

Example 178

N-[2-[4-(4-Fluorophenyl)-1-piperazinyl]-2-oxoethyl]-2,3,4,5-tetrahydro-1H-3-benzazepine-7-carboxamide trifluoroacetate

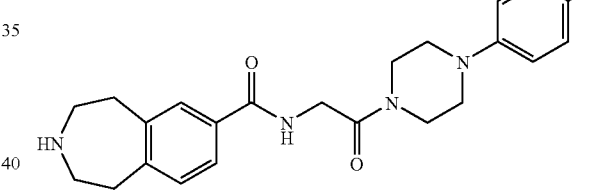

Using 2-[4-(4-fluorophenyl)-1-piperazinyl]-2-oxoethylamine dihydrochloride obtained in Reference Example 24, the title compound was obtained in the same manner as in Example 36.

MS(APCI)(M+1):411.

Example 179

N-[2-[4-(2-Methoxyphenyl)-1-piperazinyl]-2-oxoethyl]-2,3,4,5-tetrahydro-1H-3-benzazepine-7-carboxamide trifluoroacetate

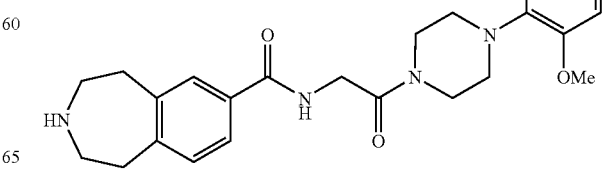

Using 2-[4-(2-methoxyphenyl)-1-piperazinyl]-2-oxoethylamine dihydrochloride obtained in Reference Example 25, the title compound was obtained in the same manner as in Example 36.

MS(APCI)(M+1):423.

Example 180

N-[2-[4-(4-Chlorophenyl)-1-piperidinyl]-2-oxoethyl]-2,3,4,5-tetrahydro-1H-2-benzazepine-8-carboxamide trifluoroacetate

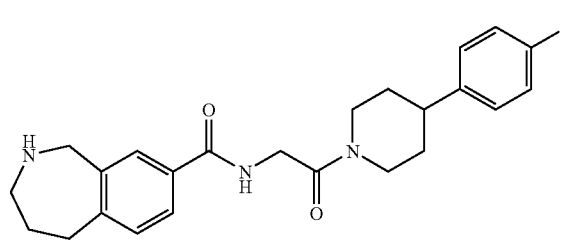

Using 2-[4-(4-chlorophenyl)-1-piperidinyl]-2-oxoethylamine hydrochloride obtained in Reference Example 22, the title compound was obtained in the same manner as in Example 36.

MS(APCI)(M+1):426.

Example 181

N-[2-[4-(2-Methylphenyl)-1-piperidinyl]-2-oxoethyl]-2,3,4,5-tetrahydro-1H-2-benzazepine-8-carboxamide trifluoroacetate

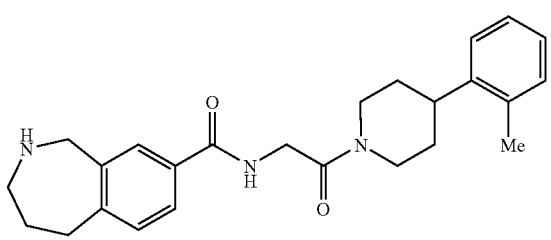

Using 2-[4-(2-methylphenyl)-1-piperidinyl]-2-oxoethylamine hydrochloride obtained in Reference Example 23, the title compound was obtained in the same manner as in Example 36.

MS(APCI)(M+1):406.

Example 182

N-[2-[4-(4-Fluorophenyl)-1-piperazinyl]-2-oxoethyl]-2,3,4,5-tetrahydro-1H-2-benzazepine-8-carboxamide trifluoroacetate

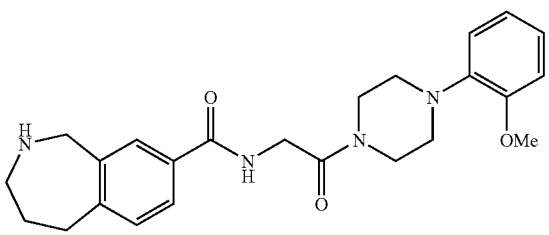

Using 2-[4-(4-fluorophenyl)-1-piperazinyl]-2-oxoethylamine dihydrochloride obtained in Reference Example 24, the title compound was obtained in the same manner as in Example 36.

MS(APCI)(M+1):411.

Example 183

N-[2-[4-(2-Methoxyphenyl)-1-piperazinyl]-2-oxoethyl]-2,3,4,5-tetrahydro-1H-2-benzazepine-8-carboxamide trifluoroacetate

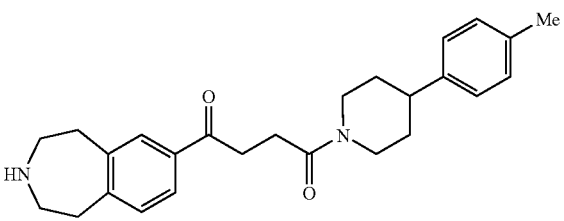

Using 2-[4-(2-methoxyphenyl)-1-piperazinyl]-2-oxoethylamine dihydrochloride obtained in Reference Example 25, the title compound was obtained by the same procedure as in Example 36.

MS(APCI)(M+1):423.

Example 184

4-[4-(4-Methylphenyl)-1-piperidinyl]-4-oxo-1-(2,3,4,5-tetrahydro-1H-3-benzazepin-7-yl)-1-butanone 1) Using 4-oxo-4-[3-(trifluoroacetyl)-2,3,4,5-tetrahydro-1H-3-benzazepin-7-yl]butanoic acid obtained in Reference Example 16, 4-[4-(4-methylphenyl)-1-piperidinyl]-4-oxo-1-[3-(trifluoroacetyl)-2,3,4,5-tetrahydro-1H-3-benzazepin-7-yl]-1-butanone was obtained as colorless powder by the same procedure as in Example 12.

¹H-NMR (CDCl₃) δ: 1.55–2.01 (4H, m), 2.33 (3H, s), 2.57–2.91 (4H, m), 2.97–3.27 (5H, m), 3.34 (2H, t, J=6.4 Hz), 3.66–3.84 (4H, m), 4.05–4.19 (1H, m), 4.67–4.83 (1H, m), 7.04–7.30 (5H, m), 7.80–7.91 (2H, m). Melting point: 132–134° C. (crystallizing solvent: diethyl ether)

2) Using 4-[4-(4-methylphenyl)-1-piperidinyl]-4-oxo-1-[3-(trifluoroacetyl)-2,3,4,5-tetrahydro-1H-3-benzazepin-7-yl]-1-butanone obtained in 1) above, the title compound was obtained as colorless powder by the same procedure as in Example 13.

¹H-NMR (CDCl₃) δ: 1.47–2.00 (5H, m), 2.33 (3H, s), 2.55–3.04 (12H, m), 3.06–3.26 (1H, m), 3.35 (2H, t, J=6.8 Hz), 4.04–4.20 (1H, m), 4.68–4.85 (1H, m), 7.05–7.24 (5H, m), 7.74–7.84 (2H, m). Melting point: 115–116° C. (crystallizing solvent: diethyl ether)

Example 185

4-[4-(3-Methylphenyl)-1-piperidinyl]-4-oxo-1-(2,3,4,5-tetrahydro-1H-3-benzazepin-7-yl)-1-butanone

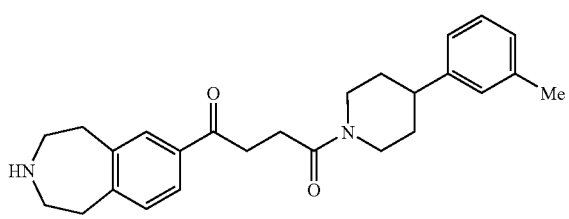

1) Using 4-oxo-4-[3-(trifluoroacetyl)-2,3,4,5-tetrahydro-1H-3-benzazepin-7-yl]butanoic acid obtained in Reference Example 16, 4-[4-(3-methylphenyl)-1-piperidinyl]-4-oxo-1-[3-(trifluoroacetyl)-2,3,4,5-tetrahydro-1H-3-benzazepin-7-yl]-1-butanone was obtained as colorless powder by the same procedure as in Example 12.

¹H-NMR (CDCl₃) δ: 1.55–2.01 (4H, m), 2.35 (3H, s), 2.56–2.93 (4H, m), 2.98–3.27 (5H, m), 3.34 (2H, t, J=6.4 Hz), 3.67–3.84 (4H, m), 4.05–4.20 (1H, m), 4.68–4.83 (1H, m), 6.96–7.10 (3H, m), 7.14–7.31 (2H, m), 7.80–7.92 (2H, m). Melting point: 128–129° C. (crystallizing solvent: diethyl ether)

2) Using 4-[4-(3-methylphenyl)-1-piperidinyl]-4-oxo-1-[3-(trifluoroacetyl)-2,3,4,5-tetrahydro-1H-3-benzazepin-7-yl]-1-butanone obtained in 1) above, the title compound was obtained as colorless powder by the same procedure as in Example 13.

¹H-NMR (CDCl₃) δ: 1.45–2.00 (5H, m), 2.34 (3H, s), 2.56–3.03 (12H, m), 3.05–3.26 (1H, m), 3.35 (2H, t, J=6.6 Hz), 4.05–4.20 (1H, m), 4.69–4.85 (1H, m), 6.95–7.08 (3H, m), 7.14–7.23 (2H, m), 7.74–7.83 (2H, m). Melting point: 91–93° C. (crystallizing solvent: diethyl ether)

Example 186

4-[4-(2-Methylphenyl)-1-piperidinyl]-4-oxo-1-(2,3,4,5-tetrahydro-1H-3-benzazepin-7-yl)-1-butanone

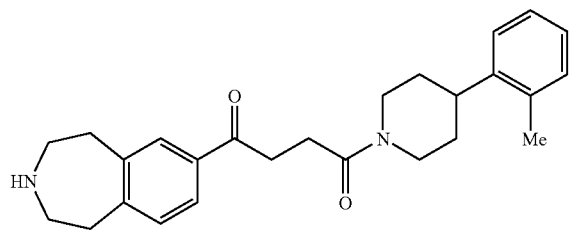

1) Using 4-oxo-4-[3-(trifluoroacetyl)-2,3,4,5-tetrahydro-1H-3-benzazepin-7-yl]butanoic acid obtained in Reference Example 16, 4-[4-(2-methylphenyl)-1-piperidinyl]-4-oxo-1-[3-(trifluoroacetyl)-2,3,4,5-tetrahydro-1H-3-benzazepin-7-yl]-1-butanone was obtained as colorless powder by the same procedure as in Example 12.

¹H-NMR (CDCl₃) δ: 1.47–1.95 (4H, m), 2.37 (3H, s), 2.58–2.77 (1H, m), 2.80–3.30 (8H, m), 3.35 (2H, t, J=6.6 Hz), 3.65–3.85 (4H, m), 4.07–4.23 (1H, m), 4.72–4.87 (1H, m), 7.10–7.32 (5H, m), 7.80–7.92 (2H, m). Melting point: 145–147° C. (crystallizing solvent: diethyl ether)

2) Using 4-[4-(2-methylphenyl)-1-piperidinyl]-4-oxo-1-[3-(trifluoroacetyl)-2,3,4,5-tetrahydro-1H-3-benzazepin-7-yl]-1-butanone obtained in 1) above, the title compound was obtained as colorless powder by the same procedure as in Example 13.

¹H-NMR (CDCl₃) δ: 1.50–1.96 (5H, m), 2.37 (3H, s), 2.57–2.76 (1H, m), 2.79–3.28 (12H, m), 3.36 (2H, t, J=6.6 Hz), 4.08–4.24 (1H, m), 4.72–4.87 (1H, m), 7.05–7.23 (5H, m), 7.75–7.84 (2H, m). Melting point: 93–95° C. (crystallizing solvent: diethyl ether)

Example 187

4-[4-(4-Fluorophenyl)-1-piperidinyl]-4-oxo-1-(2,3,4,5-tetrahydro-1H-3-benzazepin-7-yl)-1-butanone

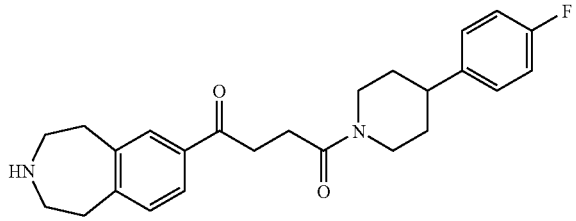

1) Using 4-oxo-4-[3-(trifluoroacetyl)-2,3,4,5-tetrahydro-1H-3-benzazepin-7-yl]butanoic acid obtained in Reference Example 16, 4-[4-(4-fluorophenyl)-1-piperidinyl]-4-oxo-1-[3-(trifluoroacetyl)-2,3,4,5-tetrahydro-1H-3-benzazepin-7-yl]-1-butanone was obtained as colorless powder by the same procedure as in Example 12.

¹H-NMR (CDCl₃) δ: 1.53–2.01 (4H, m), 2.57–2.90 (4H, m), 2.97–3.28 (5H, m), 3.34 (2H, t, J=6.6 Hz), 3.65–3.84 (4H, m), 4.05–4.20 (1H, m), 4.68–4.84 (1H, m), 6.95–7.07 (2H, m), 7.10–7.32 (3H, m), 7.80–7.90 (2H, m). Melting point: 105–102° C. (crystallizing solvent: diethyl ether)

2) Using 4-[4-(4-fluorophenyl)-1-piperidinyl]-4-oxo-1-[3-(trifluoroacetyl)-2,3,4,5-tetrahydro-1H-3-benzazepin-7-yl]-1-butanone obtained in 1) above, the title compound was obtained as colorless powder by the same procedure as in Example 13.

¹H-NMR (CDCl₃) δ: 1.47–2.00 (5H, m), 2.57–2.90 (4H, m), 2.98 (8H, br), 3.07–3.27 (1H, m), 3.35 (2H, t, J=6.8 Hz), 4.06–4.21 (1H, m), 4.70–4.86 (1H, m), 6.94–7.07 (2H, m), 7.10–7.24 (3H, m), 7.74–7.84 (2H, m). Melting point: 127–128° C. (crystallizing solvent: diethyl ether)

Example 188

4-[4-(4-Methoxyphenyl)-1-piperidinyl]-4-oxo-1-(2,3,4,5-tetrahydro-1H-3-benzazepin-7-yl)-1-butanone

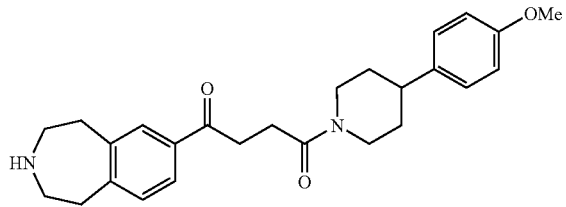

1) Using 4-oxo-4-[3-(trifluoroacetyl)-2,3,4,5-tetrahydro-1H-3-benzazepin-7-yl]butanoic acid obtained in Reference Example 16, 4-[4-(2-methylphenyl)-1-piperidinyl]-4-oxo-1-[3-(trifluoroacetyl)-2,3,4,5-tetrahydro-1H-3-benzazepin-7-yl]-1-butanone was obtained as colorless powder by the same procedure as in Example 12.

¹H-NMR (CDCl₃) δ: 1.50–1.74 (2H, m), 1.80–1.97 (2H, m), 2.59–2.78 (2H, m), 2.85 (2H, t, J=6.6 Hz), 3.00–3.09 (4H, m), 3.12–3.24 (1H, m), 3.34 (2H, t, J=6.6 Hz), 3.67–3.83 (7H, m), 4.07–4.16 (1H, m), 4.71–4.80 (1H, m), 6.86 (2H, d, J=8.6 Hz), 7.13 (2H, d, J=8.6 Hz), 7.23–7.30 (1H, m), 7.80–7.90 (2H, m). Melting point: 130–131° C. (crystallizing solvent: diethyl ether)

2) Using 4-[4-(2-methylphenyl)-1-piperidinyl]-4-oxo-1-[3-(trifluoroacetyl)-2,3,4,5-tetrahydro-1H-3-benzazepin-7-yl]-1-butanone obtained in 1) above, the title compound was obtained as colorless powder by the same procedure as in Example 13.

¹H-NMR (CDCl₃) δ: 1.51–1.97 (5H, m), 2.58–2.77 (2H, m), 2.83 (2H, t, J=6.7 Hz), 2.97 (8H, br), 3.10–3.23 (1H, m), 3.35 (2H, t, J=6.7 Hz), 3.80 (3H, s), 4.07–4.18 (1H, m), 4.73–4.83 (1H, m), 6.86 (2H, d, J=8.7 Hz), 7.13 (2H, d, J=8.7 Hz), 7.19 (1H, d, J=8.3 Hz), 7.76–7.83 (2H, m). Melting point: 99–100° C. (crystallizing solvent: diethyl ether)

Example 189

4-[4-(4-Chlorophenyl)-1-piperidinyl]-1-(2-methyl-1,2,3,4-tetrahydro-7-isoquinolinyl)-4-oxo-1-butanone

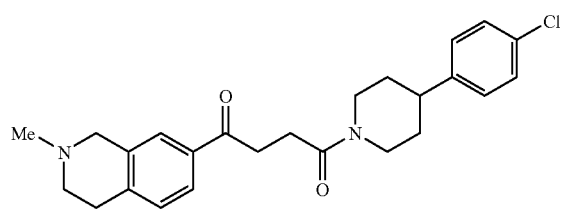

Using 4-[4-(4-chlorophenyl)piperidin-1-yl]-4-oxo-1-(1,2,3,4-tetrahydroisoquinolin-7-yl)butan-1-one obtained in Example 13, the title compound was obtained as colorless powder by the same procedure as in Example 16.

¹H-NMR (CDCl₃) δ: 1.62 (2H, m), 1.89 (2H, m), 2.48 (3H, s), 2.67–2.70 (4H, m), 2.82 (2H, t, J=6.4 Hz), 2.97 (2H, t, J=5.4 Hz), 3.23 (1H, m), 3.34 (2H, t, J=6.6 Hz), 3.62 (2H, s), 4.13 (1H, d, J=15.6 Hz), 4.76 (1H, d, J=12 Hz), 7.11–7.31 (5H, m), 7.71–7.81 (2H, m). Melting point: 139–140° C. (crystallizing solvent: ethanol-diisopropyl ether)

Example 190

4-[4-(4-Chlorophenyl)-1-piperidinyl]-1(2-ethyl-1,2,3,4-tetrahydro-7-isoquinolinyl)-4-oxo-1-butanone

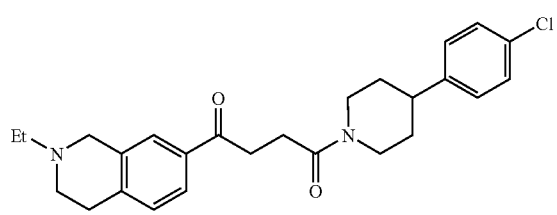

Using 4-[4-(4-chlorophenyl)piperidin-1-yl]-4-oxo-1-(1,2,3,4-tetrahydroisoquinolin-7-yl)butan-1-one obtained in Example 13, the title compound was obtained as colorless powder by the same procedure as in Example 17.

¹H-NMR (CDCl₃) δ: 1.21 (3H, t, J=7.2 Hz), 1.62 (2H, m), 1.89 (2H, m), 2.57–2.79 (6H, m), 2.82 (2H, t, J=6.4 Hz), 2.97 (2H, t, J=5.4 Hz), 3.23 (1H, m), 3.34 (2H, t, J=6.6 Hz), 3.62 (2H, s), 4.13 (1H, d, J=15.6 Hz), 4.76 (1H, d, J=12 Hz), 7.11–7.31 (5H, m), 7.71–7.81 (2H, m). Melting point: 115–116° C. (crystallizing solvent: ethanol-diisopropyl ether)

Example 191

1-(2-Benzyl-1,2,3,4-tetrahydro-7-isoquinolinyl)-4-[4-(4-chlorophenyl)-1-piperidinyl]-4-oxo-1-butanone

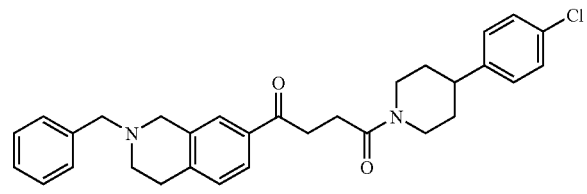

Using 4-[4-(4-chlorophenyl)piperidin-1-yl]-4-oxo-1-(1,2,3,4-tetrahydroisoquinolin-7-yl)butan-1-one obtained in Example 13, the title compound was obtained as colorless powder by the same procedure as in Example 17.

¹H-NMR (CDCl₃) δ: 1.62 (2H, m), 1.89 (2H, m), 2.58–2.80 (6H, m), 2.95 (2H, t, J=5.4 Hz), 3.23 (1H, m), 3.34 (2H, t, J=6.6 Hz), 3.67 (2H, s), 3.70 (2H, s), 4.13 (1H, d, J=15.6 Hz), 4.76 (1H, d, J=12 Hz), 7.11–7.41 (10H, m), 7.62–7.80 (2H, m). Melting point: 102–103° C. (crystallizing solvent: ethanol-diisopropyl ether)

Example 192

4-[4-(4-Chlorophenyl)-1-piperidinyl]-1-(2-isopropyl-1,2,3,4-tetrahydro-7-isoquinolinyl)-4-oxo-1-butanone

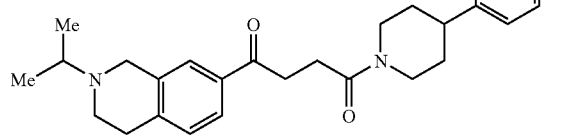

Using 4-[4-(4-chlorophenyl)piperidin-1-yl]-4-oxo-1-(1,2,3,4-tetrahydroisoquinolin-7-yl)butan-1-one obtained in Example 13, the title compound was obtained as colorless powder by the same procedure as in Example 17.

$^1$H-NMR (CDCl$_3$) δ: 1.15 (6H, d, J=6.6 Hz), 1.62 (2H, m), 1.89 (2H, m), 2.59–2.95 (9H, m), 3.18 (1H, m), 3.34 (2H, t, J=6.6 Hz), 3.77 (2H, s), 4.13 (1H, d, J=15.6 Hz), 4.76 (1H, d, J=12 Hz), 7.11–7.31 (5H, m), 7.73–7.80 (2H, m). Melting point: 113–115° C. (crystallizing solvent: ethanol-diisopropyl ether)

Example 193

4-[4-(4-Chlorophenyl)piperidin-1-yl]-1-(3-cyclohexylmethyl-2,3,4,5-tetrahydro-1H-3-benzazepin-7-yl)-4-oxobutan-1-one

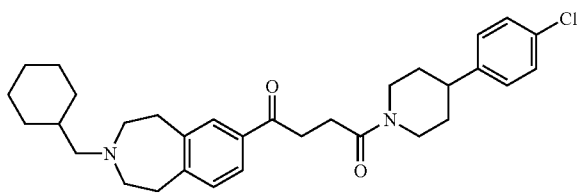

Using 4-[4-(4-chlorophenyl-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^1$H-NMR (CDCl$_3$) δ: 0.90 (2H, m), 1.24 (4H, m), 1.47–1.94 (10H, m), 2.23 (2H, d, J=6.9 Hz), 2.58–2.80 (5H, m), 2.94 (2H, t, J=6.4 Hz), 2.96 (4H, m), 3.23 (1H, m), 3.35 (2H, t, J=6.6 Hz), 4.13 (1H, m), 4.76 (1H, m), 7.35–7.11 (5H, m), 7.79 (2H, m). Melting point: 140–141° C. (crystallizing solvent: ethanol-diisopropyl ether)

Example 194

4-[4-(4-Chlorophenyl)-1-piperidinyl]-4-oxo-1-[3-(tetrahydro-2-furanylmethyl)-2,3,4,5-tetrahydro-1H-3-benzazepin-7-yl]-1-butanone

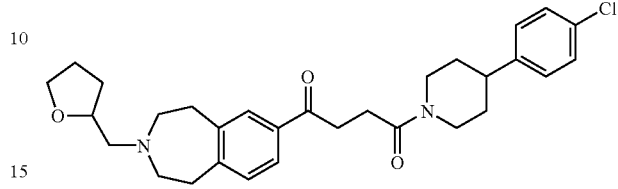

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

MS (ESI) (M+H): 509. Melting point: 123–125° C. (crystallizing solvent: ethanol-diisopropyl ether)

Example 195

4-[4-(4-Chlorophenyl)-1-piperidinyl]-1-(3-cyclohexyl-2,3,4,5-tetrahydro-1H-3-benzazepin-7-yl)-4-oxo-1-butanone

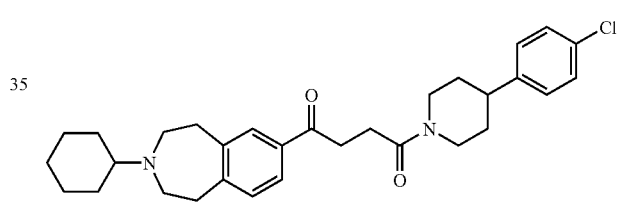

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

MS(ESI) (M+H): 507. Melting point: 128–130° C. (crystallizing solvent: ethanol-diisopropyl ether)

Example 196

4-[4-(4-Chlorophenyl)-1-piperidinyl]-1-(3-cyclopentyl-2,3,4,5-tetrahydro-1H-3-benzazepin-7-yl)-4-oxo-1-butanone

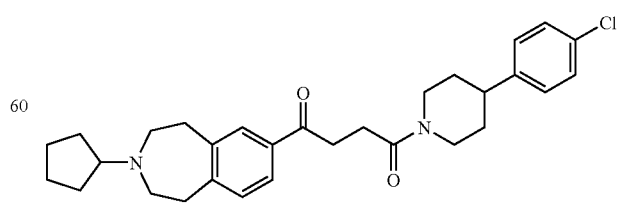

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^{1}$H-NMR (CDCl$_{3}$) δ: 1.55–1.69 (5H, m), 1.83 (3H, m), 2.59–3.03 (17H, m), 3.17 (1H, m), 3.35 (2H, t, J=6.6 Hz), 4.13 (1H, m), 4.76 (1H, m), 7.35–7.11 (5H, m), 7.79 (2H, m). Melting point: 160–162° C. (crystallizing solvent: ethanol-diisopropyl ether)

Example 197

4-[4-(4-Chlorophenyl)-1-piperidinyl]-1-(3-isobutyl-2,3,4,5-tetrahydro-1H-3-benzazepin-7-yl)-4-oxo-1-butanone

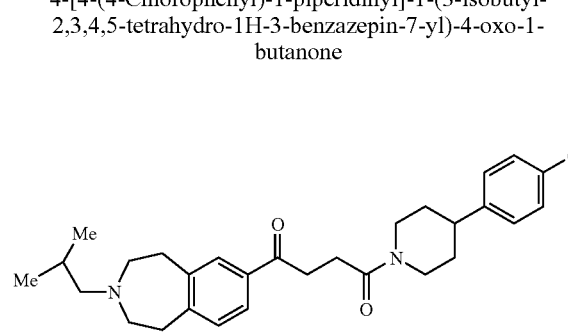

Using 4-[4-(4-chlorophenyl)-1-piperidinyl]-4-oxo-1-(2,3,4,5-tetrahydro-1H-3-benzazepin-7-yl)-1-butanone obtained in Example 15, the title compound was obtained as colorless powder by the same procedure as in Example 17.

$^{1}$H-NMR (CDCl$_{3}$) δ: 0.93 (6H, d, J=6.2 Hz), 1.62 (4H, m), 1.89 (3H, m), 2.21 (2H, d, J=7.4 Hz), 2.60–2.74 (6H, m), 2.79 (2H, t, J=6.4 Hz), 2.95 (4H, m), 3.23 (1H, m), 3.35 (2H, t, J=6.6 Hz), 4.13 (1H, m), 4.76 (1H, m), 7.35–7.11 (5H, m), 7.79 (2H, m). Melting point: 137–138° C. (crystallizing solvent: ethanol-diisopropyl ether)

Example 198

4-[4-(4-Methylphenyl)-1-piperidinyl]-1-(3-methyl-2,3,4,5-tetrahydro-1H-3-benzazepin-7-yl)-4-oxo-1-butanone

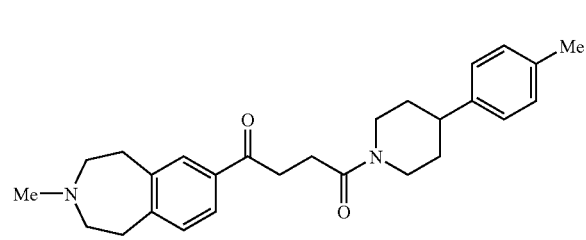

Using 4-[4-(4-methylphenyl)-1-piperidinyl]-4-oxo-1-(2,3,4,5-tetrahydro-1H-3-benzazepin-7-yl)-1-butanone obtained in Example 184, the title compound was obtained as colorless powder by the same procedure as in Example 16.

$^{1}$H-NMR (CDCl$_{3}$) δ: 1.66 (2H, m), 1.89 (2H, m), 2.33 (3H, s), 2.38 (3H, s), 2.65 (6H, m), 2.82 (2H, t, J=6.4 Hz), 2.95 (4H, m), 3.23 (1H, m), 3.35 (2H, t, J=6.6 Hz), 4.13 (1H, m), 4.76 (1H, m), 7.35–7.11 (5H, m), 7.79 (2H, m). Melting point: 111–112° C. (crystallizing solvent: ethanol-diisopropyl ether)

Example 199

1-(3-Isopropyl-2,3,4,5-tetrahydro-1H-3-benzazepin-7-yl)-4-[4-(4-methylphenyl)-1-piperidyl]-4-oxo-1-butanone hydrochloride

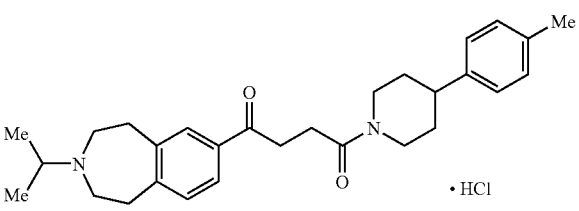

Using 4-[4-(4-methylphenyl)-1-piperidinyl]-4-oxo-1-(2,3,4,5-tetrahydro-1H-3-benzazepin-7-yl)-1-butanone obtained in Example 184, the title compound was obtained as colorless powder by the same procedure as in Example 17.

$^{1}$H-NMR (CDCl$_{3}$) δ: 1.26 (7H, m), 1.56 (1H, m), 1.78 (2H, m), 2.26 (3H, s), 2.50 (1H, m), 2.73 (2H, m), 2.94–3.64 (7H, m), 4.05 (1H, m), 4.46 (1H, m), 7.12 (4H, s), 7.40 (1H, d, J=8.4 Hz), 7.83 (2H, m). Melting point: 180° C. (decomp.) (crystallizing solvent: ethanol-diisopropyl ether)

Example 200

4-[4-(4-Methylphenyl)piperidin-1-yl]-4-oxo-1-(1,2,3,4-tetrahydroisoquinolin-7-yl)butan-1-one

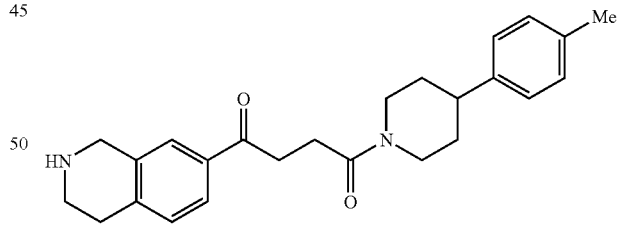

Using 4-oxo-4-[2-(trifluoroacetyl)-1,2,3,4-tetrahydro-7-isoquinolinyl]butanoic acid obtained in Reference Example 15, the title compound was obtained as colorless powder by the same procedures as in Examples 12 and 13.

$^{1}$H-NMR (CDCl$_{3}$) δ: 1.63 (2H, m), 1.95 (3H, m), 2.33 (3H, s), 2.59–2.72 (3H, m), 2.82 (4H, m), 2.97 (2H, t, J=5.4 Hz), 3.17 (2H, t, J=6.2 Hz), 3.34 (2H, t, J=6.6 Hz), 4.08 (2H, s), 4.13 (1H, d, J=15.6 Hz), 4.76 (1H, d, J=12 Hz), 7.11–7.20 (5H, m), 7.71–7.81 (2H, m). Melting point: 119–120° C. (crystallizing solvent: ethanol-diisopropyl ether)

Example 201

4-[4-(4-Methylphenyl)-1-piperidinyl]-1-(2-methyl-1,2,3,4-tetrahydro-7-isoquinolinyl)-4-oxo-1-butanone

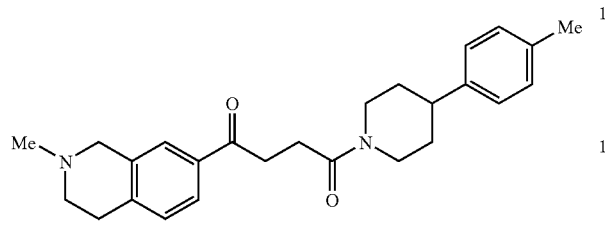

Using 4-[4-(4-methylphenyl) piperidin-1-yl]-4-oxo-1-(1,2,3,4-tetrahydroisoquinolin-7-yl)butan-1-one obtained in Example 200, the title compound was obtained as colorless powder by the same procedure as in Example 16.

$^1$H-NMR (CDCl$_3$) δ: 1.62 (2H, m), 1.89 (2H, m), 2.34 (3H, s), 2.48 (3H, s), 2.60–2.73 (4H, m), 2.82 (2H, t, J=6.4 Hz), 2.97 (2H, t, J=5.4 Hz), 3.23 (1H, m), 3.34 (2H, t, J=6.6 Hz), 3.62 (2H, s), 4.13 (1H, d, J=15.6 Hz), 4.76 (1H, d, J=12 Hz), 7.11–7.31 (5H, m), 7.71–7.81 (2H, m). Melting point: 97–99° C. (crystallizing solvent: ethanol-diisopropyl ether)

Example 202

1-(2-Isopropyl-1,2,3,4-tetrahydro-7-isoquinolinyl)-4-[4-(4-methylphenyl)-1-piperidinyl]-4-oxo-1-butanone

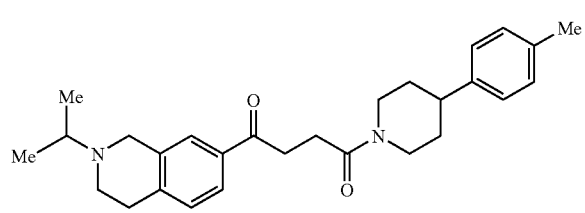

Using 4-[4-(4-methylphenyl)piperidin-1-yl]-4-oxo-1-(1,2,3,4-tetrahydroisoquinolin-7-yl)butan-1-one obtained in Example 200, the title compound was obtained as colorless powder by the same procedure as in Example 17.

$^1$H-NMR (CDCl$_3$) δ: 1.15 (6H, d, J=6.6 Hz), 1.62 (2H, m), 1.89 (2H, m), 2.64 (3H, s), 2.65–2.95 (9H, m), 3.18 (1H, m), 3.34 (2H, t, J=6.6 Hz), 3.77 (2H, s), 4.13 (1H, d, J=15.6 Hz), 4.76 (1H, d, J=12 Hz), 7.11–7.31 (5H, m), 7.73–7.80 (2H, m). Melting point: 78–80° C. (crystallizing solvent: ethanol-diisopropyl ether)

Example 203

1-(2-Benzyl-1,2,3,4-tetrahydro-7-isoquinolinyl)-4-[4-(4-methylphenyl)-1-piperidinyl]-4-oxo-1-butanone hydrochloride

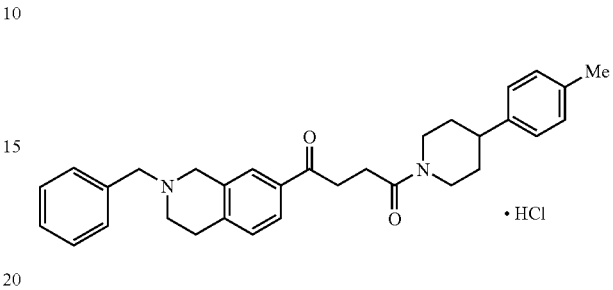

Using 4-[4-(4-methylphenyl)piperidin-1-yl]-4-oxo-1-(1,2,3,4-tetrahydroisoquinolin-7-yl)butan-1-one obtained in Example 200, the title compound was obtained as colorless powder by the same procedure as in Example 17.

$^1$H-NMR (CDCl$_3$) δ: 1.36 (1H, m), 1.56 (1H, m), 1.78 (2H, m), 2.26 (3H, s), 2.50 (1H, m), 2.73 (2H, m), 3.08–3.43 (8H, m), 3.67 (1H, m), 4.05 (1H, m), 4.46 (4H, m), 7.12 (4H, s), 7.41 (1H, d, J=8.4 Hz), 7.53 (3H, m), 7.67 (2H, m), 7.86 (2H, m). Melting point: 72° C. (decomp) (crystallizing solvent: ethanol-diisopropyl ether)

Example 204

5-[4-(4-Chlorophenyl)-1-piperidinyl]-5-oxo-1-[3-(trifluoroacetyl)-2,3,4,5-tetrahydro-1H-3-benzazepin-7-yl]-1-pentanone

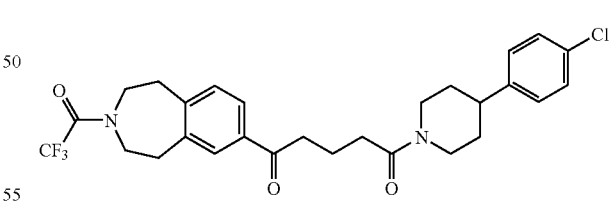

Using 2,3,4,5-tetrahydro-1H-3-benzazepine, the title compound was obtained as colorless amorphous powder by the same procedures as in Reference Example 15 and in Example 12.

$^1$H NMR (CDCl$_3$) δ: 1.57 (2H, m), 1.89 (2H, m), 2.10 (2H, m), 2.49 (2H, m), 2.58–2.76 (2H, m), 3.01–3.17 (7H, m), 3.75 (4H, m), 4.04 (1H, m), 4.79 (1H, m), 7.11 (2H, m), 7.28 (3H, m), 7.82 (2H, m).

Example 205

5-[4-(4-Chlorophenyl)-1-piperidinyl]-5-oxo-1-(2,3,4,5-tetrahydro-1H-3-benzazepin-7-yl)-1-pentanone

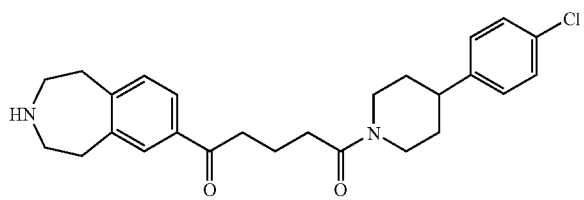

Using 5-[4-(4-chlorophenyl)-1-piperidinyl]-5-oxo-1-[3-(trifluoroacetyl)-2,3,4,5-tetrahydro-1H-3-benzazepin-7-yl]-1-pentanone obtained in Example 204, the title compound was obtained as colorless powder by the same procedure as in Example 13.

$^1$H NMR (CDCl$_3$) δ: 1.57 (2H, m), 1.87 (2H, m), 2.10 (2H, m), 2.48 (2H, m), 2.58–2.75 (2H, m), 2.96 (8H, m), 3.10 (3H, m), 4.04 (1H, m), 4.79 (1H, m), 7.11 (2H, m), 7.18 (1H, m), 7.28 (2H, m), 7.73 (2H, m). FABMS(pos) 439[M+H]$^+$. Melting point: 112–113° C. (crystallizing solvent: ethyl acetate-diisopropyl ether)

Example 206 tert-Butyl 8-[3-[4-(4-chlorophenyl)-1-piperidinyl]propoxy]-1,3,4,5-tetrahydro-2H-2-benzazepine-2-carboxylate

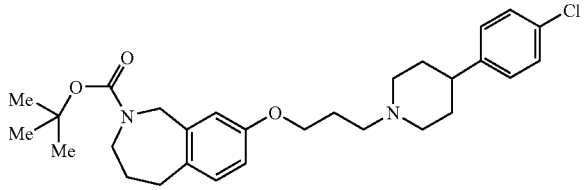

A solution of tert-butyl 8-hydroxy-1,3,4,5-tetrahydro-2H-2-benzazepine-2-carboxylate (1.00 g, 3.80 mmol) obtained in Reference Example 27, 3-bromo-1-chloropropane (0.451 ml, 4.56 mmol) and potassium carbonate (2.62 g, 19.0 mmol) in dimethylformamide (10 ml) was stirred at 80° C. for 3 hours. Ethyl acetate was added to the resultant solution which was then washed with a saturated saline solution and dried over anhydrous sodium sulfate. After the solvent was concentrated under reduced pressure, the resultant residues were purified by alumina column chromatography (developing solvent; ethyl acetate). The resultant oily matter and a solution of 4-(4-chlorophenyl) piperidine (882 mg, 3.80 mmol), potassium carbonate (2.62 g, 19.0 mmol) and sodium iodide (569 mg, 3.80 mmol) in dimethylformamide (10 ml) were stirred at 80° C. for 3 hours. Ethyl acetate was added to the resultant solution which was then washed with a saturated saline solution and dried over anhydrous sodium sulfate. After the solvent was concentrated under reduced pressure, the resultant residues were purified by silica gel column chromatography (developing solvent; hexane:ethyl acetate=3:1), whereby the title compound (1.25 g) was obtained.

$^1$H NMR (CDCl$_3$) δ: 1.41 (9H, s), 1.72–1.82 (6H, m), 1.96–2.05 (4H, m), 2.48–2.58 (3H, m), 2.88 (2H, m), 3.03–3.09 (2H, m), 3.66 (2H, m), 4.01 (2H, m), 4.32–4.39 (2H, m), 6.66–6.75 (2H, m), 7.01–7.05 (1H, m), 7.15 (2H, d, J=8.6 Hz), 7.26 (2H, d, J=8.6 Hz).

Example 207

8-[3-[4-(4-Chlorophenyl)-1-piperidinyl]propoxy]-2,3,4,5-tetrahydro-1H-2-benzazepine

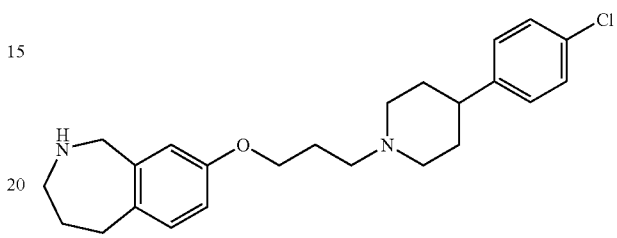

A solution of tert-butyl 8-[3-[4-(4-chlorophenyl)-1-piperidinyl]propoxy]-1,3,4,5-tetrahydro-2H-2-benzazepine-2-carboxylate (1.10 g, 2.20 mmol) obtained in Example 206 in trifluoroacetic acid (10 ml) was stirred for 1 hour and then concentrated under reduced pressure. Ethyl acetate was added to the resultant oily matter which was then washed with an aqueous potassium carbonate solution and a saturated saline solution and dried over anhydrous sodium sulfate. The solvent was concentrated under reduced pressure, and the resultant residues were formed into powder with hexane, to give the title compound (682 mg).

$^1$H NMR (DMSO-d$_6$) δ: 1.57–2.03 (10H, m), 2.43 (3H, m), 2.78 (2H, m), 3.00 (4H, m), 3.72 (2H, m), 3.96 (2H, m), 6.55–6.70 (2H, m), 7.02 (1H, d, J=8.0 Hz), 7.24–7.36 (4H, m). Melting point: 97–99° C. (crystallizing solvent: diisopropyl ether-hexane)

Example 208

8-[3-[4-(4-Chlorophenyl)-1-piperidinyl]propoxy]-2-methyl-2,3,4,5-tetrahydro-1H-2-benzazepine hydrochloride

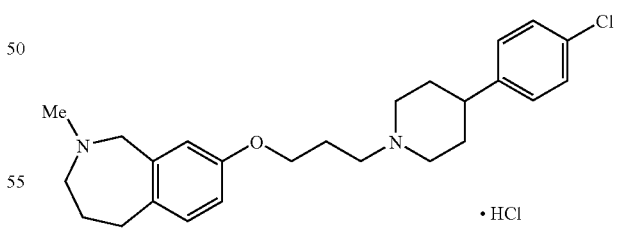

Using 8-[3-[4-(4-chlorophenyl)-1-piperidinyl]propoxy]-2,3,4,5-tetrahydro-1H-2-benzazepine obtained in Example 207, the title compound was obtained as colorless amorphous powder by the same procedure as in Example 16.

$^1$H NMR (CDCl$_3$, free base) δ: 1.71–1.80 (6H, m), 1.96–2.07 (4H, m), 2.31 (3H, s), 2.45–2.57 (3H, m), 2.81 (2H, m), 2.98–3.09 (4H, m), 3.75 (2H, s), 3.99 (2H, t, J=6.3 Hz), 6.65–6.71 (2H, m), 7.01 (1H, d, J=7.2 Hz), 7.15 (2H, d, J=8.7 Hz), 7.26 (2H, d, J=8.7 Hz).

Example 209

2-Acetyl-8-[3-[4-(4-chlorophenyl)-1-piperidinyl]propoxy]-2,3,4,5-tetrahydro-1H-2-benzazepine hydrochloride

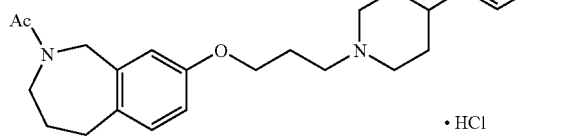

Using 8-[3-[4-(4-chlorophenyl)-1-piperidinyl]propoxy]-2,3,4,5-tetrahydro-1H-2-benzazepine obtained in Example 207 and acetic anhydride, the title compound was obtained as colorless amorphous powder by the same procedure as in Example 17.

$^1$H NMR (DMSO-$d_6$) δ: 1.84 (2H, m), 2.01 (2H, m), 2.32 (3H, s), 2.47–2.62 (4H, m), 2.75–2.95 (5H, m), 3.24 (2H, m), 3.70–3.82 (4H, m), 4.09 (2H, m), 4.57 (2H, m), 6.72–6.90 (2H, m), 7.09 (1H, m), 7.21–7.30 (4H, m).

Example 210

4-[4-(4-Chlorophenyl)-1-piperidinyl]-1-(3-isopropyl-2,3,4,5-tetrahydro-1H-3-benzazepin-7-yl)-1-butanone dihydrochloride

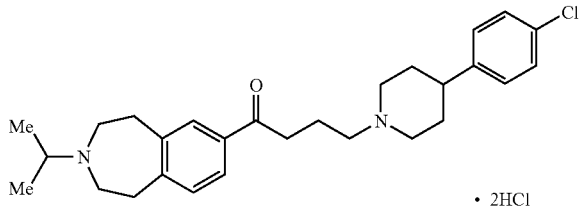

Using 4-[4-(4-chlorophenyl)-1-piperidinyl]-1-(2,3,4,5-tetrahydro-1 H-3-benzazepin-7-yl)-1-butanone obtained in Example 34, the title compound was obtained as colorless powder by the same procedure as in Example 17.

$^1$H-NMR (CDCl$_3$) δ:1.02 (6H, d, J=6.6 Hz), 1.62–1.74 (6H, m), 1.93–2.05 (4H, m), 2.44 (2H, t like), 2.63–2.67 (2H, m), 2.89–3.05 (10H, m), 7.09–7.27 (5H, m), 7.72–7.75 (2H, m). Melting point: 236° C. (decomp) (crystallizing solvent: ethyl acetate-hexane)

Example 211

1-(3-Benzyl-2,3,4,5-tetrahydro-1H-3-benzazepin-7-yl)-4-[4-(4-chlorophenyl)-1-piperidinyl]-1-butanone

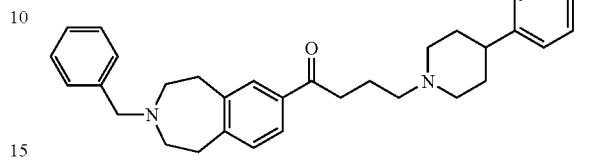

Using 4-[4-(4-chlorophenyl)-1-piperidinyl]-1-(2,3,4,5-tetrahydro-1 H-3-benzazepin-7-yl)-1-butanone obtained in Example 34, the title compound was obtained as colorless powder by the same procedure as in Example 17.

$^1$H-NMR (CDCl$_3$) δ: 1.60–1.79 (6H, m), 1.96–2.08 (4H, m), 2.43 (2H, t like), 2.61–2.65 (2H, m), 2.94–3.04 (9H, m), 3.63 (2H, s), 7.09–7.36 (10H, m), 7.71–7.75 (2H, m). Melting point: 99–100° C. (crystallizing solvent: ethyl acetate-hexane)

Example 212

4-[4-(4-Chlorophenyl)-1-piperidinyl]-1-(3-isopropyl-2,3,4,5-tetrahydro-1H-3-benzazepin-7-yl)-4-oxo-1-butanol

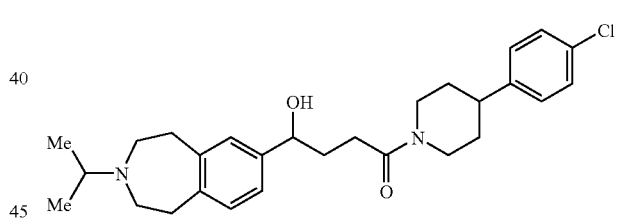

Sodium borohydride (81 mg, 2.14 mmol) was added to a suspension of 4-[4-(4-chlorophenyl)-1-piperidinyl]-1-(3-isopropyl-2,3,4,5-tetrahydro-1H-3-benzazepin-7-yl)-4-oxo-1-butanone (0.50 g, 1.07 mmol) obtained in Example 30 in methanol (20 mL), and the mixture was stirred at room temperature for 30 minutes. The reaction solution was concentrated under reduced pressure, and the residues were partitioned into ethyl acetate and water. The ethyl acetate layer was washed with a saturated saline solution and dried over magnesium sulfate. The solvent was distilled away under reduced pressure, whereby the title compound was obtained as amorphous powder.

$^1$H-NMR (CDCl$_3$) δ: 1.02 (6H, d, J=6.6 Hz), 1.54–1.63 (2H, m), 1.85–1.91 (2H, br m), 2.05–2.17 (2H, m), 2.54 (2H, t like), 2.66–2.78 (6H, m), 2.89–2.93 (5H, m), 3.12 (1H, m), 3.95 (1H, br d), 4.72–4.85 (2H, m), 7.04–7.14 (5H, m), 7.30–7.31 (2H, m).

Example 213

7-[(E)-4-[4-(4-Chlorophenyl)-1-piperidinyl]-4-oxo-1-butenyl]-3-isopropyl-2,3,4,5-tetrahydro-1H-3-benzazepine hydrochloride

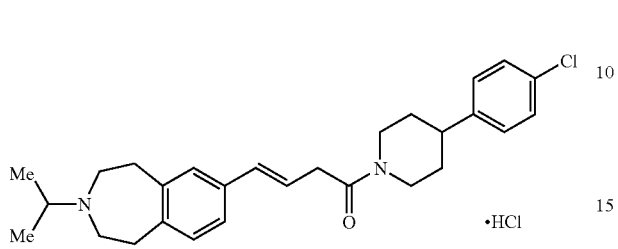

A solution of 4-[4-(4-chlorophenyl)-1-piperidinyl]-1-(3-isopropyl-2,3,4,5-tetrahydro-1H-3-benzazepin-7-yl)-4-oxo-1-butanol (0.14 g, 0.30 mmol) obtained in Example 212 and p-toluenesulfonic acid monohydrate (0.03 g, 0.16 mmol) in toluene (10 mL) was refluxed for 24 hours under heating. The reaction solution was concentrated under reduced pressure, and the resultant residues were purified by alumina column chromatography (developing solvent; hexane:ethyl acetate=1:1), whereby 0.09 g free base of the title compound was obtained as colorless amorphous powder. The resultant powder was dissolved in ethyl acetate and treated with 4 N hydrochloric acid in ethyl acetate under cooling with ice-bath, whereby 0.04 g of the title compound was obtained as colorless amorphous powder.

1H-NMR (CDCl$_3$) δ: 1.02 (6H, d, J=6.6 Hz), 1.50–1.71 (2H, m), 1.86–1.92 (2H, m), 2.57–2.72 (6H, m), 2.87–3.00 (5H, m), 2.64 (1H, m), 3.34 (2H, d, J=6.2 Hz), 4.01–4.07 (1H, br d like), 4.78–4.85 (1H, br d like), 6.26–6.37 (1H, m), 6.46 (1H, d, J=16.2 Hz), 7.05–7.29 (7H, m).

Example 214

1-(3-Acetyl-2,3,4,5-tetrahydro-1H-3-benzazepin-7-yl)-4-[4-(4-chlorophenyl)-1-piperidinyl]-1-butanol

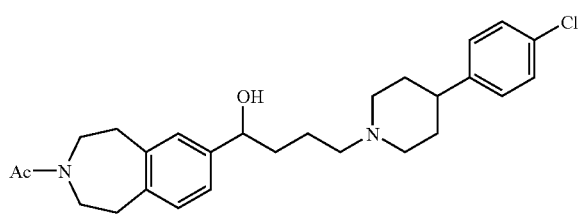

Using 1-(3-acetyl-2,3,4,5-tetrahydro-1 H-3-benzazepin-7-yl)-4-[4-(4-chlorophenyl)-1-piperidinyl]-1-butanone obtained in Example 33, the title compound was obtained as colorless powder by the same procedure as in Example 212.

$^1$H-NMR (CDCl$_3$) δ: 1.50–2.27 (14H, m), 2.42–2.60 (3H, m), 2.85–2.97 (4H, m), 3.01–3.10 (1H, m), 3.23–3.32 (1H, m), 3.47–3.82 (4H, m), 4.64 (1H, brd, J=5.4 Hz), 7.05–7.30 (7H, m). Melting point: 113–114° C. (crystallizing solvent: diethyl ether)

Example 215

3-Acetyl-7-[(E)-4-[4-(4-chlorophenyl)-1-piperidinyl]-1-butenyl]-2,3,4,5-tetrahydro-1H-3-benzazepine

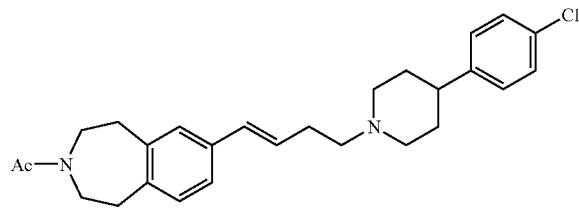

Using 1-(3-acetyl-2,3,4,5-tetrahydro-1 H-3-benzazepin-7-yl)-4-[4-(4-chlorophenyl)-1-piperidinyl]-1-butanol obtained in Example 214, the title compound was obtained as colorless powder by the same procedure as in Example 213.

$^1$H-NMR (CDCl$_3$) δ: 1.57–1.90 (4H, m), 2.04–2.17 (2H, m), 2.19 (3H, s), 2.39–2.58 (5H, m), 2.84–2.95 (4H, m), 3.05–3.15 (2H, m), 3.52–3.61 (2H, m), 3.68–3.77 (2H, m), 6.13–6.27 (1H, m), 6.39 (1H, d, J=15.7 Hz), 7.03–7.20 (5H, m), 7.23–7.30 (2H, m). Melting point: 153–155° C. (crystallizing solvent: diethyl ether)

Example 216

N-[2-(4-Chlorophenoxy) ethyl]-4-oxo-4-[3-(trifluoroacetyl)-2,3,4,5-tetrahydro-1H-3-benzazepin-7-yl]butanamide

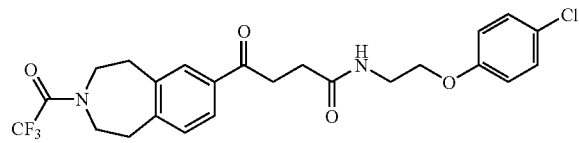

Using 4-oxo-4-[3-(trifluoroacetyl)-2,3,4,5-tetrahydro-1 H-3-benzazepin-7-yl]butanoic acid obtained in Reference Example 16 and 2-(4-chlorophenoxy)ethylamine obtained in Reference Example 26, the title compound was obtained as oily matter by the same procedure as in Example 12.

$^1$H-NMR (CDCl$_3$) δ: 2.65 (2H, t, J=6.6 Hz), 3.02 (4H, m), 3.32 (2H, t, J=6.6 Hz), 3.62–3.69 (4H, m), 3.78 (2H, m), 3.97 (2H, t, J=5.4 Hz), 6.24 (1H, m), 6.81 (2H, m), 7.22–7.28 (3H, m), 7.78 (2H, m).

Example 217

N-[2-(4-Chlorophenoxyl)ethyl]-4-oxo-4-(2,3,4,5-tetrahydro-1H-3-benzazepin-7-yl]butanamide hydrochloride

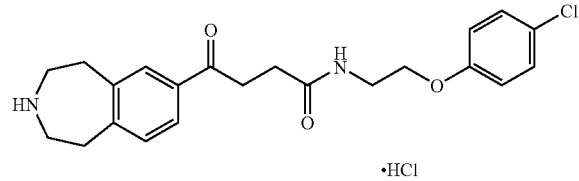

Using N-[2-(4-chlorophenoxy)ethyl]-4-oxo-4-[3-(trifluoroacetyl)-2,3,4,5-tetrahydro-1H-3-benzazepin-7-yl]butanamide obtained in Example 216, the title compound was obtained as amorphous powder by the same procedure as in Example 13.

$^1$H-NMR (CDCl$_3$, free base) δ: 2.02 (1H, m), 2.65 (2H, t, J=6.6 Hz), 2.99 (8H, m), 3.33 (2H, t, J=6.6 Hz), 3.66 (2H, m), 3.97 (2H, t, J=5.4 Hz), 6.31 (1H, m), 6.81 (2H, m), 7.16–7.27 (3H, m), 7.70 (2H, m).

Example 218

N-[3-(4-Chlorophenyl)propyl]-N-methyl-4-oxo-4-[3-(trifluoroacetyl)-2,3,4,5-tetrahydro-1H-3-benzazepin-7-yl]butanamide

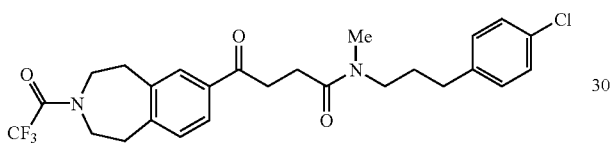

3-(4-Chlorophenyl)propylamine (1.69 g, 9.96 mmol) and 37% aqueous formaldehyde (0.811 ml, 10.0 mmol) was stirred at 100° C. for 7 hours in formic acid (10 ml). The resultant mixture was cooled to room temperature, and the formic acid was distilled away, and the reaction solution was made basic with 8 N aqueous sodium hydroxide and extracted with ethyl acetate. The extract was washed with an aqueous saturated NaCl solution and dried over anhydrous magnesium sulfate. The solvent was distilled away under reduced pressure, and the resultant residues, 4-oxo-4-[3-(trifluoroacetyl)-2,3,4,5-tetrahydro-1H-3-benzazepin-8-yl] butanoic acid (3.4 g, 9.96 mmol) obtained in Reference Example 16, and triethylamine (1.39 ml, 9.96 mmol) were stirred in dimethylformamide (5 ml) at room temperature for 30 minutes and then cooled to 0° C., followed by adding diethyl cyanophosphate (1.51 ml, 9.96 mmol). The resultant mixture was stirred for 1 hour, poured into water and extracted with ethyl acetate. The extract was washed with an aqueous saturated NaCl solution and dried over anhydrous magnesium sulfate. After the solvent was distilled away under reduced pressure, the residues were purified by silica gel column chromatography (developing solvent; ethyl acetate:hexane:1:1), whereby 1.44 g of the title compound was obtained as oily matter.

$^1$H-NMR (CDCl$_3$) δ: 1.86 (2H, m), 2.57–2.80 (4H, m), 3.05 (7H, m), 3.30–3.36 (4H, m), 3.77–3.79 (4H, m), 7.10–7.33 (5H, m), 7.76 (2H, m).

Example 219

N-[3-(4-Chlorophenyl)propyl]-N-methyl-4-oxo-4-(2,3,4,5-tetrahydro-1H-3-benzazepin-7-yl)butanamide hydrochloride

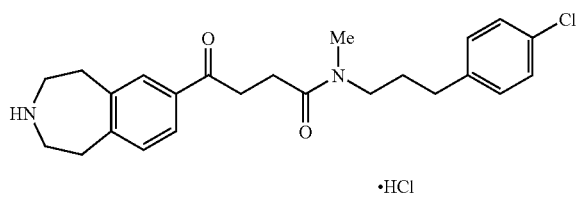

Using N-[3-(4-chlorophenyl) propyl]-N-methyl-4-oxo-4-[3-(trifluoroacetyl)-2,3,4,5-tetrahydro-1 H-3-benzazepin-7-yl]butanamide obtained in Example 218, the title compound was obtained as amorphous powder by the same procedure as in Example 13.

$^1$H-NMR (CDCl$_3$, free base) δ: 1.76–2.05 (3H, m), 2.51–2.68 (6H, m), 3.00 (7H, m), 3.24–3.41 (4H, m), 3.90 (2H, m), 7.07–7.30 (5H, m), 7.76 (2H, m).

Example 220

(E)-3-(Dimethylamino)-1-[1-[[6-(4-methylphenyl)-3-pyridinyl]carbonyl]-1,2,3,4-tetrahydro-6-quinolinyl]-2-propen-1-one

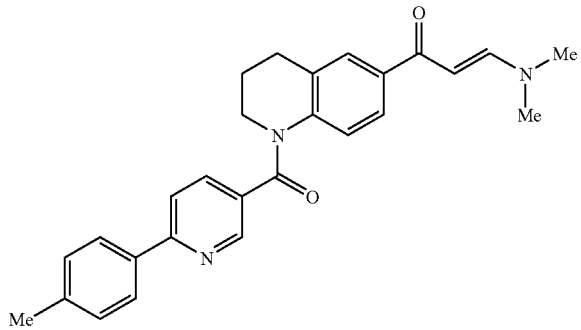

1) Using 6-acetyl-1,2,3,4-tetrahydroquinoline and 6-(4-methylphenyl)nicotinic acid, 1-[1-[[6-(4-methylphenyl)-3-pyridinyl]carbonyl]-1,2,3,4-tetrahydro-6-quinolinyl]ethanone was obtained as pale yellow powder by the same procedure as in Reference Example 5.

$^1$H-NMR (DMSO-d$_6$) δ: 2.00 (2H, m), 2.36 (3H, s), 2.49 (3H, s), 2.93 (2H, dd, J=6.3 and 6.6 Hz), 3.83 (2H, dd, J=6.1 and 6.3 Hz), 7.00 (1H, d, J=9.3 Hz), 7.30 (2H, d, J=8.1 Hz), 7.52 (1H, dd, J=1.5 and 8.3 Hz), 7.83 (2H, m), 7.95 (1H, d, J=8.3 Hz), 8.01 (2H, d, J=8.1 Hz), 8.59 (1H, m).

2) Using 1-[1-[[6-(4-methylphenyl)-3-pyridinyl]carbonyl]-1,2,3,4-tetrahydro-6-quinolinyl]ethanone obtained in 1) above, the title compound was obtained as pale yellow powder by the same procedure as in Reference Example 6.

$^1$H-NMR (DMSO-d$_6$) δ: 2.00 (2H, tt, J=6.3, 6.3 Hz), 2.35 (3H, s), 2.87 (3H, br s), 2.91 (2H, t, J=6.3 Hz), 3.11 (3H, br s), 3.83 (2H, t, J=6.3 Hz), 5.78 (1H, d, J=12.5 Hz), 6.86 (1H, d, J=8.1 Hz), 7.30 (2H, d, J=8.3 Hz), 7.66 (1H, d, J=12.5 Hz), 7.80 (3H, m), 7.94 (1H, d, J=8.3 Hz), 8.00 (2H, d, J=8.1 Hz), 8.57 (1H, m).

Example 221

(E)-N,N-Dimethyl-3-[1-[[6-(4-methylphenyl)-3-pyridinyl]carbonyl]-1,2,3,4-tetrahydro-6-quinolinyl]-2-propene-1-amine hydrochloride

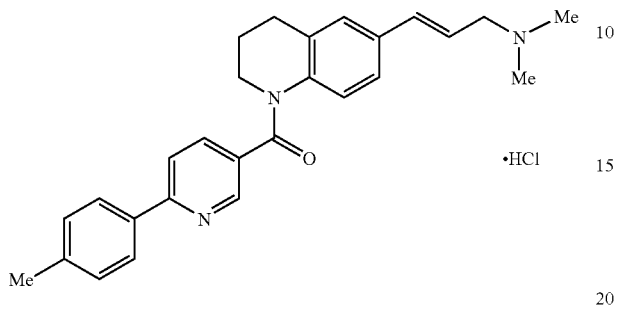

Using (E)-3-(dimethylamino)-1-[1-[[6-(4-methylphenyl)-3-pyridinyl]carbonyl]-1,2,3,4-tetrahydro-6-quinolinyl]-2-propen-1-one obtained in Example 220, the title compound was obtained as yellow crystals by the same procedures as in Examples 4 and 5.

$^1$H-NMR (DMSO-$d_6$) δ: 1.98 (2H, m), 2.36 (3H, s), 2.70 (3H, s), 2.71 (3H, s), 2.86 (2H, t, J=6.3 Hz), 3.00 (2H, m), 3.79 (2H, t, J=6.3 Hz), 5.66 (1H, m), 6.98 (2H, s), 7.24 (1H, s), 7.31 (2H, d, J=8.1 Hz), 7.86 (1H, m), 7.96 (1H, m), 8.00 (2H, d, J=8.1 Hz), 8.57 (1H, m), 10.42 (1H, br s).

Example 222

1-[1-[(4-Phenyl-1-piperidinyl)carbonyl]-1,2,3,4-tetrahydro-6-quinolinyl]-3-(1-pyrrolidinyl)-1-propanone

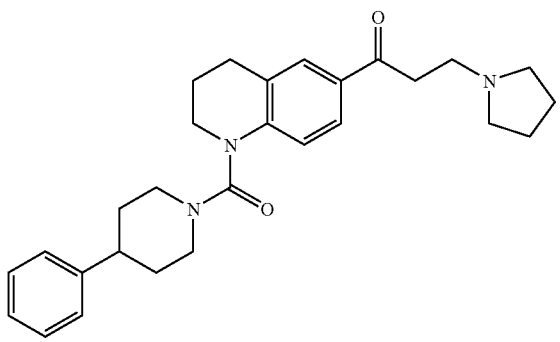

Using 1-[(4-phenyl-1-piperidinyl)carbonyl]-1,2,3,4-tetrahydroquinoline obtained in Reference Example 28, the title compound was obtained as colorless solution by the same procedures as in Reference Examples 7 and 8.

$^1$H-NMR (CDCl$_3$) δ: 1.70 (2H, m), 1.79 (4H, m), 1.84 (2H, m), 2.01 (2H, m), 2.56 (4H, m), 2.69 (1H, m), 2.84 (2H, t, J=6.6 Hz), 2.89 (2H, dd, J=7.0 and 8.0 Hz), 2.91 (2H, m), 3.14 (2H, dd, J=7.0 and 8.0 Hz), 3.64 (2H, t, J=5.8 Hz), 4.05 (2H, m), 7.02 (1H, d, J=8.8 Hz), 7.19–7.33 (5H, m), 7.73 (2H, m).

Example 223

1-[(4-Phenyl-1-piperidinyl)carbonyl]-6-[(E)-3-(1-pyrrolidinyl)-1-propenyl]-1,2,3,4-tetrahydroquinoline hydrochloride Using 1-[1-[(4-phenyl-1-piperidinyl)carbonyl]-1,2,3,4-tetrahydro-6-quinolinyl]-3-(1-pyrrolidinyl)-1-propanone obtained in Example 222, the title compound was obtained as yellow amorphous powder by the same procedures as in Examples 4 and 5.

$^1$H-NMR (DMSO-$d_6$) δ: 1.70 (2H, m), 1.83 (2H, m), 1.97 (2H, m), 2.07 (2H, m), 2.23 (2H, m), 2.68 (1H, m), 2.79 (2H, m), 2.88 (4H, m), 3.64 (2H, m), 3.72 (2H, m), 3.78 (2H, m), 4.00 (2H, m), 6.32 (1H, m), 6.82 (1H, d, J=15.8 Hz), 7.14–7.33 (8H, m), 12.54 (1H, br s).

| Preparation Example 1 | |
| --- | --- |
| (1) Compound obtained in Example 1 | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Carboxymethylcellulose calcium | 20 mg |
| Total | 120 mg |

In accordance with a conventional manner, the above (1) to (6) are admixed and tableted using a tableting machine to give tablets.

| Preparation Example 2 | |
| --- | --- |
| (1) Compound obtained in Example 5 | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Carboxymethylcellulose calcium | 20 mg |
| Total | 120 mg |

In accordance with a conventional manner, the above (1) to (6) are admixed and tableted using a tableting machine to give tablets.

Reference Example 1-1

Amplification of Rat SLC-1 Receptor cDNA by PCR Method Using Rat-Brain-Originated cDNA Reverse transcription reaction was carried out using random primer, with rat-brain-originated poly (A)$^+$RNA (Clone Tech Co.) as a template. The reagent from the TaKaRa RNA PCR ver. 2 kit was used for the reverse transcription reaction. Next, using this reverse transcription product as a template, amplification was carried out by a PCR method using synthetic DNA primers with SEQ ID NOS: 1 and 2. Synthetic DNA primers were constructed to amplify genes in the domain where genes were translated into the receptor protein. At that time, individual restriction enzyme recognition sequences were also added to the 5' side and 3' side of the gene so as to add a nucleotide sequence recognizing the restriction enzyme Sal I to the 5' side of the gene, and to add a nucleotide sequence recognizing the restriction enzyme Spe I to the 3' side of the gene. The reaction mixture was composed of 5 μl of cDNA template, 0.4 μM of synthetic DNA primer, 0.25 mM of dNTPs, 0.5 μl of Pfu (StrataGene Co.) DNA polymerase, and buffers attached to enzymes, with setting total reaction quantity at 50 μl.

A thermal cycler (Parkin Elmer Co.) was used to produce cycles for amplification. After heating at 94° C. for 60 seconds, the cycle consisting of 94° C. for 60 seconds, 60° C. for 30 seconds, and 72° C. for 150 seconds, was repeated 35 times, and finally reaction was conducted at 72° C. for 10 minutes. After 0.8% agarose gel electrophoresis, the amplified products were confirmed by ethidium bromide dying.

Reference Example 1-2

Subcloning of PCR Products into Plasmid Vector, and Confirmation of an Amplified cDNA Sequence by Decoding of a Nucleotide Sequence in an Inserted cDNA Portion The reaction product after PCR conducted in Reference Example 1-1 was separated using 0.8% low-melting point agarose gel. After the band section was cut out using a razor, DNA was recovered by conducting fragmentation, phenol extraction, phenol-chloroform extraction and ethanol precipitation. The recovered DNA was subcloned on plasmid vector PCR-Script Amp SK(+) in accordance with prescription of the PCR-Script™ Amp SK(+) cloning kit (Stratagene Co.). After this was introduced into *Escherichia coli* XL-1 Blue (Stratagene Co.) by transformation, the clones with fragments of inserted cDNA were selected in LB agar culture medium containing ampicillin and X-gal. Only clones showing white color were separated using a sterilized toothpick, and transformant *E. coli* XL-1 Blue/rat SLC-1 was obtained.

Each clone was cultured overnight in LB culture medium containing ampicillin, and plasmid DNA was prepared using QIA prep8 mini prep (Qiagen). A portion of the prepared DNA was digested with Sal I and Spe I, and the size of the inserted receptor cDNA fragment was confirmed. Reactions to determine nucleotide sequences were carried out using a DyeDeoxy Terminator Cycle Sequence Kit (Parkin Elmer Co.), and decoded using a fluorescent light automatic sequencer. The sequences of the 3 clones obtained were analyzed, and it was confirmed that all of them match the reported gene sequence (SEQ ID NO: 4) in which the Sal I recognition sequence was added to the 5' side and the Spe I recognition sequence was added to the 3' side of the cDNA sequence (Lakaye, B., et al., Biochim. Biophys. Acta, Vol. 1401, pp. 216–220 (1998), accession No. AF08650) coding rat SLC-1 protein (SEQ ID NO: 3).

Reference Example 1-3

Preparation of CHO Cells for Rat SLC-1 Expression

The full-length amino acid sequence of rat brain originated SLC-1, which was confirmed in Reference Example 1-2, was coded, and plasmid was prepared using a plasmid Midi Kit (Qiagen) from the *E. coli* transformed by the plasmid, to which the gene with Sal I recognition sequence added to the 5' side and Spe I recognition sequence added to the 3' side, had been introduced. Then, the insert section was cut out by digesting with Sal I and Spe I. The insert DNA was cut out with a razor from the agarose gel after electrophoresis.

Next, fragmentation, phenol extraction, phenol-chloroform extraction, and ethanol precipitation, were conducted and the DNA was recovered. This insert DNA was added to vector plasmid pAKKO-111H (the same vector plasmid as pAKKO1.11H described in Hinuma, S., et al., Biochim. Biophys. Acta, Vol. 1219, pp. 251–259 (1994)) for animal cell expression which was digested with Sal I and Spe I, and ligation was conducted using T4 ligase (TaKaRa Shuzo), to construct pAKKO-SLC-1 plasmid for protein expression.

After *E. coli* DH5 (TOYOBO) transformed by pAKKO-SLC-1 was cultured, pAKKO-SLC-1 plasmid DNA was prepared using a Plasmid Midi Kit (Qiagen). This was introduced into CHO dhfr$^-$ cells in accordance with the attached protocol, using a CellPhect Transfection Kit (Amersham Pharmacia Biotech Co.). A coprecipitating suspension of 10 μg of DNA and calcium phosphate was prepared, and this suspension was added to 10 cm Petri dishes in which $5 \times 10^5$ or $1 \times 10^6$ of CHO dhfr$^-$ cells had been seeded 24 hours previously. After these cells were cultured for 1 day in MEMα culture medium containing 10% fetal bovine serum, subculture was conducted, and cultivation was conducted in selective culture medium, MEMα culture medium containing no nucleic acid but containing 10% dialyzed fetal bovine serum. 56 Clones of colonies of the transformed CHO cells expressing SLC-1, proliferated in the selective culture medium, were selected.

Reference Example 1-4

Selection of CHO/SLC-1 Cell Strain Expressing a Large Quantity of Full-Length rat SLC-1 Receptor Protein mRNA The quantity of expressed full-length rat SLC-1 receptor protein mRNA of 56 clones of the CHO/SLC-1 strains established in Reference Example 1-3, was measured using a Cytostar T Plate (Amersham Pharmacia Biotech Co.) as shown below according to the attached protocol. Each well of the Cytostar T Plate was seeded with each clone of the CHO/SLC-1 strain by $2.5 \times 10^4$, and cultured for 24 hours, then the cells were fixed using 10% formalin. After 0.25% Triton X-100 was added to each well to increase cell permeability, $^{35}$S-labeled riboprobes with SEQ ID NO: 5 were added and hybridized. 20 mg/ml of RNaseA was added to each well to digest free riboprobes. After the plate was thoroughly washed, the radioactivity of the hybridized riboprobes was determined using a Topcounter. Strains with high radioactivity showed large amounts of mRNA expression. In particular, mainly used was Clone number 44 among 3 clones which showed large amounts of mRNA expression.

Reference Example 1-5

Isolation of Plasmid Containing Human SLC-1 cDNA

After nicks were inserted into the DNA of Human fetal brain originated cDNA library (SUPERSCRIPT™ cDNA Library; GIBCOBRL Co.) according to the manual of the Genetrapper cDNA positive selection system (GIBCOBRL Co.), using pharge F1 endonuclease, single stranded human fetal brain originated cDNA library was prepared by digesting the above-mentioned library with *Escherichia coli* exonuclease III.

Biotin-14-dCTP was added to the 3' end of synthetic oligonucleotide (equivalent to 1434–1451 of accession No. U71092), SEQ ID NO: 6 which was prepared according to the report by Kolakowski Jr., et al. (Kolakowski Jr., et al. (1996) FEBS Lett. Vol. 398, pp. 253–258) using Terminal Deoxynucleotidyl Transferase, and biotinated oligonucleotide was prepared. The above manual was followed regarding composition of a reaction mixture and reaction time.

After 4 µg of single stranded human fetal brain originated cDNA library was kept at 95° C. for 1 minute, the library was rapidly cooled on ice. 20 ng of Biotinated oligonucleotide was added, which was hybridized using the attached hybridization buffer at 37° C. for 1 hour. Streptoavidin beads were added to the mixture, then single stranded human fetal brain originated cDNA hybridized by biotinated oligonucleotide, was isolated using a MAGNA-SEP Magnetic Particle Separator (GIBCOBRL Co.). The complementary strand was synthesized according to the manual, using as primer 50 ng of synthetic oligonucleotide (equivalent to 1011–1028 of accession No. U71092) of SEQ ID NO: 7, prepared based on the report by Kolakowski Jr., et al (Kolakowski Jr., et al. (1996) FEBS Lett. Vol. 398, pp. 253–258), to give the double stranded plasmid.

Reference Example 1-6

Determination of Nucleotide Sequence of Plasmid Containing Isolated Human SLC-1 cDNA After the plasmid obtained in Reference Example 1-5 was introduced into ELECTROMAX™DH10B™ Cells by the electroporation method, clones with cDNA inserted fragments were selected in LB agar culture medium containing ampicillin and X-gal. Using a sterilized toothpick, only the clones showing white color were separated to give transformant *E. coli* DH10B/hSLC-1. Individual clones were cultured overnight in LB culture medium containing ampicillin, and the plasmid DNA was refined using QIA prep8 mini prep (Qiagen). The reactions to determine nucleotide sequence were conducted using a DyeDeoxy Terminator Cycle Sequence Kit (Parkin Elmer Co.), and the nucleotide sequence was decoded using a fluorescent light automatic sequencer.

As the results, obtained was the sequence shown in SEQ ID NO: 8. The amino acid sequence (SEQ ID NO: 9) coded by the nucleotide sequence obtained here, differs from the human SLC-1 amino acid sequence predicted as the sequence analogized from rat SLC-1 based on human chromosome DNA sequence (accession number: Z86090) containing human SLC-1 sequence, in the report by Lakaye, et al. (Lakaye, B., et al. (1998) Biochim. Biophys. Acta. Vol. 1401, pp. 216–220). This shows the presence of ATG, the initiation codon, on mRNA, in the 69 and 64 amino acids upstream from the estimated sequence. *Escherichia coli* DH10B/phSLC1L8, the transformant produced by the plasmid containing DNA coding this sequence was deposited at IFO and NIBH.

Reference Example 1-7

Amplification of Human SLC-1cDNA by PCR Method Using Human Fetal Brain Originated cDNA Amplification by the PCR method was conducted using as the template plasmid containing human SLC-1 DNA sequence cloned by the gene trap method, and using synthetic DNA primers of SEQ ID NO: 10 and SEQ ID NO: 11, and synthetic DNA primers of SEQ ID NO: 12 and SEQ ID NO: 13, respectively. The former amplified DNA and the latter amplified DNA were named as "human SLC-1(S)" and "human SLC-1(L)", respectively. The synthetic DNA primer was constructed so that the genes in the domain translated to the receptor protein were amplified. At that time, a recognition sequence for each restriction enzyme was added to the 5' side and 3' side, so that the nucleotide sequence recognized by restriction enzyme Sal I would be added to the 5' side of the gene, and the nucleotide sequence recognized by restriction enzyme Spe I would be added to the 3' side. The composition of the reaction mixture for human SLC-1(S) amplification was: 5 µl of plasmid template containing human SLC-1 DNA sequence, 0.4 µM of respective synthetic DNA primers, 0.2 mM of dNTPs and 0.5 µl of Pfu DNA polymerase and buffers attached to the enzyme, with setting total quantity for reaction at 50 µl. A thermal cycler (Parkin Elmer Co.) was used for the cycles for amplification. After heating at 94° C. for 60 seconds, the cycle consisting of 94° C. for 60 seconds, 57° C. for 60 seconds, and 72° C. for 150 seconds, was repeated 25 times, and finally the temperature of the reactant was maintained at 72° C. for 10 minutes. The composition of the reaction mixture for human SLC-1(L) amplification was 5 µl of plasmid template containing human SLC-1 DNA sequence, 0.4 µM of respective synthetic DNA primers, 0.2 mM of dNTPs, 0.5 µl of Pfu DNA polymerase and buffers attached to the enzymes, with setting total quantity for reaction at 50 µl. A thermal cycler (Parkin Elmer Co.) was used for the cycles for amplification. After heating at 94° C. for 60 seconds, the cycle consisting of 94° C. for 60 seconds, 60° C. for 60 seconds, and 72° C. for 3 minutes, was repeated 25 times, and finally the temperature of the reactant was maintained at 72° C. for 10 minutes. After 0.8% agarose gel electrophoresis, confirmation of amplified products was conducted by ethidium bromide dying.

Reference Example 1-8

Subcloning of PCR Product Into Plasmid Vector and Confirmation of Amplified cDNA Sequence by Decoding of Nucleotide Sequence of Inserted cDNA Section The reaction product after PCR in Reference Example 1-7 was separated using 0.8% low-melting point agarose gel, and the band section was cut out using a razor. After that, fragmentation, phenol extraction, phenol-chloroform extraction, and ethanol precipitation were conducted, and the DNA was recovered. The recovered DNA was subcloned into pCR-Script Amp SK(+) plasmid vector, as prescribed by the PCR-Script™ Amp SK(+) cloning kit (Stratagene Co.). After this was introduced into *Escherichia coli* DH5α competent cells (TOYOBO) and transformed, the clones with cDNA inserted fragments were selected in LB agar culture medium containing ampicillin and X-gal. Using a sterilized toothpick, only clones showing white color were separated to give *E. coli* DH5α/hSLC-1(S), which is a transformant of human SLC-1 (S), and *E. coli* DH5α/hSLC-1(L), which is a transformant of human SLC-1 (L). Each clone was cultured overnight in LB culture medium containing ampicillin, and plasmid DNA was prepared using QIA prep8 mini prep (Qiagen). Some of the prepared DNA was digested with Sal I and Spe I restriction enzymes, and the size of the receptor cDNA fragments inserted was confirmed. The reactions to determine nucleotide sequence were conducted using a DyeDeoxy Terminator Cycle Sequence Kit (Parkin Elmer Co.) and the nucleotide sequence was decoded using a fluorescent light automatic sequencer. The sequence of the obtained clones respectively matched the DNA sequence (SEQ ID NO: 14) which should be amplified by synthetic DNA primers of SEQ ID NO: 10 and SEQ ID NO: 11 using human SLC-1 gene as a template, and the DNA sequence (SEQ ID NO: 15) which should be amplified by synthetic DNA primers of SEQ ID NO: 12 and SEQ ID NO: 13 using human SLC-1 gene as a template.

Reference Example 1-9

Preparation of CHO Cells for Expression of Human SLC-1(S), and CHO Cells for Expression of Human SLC-1(L)

Plasmid was prepared from the *E. coli* clones transformed by the plasmid wherein inserted were human SLC-1(S) and human SLC-1(L) whose sequences were confirmed in Reference Example 1-8, using a Plasmid Midi Kit (Qiagen), and the insert section was cut out using Sal I and Spe I restriction enzymes. After electrophoresis was conducted, the insert DNA was cut out from agarose gel using a razor. Next, fragmentation, phenol extraction, phenol-chloroform extraction, and ethanol precipitation were conducted, and the insert DNA was recovered.

This insert DNA was added to pAKKO-111H vector plasmid for animal cell expression, digested with Sal I and Spe I (the same vector plasmid as the pAKKO1.11H described in Hinuma, S., et al., Biochim. Biophys. Acta, Vol. 1219, pp. 251–259 (1994)), and ligation was conducted by adding T4 ligase (TaKaRa Shuzo), to construct pAKKO-hSLC-1(S) and pAKKO-hSLC-1(L) plasmids for protein expression.

After *E. coli* DH5α (TOYOBO) transformed by pAKKO-hSLC-1(S) and pAKKO-hSLC-1(L) was cultured, pAKKO-hSLC-1(S) and pAKKO-hSLC-1(L) plasmid DNAs were prepared using a Plasmid Midi Kit (Qiagen). These were introduced into CHO dhfr⁻ cells in accordance with the attached protocol, using a CellPhect Transfection Kit (Amersham Pharmacia Biotech Co.). A coprecipitative suspension of 10 μg of DNA with calcium phosphate was made, which was added to 10 cm Petri dishes seeded 24 hours in advance with $5 \times 10^5$ or $1 \times 10^6$ CHO dhfr⁻ cells. After the above was cultured for 1 day in MEMα culture medium containing 10% fetal bovine serum, subculture was conducted, and then cultivation was conducted in MEMα culture medium containing no nucleic acid but containing 10% dialyzed fetal bovine serum, which is a selective culture medium. 56 clones of colonies of transformed cells which are human SLC-1(S) gene introduced CHO cells, and 61 clones of colonies of transformed cells which are human SLC-1(L) gene introduced CHO cells, both of which proliferated in the selective culture medium, were selected.

Reference Example 1-10

Selection of Cell Colonies into which Genes with Large Quantities of Human SLC-1(S) and Human SLC-1 (L) mRNA Expression have been Introduced The quantities of expressed mRNA of 56 clones of CHO/hSLC-1(S) colonies and 61 clones of CHO/hSLC-1(L) colonies, both of which were established in Reference Example 1-9, were measured in accordance with the attached protocol using a Cytostar T Plate (Amersham Pharmacia Biotech Co.) as shown below.

After each well of the Cytostar T Plate was seeded with each clone of CHO/hSLC-1(S) colonies and CHO/hSLC-1 (L) colonies by $2.5 \times 10^4$, and cultured for 24 hours, the cells were fixed using 10% formalin.

After 0.25% Triton X-100 was added to each well to increase cell permeability, $^{35}$S-labeled riboprobe of SEQ ID NO: 16 was added and hybridization was conducted.

20 mg/ml of RNaseA was added to each well to digest free riboprobe. After the plate was washed well, the radioactivity of the hybridized riboprobe was determined using a Topcounter. Colonies showing high radioactivity expressed large quantities of mRNA. Of the 7 clones which expressed large quantities of mRNA, mainly used was Clone number 57.

Experimental Example 1

Determination of Antagonist Activity using GTPγS Binding Assay of Test Compound

Membrane fraction was prepared by the following method, using the human SLC-1 expressing CHO cell clone 57 obtained in Reference Example 1-10, and the rat SLC-1 expressing CHO cell clone 44 obtained in Reference Example 1-4.

The human and rat SLC-1 expressing CHO cells ($1 \times 10^8$) were scraped in buffer saline phosphate (pH 7.4) to which 5 mM EDTA (ethylenediaminetetraacetic acid) had been added, and centrifuged. 10 ml of homogenized buffer (10 mM NaHCO$_3$, 5 mM EDTA, pH 7.5) was added to the cell pellets, and they were homogenized using a Polytron homogenizer. The supernatant obtained by centrifugation at 400×g for 15 minutes was further centrifuged at 100,000×g for 1 hour, to obtain the membrane fraction precipitate. This precipitate was suspended in 2 ml of assay buffer [50 mM Tris-HCl(pH 7.5), 1 mM EDTA, 0.1% BSA (bovine serum albumin), 10 mM MgCl$_2$, 100 mM NaCl, 1 μM GDP (guanosine 5'-diphosphate), 0.25 mM PMSF (phenylmethylsulfonyl fluoride), 1 mg/ml pepstatin, 20 mg/ml leupeptin, 10 mg/ml phosphoramidon], which was centrifuged at 100,000×g for 1 hour. The membrane fraction recovered as precipitate was suspended again in 20 ml of assay buffer, and after the suspension was divided, individual portions were preserved at −80° C. and thawed before every use.

Determination of antagonist activity of the test compound was conducted as shown below. After 171 μl of SLC-1 expressing CHO cell membrane fractions diluted with assay buffer was poured into each well of a 96-well polypropylene plate, 2 μl of $3 \times 10^{-10}$M MCH diluted with DMSO solution, 2 μl of test compound solution diluted to various concentrations, and 25 μl of [$^{35}$S]-Guanosine 5'-(γ-thio) triphosphate (produced by Daiichi Kagaku Yakuhin) were added respectively. (Final concentration of cell membrane: 20 μg/ml, final concentration of [$^{35}$S]-Guanosine 5'-(γ-thio) triphosphate: 0.33 nM).

After this reaction mixture was allowed to react at 25° C. for 1 hour under stirring, it was filtered under vacuum using a glass filter (GF-C), then the filter was washed 3 times with 300 μl of washing solution (50 mM Tris-HCl buffer solution pH 7.5). 50 ml of liquid scintillator was added to the glass filter, and residual radioactivity was determined using a liquid scintillation counter.

The IC$_{50}$ value of the compound was calculated from the binding inhibition rate (%), based on the definition that the binding inhibition rate (%)=(radioactivity when compound and MCH were added−radioactivity when DMSO solution was added)/(radioactivity when MCH was added−radioactivity when DMSO solution was added)×100.

The results were shown below.

| Compound Number | Inhibition Activity (IC$_{50}$ value: μM) |
| --- | --- |
| Example 1 | 0.3 |
| Example 5 | 0.02 |

INDUSTRIAL APPLICABILITY

Compounds (I), (I'), (I"), (I''') and salts thereof possess excellent MCH receptor antagonistic activities, and are useful as an agent for preventing or treating obesity, etc.

---

What is claimed is:

1. A compound represented by the formula:

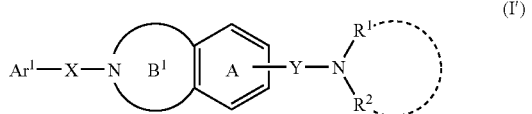

(I')

wherein Ar¹ is a cyclic group which may be substituted, and said cyclic group which may be substituted is (1) phenyl, (2) a group which formed by removing an optional one hydrogen atom from a 5- or 6-membered aromatic heterocyclic ring containing 1 to 3 hetero atoms selected from nitrogen, sulfur and oxygen atoms in addition to carbon atoms, (3) a group which formed by removing an optional one hydrogen atom from a $C_{9-14}$ condensed polycyclic aromatic hydrocarbon, (4) a group which formed by removing an optional one hydrogen atom from a 9- or 14-membered condensed polycyclic aromatic heterocyclic ring containing 1 to 4 hetero atoms selected from nitrogen, sulfur and oxygen atoms in addition to carbon atoms, (5) a group which formed by removing an optional one hydrogen atom from an aromatic ring assemble comprising 2 or 3 aromatic rings selected from benzene, naphthalene, pyridine, pyrimidine, thiophene, furan, thiazole, isothiazole, oxazole, isoxazole, 1,2,4-oxadiazole, 1,3,4-oxadiazole, 1,2,4-thiadiazole, 1,3,4-thiadiazole, quinoline, isoquinoline, indole, benzothiophene, benzoxazole, benzothiazole and benzofuran, (6) a $C_{3-8}$ cycloalkyl or a $C_{3-8}$ cycloalkenyl, (7) a group which formed by removing an optional one hydrogen atom from a 5- to 8-membered monocyclic non-aromatic heterocyclic ring containing 1 to 3 hetero atoms selected from nitrogen, sulfur and oxygen atoms in addition to carbon atoms, or (8) a group which formed by removing an optional one hydrogen atom from a 9- to 14-membered condensed polycyclic non-aromatic heterocyclic rings which contain 1 to 4 hetero atoms selected from nitrogen, sulfur and oxygen atoms in addition to carbon atoms, and each of the above said cyclic group which may be substituted (1) to (8) may have 1 to 5 substituents selected from the group consisting of 1) oxo,
2) halogen atoms,
3) $C_{1-3}$ alkylenedioxy,
4) nitro,
5) cyano,
6) optionally halogenated $C_{1-6}$ alkyl,
7) hydroxy-$C_{1-6}$ alkyl,
8) $C_{6-14}$ aryloxy-$C_{1-6}$ alkyl,
9) $C_{1-6}$ alkyl-$C_{6-14}$ aryl-$C_{2-6}$ alkenyl,
10) optionally halogenated $C_{3-6}$ cycloalkyl,
11) optionally halogenated $C_{1-6}$ alkoxy,
12) optionally halogenated $C_{1-6}$ alkylthio,
13) $C_{7-19}$ aralkyl,
14) hydroxy,
15) $C_{6-14}$ aryloxy,
16) $C_{7-19}$ aralkyloxy,
17) $C_{6-14}$ aryl-carbamoyl,
18) amino,
19) amino-$C_{1-6}$ alkyl,
20) mono-$C_{1-6}$ alkylamino,
21) di-$C_{1-6}$ alkylamino,
22) mono-$C_{1-6}$ alkylamino-$C_{1-6}$ alkyl,
23) di-$C_{1-6}$ alkylamino-$C_{1-6}$ alkyl,
24) 5- to 7-membered saturated cyclic amino,
25) 5- to 7-membered non-aromatic heterocyclic groups,
26) acyl,
27) acylamino and
28) acyloxy
  wherein the above substituents 24) and 25) of each said cyclic group which may be substituted (1) to (8) may have 1 to 5 substituents selected from the group consisting of:
  24a) oxo,
  24b) optionally halogenated $C_{1-6}$ alkyl,
  24c) optionally halogenated $C_{1-6}$ alkyl-carbonyl,
  24d) optionally halogenated $C_{1-6}$ alkylsulfonyl,
  24e) $C_{6-14}$ aryl,
  24f) $C_{7-19}$ aralkyl,
  24g) $C_{6-14}$ aryl-carbonyl,
  24h) 5- to 10-membered aromatic heterocyclic group which may have 1 to 5 substituents selected from the group consisting of (A) halogen atom, (B) $C_{1-3}$ alkylenedioxy, (C) nitro, (D) cyano, (E) optionally halogenated $C_{1-6}$ alkyl, (F) $C_{6-14}$ aryloxy-$C_{1-6}$ alkyl, (G) $C_{1-6}$ alkyl-$C_{6-14}$ aryl-$C_{2-6}$ alkenyl, (H) optionally halogenated $C_{3-6}$ cycloalkyl, (I) optionally halogenated $C_{1-6}$ alkoxy, (J) optionally halogenated $C_{1-6}$ alkylthio, (K) $C_{7-19}$ aralkyl, (L) hydroxy, (M) $C_{6-14}$ aryloxy, (N) $C_{7-19}$ aralkyloxy, (O) amino, (P) amino-$C_{1-6}$ alkyl, (Q) mono-$C_{1-6}$ alkylamino, (R) di-$C_{1-6}$ alkylamino, (S) mono-$C_{1-6}$ alkylamino-$C_{1-6}$ alkyl, (T) di-$C_{1-6}$ alkylamino-$C_{1-6}$ alkyl, (U) 5- to 7-membered saturated cyclic amino, (V) acyl, (W) acylamino and (X) acyloxy,
  24i) hydroxy,
  24j) 5- to 8-membered monocyclic non-aromatic heterocyclic group,
  24k) carbamoyl,
  24l) hydroxy-$C_{1-6}$ alkyl,
  24m) $C_{1-6}$ alkoxy-carbonyl-$C_{1-6}$ alkyl,
  24n) $C_{8-19}$ arylalkenyl,
  24o) $C_{1-6}$ alkyl-carboxamide,
  24p) (N—$C_{1-6}$ alkyl)-$C_{1-6}$ alkyl-carboxamide,
  24q) amino,
  24r) mono-$C_{1-6}$ alkylamino,
  24s) di-$C_{1-6}$ alkylamino,
  24t) 5- to 8-membered monocyclic non-aromatic heterocyclic group-$C_{1-6}$ alkyl and
  24u) $C_{6-14}$ aryl-amino-$C_{1-6}$ alkyl which may be substituted with one to three $C_{1-6}$ alkyl,
  wherein each of the above said cyclic group which may be substituted (6) to (8) may further have a substituent selected from the group consisting of
  (6a) $C_{6-14}$ aryl which may have 1 to 3 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-4}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl, and
  (6b) 5- to 10-membered aromatic heterocyclic groups which may have 1 to 3 substituents selected from the group consisting of (6ba) halogen atom, (6bb) $C_{1-3}$ alkylenedioxy, (6bc) nitro, (6bd) cyano, (6be) optionally halogenated $C_{1-6}$ alkyl, (6bf) $C_{6-14}$ aryloxy-$C_{1-6}$ alkyl, (6bg) $C_{1-6}$ alkyl-$C_{6-14}$ aryl-$C_{2-6}$ alkenyl, (6bh) optionally halogenated $C_{3-6}$ cycloalkyl, (6bi) optionally halogenated $C_{1-6}$ alkoxy, (6bj) optionally halogenated $C_{1-6}$ alkylthio, (6bk) $C_{7-19}$ aralkyl, (6bl) hydroxy, (6bm) $C_{6-14}$ aryloxy, (6bn) $C_{7-19}$ aralkyloxy, (6bo) amino, (6bp) amino-$C_{1-6}$ alkyl, (6bq) mono-$C_{1-6}$ alkylamino, (6br) di-$C_{1-6}$ alkylamino, (6bs) mono-$C_{1-6}$ alkylamino-$C_{1-6}$ alkyl, (6bt) di-$C_{1-6}$ alkylamino-$C_{1-6}$ alkyl, (6bu) 5- to 7-membered saturated cyclic amino, (6bv) acyl, (6bw) acylamino and (6bx) acyloxy,
  wherein the above substituents 13), 15), 16), 17), 24e), 24f), 24g), 24K), 24hM), 24hN), (6bk), (6bm) and (6bn) may have 1 to 5 substituents selected from the group consisting of
  halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl;
X is a bond or a bivalent group consisting of 1 to 3 members selected from —O—, —S—, —CO—, —SO—, —SO$_2$—; —NR$^8$—(R$^8$ is hydrogen atom, optionally halogenated $C_{1-6}$ alkyl, optionally halogenated $C_{1-6}$ alkyl-carbonyl or optionally halogenated $C_{1-6}$ alkylsulfonyl), and a divalent $C_{1-6}$ non-cyclic hydrocarbon group which may have 1 to 5 substituents selected front the group consisting of halogen atom, hydroxy, nitro, cyano, optionally halogenated $C_{1-6}$ alkoxy, optionally halogenated $C_{1-6}$ alkylthio, amino, mono-$C_{1-6}$ alkylamino, di-$C_{1-6}$ alkylamino, formyl, carboxy, carbamoyl, thiocarbamoyl, optionally halogenated $C_{1-6}$ alkyl-carbonyl, $C_{1-6}$ alkoxy-carbonyl and optionally halogenated $C_{1-6}$ alkylsulfonyl, wherein the bivalent $C_{1-6}$ non-cyclic hydrocarbon group is selected from a $C_{1-6}$ alkylene, a $C_{2-6}$ alkenylene and a $C_{2-6}$ alkynylene;

Y is —CO(CH$_2$)$_{w7}$CO— wherein w7 is an integer of 0 to 4;

the group represented by the formula

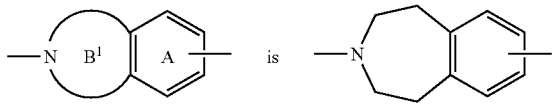

is which may have 1 to 5 further substituents selected from the group consisting of i) oxo,
ii) halogen atoms,
iii) $C_{1-3}$ alkylenedioxy,
iv) nitro,
v) cyano,
vi) optionally halogenated $C_{1-6}$ alkyl,
vii) hydroxy-$C_{1-6}$ alkyl,
viii) $C_{6-14}$ aryloxy-$C_{1-6}$ alkyl,
ix) $C_{1-6}$ alkyl-$C_{6-14}$ aryl-$C_{2-6}$ alkenyl,
x) optionally halogenated $C_{3-6}$ cycloalkyl,
xi) optionally halogenated $C_{1-6}$ alkoxy,
xii) optionally halogenated $C_{1-6}$ alkylthio,
xiii) $C_{7-19}$ aralkyl,
xiv) hydroxy,
xv) $C_{6-14}$ aryloxy,
xvi) $C_{7-19}$ aralkyloxy,
xvii) $C_{6-14}$ aryl-carbamoyl,
xviii) amino,
xix) amino-$C_{1-6}$ alkyl,
xx) mono-$C_{1-6}$ alkylamino,
xxi) di-$C_{1-6}$ alkylamino,
xxii) mono-$C_{1-6}$ alkylamino-$C_{1-6}$ alkyl,
xxiii) di-$C_{1-6}$ alkylamino-$C_{1-6}$ alkyl,
xxiv) 5- to 7-membered saturated cyclic amino,
xxv) 5- to 7-membered non-aromatic heterocyclic groups,
xxvi) acyl,
xxvii) acylamino,
xxviii) acyloxy,
xxix) $C_{6-14}$ aryl which may have 1 to 3 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl, and xxx) 5- to 10-membered aromatic heterocyclic groups which may have 1 to 3 substituents selected from the group consisting of 30a) halogen atom, 30b) $C_{1-3}$ alkylenedioxy, 30c) nitro, 30d) cyano, 30e) optionally halogenated $C_{1-6}$ alkyl, 30f) $C_{6-14}$ aryloxy-$C_{1-6}$ alkyl, 30g) $C_{1-6}$ alkyl-$C_{6-14}$ aryl-$C_{2-6}$ alkenyl, 30h) optionally halogenated $C_{3-6}$ cycloalkyl, 30i) optionally halogenated $C_{1-6}$ alkoxy, 30j) optionally halogenated $C_{1-6}$ alkylthio, 30k) $C_{7-19}$ aralkyl, 30l) hydroxy, 30m) $C_{6-14}$ aryloxy, 30n) $C_{7-19}$ aralkyloxy, 30o) amino, 30p) amino-$C_{1-6}$ alkyl, 30q) mono-$C_{1-6}$ alkylamino, 30r) di-$C_{1-6}$ alkylamino, 30s) mono-$C_{1-6}$ alkylamino-$C_{1-6}$ alkyl, 30t) di-$C_{1-6}$ alkylamino-$C_{1-6}$ alkyl, 30u) 5- to 7-membered saturated cyclic amino, 30v) acyl, 30w) acylamino and 30x) acyloxy, wherein the above substituents xxiv) and xxv) may have 1 to 5 substituents selected from the group consisting of 25a) oxo,
25b) optionally halogenated $C_{1-6}$ alkyl,
25c) optionally halogenated $C_{1-6}$ alkyl-carbonyl,
25d) optionally halogenated $C_{1-6}$ alkylsulfonyl,
25e) $C_{6-14}$ aryl,
25f) $C_{7-19}$ aralkyl,
25g) $C_{6-14}$ aryl-carbonyl,
25h) 5- to 10-membered aromatic heterocyclic group which may have 1 to 5 substituents selected from the group consisting of 25ha) halogen atom, 25hb) $C_{1-3}$ alkylenedioxy, 25hc) nitro, 25hd) cyano, 25he) optionally halogenated $C_{1-6}$ alkyl, 25hf) $C_{6-14}$ aryloxy-$C_{1-6}$ alkyl, 25hg) $C_{1-6}$ alkyl-$C_{6-14}$ aryl-$C_{2-6}$ alkenyl, 25hh) optionally halogenated $C_{3-6}$ cycloalkyl, 25hi) optionally halogenated $C_{1-6}$ alkoxy, 25hj) optionally halogenated $C_{1-6}$ alkylthio, 25hk) $C_{7-19}$ aralkyl, 25hl) hydroxy, 25hm) $C_{6-14}$ aryloxy, 25hn) $C_{7-19}$ aralkyloxy, 25ho) amino, 25hp) amino-$C_{1-6}$ alkyl, 25hq) mono-$C_{1-6}$ alkylamino, 25hr) di-$C_{1-6}$ alkylamino, 25hs) mono-$C_{1-6}$ alkylamino-$C_{1-6}$ alkyl, 25ht) di-$C_{1-6}$ alkylamino-$C_{1-6}$ alkyl, 25hu) 5-to 7-membered saturated cyclic amino, 25hv) acyl, 25hw) acylamino and 25hx) acyloxy, 25i) hydroxy,
25j) 5- to 8-membered monocyclic non-aromatic heterocyclic group,
25k) carbamoyl,
25l) hydroxy-$C_{1-6}$ alkyl,
25m) $C_{1-6}$ alkoxy-carbonyl-$C_{1-6}$ alkyl,
25n) $C_{8-19}$ arylalkenyl,
25o) $C_{1-6}$ alkyl-carboxamide,
25p) (N—$C_{1-6}$ alkyl)-$C_{1-6}$ alkyl-carboxamide,
25q) amino,
25r) mono-$C_{1-6}$ alkylamino,
25s) di-$C_{1-6}$ alkylamino,
25t) 5- to 8-membered monocyclic non-aromatic heterocyclic group-$C_{1-6}$ alkyl and 25u) $C_{6-14}$ aryl-amino-$C_{1-6}$ alkyl which may be substituted with one to three $C_{1-6}$ alkyl, wherein the above xiii), xv), xvi), xvii), 25e), 25f), 25g), 25hk), 25hm), 25hn), 30k), 30m) and 30n) may have 1 to 5 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl; and $R^1$ and $R^2$, together with the adjacent nitrogen atom, form aziridine, azetidine, morpholine, thiomorpholine, piperidine, piperazine, pyrrolidine, hexamethyleneimine, heptamethyleneimine, hexahydropyrimidine, 1,4-diazepan, dihydroisoquinoline, 1,2,5,6-tetrahydropyridine, 1,4-diazepin, or octahydroisoquinoline, each of which may have 1 to 5 substituents selected from the group consisting of <1> oxo,
<2> optionally halogenated $C_{1-6}$ alkyl,
<3> optionally halogenated $C_{1-6}$ alkyl-carbonyl,
<4> optionally halogenated $C_{1-6}$ alkylsulfonyl,
<5> $C_{6-14}$ aryl,
<6> $C_{7-19}$ aralkyl,
<7> $C_{6-14}$ aryl-carbonyl,
<8> 5- to 10-membered aromatic heterocyclic group which may have 1 to 5 substituents selected from the group consisting of 8a) halogen atom, 8b) $C_{1-3}$ alkylenedioxy, 8c) nitro, 8d) cyano, 8e) optionally halogenated $C_{1-6}$ alkyl, 8f) $C_{6-14}$ aryloxy-$C_{1-6}$ alkyl, 8g) $C_{1-6}$ alkyl-$C_{6-14}$ aryl-$C_{2-6}$ alkenyl, 8h) optionally halogenated $C_{3-6}$ cycloalkyl, 8i) optionally halogenated $C_{1-6}$ alkoxy, 8j) optionally halogenated $C_{1-6}$ alkylthio, 8k) $C_{7-19}$ aralkyl, 8l) hydroxy, 8m) $C_{6-14}$ aryloxy, 8n) $C_{7-19}$ aralkyloxy, 8o) amino, 8p) amino-$C_{1-6}$ alkyl, 8q) mono-$C_{1-6}$ alkylamino, 8r) di-$C_{1-6}$ alkylamino, 8s) mono-$C_{1-6}$ alkylamino-$C_{1-6}$ alkyl, 8t) di-$C_{1-6}$ alkylamino-$C_{1-6}$ alkyl, 8u) 5- to 7-membered saturated cyclic amino, 8v) acyl, 8w) acylamino and 8x) acyloxy,
<9> hydroxy,
<10> 5- to 8-membered monocyclic non-aromatic heterocyclic group,
<11> carbamoyl,
<12> hydroxy-$C_{1-6}$ alkyl,
<13> $C_{1-6}$ alkoxy-carbonyl-$C_{1-6}$ alkyl,
<14> $C_{8-19}$ arylalkenyl,
<15> $C_{1-6}$ alkyl-carboxamide,
<16> (N—$C_{1-6}$ alkyl)-$C_{1-6}$ alkyl-carboxamide,
<17> amino,
<18> mono-$C_{1-6}$ alkylamino,
<19> di-$C_{1-6}$ alkylamino,
<20> 5- to 8-membered monocyclic non-aromatic heterocyclic group-$C_{1-6}$ alkyl and
<21> $C_{6-14}$ aryl-amino-$C_{1-6}$ alkyl which may be substituted with one to three $C_{1-6}$ alkyl, wherein the above <5>, <6>, <7>, 8k), 8m) and 8n) may have 1 to 5 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl;

or a salt thereof.

2. The compound according to claim 1, wherein the cyclic group represented by $Ar^1$ is (1) phenyl, (2) a group which formed by removing an optional one hydrogen atom from a 5- or 6-membered aromatic heterocyclic ring containing 1 to 3 hetero atoms selected from nitrogen, sulfur and oxygen atoms in addition to carbon atoms, (3) a group which formed by removing an optional one hydrogen atom from a $C_{9-14}$ condensed polycyclic aromatic hydrocarbon, (4) a group which formed by removing an optional one hydrogen atom from a 9- or 14-membered condensed polycyclic aromatic heterocyclic ring containing 1 to 4 hetero atoms selected from nitrogen, sulfur and oxygen atoms in addition to carbon atoms, or (5) a group which formed by removing an optional one hydrogen atom from an aromatic ring assemble comprising 2 or 3 aromatic rings selected from benzene, naphthalene, pyridine, pyrimidine, thiophene, furan, thiazole, isothiazole, oxazole, isoxazole, 1,2,4-oxadiazole, 1,3,4-oxadiazole, 1,2,4-thiadiazole, 1,3,4-thiadiazole, quinoline, isoquinoline, indole, benzothiophene, benzoxazole, benzothiazole and benzofuran.

3. The compound according to claim 2, wherein the cyclic group represented by $Ar^1$ is a group formed by removing an optional one hydrogen atom from an aromatic ring assembly comprising 2 or 3 aromatic rings selected from benzene, naphthalene, pyridine, pyrimidine, thiophene, furan, thiazole, isothiazole, oxazole, isoxazole, 1,2,4-oxadiazole, 1,3,4-oxadiazole, 1,2,4-thiadiazole, 1,3,4-thiadiazole, quinoline, isoquinoline, indole, benzothiophene, benzoxazole, benzothiazole and benzofuran.

4. The compound according to claim 1, wherein X is CO.

5. A pharmaceutical composition comprising the compound according to claim 1, or a salt thereof and a pharmacologically acceptable carrier, excipient or diluent.

6. A process for producing a compound according to claim 1, or a salt thereof, which comprises reacting a compound represented by the formula:

(IIb)

wherein L is a leaving group and the other symbols are as defined in claim 5, or a salt thereof with a compound represented by the formula:

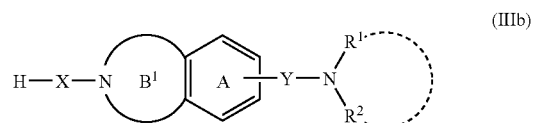

(IIIb)

wherein each symbol is as defined in claim 1, or a salt thereof.

7. A compound represented byte formula:

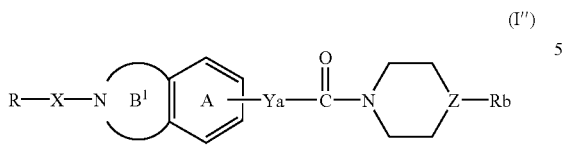

wherein R is hydrogen atom, a halogen atom or a cyclic group which may be substituted,
wherein said cyclic group which may be substituted is
(1) phenyl,
(2) a group which formed by removing an optional one hydrogen atom from a 5- or 6membered aromatic heterocyclic ring containing 1 to 3 hetero atoms selected from nitrogen, sulfur and oxygen atoms in addition to carbon atoms,
(3) a group which formed by removing an optional one hydrogen atom from a $C_{9-14}$ condensed polycyclic aromatic hydrocarbon,
(4) a group which formed by removing an optional one hydrogen atom from a 9- or 14-membered condensed polycyclic aromatic heterocyclic ring containing 1 to 4 hetero atoms selected from nitrogen, sulfur and oxygen atoms in addition to carbon atoms,
(5) a group which formed by removing an optional one hydrogen atom from an aromatic ring assemble comprising 2 or 3 aromatic rings selected from benzene, naphthalene, pyridine, pyrimidine, thiophene, furan, thiazole, isothiazole, oxazole, isoxazole, 1,2,4-oxadiazole, 1,3,4-oxadiazole, 1,2,4-thiadiazole, 1,3,4-thiadiazole, quinoline, isoquinoline, indole, benzothiophene, benzoxazole, benzothiazole and benzofuran,
(6) a $C_{3-8}$ cycloalkyl or a $C_{3-8}$ cycloalkenyl,
(7) a group which formed by removing an optional one hydrogen atom from a 5- to 8-membered monocyclic non-aromatic heterocyclic ring containing 1 to 3 hetero atoms selected from nitrogen, sulfur and oxygen atoms in addition to carbon atoms, or
(8) a group which formed by removing an optional one hydrogen atom from a 9- to 1 4-membered condensed polycyclic non-aromatic heterocyclic rings which contain 1 to 4 hetero atoms selected from nitrogen, sulfur and oxygen atoms in addition to carbon atoms,
wherein the above (1) to (8) may have 1 to 5 substituents selected from the group consisting of
1) oxo,
2) halogen atoms,
3) $C_{1-3}$ alkylenedioxy,
4) nitro,
5) cyano,
6) optionally halogenated $C_{1-6}$ alkyl,
7) hydroxy-$C_{1-6}$ alkyl,
8) $C_{6-14}$ aryloxy-$C_{1-6}$ alkyl,
9) $C_{1-6}$ alkyl-$C_{6-14}$ aryl-$C_{2-6}$ alkenyl,
10) optionally halogenated $C_{3-6}$ cycloalkyl,
11) optionally halogenated $C_{1-6}$ alkoxy,
12) optionally halogenated $C_{1-6}$ alkylthio,
13) $C_{7-19}$ aralkyl,
14) hydroxy,
15) $C_{6-14}$ aryloxy,
16) $C_{7-9}$ aralkyloxy,
17) $C_{6-14}$ aryl-carbamoyl,
18) amino,
19) amino-$C_{1-6}$ alkyl,
20) mono-$C_{1-6}$ alkylamino,
21) di-$C_{1-6}$ alkylamino,
22) mono-$C_{1-6}$ alkylamino-$C_{1-6}$ alkyl,
23) di-$C_{1-6}$ alkylamino-$C_{1-6}$ alkyl,
24) 5- to 7-membered saturated cyclic amino,
25) 5- to 7-membered non-aromatic heterocyclic groups,
26) acyl,
27) acylamino and
28) acyloxy
wherein the above 24) and 25) may have 1 to 5 substituents selected from the group consisting of
24a) oxo,
24b) optionally halogenated $C_{1-6}$ alkyl,
24c) optionally halogenated $C_{1-6}$ alkyl-carbonyl,
24d) optionally halogenated $C_{1-6}$ alkylsulfonyl,
24e) $C_{6-14}$ aryl,
24f) $C_{7-19}$ aralkyl,
24g) $C_{6-14}$ aryl-carbonyl,
24h) 5- to 10-membered aromatic heterocyclic group which may have 1 to 5 substituents selected from the group consisting of 24ha) halogen atom, 24hb) $C_{1-3}$ alkylenedioxy, 24hc) nitro, 24hd) cyano, 24he) optionally halogenated $C_{1-6}$ alkyl, 24hf) $C_{6-14}$ aryloxy-$C_{1-6}$ alkyl, 24hg) $C_{1-6}$ alkyl-$C_{6-14}$ aryl-$C_{2-6}$ alkenyl, 24hh) optionally halogenated $C_{3-6}$ cycloalkyl, 24hi) optionally halogenated $C_{1-6}$ alkoxy, 24hj) optionally halogenated $C_{1-6}$ alkylthio, 24hk) $C_{7-19}$ aralkyl, 24hl) hydroxy, 24hm) $C_{6-14}$ aryloxy, 24hn) $C_{7-19}$ aralkyloxy, 24ho) amino, 24hp) amino-$C_{1-6}$ alkyl, 24hq) mono-$C_{1-6}$ alkylamino, 24hr) di-$C_{1-6}$ alkylamino, 24hs) mono-$C_{1-6}$ alkylamino-$C_{1-6}$ alkyl, 24ht) di-$C_{1-6}$ alkylamino-$C_{1-6}$ alkyl, 24hu) 5- to 7-membered saturated cyclic amino, 24hv) acyl, 24hw) acylamino and 24hx) acyloxy,
24i) hydroxy,
24j) 5- to 8-membered monocyclic non-aromatic heterocyclic group,
24k) carbamoyl,
24l) hydroxy-$C_{1-6}$ alkyl,
24m) $C_{1-6}$ alkoxy-carbonyl-$C_{1-6}$ alkyl,
24n) $C_{8-19}$ arylalkenyl,
24o) $C_{1-6}$ alkyl-carboxamide,
24p) (N—$C_{1-6}$ alkyl)-$C_{1-6}$ alkyl-carboxamide,
24q) amino,
24r) mono-$C_{1-6}$ alkylamino,
24s) di-$C_{1-6}$ alkylamino,
24t) 5- to 8-membered monocyclic non-aromatic heterocyclic group-$C_{1-6}$ alkyl and
24u) $C_{6-14}$ aryl-amino-$C_{1-6}$ alkyl which may be substituted with one to three $C_{1-6}$ alkyl,
wherein the above (6) to (8) may further have a substituent selected from the group consisting of
(6a) $C_{6-14}$ aryl which may have 1 to 3 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl, and (6b) 5- to 10-membered aromatic heterocyclic groups which may have 1 to 3 substituents selected from the group consisting of (6ba) halogen atom, (6bb) $C_{1-3}$ alkylenedioxy, (6bc) nitro, (6bd) cyano, (6be) optionally halogenated $C_{1-6}$ alkyl, (6bf) $C_{6-14}$ aryloxy-$C_{1-6}$ alkyl, (6bg) $C_{1-6}$ alkyl-$C_{6-14}$ aryl-$C_{2-6}$ alkenyl, (6bh) optionally halogenated $C_{3-6}$ cycloalkyl, (6bi) optionally halogenated $C_{1-6}$ alkoxy, (6bj) optionally halogenated $C_{1-6}$ alkylthio, (6bk) $C_{7-19}$ aralkyl, (6bl) hydroxy, (6bm) $C_{6-14}$ aryloxy, (6bn) $C_{7-19}$ aralkyloxy, (6bo) amino, (6bp) amino-$C_{1-6}$ alkyl, (6bq) mono-$C_{1-6}$ alkylamino, (6br) di-$C_{1-6}$ alkylamino, (6bs) mono-$C_{1-6}$ alkylamino-$C_{1-6}$ alkyl, (6bt) di-$C_{1-6}$ alkylamino-$C_{1-6}$ alkyl, (6bu) 5- to 7-membered saturated cyclic amino, (6bv) acyl, (6bw) acylamino and (6bx) acyloxy, wherein the above 13), 15), 16), 17), 24e), 24f, 24g), 24hk), 24hm), 24hn), (6bk), (6bm and (6bn) may have 1 to 5 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl;

X is a bond or a bivalent group consisting of 1 to 3 members selected from —O—, —S—, —CO—, —SO—, —SO$_2$—, —NR$^8$— (R$^8$ is hydrogen atom, optionally halogenated $C_{1-6}$ alkyl, optionally halogenated $C_{1-6}$ alkyl-carbonyl or optionally halogenated $C_{1-6}$ alkylsulfonyl), and a divalent $C_{1-6}$ non-cyclic hydrocarbon group which may have 1 to 5 substituents selected from the group consisting of halogen atom, hydroxy, nitro, cyano, optionally halogenated $C_{1-6}$ alkoxy, optionally halogenated $C_{1-6}$ alkylthio, amino, mono-$C_{1-6}$ alkylamino, di-$C_{1-6}$ alkylamino, formyl, carboxy, carbamoyl, thiocarbamoyl, optionally halogenated $C_{1-6}$ alkyl-carbonyl, $C_{1-6}$ alkoxy-carbonyl and optionally halogenated $C_{1-6}$ alkylsulfonyl, wherein the bivalent $C_{1-6}$ non-cyclic hydrocarbon group is selected from a $C_{1-6}$ alkylene, a $C_{26}$ alkenylene and a $C_{2-6}$ alkynylene;

Ya is —CO(CH$_2$)$_{w7}$— wherein w7 is an integer of 0 to 4; the group represented by the formula:

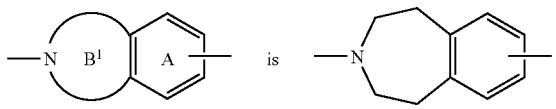

which may have 1 to 5 further substituents selected from the group consisting of 1) oxo,
2) halogen atoms,
3) $C_{1-3}$ alkylenedioxy,
4) nitro,
5) cyano,
6) optionally halogenated $C_{1-6}$ alkyl,
7) hydroxy-$C_{1-6}$ alkyl,
8) $C_{6-14}$ aryloxy-$C_{1-6}$ alkyl,
9) $C_{1-6}$ alkyl-$C_{6-14}$ aryl-$C_{2-6}$ alkenyl,
10) optionally halogenated $C_{3-6}$ cycloalkyl,
11) optionally halogenated $C_{1-6}$ alkoxy,
12) optionally halogenated $C_{1-6}$ alkylthio,
13) $C_{7-19}$ aralkyl,
14) hydroxy,
15) $C_{6-14}$ aryloxy,
16) $C_{7-19}$ aralkyloxy,
17) $C_{6-14}$ aryl-carbamoyl,
18) amino,
19) amino-$C_{1-6}$ alkyl,
20) mono-$C_{1-6}$ alkylamino,
21) di-$C_{1-6}$ alkylamino,
22) mono-$C_{1-6}$ alkylamino-$C_{1-6}$ alkyl,
23) di-$C_{1-6}$ alkylamino-$C_{1-6}$ alkyl,
24) 5- to 7-membered saturated cyclic amino,
25) 5- to 7-membered non-aromatic heterocyclic groups,
26) acyl,
27) acylamino,
28) acyloxy,
29) $C_{6-14}$ aryl which may have 1 to 3 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl, and
30) 5- to 10-membered aromatic heterocyclic groups which may have 1 to 3 substituents selected from the group consisting of 30a) halogen atom, 30b) $C_{1-3}$ alkylenedioxy, 30c) nitro, 30d) cyano, 30e) optionally halogenated $C_{1-6}$ alkyl, 30f) $C_{6-14}$ aryloxy-$C_{1-6}$ alkyl, 30g) $C_{1-6}$ alkyl-$C_{6-14}$ aryl-$C_{2-6}$ alkenyl, 30h) optionally halogenated $C_{1-6}$ cycloalkyl, 30i) optionally halogenated $C_{1-6}$ alkoxy, 30j) optionally halogenated $C_{1-6}$ alkylthio, 30k) $C_{7-19}$ aralkyl, 30l) hydroxy, 30m) $C_{6-14}$ aryloxy, 30n) $C_{7-19}$ aralkyloxy, 30o) amino, 30p) amino-$C_{1-6}$ alkyl, 30q) mono-$C_{1-6}$ alkylamino, 30r) di-$C_{1-6}$alkylamino, 30s) mono-$C_{1-6}$ alkylamino-$C_{1-6}$alkyl, 3t) di-$C_{1-6}$ alkylamino-$C_{1-6}$ alkyl, 30u) 5- to 7-membered saturated cyclic amino, 30v) acyl, 30w) acylamino and 30x) acyloxy, wherein the above 24) and 25) may have 1 to 5 substituents selected from the group consisting of
24a) oxo,
24b) optionally halogenated $C_{1-6}$ alkyl,
24c) optionally halogenated $C_{1-5}$ alkyl-carbonyl,
24d) optionally halogenated $C_{1-6}$ alkylsulfonyl,
24e) $C_{6-14}$ aryl, 24f) $C_{7-19}$ aralkyl,
24g) $C_{6-14}$ aryl-carbonyl,
24h) 5- to 10-membered aromatic heterocyclic group which may have 1 to 5 snbstituents selected from the group consisting of 24ha) halogen atom, 24hb) $C_{1-3}$ alkylenedioxy, 24hc) nitro, 24hd) cyano, 24he) optionally halogenated $C_{1-6}$ alkyl), 24hf) $C_{6-14}$ aryloxy-$C_{1-6}$ alkyl, 24hg) $C_{1-6}$ alkyl-$C_{6-14}$ aryl-$C_{2-6}$ alkenyl, 24hh) optionally halogenated $C_{3-6}$ cycloalkyl, 24hi) optionally halogenated $C_{1-6}$ alkoxy, 24hj) optionally halogenated $C_{1-6}$ alkylthio, 24hk) $C_{7-19}$ aralkyl, 24hl) hydroxy, 24hm) $C_{6-14}$ aryloxy, 24hn) $C_{7-19}$ aralkyloxy, 24ho) amino, 24hp) amino-$C_{1-6}$ alkyl,
24hq) mono-$C_{1-6}$ alkylamino, 24hr) di-$C_{1-6}$ alkylamino, 24hs) mono-$C_{1-6}$ alkylamino-$C_{1-6}$ alkyl,
24ht) di-$C_{1-6}$ alkylamino-$C_{1-6}$ alkyl, 24hu) 5- to 7-membered saturated cyclic amino, 24hv) acyl,
24hw) acylamino and 24hx) acyloxy,
24i) hydroxy,
24j) 5- to 8-membered monocyclic non-aromatic heterocyclic group,
24k) carbamoyl,
24l) hydroxy-$C_{1-6}$ alkyl,
24m) $C_{1-6}$ alkoxy-carbonyl-$C_{1-6}$ alkyl,
24n) $C_{8-19}$ arylalkenyl,
24o) $C_{1-6}$ alkyl-carboxamide,
24p) (N—$C_{1-6}$ alkyl)-$C_{1-6}$ alkyl-carboxamide,
24q) amino,
24r) mono-$C_{1-6}$ alkylamino,
24s) di-$C_{1-6}$ alkylamino,
24t) 5- to 8-membered monocyclic non-aromatic heterocyclic group-$C_{1-6}$ alkyl and
24u) $C_{6-14}$ aryl-amino-$C_{1-6}$ alkyl which may be substituted with one to three $C_{1-6}$ alkyl,
wherein the above 13), 15), 16), 17), 24e), 24f, 24g), 24hk), 24hm), 24hn), 30k), 30m) and 30n) may have 1 to 5 substituents selected from the group consisting of halogen atom, $C_{3-6}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl;
Z is CH or N; and
Rb is 1) hydrogen atom, 2) optionally halogenated $C_{1-6}$ alkyl, 3) $C_{6-14}$ aryl which may have 1 to 3 substituents selected from halogen atom, optionally halogenated $C_{1-6}$ alkyl and optionally halogenated $C_{1-6}$ alkoxy, 4) hydroxy-$C_{1-6}$ alkyl, 5) $C_{1-6}$ alkoxy-carbonyl-$C_{1-6}$ alkyl, 6) $C_{7-19}$ aralkyl which may be substituted with $C_{1-3}$ alkylenedioxy, 7) $C_{8-19}$ arylalkenyl, 8) 5- to 8-monocyclic non-aromatic heterocyclic group-$C_{1-6}$ alkyl or 9) $C_{6-14}$ aryl-amino-$C_{1-6}$ alkyl which may be substituted with 1 to 3 $C_{1-6}$ alkyl;
or a salt thereof.

8. The compound according to claim 7, wherein R is hydrogen atom.

9. The compound according to claim 7, wherein Z is CH.

10. The compound according to claim 7, wherein Rb is $C_{6-14}$ aryl which may have 1 to 3 substituents selected from halogen atom, optionally halogenated $C_{1-6}$ alkyl and $C_{1-6}$ alkoxy.

11. A pharmaceutical composition comprising the compound according to claim 7, or a salt thereof and a pharmacologically acceptable carrier, excipient or diluent.

12. A process for producing a compound according to claim 7, or a salt thereof which comprises reacting a compound represented by the formula:

$$R\text{—}X\text{-}L \qquad (IIa)$$

wherein L is a leaving group and the other symbols are as defined in claim 7, or a salt thereof with a compound represented by the formula:

$$\text{H}\text{—}\text{N}\underset{}{\bigcirc}\text{B}\underset{}{\bigcirc}\text{A}\text{—}Y_a\text{—}\overset{O}{\underset{\|}{C}}\text{—}\text{N}\underset{}{\bigcirc}Z\text{—}Rb \qquad (IIIc)$$

wherein each symbol is as defined in claim 7, or a salt thereof.

13. A compound represented by the formula $$R\text{—}X\text{—}N\underset{}{\bigcirc}\text{B}\underset{}{\bigcirc}\text{A}\text{—}\overset{O}{\underset{\|}{C}}\text{—}(CH_2)_{w7}\text{—}\overset{O}{\underset{\|}{C}}\text{—}N\underset{R^2}{\overset{R^1}{\diagup}} \qquad (I'''')$$

wherein R is hydrogen atom, a halogen atom or a cyclic group which may be substituted;
wherein said cyclic group which may be substituted is
(1) phenyl,
(2) a group which formed by removing an optional one hydrogen atom from a 5- or 6-membered aromatic heterocyclic ring containing 1 to 3 hetero atoms selected from nitrogen, sulfur and oxygen atoms in addition to carbon atoms,
(3) a group which formed by removing an optional one hydrogen atom from a $C_{9-14}$ condensed polycyclic aromatic hydrocarbon,
(4) a group which formed by removing an optional one hydrogen atom from a 9- or 14-membered condensed polycyclic aromatic heterocyclic ring containing 1 to 4 hetero atoms selected from nitrogen, sulfur and oxygen atoms in addition to carbon atoms,
(5) a group which formed by removing an optional one hydrogen atom from an aromatic ring assemble comprising 2 or 3 aromatic rings selected from benzene, naphthalene, pyridine, pyrimidine, thiophene, furan, thiazole, isothiazole, oxazole, isoxazole, 1,2,4-oxadiazole, 1,3,4-oxadiazole, 1,2,4-thiadiazole, 1,3,4thiadiazole, quinoline, isoquinoline, indole, benzothiophene, benzoxazole, benzothiazole and benzofuran,
(6) a $C_{3-8}$ cycloalkyl or a $C_{3-8}$ cycloalkenyl,
(7) a group which formed by removing an optional one hydrogen atom from a 5- to 8-membered monocyclic non-aromatic heterocyclic ring containing 1 to 3 hetero atoms selected from nitrogen, sulfur and oxygen atoms in addition to carbon atoms, or (8) a group which formed by removing an optional one hydrogen atom from a 9- to 14-membered condensed polycyclic non-aromatic heterocyclic rings which contain 1 to 4 hetero atoms selected from nitrogen, sulfur and oxygen atoms in addition to carbon atoms, wherein the above (1) to (8) may have 1 to 5 substituents selected from the group consisting of 1) oxo,
2) halogen atoms,
3) $C_{1-3}$ alkylenedioxy,
4) nitro,
5) cyano,
6) optionally halogenated $C_{1-6}$ alkyl,
7) hydroxy-$C_{1-6}$ alkyl,
8) $C_{1-6}$ aryloxy-$C_{1-6}$ alkyl,
9) $C_{1-6}$ alkyl-$C_{6-14}$ aryl-$C_{2-6}$ alkenyl,
10) optionally halogenated $C_{3-6}$ cycloalkyl,
11) optionally halogenated $C_{1-6}$ alkoxy,
12) optionally halogenated $C_{1-6}$ alkylthio,
13) $C_{7-19}$ aralkyl,
14) hydroxy,
15) $C_{1-6}$ aryloxy,
16) $C_{7-19}$ aralkyloxy,
17) $C_{6-14}$ aryl-carbamoyl,
18) amino,
19) amino-$C_{1-6}$ alkyl,
20) mono-$C_{1-6}$ alkylamino,
21) di-$C_{1-6}$ alkylamino,
22) mono-$C_{1-6}$ alkylamino-$C_{1-6}$ alkyl
23) di-$C_{1-6}$ alkylamino-$C_{1-6}$ alkyl,
24) 5- to 7-membered saturated cyclic amino,
25) 5- to 7-membered non-aromatic heterocyclic groups,
26) acyl,
27) acylamino and
28) acyloxy wherein the above 24) and 25) may have 1 to 5 substituents selected from the group consisting of 24a) oxo,
24b) optionally halogenated $C_{1-6}$ alkyl,
24c) optionally halogenated $C_{1-6}$ alkyl-carbonyl,
24d) optionally halogenated $C_{1-6}$ alkyl-sulfonyl,
24e) $C_{6-14}$ aryl,
24f) $C_{7-19}$ aralkyl,
24g) $C_{6-14}$ aryl-carbonyl,
24h) 5- to 10-membered aromatic heterocyclic group which may have 1 to 5 substituents selected from the group consisting of 24ha) halogen atom, 24hb) $C_{1-3}$ alkylenedioxy, 24hc) nitro, 24hd) cyano, 24he) optionally halogenated $C_{1-6}$ alkyl, 24hf) $C_{6-14}$ aryloxy-$C_{1-6}$ alkyl, 24hg) $C_{1-6}$ alkyl-$C_{6-14}$ aryl-$C_{2-6}$ alkenyl, 24hh) optionally halogenated $C_{3-6}$ cycloalkyl, 24hi) optionally halogenated $C_{1-6}$ alkoxy, 24hj) optionally halogenated $C_{1-6}$ alkylthio, 24hk) $C_{7-19}$ aralkyl, 24hl) hydroxy, 24hm) $C_{1-6}$ aryloxy, 24hn) $C_{7-19}$ aralkyloxy, 24ho) amino, 24hp) amino-$C_{1-6}$ alkyl,
24hq) mono-$C_{1-6}$ alkylamino, 24hr) di-$C_{1-6}$ alkylamino, 24hs) mono-$C_{1-6}$ alkylamino-$C_{1-6}$ alkyl,
24ht) di-$C_{1-6}$ alkylamino-$C_{1-6}$ alkyl, 24hu) 5- to 7-membered saturated cyclic amino, 24hv) acyl,
24hw) acylamino and 24hx) acyloxy,
24i) hydroxy,
24j) 5- to 8-membered monocyclic non-aromatic heterocyclic group,
24k) carbamoyl,
24l) hydroxy-$C_{1-6}$ alkyl,
24m) $C_{1-6}$ alkoxy-carbonyl-$C_{1-6}$ alkyl,
24n) $C_{8-19}$ arylalkenyl,
24o) $C_{1-6}$ alkyl-carboxamide,
24p) (N—$C_{1-6}$ alkyl)-$C_{1-6}$ alkyl-carboxamide,
24q) amino,
24r) mono-$C_{1-6}$ alkylamino,
24s) di-$C_{1-6}$ alkylamino,
24t) 5- to 8-membered monocyclic non-aromatic heterocyclic group-$C_{1-6}$ alkyl and
24u) $C_{6-14}$ aryl-amino-$C_{1-6}$ alkyl which may be substituted with one to three $C_{1-6}$ alkyl, wherein the above (6) to (8) may further have a substituent selected from the group consisting of (6a) $C_{6-14}$ aryl which may have 1 to 3 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_6$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl, and (6b) 5- to 10-membered aromatic heterocyclic groups which may have 1 to 3 substituents selected from the group consisting of (6ba) halogen atom, (6bb) $C_{1-3}$ alkylenedioxy, (6bc) nitro, (6bd) cyano, (6be) optionally halogenated $C_{1-6}$ alkyl, (6bf) $C_{6-14}$ aryloxy-$C_{1-6}$ alkyl, (6bg) $C_{1-6}$ alkyl-$C_{6-14}$ aryl-$C_{2-6}$ alkenyl, (6bh) optionally halogenated $C_{3-6}$ cycloalkyl, (6bi) optionally halogenated $C_{1-6}$ alkoxy, (6bj) optionally halogenated $C_{1-6}$ alkylthio, (6bk) $C_{7-19}$ aralkyl, (6bl) hydroxy, (6bm) $C_{6-14}$ aryloxy, (6bn) $C_{7-19}$ aralkyloxy, (6bo) amino, (6bp) amino-$C_{1-6}$ alkyl, (6bq) mono-$C_{1-6}$ alkylamino, (6br) di-$C_{1-6}$ alkylamino, (6bs) mono-$C_{1-6}$ alkylamino-$C_{1-6}$ alkyl, (6bt) di-$C_{1-6}$ alkylamino-$C_{1-6}$ alkyl, (6bu) 5- to 7-membered saturated cyclic amino, (6bv) acyl, (6bw) acylamino and (6bx) acyloxy, wherein the above 13), 15), 16), 17), 24e), 24f, 24g), 24hk), 24hm), 24hn), (6bk), (6bm) and (6bn) may have 1 to 5 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl;

X is a bond or a bivalent group consisting of 1 to 3 members selected from —O—, —S—, —CO—, —SO—, —SO$_2$—, —NR$^8$— (R$^8$ is hydrogen atom, optionally halogenated C$_{1-6}$ alkyl, optionally halogenated C$_{1-6}$ alkyl-carbonyl or optionally halogenated C$_{1-6}$ alkylsulfonyl), and a divalent C$_{1-6}$ non-cyclic hydrocarbon group which may have 1 to 5 substituents selected from the group consisting of halogen atom, hydroxy, nitro, cyano, optionally halogenated C$_{1-6}$ alkoxy, optionally halogenated C$_{1-6}$ alkylthio, amino, mono-C$_{1-6}$ alkylamino, di-C$_{1-6}$ alkylamino, formyl, carboxy, carbamoyl, thiocarbamoyl, optionally halogenated C$_{1-6}$ alkyl-carbonyl, C$_{1-6}$ alkoxy-carbonyl and optionally halogenated C$_{1-6}$ alkylsulfonyl, wherein the bivalent C$_{1-6}$ non-cyclic hydrocarbon group is selected from a C$_{1-6}$ alkylene, a C$_{2-6}$ alkenylene and a C$_{2-6}$ alkynylene;

the group represented by the formula:

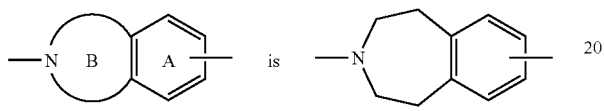

which may have 1 to 5 further substituents selected from the group consisting of
1) oxo,
2) halogen atoms,
3) C$_{1-3}$ alkylenedioxy,
4) nitro,
5) cyano,
6) optionally halogenated C$_{1-6}$ alkyl,
7) hydroxy-C$_{1-6}$ alkyl,
8) C$_{6-14}$ aryloxy-C$_{1-6}$ alkyl,
9) C$_{1-6}$ alkyl-C$_{6-14}$ aryl-C$_{2-6}$ alkenyl,
10) optionally halogenated C$_{3-6}$ cycloalkyl,
11) optionally halogenated C$_{1-6}$ alkoxy,
12) optionally halogenated C$_{1-6}$ alkylthio,
13) C$_{7-19}$ aralkyl,
14) hydroxy,
15) C$_{6-14}$ aryloxy,
16) C$_{7-19}$ aralkyloxy,
17) C$_{6-14}$ aryl-carbamoyl,
18) amino,
19) amino-C$_{1-6}$ alkyl,
20) mono-C$_{1-6}$ alkylamino,
21) di-C$_{1-6}$ alkylamino,
22) mono-C$_{1-6}$ alkylamino-C$_{1-6}$ alkyl,
23) di-C$_{1-6}$ alkylamino-C$_{1-6}$ alkyl,
24) 5- to 7-membered saturated cyclic amino,
25) 5-to 7-membered non-aromatic heterocyclic groups,
26) acyl,
27) acylamino,
28) acyloxy,
29) C$_{6-14}$ aryl which may have 1 to 3 substituents selected from the group consisting of halogen atom, C$_{1-3}$ alkylenedioxy, nitro, cyano, optionally halogenated C$_{1-6}$ alkyl, optionally halogenated C$_{3-6}$ cycloalkyl, optionally halogenated C$_{1-6}$ alkoxy, optionally halogenated C$_{1-6}$ alkylthio, hydroxy, amino, mono-C$_{1-6}$ alkylamino, di-C$_{1-6}$ alkylamino, amino-C$_{1-6}$ alkyl mono-C$_{1-6}$ alkylamino-C$_{1-6}$ alkyl, di-C$_{1-6}$ alkylamino-C$_{1-6}$ alkyl, formyl, carboxy, carbamoyl, thiocarbamoyl, optionally halogenated C$_{1-6}$ alkyl-carbonyl, C$_{1-6}$ alkoxy-carbonyl, mono-C$_{1-6}$ alkyl-carbamoyl, di-C$_{1-6}$ alkyl-carbamoyl, optionally halogenated C$_{1-6}$ alkylsulfonyl, formylamino, optionally halogenated C$_{1-6}$ alkyl-carboxamide, C$_{1-6}$ alkoxy-carboxamide, C$_{1-6}$ alkylsulfonylamino, C$_{1-6}$ alkyl-carbonyloxy, C$_{1-6}$ alkoxy-carbonyloxy, mono-C$_{1-6}$ alkyl-carbamoyloxy, di-C$_{1-6}$ alkyl-carbamoyloxy and hydroxy-C$_{1-6}$ alkyl, and 30) 5- to 10-membered aromatic heterocyclic groups which may have 1 to 3 substituents selected from the group consisting of 30a) halogen atom, 30b) C$_{1-3}$ alkylenedioxy, 30c) nitro, 30d) cyano, 30e) optionally halogenated C$_{1-6}$ alkyl, 30f) C$_{6-14}$ aryloxy-C$_{1-6}$ alkyl, 30g) C$_{1-6}$ alkyl-C$_{6-14}$ aryl-C$_{2-6}$ alkenyl, 30h) optionally halogenated C$_{3-6}$ cycloalkyl, 30i) optionally halogenated C$_{1-6}$ alkoxy, 30j) optionally halogenated C$_{1-6}$ alkylthio, 30k) C$_{7-19}$ aralkyl, 30l) hydroxy, 30m) C$_{6-14}$ aryloxy, 30n) C$_{7-19}$ aralkyloxy, 30o) amino, 30p) amino-C$_{1-6}$ alkyl, 30q) mono-C$_{1-6}$ alkylamino, 30r) di-C$_{1-6}$ alkylamino, 30s) mono-C$_{1-6}$ alkylamino-C$_{1-6}$ alkyl, 30t) di-C$_{1-6}$ alkylamino-C$_{1-6}$ alkyl, 30u) 5- to 7-membered saturated cyclic amino, 30v) acyl, 30w) acylamino and 30x) acyloxy, wherein to above 24) and 25) may have 1 to 5 substituents selected from the group consisting of
24a) oxo,
24b) optionally halogenated C$_{1-6}$ alkyl,
24c) optionally halogenated C$_{1-6}$ alkyl-carbonyl,
24d) optionally halogenated C$_{1-6}$ alkylsulfonyl,
24e) C$_{6-14}$ aryl,
24f) C$_{7-19}$ aralkyl,
24g) C$_{6-14}$ aryl-carbonyl,
24h) 5- to 10-membered aromatic heterocyclic group which may have 1 to 5 substituents selected from the group consisting of 24ha) halogen atom, 24hb) C$_{1-3}$ alkylenedioxy, 24hc) nitro, 24hd) cyano, 24he) optionally halogenated C$_{1-6}$ alkyl, 24hf) C$_{6-14}$ aryloxy-C$_{1-6}$ alkyl, 24hg) C$_{1-6}$ alkyl-C$_{6-14}$ aryl-C$_{2-6}$ alkenyl, 24hh) optionally halogenated C$_{3-6}$ cycloalkyl, 24hi) optionally halogenated C$_{1-6}$ alkoxy, 24hj) optionally halogenated C$_{1-6}$ alkylthio, 24hk) C$_{7-19}$ aralkyl, 24hl) hydroxy, 24hm) C$_{6-14}$ aryloxy, 24hn) C$_{7-19}$ aralkyloxy, 24ho) amino, 24hp) amino-C$_{1-6}$ alkyl, 24hq) mono-C$_{1-6}$ alkylamino, 24hr) di-C$_{1-6}$ alkylamino, 24hs) mono-C$_{1-6}$ alkylamino-C$_{1-6}$ alkyl, 24ht) di-C$_{1-6}$ alkylamino-C$_{1-6}$ alkyl, 24hu) 5- to 7-membered saturated cyclic amino, 24hv) acyl, 24hw) acylamino and 24hx) acyloxy,
24i) hydroxy,
24j) 5- to 8-membered monocyclic non-aromatic heterocyclic group,
24k) carbamoyl,
24l) hydroxy-C$_{1-6}$ alkyl,
24m) C$_{1-6}$ alkoxy-carbonyl-C$_{1-6}$ alkyl,
24n) C$_{8-19}$ arylalkenyl,
24o) C$_{1-6}$ alkyl-carboxamide,
24p) (N—C$_{1-6}$ alkyl)-C$_{1-6}$ alkyl-carboxamide,
24q) amino,
24r) mono-C$_{1-6}$ alkylamino,
24s) di-C$_{1-6}$ alkylamino,
24t) 5-to 8-membered monocyclic non-aromatic heterocyclic group-C$_{1-6}$ alkyl and
24u) C$_{6-14}$ aryl-amino-C$_{1-6}$ alkyl which may be substituted with one to three C$_{1-6}$ alkyl, wherein the above 13), 15), 16), 17), 24e), 24f, 24g), 24hk), 24hm), 24hn), 30k), 30m) and 30n) may have 1 to 5 substituents selected from the group consisting of halogen atom, C$_{1-3}$ alkylenedioxy, nitro, cyano, optionally halogenated C$_{1-6}$ alkyl, optionally halogenated C$_{3-6}$ cycloalkyl, optionally halogenated C$_{1-6}$ alkoxy, optionally halogenated C$_{1-6}$ alkylthio, hydroxy, amino, mono-C$_{1-6}$ alkylamino, di-C$_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl;

w7 is an integer of 0 to 4; and $R^1$ and $R^{2}$ together with the adjacent nitrogen atom, form aziridine, azetidine, morpholine, thiomorpholine, piperidine, piperazine, pyrrolidine, hexamethyleneimine, heptamethyleneimine, hexahydropyrimidine, 1,4-diazepan, dihydroisoquinoline, 1,2,5,6-tetrahydropyridine, 1,4-diazepin, or octahydroisoquinoline, each of which may have 1 to 5 substituents selected from the group consisting of 1) oxo,
2) optionally halogenated $C_{1-6}$ alkyl,
3) optionally halogenated $C_{1-6}$ alkyl-carbonyl,
4) optionally halogenated $C_{1-6}$ alkylsulfonyl,
5) $C_{6-14}$ aryl,
6) $C_{7-19}$ aralkyl,
7) $C_{6-14}$ aryl-carbonyl,
5) 5- to 10-membered aromatic heterocyclic group which may have 1 to 5 substituents selected from the group consisting of 8a) halogen atom, 8b) $C_{1-3}$ alkylenedioxy, 8c) nitro, 8d) cyano, 8e) optionally halogenated $C_{1-6}$ alkyl, 8f) $C_{6-14}$ aryloxy-$C_{1-6}$ alkyl, 8g) $C_{1-6}$ alkyl-$C_{6-14}$ aryl-$C_{2-6}$ alkenyl, 8h) optionally halogenated $C_{3-6}$ cycloalkyl, 8i) optionally halogenated $C_{1-6}$ alkoxy, 8j) optionally halogenated $C_{1-6}$ alkylthio, 8k) $C_{7-19}$ aralkyl, 8l) hydroxy, 8m) $C_{6-14}$ aryloxy 8n) $C_{7-19}$ aralkyloxy, 8o) amino, 8p) amino-$C_{1-6}$ alkyl, 8q) mono-$C_{1-6}$ alkylamino, 8r) di-$C_{1-6}$ alkylamino, 8s) mono-$C_{1-6}$ alkylamino-$C_{1-6}$ alkyl, 8t) di-$C_{1-6}$ alkylamino-$C_{1-6}$ alkyl, 8u) 5- to 7-membered saturated cyclic amino, 8v) acyl, 8w) acylamino and 8x) acyloxy,
9) hydroxy,
10) 5- to 8-membered monocyclic non-aromatic heterocyclic group,
11) carbamoyl,
12) hydroxy-$C_{1-6}$ alkyl,
13) $C_{1-6}$ alkoxy-carbonyl-$C_{1-6}$ alkyl,
14) $C_{8-19}$ arylalkenyl,
15) $C_{1-6}$ alkyl-carboxamide,
16) (N—$C_{1-6}$ alkyl)-$C_{1-6}$ alkyl-carboxamide,
17) amino,
18) mono-$C_{1-6}$ alkylamino,
19) di-$C_{1-6}$ alkylamino,
20) 5- to 8-membered monocyclic non-aromatic heterocyclic group-$C_{1-6}$ alkyl and
21) $C_{6-14}$ aryl-amino-$C_{1-6}$ alkyl which may be substituted with one to three $C_{1-6}$ alkyl, wherein the above 5), 6), 7), 8k), 8m) and 8n) may have 1 to 5 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl;

or a salt thereof.

14. A pharmaceutical composition comprising the compound according to claim 13 or a salt thereof and a pharmaceutically acceptable carrier, excipient or diluent.

15. A method for treating obesity in a mammal in need thereof, which comprises administering to said mammal an effective amount of a compound represented by the formula:

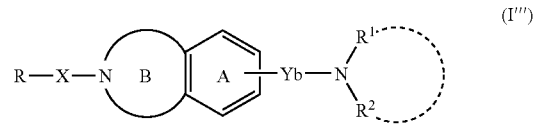

(I''')

wherein R is hydrogen atom, a halogen atom or a cyclic group which may be substituted;

wherein said cyclic group which may be substituted is (1) phenyl,
(2) a group which formed by removing an optional one hydrogen atom from a 5- or 6-membered aromatic heterocyclic ring containing 1 to 3 hetero atoms selected from nitrogen, sulfur and oxygen atoms in addition to carbon atoms,
(3) a group which formed by removing an optional one hydrogen atom from a $C_{9-14}$ condensed polycyclic aromatic hydrocarbon,
(4) a group which formed by removing an optional one hydrogen atom from a 9- or 14-membered condensed polycyclic aromatic heterocyclic ring containing 1 to 4 hetero atoms selected from nitrogen, sulfur and oxygen atoms in addition to carbon atoms,
(5) a group which formed by removing an optional one hydrogen atom from an aromatic ring assemble comprising 2 or 3 aromatic rings selected from benzene, naphthalene, pyridine, pyrimidine, thiophene, furan, thiazole, isothiazole, oxazole, isoxazole, 1,2,4-oxadiazole, 1,3,4-oxadiazole, 1,2,4-thiadiazole, 1,3,4-thiadiazole, quinoline, isoquinoline, indole, benzothiophene, benzoxazole, benzothiazole and benzofuran,
(6) a $C_{3-8}$ cycloalkyl or a $C_{3-8}$ cycloalkenyl,
(7) a group which formed by removing an optional one hydrogen atom from a 5- to 8-membered monocyclic non-aromatic heterocyclic ring containing 1 to 3 hetero atoms selected from nitrogen, sulfur and oxygen atoms in addition to carbon atoms, or
(8) a group which formed by removing an optional one hydrogen atom from a 9- to 14-membered condensed polycyclic non-aromatic heterocyclic rings which contain 1 to 4 hetero atoms selected from nitrogen, sulfur and oxygen atoms in addition to carbon atoms, wherein the above (1) to (8) may have 1 to 5 substituents selected from the group consisting of 1) oxo,
2) halogen atoms,
3) $C_{1-3}$ alkylenedioxy, 4) nitro,
5) cyano,
6) optionally halogenated $C_{1-6}$ alkyl,
7) hydroxy-$C_{1-6}$ alkyl,
8) $C_{6-14}$ aryloxy-$C_{1-6}$ alkyl,
9) $C_{1-6}$ alkyl-$C_{6-14}$ aryl-$C_{2-6}$ alkenyl,
10) optionally halogenated $C_{3-6}$ cycloalkyl,
11) optionally halogenated $C_{1-6}$ alkoxy,
12) optionally halogenated $C_{1-6}$ alkylthio,
13) $C_{7-19}$ aralkyl,
14) hydroxy,
15) $C_{6-14}$ aryloxy,
16) $C_{7-19}$ aralkyloxy,
17) $C_{6-14}$ aryl-carbamoyl,
18) amino,
19) amino-$C_{1-6}$ alkyl,
20) mono-$C_{1-6}$ alkylamino,
21) di-$C_{1-6}$ alkylamino,
22) mono-$C_{1-6}$ alkylamino-$C_{1-6}$ alkyl,
23) di-$C_{1-6}$ alkylamino-$C_{1-6}$ alkyl,
24) 5- to 7-membered saturated cyclic amino,
25) 5- to 7-membered non-aromatic heterocyclic groups,
26) acyl,
27) acylamino and
28) acyloxy
   wherein the above 24) and 25) may have 1 to 5 substituents selected from the group consisting of
   24a) oxo,
   24b) optionally halogenated $C_{1-6}$ alkyl,
   24c) optionally halogenated $C_{1-6}$ alkyl-carbonyl,
   24d) optionally halogenated $C_{1-6}$ alkylsulfonyl,
   24e) $C_{6-14}$ aryl,
   24f) $C_{7-19}$ aralkyl,
   24g) $C_{6-14}$ aryl-carbonyl,
   24h) 5- to 10-membered aromatic heterocyclic group which may have 1 to 5 substituents selected from the group consisting of (A) halogen atom, (B) $C_{1-3}$ alkylenedioxy, (C) nitro, (D) cyano, (E) optionally halogenated $C_{1-6}$ alkyl, (F) $C_{6-14}$ aryloxy-$C_{1-6}$ alkyl, (G) $C_{1-6}$ alkyl-$C_{6-14}$ aryl-$C_{2-6}$ alkenyl, (H) optionally halogenated $C_{3-6}$ cycloalkyl, (I) optionally halogenated $C_{1-6}$ alkoxy, (J) optionally halogenated $C_{1-6}$ alkylthio, (K) $C_{7-19}$ aralkyl, (L) hydroxy, (M) $C_{6-14}$ aryloxy, (N) $C_{7-19}$ aralkyloxy, (O) amino, (P) amino-$C_{1-6}$ alkyl, (Q) mono-$C_{1-6}$ alkylamino, (R) di-$C_{1-6}$ alkylamino, (S) mono-$C_{1-6}$ alkylamino-$C_{1-6}$ alkyl, (T) di-$C_{1-6}$ alkylamino-$C_{1-6}$ alkyl, (U) 5- to 7-membered saturated cyclic amino, (V) acyl, (W) acylamino and (X) acyloxy,
   24i) hydroxy,
   24j) 5- to 8-membered monocyclic non-aromatic heterocyclic group,
   24k) carbamoyl,
   24l) hydroxy-$C_{1-6}$ alkyl,
   24m) $C_{1-6}$ alkoxy-carbonyl-$C_{1-6}$ alkyl,
   24n) $C_{8-19}$ arylalkenyl,
   24o) $C_{1-6}$ alkyl-carboxamide,
   24p) (N—$C_{1-6}$ alkyl)-$C_{1-6}$ alkyl-carboxamide,
   24q) amino,
   24r) mono-$C_{1-6}$ alkylamino,
   24s) di-$C_{1-6}$ alkylamino,
   24t) 5- to 8-membered monocyclic non-aromatic heterocyclic group-$C_{1-6}$ alkyl and
   24u) $C_{6-14}$ aryl-amino-$C_{1-6}$ alkyl which may be substituted with one to three $C_{1-6}$ alkyl,
   wherein the above (6) to (8) may further have a substituent selected from the group consisting of (6a) $C_{6-14}$ aryl which may have 1 to 3 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-4}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl, and (6b) 5- to 10-membered aromatic heterocyclic groups which may have 1 to 3 substituents selected from the group consisting of (6ba) halogen atom, (6bb) $C_{1-3}$ alkylenedioxy, (6bc) nitro, (6bd) cyano, (6be) optionally halogenated $C_{1-6}$ alkyl, (6bf) $C_{6-14}$ aryloxy-$C_{1-6}$ alkyl, (6bg) $C_{1-6}$ alkyl-$C_{6-14}$ aryl-$C_{2-6}$ alkenyl, (6bh) optionally halogenated $C_{3-6}$ cycloalkyl, (6bi) optionally halogenated $C_{1-6}$ alkoxy, (6bj) optionally halogenated $C_{1-6}$ alkylthio, (6bk) $C_{7-19}$ aralkyl, (6bl) hydroxy, (6bm) $C_{6-14}$ aryloxy, (6bn) $C_{7-19}$ aralkyloxy, (6bo) amino, (6bp) amino-$C_{1-6}$ alkyl, (6bq) mono-$C_{1-6}$ alkylamino, (6br) di-$C_{1-6}$ alkylamino, (6bs) mono-$C_{1-6}$ alkylamino-$C_{1-6}$ alkyl, (6bt) di-$C_{1-6}$ alkylamino-$C_{1-6}$ alkyl, (6bu) 5- to 7-membered saturated cyclic amino, (6bv) acyl, (6bw) acylamino and (6bx) acyloxy,
   wherein the above 13), 15), 16), 17), 24e), 24f), 24g), 24k), 24hm), 24hn), (6bk), (6bm) and (6bn) may have 1 to 5 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl;

X is a bond or a bivalent group consisting of 1 to 3 members selected from —O—, —S—, —CO—, —SO—, —$SO_2$—; —$NR^8$—($R^8$ is hydrogen atom, optionally halogenated $C_{1-6}$ alkyl, optionally halogenated $C_{1-6}$ alkyl-carbonyl or optionally halogenated $C_{1-6}$ alkylsulfonyl), and a divalent $C_{1-6}$ non-cyclic hydrocarbon group which may have 1 to 5 substituents selected front the group consisting of halogen atom, hydroxy, nitro, cyano, optionally halogenated $C_{1-6}$ alkoxy, optionally halogenated $C_{1-6}$ alkylthio, amino, mono-$C_{1-6}$ alkylamino, di-$C_{1-6}$ alkylamino, formyl, carboxy, carbamoyl, thiocarbamoyl, optionally halogenated $C_{1-6}$ alkyl-carbonyl, $C_{1-6}$ alkoxy-carbonyl and optionally halogenated $C_{1-6}$ alkylsulfonyl, wherein the bivalent $C_{1-6}$ non-cyclic hydrocarbon group is selected from a $C_{1-6}$ alkylene, a $C_{2-6}$ alkenylene and a $C_{2-6}$ alkynylene;

Yb is —CO(CH$_2$)$_{w7}$CO— wherein w7 is an integer of 0 to 4;

the group represented by the formula

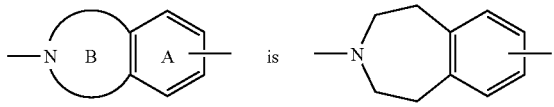

which may have 1 to 5 further substituents selected from the group consisting of
1) oxo,
2) halogen atoms,
3) $C_{1-3}$ alkylenedioxy,
4) nitro,
5) cyano,
6) optionally halogenated $C_{1-6}$ alkyl,
7) hydroxy-$C_{1-6}$ alkyl,
8) $C_{6-14}$ aryloxy-$C_{1-6}$ alkyl,
9) $C_{1-6}$ alkyl-$C_{6-14}$ aryl-$C_{2-6}$ alkenyl,
10) optionally halogenated $C_{3-6}$ cycloalkyl,
11) optionally halogenated $C_{1-6}$ alkoxy,
12) optionally halogenated $C_{1-6}$ alkylthio,
13) $C_{7-19}$ aralkyl,
14) hydroxy,
15) $C_{6-14}$ aryloxy,
16) $C_{7-19}$ aralkyloxy,
17) $C_{6-14}$ aryl-carbamoyl,
18) amino,
19) amino-$C_{1-6}$ alkyl,
20) mono-$C_{1-6}$ alkylamino,
21) di-$C_{1-6}$ alkylamino,
22) mono-$C_{1-6}$ alkylamino-$C_{1-6}$ alkyl,
23) di-$C_{1-6}$ alkylamino-$C_{1-6}$ alkyl,
24) 5- to 7-membered saturated cyclic amino,
25) 5- to 7-membered non-aromatic heterocyclic groups,
26) acyl,
27) acylamino,
28) acyloxy,
29) $C_{6-14}$ aryl which may have 1 to 3 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl, and
30) 5- to 10-membered aromatic heterocyclic groups which may have 1 to 3 substituents selected from the group consisting of 30a) halogen atom, 30b) $C_{1-3}$ alkylenedioxy, 30c) nitro, 30d) cyano, 30e) optionally halogenated $C_{1-6}$ alkyl, 30f) $C_{6-14}$ aryloxy-$C_{1-6}$ alkyl, 30g) $C_{1-6}$ alkyl-$C_{6-14}$ aryl-$C_{2-6}$ alkenyl, 30h) optionally halogenated $C_{3-6}$ cycloalkyl, 30i) optionally halogenated $C_{1-6}$ alkoxy, 30j) optionally halogenated $C_{1-6}$ alkylthio, 30k) $C_{7-19}$ aralkyl, 30l) hydroxy, 30m) $C_{6-14}$ aryloxy, 30n) $C_{7-19}$ aralkyloxy, 30o) amino, 30p) amino-$C_{1-6}$ alkyl, 30q) mono-$C_{1-6}$ alkylamino, 30r) di-$C_{1-6}$ alkylamino, 30s) mono-$C_{1-6}$ alkylamino-$C_{1-6}$ alkyl, 30t) di-$C_{1-6}$ alkylamino-$C_{1-6}$ alkyl, 30u) 5- to 7-membered saturated cyclic amino, 30v) acyl, 30w) acylamino and 30x) acyloxy, wherein the above 24) and 25) may have 1 to 5 substituents selected from the group consisting of
24a) oxo,
24b) optionally halogenated $C_{1-6}$ alkyl,
24c) optionally halogenated $C_{1-6}$ alkyl-carbonyl,
24d) optionally halogenated $C_{1-6}$ alkylsulfonyl,
24e) $C_{6-14}$ aryl,
24f) $C_{7-19}$ aralkyl,
24g) $C_{6-14}$ aryl-carbonyl,
24h) 5- to 10-membered aromatic heterocyclic group which may have 1 to 5 substituents selected from the group consisting of24ha) halogen atom, 24hb) $C_{1-3}$ alkylenedioxy, 24hc) nitro, 24hd) cyano, 24he) optionally halogenated $C_{1-6}$ alkyl, 24hf) $C_{6-14}$ aryloxy-$C_{1-6}$ alkyl, 24hg) $C_{1-6}$ alkyl-$C_{6-14}$ aryl-$C_{2-6}$ alkenyl, 24hh) optionally halogenated $C_{3-6}$ cycloalkyl, 24hi) optionally halogenated $C_{1-6}$ alkoxy, 24hj) optionally halogenated $C_{1-6}$ alkylthio, 24hk) $C_{7-19}$ aralkyl, 24hl) hydroxy, 24hm) $C_{6-14}$ aryloxy, 24hn) $C_{7-19}$ aralkyloxy, 24ho) amino, 24hp) amino-$C_{1-6}$ alkyl, 24hq) mono-$C_{1-6}$ alkylamino, 24hr) di-$C_{1-6}$ alkylamino, 24hs) mono-$C_{1-6}$ alkylamino-$C_{1-6}$ alkyl, 24ht) di-$C_{1-6}$ alkylamino-$C_{1-6}$ alkyl, 24hu) 5-to 7-membered saturated cyclic amino, 24hv) acyl, 24hw) acylamino and 24hx) acyloxy,
24i) hydroxy,
24j) 5- to 8-membered monocyclic non-aromatic heterocyclic group,
24k) carbamoyl,
24l) hydroxy-$C_{1-6}$ alkyl,
24m) $C_{1-6}$ alkoxy-carbonyl-$C_{1-6}$ alkyl,
24n) $C_{8-19}$ arylalkenyl,
24o) $C_{1-6}$ alkyl-carboxamide,
24p) (N—$C_{1-6}$ alkyl)-$C_{1-6}$ alkyl-carboxamide,
24q) amino,
24r) mono-$C_{1-6}$ alkylamino,
24s) di-$C_{1-6}$ alkylamino,
24t) 5- to 8-membered monocyclic non-aromatic heterocyclic group-$C_{1-6}$ alkyl and 24u) $C_{6-14}$ aryl-amino-$C_{1-6}$ alkyl which may be substituted with one to three $C_{1-6}$ alkyl, wherein the above 13), 15), 16), 17), 24e), 24f), 24g), 24hk), 24hm), 24hn), 30k), 30m) and 30n) may have 1 to 5 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl; and $R^1$ and $R^2$, together with the adjacent nitrogen atom, form aziridine, azetidine, morpholine, thiomorpholine, piperidine, piperazine, pyrrolidine, hexamethyleneimine, heptamethyleneimine, hexahydropyrimidine, 1,4-diazepan, dihydroisoquinoline, 1,2,5,6-tetrahydropyridine, 1,4-diazepin, or octahydroisoquinoline, each of which may have 1 to 5 substituents selected from the group consisting of 1) oxo,
2) optionally halogenated $C_{1-6}$ alkyl,
3) optionally halogenated $C_{1-6}$ alkyl-carbonyl,
4) optionally halogenated $C_{1-6}$ alkylsulfonyl,
5) $C_{6-14}$ aryl,
6) $C_{7-19}$ aralkyl,
7) $C_{6-14}$ aryl-carbonyl,
8) 5- to 10-membered aromatic heterocyclic group which may have 1 to 5 substituents selected from the group consisting of 8a) halogen atom, 8b) $C_{1-3}$ alkylenedioxy, 8c) nitro, 8d) cyano, 8e) optionally halogenated $C_{1-6}$ alkyl, 8f) $C_{6-14}$ aryloxy-$C_{1-6}$ alkyl, 8g) $C_{1-6}$ alkyl-$C_{6-14}$ aryl-$C_{2-6}$ alkenyl, 8h) optionally halogenated $C_{3-6}$ cycloalkyl, 8i) optionally halogenated $C_{1-6}$ alkoxy, 8j) optionally halogenated $C_{1-6}$ alkylthio, 8k) $C_{7-19}$ aralkyl, 8l) hydroxy, 8m) $C_{6-14}$ aryloxy, 8n) $C_{7-19}$ aralkyloxy, 8o) amino, 8p) amino-$C_{1-6}$ alkyl, 8q) mono-$C_{1-6}$ alkylamino, 8r) di-$C_{1-6}$ alkylamino, 8s) mono-$C_{1-6}$ alkylamino-$C_{1-6}$ alkyl, 8t) di-$C_{1-6}$ alkylamino-$C_{1-6}$ alkyl, 8u) 5- to 7-membered saturated cyclic amino, 8v) acyl, 8w) acylamino and 8x) acyloxy,
9) hydroxy,
10) 5- to 8-membered monocyclic non-aromatic heterocyclic group,
11) carbamoyl,
12) hydroxy-$C_{1-6}$ alkyl,
13) $C_{1-6}$ alkoxy-carbonyl-$C_{1-6}$ alkyl,
14) $C_{8-19}$ arylalkenyl,
15) $C_{1-6}$ alkyl-carboxamide,
16) (N—$C_{1-6}$ alkyl)-$C_{1-6}$ alkyl-carboxamide,
17) amino,
18) mono-$C_{1-6}$ alkylamino,
19) di-$C_{1-6}$ alkylamino,
20> 5- to 8-membered monocyclic non-aromatic heterocyclic group-$C_{1-6}$ alkyl and
21) $C_{6-14}$ aryl-amino-$C_{1-6}$ alkyl which may be substituted with one to three $C_{1-6}$ alkyl, wherein the above 5), 6), 7), 8k), 8m) and 8n) may have 1 to 5 substituents selected from the group consisting of halogen atom, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, amino-$C_{1-6}$ alkyl, mono-$C_{1-6}$ alkylamino-$C_{1-6}$ alkyl, di-$C_{1-6}$ alkylamino-$C_{1-6}$ alkyl, formyl, carboxy, carbamoyl, thiocarbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy and hydroxy-$C_{1-6}$ alkyl;

or a salt thereof.

\* \* \* \* \*

SEQUENCE LISTING

<160> NUMBER OF SEQ ID NOS: 16

<210> SEQ ID NO 1
<211> LENGTH: 32
<212> TYPE: DNA
<213> ORGANISM: Artificial Sequence
<220> FEATURE:
<223> OTHER INFORMATION: primer

<400> SEQUENCE: 1
gtcgacatgg atctgcaaac ctcgttgctg tg                         32

<210> SEQ ID NO 2
<211> LENGTH: 32
<212> TYPE: DNA
<213> ORGANISM: Artificial Sequence
<220> FEATURE:
<223> OTHER INFORMATION: primer

<400> SEQUENCE: 2
actagttcag gtgcctttgc tttctgtcct ct                         32

<210> SEQ ID NO 3
<211> LENGTH: 353
<212> TYPE: PRT
<213> ORGANISM: Rat

<400> SEQUENCE: 3

Met Asp Leu Gln Thr Ser Leu Leu Ser Thr Gly Pro Asn Ala Ser Asn
1               5                   10                  15

Ile Ser Asp Gly Gln Asp Asn Leu Thr Leu Pro Gly Ser Pro Pro Arg
            20                  25                  30

Thr Gly Ser Val Ser Tyr Ile Asn Ile Ile Met Pro Ser Val Phe Gly
        35                  40                  45

Thr Ile Cys Leu Leu Gly Ile Val Gly Asn Ser Thr Val Ile Phe Ala
    50                  55                  60

Val Val Lys Lys Ser Lys Leu His Trp Cys Ser Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly

```
                  100                 105                 110
Glu Thr Met Cys Thr Leu Ile Thr Ala Met Asp Ala Asn Ser Gln Phe
            115                 120                 125

Thr Ser Thr Tyr Ile Leu Thr Ala Met Thr Ile Asp Arg Tyr Leu Ala
        130                 135                 140

Thr Val His Pro Ile Ser Ser Thr Lys Phe Arg Lys Pro Ser Met Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Lys Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Thr
                325                 330                 335

Val Ser Asn Ala Gln Thr Ala Asp Glu Glu Arg Thr Glu Ser Lys Gly
            340                 345                 350

Thr
```

<210> SEQ ID NO 4
<211> LENGTH: 1074
<212> TYPE: DNA
<213> ORGANISM: Rat

<400> SEQUENCE: 4

```
gtcgacatgg atctgcaaac ctcgttgctg tccactggcc ccaatgccag caacatctcc     60
gatggccagg ataatctcac attgccgggg tcacctcctc gcacagggag tgtctcctac    120
atcaacatca ttatgccttc cgtgtttggt accatctgtc tcctgggcat cgtgggaaac    180
tccacggtca tctttgctgt ggtgaagaag tccaagctac actggtgcag caacgtcccc    240
gacatcttca tcatcaacct ctctgtggtg gatctgctct tcctgctggg catgcctttc    300
atgatccacc agctcatggg gaacggcgtc tggcactttg ggaaaccat gtgcaccctc    360
atcacagcca tggacgccaa cagtcagttc actagcacct catcctgac tgccatgacc    420
attgaccgct acttggccac cgtccacccc atctcctcca ccaagttccg gaagccctcc    480
atggccaccc tggtgatctg cctcctgtgg gcgctctcct tcatcagtat caccccctgtg   540
tggctctacg ccaggctcat tcccttccca gggggtgctg tgggctgtgg catccgcctg    600
ccaaacccgg acactgacct ctactggttc actctgtacc agtttttcct ggcctttgcc    660
```

-continued

```
cttccgtttg tggtcattac cgccgcatac gtgaaaatac tacagcgcat gacgtcttcg    720 gtggcccag cctcccaacg cagcatccgg cttcggacaa agagggtgac ccgcacggcc    780
attgccatct gtctggtctt ctttgtgtgc tgggcaccct actatgtgct gcagctgacc    840
cagctgtcca tcagccgccc gaccctcacg tttgtctact tgtacaacgc ggccatcagc    900
ttgggctatg ctaacagctg cctgaacccc tttgtgtaca tagtgctctg tgagaccttt    960
cgaaaacgct tggtgttgtc agtgaagcct gcagcccagg ggcagctccg cacggtcagc   1020
aacgctcaga cagctgatga ggagaggaca gaaagcaaag gcacctgaac tagt         1074
```

<210> SEQ ID NO 5
<211> LENGTH: 262
<212> TYPE: RNA
<213> ORGANISM: Rat

<400> SEQUENCE: 5

```
gcgaauuggg uaccgggccc ccccucgagg ucgacgguau cgauaagcuu gauaucgaau     60
uccugcagcc cggggauccg cccacuagu ucaggugccu ugcuuucug uccucuccuc    120 aucagcuguc ugagcguugc ugaccgucg gagcugcccc ugggcugcag gcuucacuga    180
caacaccaag cguuucgaa aggucucaca gagcacuaug uacacaaagg ggucaggca    240 gcuguuagca uagcccaagc ug                                            262
```

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6

```
caacagctgc ctcaaccc                                                  18
```

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7

```
cctggtgatc tgcctcct                                                  18
```

<210> SEQ ID NO 8
<211> LENGTH: 1275
<212> TYPE: DNA
<213> ORGANISM: Human

<400> SEQUENCE: 8

```
taggtgatgt cagtgggagc catgaagaag ggagtgggga gggcagttgg gcttggaggc     60
ggcagcggct gccaggctac ggaggaagac ccccttccca actgcggggc ttgcgctccg    120
ggacaaggtg gcaggcgctg gaggctgccg cagcctgcgt gggtggaggg gagctcagct    180
cggttgtggg agcaggcgac cggcactggc tggatggacc tggaagcctc gctgctgccc    240
actggtccca acgccagcaa cacctctgat ggccccgata acctcacttc ggcaggatca    300
cctcctcgca cggggagcat ctcctacatc aacatcatca tgccttcggt gttcggcacc    360
atctgcctcc tgggcatcat cgggaactcc acggtcatct tcgcggtcgt gaagaagtcc    420
aagctgcact ggtgcaacaa cgtccccgac atcttcatca tcaacctctc ggtagtagat    480
```

-continued

```
ctcctctttc tcctgggcat gcccttcatg atccaccagc tcatgggcaa tggggtgtgg      540
cactttgggg agaccatgtg caccctcatc acggccatgg atgccaatag tcagttcacc      600
agcacctaca tcctgaccgc catggccatt gaccgctacc tggccactgt ccacccatc       660 tcttccacga agttccggaa gccctctgtg gccaccctgg tgatctgcct cctgtgggcc      720
ctctccttca tcagcatcac ccctgtgtgg ctgtatgcca gactcatccc cttcccagga      780
ggtgcagtgg gctgcggcat acgcctgccc aacccagaca ctgacctcta ctggttcacc      840
ctgtaccagt ttttcctggc ctttgccctg ccttttgtgg tcatcacagc cgcatacgtg      900
aggatcctgc agcgcatgac gtcctcagtg gcccccgcct cccagcgcag catccggctg      960
cggacaaaga gggtgacccg cacagccatc gccatctgtc tggtcttctt tgtgtgctgg     1020
gcaccctact atgtgctaca gctgacccag ttgtccatca gccgcccgac cctcaccttt     1080
gtctacttat acaatgcggc catcagcttg ggctatgcca acagctgcct caacccctttt    1140 gtgtacatcg tgctctgtga gacgttccgc aaacgcttgg tcctgtcggt gaagcctgca     1200 gcccagggc  agcttcgcgc tgtcagcaac gctcagacgg ctgacgagga gaggacagaa     1260
agcaaaggca cctga                                                       1275
```

<210> SEQ ID NO 9
<211> LENGTH: 422
<212> TYPE: PRT
<213> ORGANISM: Human

<400> SEQUENCE: 9

```
MeT Ser Val Gly Ala MeT Lys Lys Gly Val Gly Arg Ala Val Gly Leu
1               5                  10                  15

Gly Gly Gly Ser Gly Cys Gln Ala Thr Glu Glu Asp Pro Leu Pro Asn
                20                  25                  30

Cys Gly Ala Cys Ala Pro Gly Gln Gly Gly Arg Arg Trp Arg Leu Pro
            35                  40                  45

Gln Pro Ala Trp Val Glu Gly Ser Ser Ala Arg Leu Trp Glu Gln Ala
        50                  55                  60

Thr Gly Thr Gly Trp MeT Asp Leu Glu Ala Ser Leu Leu Pro Thr Gly
65                  70                  75                  80

Pro Asn Ala Ser Asn Thr Ser Asp Gly Pro Asp Asn Leu Thr Ser Ala
                85                  90                  95

Gly Ser Pro Pro Arg Thr Gly Ser Ile Ser Tyr Ile Asn Ile Ile MeT
                100                 105                 110

Pro Ser Val Phe Gly Thr Ile Cys Leu Leu Gly Ile Ile Gly Asn Ser
            115                 120                 125

Thr Val Ile Phe Ala Val Val Lys Ser Lys Leu His Trp Cys Asn
        130                 135                 140

Asn Val Pro Asp Ile Phe Ile Ile Asn Leu Ser Val Val Asp Leu Leu
145                 150                 155                 160

Phe Leu Leu Gly MeT Pro Phe MeT Ile His Gln Leu MeT Gly Asn Gly
                165                 170                 175

Val Trp His Phe Gly Glu Thr MeT Cys Thr Leu Ile Thr Ala MeT Asp
                180                 185                 190

Ala Asn Ser Gln Phe Thr Ser Thr Tyr Ile Leu Thr Ala MeT Ala Ile
            195                 200                 205

Asp Arg Tyr Leu Ala Thr Val His Pro Ile Ser Ser Thr Lys Phe Arg
        210                 215                 220
```

```
Lys Pro Ser Val Ala Thr Leu Val Ile Cys Leu Leu Trp Ala Leu Ser
225                 230                 235                 240

Phe Ile Ser Ile Thr Pro Val Trp Leu Tyr Ala Arg Leu Ile Pro Phe
            245                 250                 255

Pro Gly Gly Ala Val Gly Cys Gly Ile Arg Leu Pro Asn Pro Asp Thr
        260                 265                 270

Asp Leu Tyr Trp Phe Thr Leu Tyr Gln Phe Phe Leu Ala Phe Ala Leu
            275                 280                 285

Pro Phe Val Val Ile Thr Ala Ala Tyr Val Arg Ile Leu Gln Arg MeT
        290                 295                 300

Thr Ser Ser Val Ala Pro Ala Ser Gln Arg Ser Ile Arg Leu Arg Thr
305                 310                 315                 320

Lys Arg Val Thr Arg Thr Ala Ile Ala Ile Cys Leu Val Phe Phe Val
                325                 330                 335

Cys Trp Ala Pro Tyr Tyr Val Leu Gln Leu Thr Gln Leu Ser Ile Ser
            340                 345                 350

Arg Pro Thr Leu Thr Phe Val Tyr Leu Tyr Asn Ala Ala Ile Ser Leu
        355                 360                 365

Gly Tyr Ala Asn Ser Cys Leu Asn Pro Phe Val Tyr Ile Val Leu Cys
370                 375                 380

Glu Thr Phe Arg Lys Arg Leu Val Leu Ser Val Lys Pro Ala Ala Gln
385                 390                 395                 400

Gly Gln Leu Arg Ala Val Ser Asn Ala Gln Thr Ala Asp Glu Glu Arg
                405                 410                 415

Thr Glu Ser Lys Gly Thr
            420

<210> SEQ ID NO 10
<211> LENGTH: 31
<212> TYPE: DNA
<213> ORGANISM: Artificial Sequence
<220> FEATURE:
<223> OTHER INFORMATION: primer

<400> SEQUENCE: 10
gtcgacatgg acctggaagc ctcgctgctg c                              31

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
actagttcag gtgcctttgc tttctgtcct c                              31

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
agtcgacatg tcagtgggag ccatgaagaa ggg                            33

<210> SEQ ID NO 13
<211> LENGTH: 33
<212> TYPE: DNA
```

```
<213> ORGANISM: Artificial Sequence
<220> FEATURE:
<223> OTHER INFORMATION: primer

<400> SEQUENCE: 13
aactagttca ggtgcctttg ctttctgtcc tct                                    33

<210> SEQ ID NO 14
<211> LENGTH: 1074
<212> TYPE: DNA
<213> ORGANISM: Human

<400> SEQUENCE: 14
gtcgacatgg aacctggaagc ctcgctgctg cccactggtc ccaacgccag caacacctct       60
gatggccccg ataacctcac ttcggcagga tcacctcctc gcacgggag catctcctac        120 atcaacatca tcatgccttc ggtgttcggc accatctgcc tcctgggcat catcgggaac       180
tccacggtca tcttcgcggt cgtgaagaag tccaagctgc actggtgcaa caacgtcccc       240
gacatcttca tcatcaacct ctcggtagta gatctcctct ttctcctggg catgcccttc       300
atgatccacc agctcatggg caatggggtg tggcactttg gggagaccat gtgcaccctc       360
atcacggcca tggatgccaa tagtcagttc accagcacct acatcctgac cgccatggcc       420
attgaccgct acctggccac tgtccacccc atctcttcca cgaagttccg gaagccctct       480
gtggccaccc tggtgatctg cctcctgtgg gccctctcct tcatcagcat caccctgtg       540 tggctgtatg ccagactcat ccccttccca ggaggtgcag tgggctgcgg catacgcctg       600
cccaacccag acactgacct ctactggttc accctgtacc agttttttcct ggcctttgcc       660 ctgcctttttg tggtcatcac agccgcatac gtgaggatcc tgcagcgcat gacgtcctca       720
gtggcccccg cctcccagcg cagcatccgg ctgcggacaa agagggtgac ccgcacagcc       780
atcgccatct gtctggtctt cttttgtgtgc tgggcaccct actatgtgct acagctgacc       840
cagttgtcca tcagccgccc gaccctcacc tttgtctact tatacaatgc ggccatcagc       900
ttgggctatg ccaacagctg cctcaacccc tttgtgtaca tcgtgctctg tgagacgttc       960
cgcaaacgct tggtcctgtc ggtgaagcct gcagcccagg ggcagcttcg cgctgtcagc      1020
aacgctcaga cggctgacga ggagaggaca gaaagcaaag gcacctgaac tagt           1074

<210> SEQ ID NO 15
<211> LENGTH: 1283
<212> TYPE: DNA
<213> ORGANISM: Human

<400> SEQUENCE: 15
agtcgacatg tcagtgggag ccatgaagaa gggagtgggg agggcagttg ggcttggagg        60
cggcagcggc tgccaggcta cggaggaaga ccccttccc aactgcgggg cttgcgctcc       120
gggacaaggt ggcaggcgct ggaggctgcc gcagcctgcg tgggtggagg ggagctcagc       180
tcggttgtgg gagcaggcga ccggcactgg ctggatggac ctggaagcct cgctgctgcc       240
cactggtccc aacgccagca acacctctga tggccccgat aacctcactt cggcaggatc       300
acctcctcgc acgggagca tctcctacat caacatcatc atgccttcgg tgttcggcac       360
catctgcctc ctgggcatca tcgggaactc cacggtcatc ttcgcggtcg tgaagaagtc       420
caagctgcac tggtgcaaca acgtccccga catcttcatc atcaacctct cggtagtaga       480
tctcctcttt ctcctgggca tgcccttcat gatccaccag ctcatgggca atggggtgtg       540
gcactttggg gagaccatgt gcaccctcat cacggccatg gatgccaata gtcagttcac       600
```

```
cagcacctac atcctgaccg ccatggccat tgaccgctac ctggccactg tccaccccat    660
ctcttccacg aagttccgga agccctctgt ggccaccctg gtgatctgcc tcctgtgggc    720
cctctccttc atcagcatca cccctgtgtg gctgtatgcc agactcatcc ccttcccagg    780
aggtgcagtg ggctgcggca tacgcctgcc caacccagac actgacctct actggttcac    840
cctgtaccag tttttcctgg cctttgccct gccttttgtg gtcatcacag ccgcatacgt    900
gaggatcctg cagcgcatga cgtcctcagt ggcccccgcc tcccagcgca gcatccggct    960
gcggacaaag agggtgaccc gcacagccat cgccatctgt ctggtcttct ttgtgtgctg   1020
ggcaccctac tatgtgctac agctgaccca gttgtccatc agccgcccga ccctcacctt   1080
tgtctactta tacaatgcgg ccatcagctt gggctatgcc aacagctgcc tcaaccccct   1140
tgtgtacatc gtgctctgtg agacgttccg caaacgcttg gtcctgtcgg tgaagcctgc   1200
agcccagggg cagcttcgcg ctgtcagcaa cgctcagacg gctgacgagg agaggacaga   1260
aagcaaaggc acctgaacta gtt                                           1283

<210> SEQ ID NO 16
<211> LENGTH: 420
<212> TYPE: RNA
<213> ORGANISM: Human

<400> SEQUENCE: 16
caaaagcugg agcuccaccg cgguggcggc cgcucuagcc cacuaguuca ggugccuuug     60
cuuucugucc ucuccucguc agccgucuga gcguugcuga cagcgcgaag cugccccugg    120
gcugcaggcu ucaccgacag gaccaagcgu uugcggaacg ucucacagag cacgauguac    180
acaaaggggu ugaggcagcu guuggcauag cccaagcuga uggccgcauu guauaaguag    240
acaaagguga gggucgggcg gcugauggac aacggguca gcuguagcac auaguagggu     300
gcccagcaca caaagaagac cagacagaug gcgauggcug ugcgggucac ccucuuuguc    360
cgcagccgga ugcugcgcug ggaggcgggg gccacugagg acgucaugcg cugcaggauc    420
```